US009259407B2

(12) United States Patent
Baker, Jr. et al.

(10) Patent No.: US 9,259,407 B2
(45) Date of Patent: *Feb. 16, 2016

(54) NANOEMULSION THERAPEUTIC COMPOSITIONS AND METHODS OF USING THE SAME

(71) Applicant: THE REGENTS OF THE UNIVERSITY OF MICHIGAN, Ann Arbor, MI (US)

(72) Inventors: James R. Baker, Jr., Ann Arbor, MI (US); Mark R. Hemmila, Superior Township, MI (US); Stewart C. Wang, Ann Arbor, MI (US); Tarek Hamouda, Milan, MI (US); John J. LiPuma, Ann Arbor, MI (US); Jessica Ann Knowlton, Ypsilanti, MI (US); Paul E. Makidon, Webberville, MI (US); Luz Blanco, Ann Arbor, MI (US); Jeffery V. Groom, II, Utica, MI (US); Anna U. Bielinska, Ypsilanti, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/628,886

(22) Filed: Feb. 23, 2015

(65) Prior Publication Data

US 2015/0216826 A1 Aug. 6, 2015

Related U.S. Application Data

(63) Continuation of application No. 12/567,571, filed on Sep. 25, 2009, now Pat. No. 8,962,026.

(60) Provisional application No. 61/100,559, filed on Sep. 26, 2008.

(51) Int. Cl.
*A61K 9/107* (2006.01)
*A01N 25/04* (2006.01)

(Continued)

(52) U.S. Cl.
CPC ............ *A61K 31/198* (2013.01); *A61K 9/1075* (2013.01); *A61K 45/06* (2013.01)

(58) Field of Classification Search
CPC .......................... A01N 25/04; A01N 2300/00
USPC .................................. 424/400, 489, 405, 447
See application file for complete search history.

(56) References Cited

U.S. PATENT DOCUMENTS 4,596,556 A 6/1986 Morrow et al.
4,604,384 A 8/1986 Smith et al.

(Continued)

FOREIGN PATENT DOCUMENTS

EP 0468520 1/1992
EP 0517565 12/1992

(Continued)

OTHER PUBLICATIONS

Mestecky, The common mucosal immune system and current strategies for induction of immune responses in external secretions, J Clin Immunol. Jul. 1987;7(4):265-76.

(Continued)

*Primary Examiner* — Albert Navarro
*Assistant Examiner* — Ginny Portner
(74) *Attorney, Agent, or Firm* — Tyler J. Sisk; Casimir Jones, S.C.

(57) ABSTRACT

The present invention relates to therapeutic nanoemulsion compositions and to methods of utilizing the same. In particular, nanoemulsion compositions are described herein that find use in the treatment and/or prevention of infection (e.g., respiratory infection (e.g., associated with cystic fibrosis)), in burn wound management, and in immunogenic compositions (e.g., comprising a *Burkholderia* antigen) that generate an effective immune response (e.g., against a bacterial species of the genus *Burkholderia*) in a subject administered the immunogenic composition. Compositions and methods of the present invention find use in, among other things, clinical (e.g. therapeutic and preventative medicine), industrial, and research applications.

12 Claims, 39 Drawing Sheets

(51) Int. Cl.
*A61K 45/06* (2006.01)
*A61K 31/198* (2006.01)

(56) References Cited

U.S. PATENT DOCUMENTS

| | | | |
|---|---|---|---|
| 4,895,452 | A | 1/1990 | Yiournas |
| 5,057,540 | A | 10/1991 | Kensil |
| 5,103,497 | A | 4/1992 | Hicks |
| 5,284,656 | A | 2/1994 | Platz |
| 5,451,569 | A | 9/1995 | Wong |
| 5,510,104 | A | 4/1996 | Allen |
| 5,547,677 | A | 8/1996 | Wright |
| 5,549,901 | A | 8/1996 | Wright |
| 5,576,016 | A | 11/1996 | Amselem et al. |
| 5,618,840 | A | 4/1997 | Wright |
| 5,662,957 | A | 9/1997 | Wright |
| 5,700,679 | A | 12/1997 | Wright |
| 5,716,637 | A | 2/1998 | Anselem et al. |
| 5,951,988 | A | 9/1999 | Littel-van den Hurk et al. |
| 5,961,970 | A | 10/1999 | Lowell et al. |
| 5,993,412 | A | 11/1999 | Deily |
| 6,005,099 | A | 12/1999 | Davies |
| 6,015,832 | A | 1/2000 | Baker, Jr. et al. |
| 6,039,936 | A | 3/2000 | Restle et al. |
| 6,165,500 | A | 12/2000 | Cevc |
| 6,491,919 | B2 | 12/2002 | Crane |
| 6,492,395 | B1 | 12/2002 | Scheiwe et al. |
| 6,506,803 | B1 | 1/2003 | Baker, Jr. et al. |
| 6,558,695 | B2 | 5/2003 | Luo et al. |
| 6,559,189 | B2 | 5/2003 | Baker, Jr. et al. |
| 6,565,873 | B1 | 5/2003 | Shefer et al. |
| 6,635,676 | B2 | 10/2003 | Baker, Jr. et al. |
| 6,651,655 | B1 | 11/2003 | Licalsi |
| 7,314,624 | B2 | 1/2008 | Baker et al. |
| 7,655,252 | B2 | 2/2010 | Baker, Jr. et al. |
| 7,767,216 | B2 * | 8/2010 | Baker et al. .................. 424/405 |
| 7,858,580 | B2 | 12/2010 | Lersch et al. |
| 7,887,839 | B2 * | 2/2011 | Wen ...................... A61K 9/107 424/451 |
| 8,039,450 | B2 * | 10/2011 | Akama et al. .................. 514/64 |
| 8,226,965 | B2 * | 7/2012 | Baker et al. .................. 424/405 |
| 8,232,320 | B2 | 7/2012 | Baker et al. |
| 8,236,335 | B2 | 8/2012 | Baker et al. |
| 8,389,021 | B2 | 3/2013 | Baker |
| 8,464,435 | B2 * | 6/2013 | Johnson et al. ................ 33/600 |
| 8,703,164 | B2 * | 4/2014 | Annis et al. .................. 424/405 |
| 8,747,872 | B2 * | 6/2014 | Baker et al. .................. 424/405 |
| 8,877,208 | B2 * | 11/2014 | Baker et al. ............... 424/203.1 |
| 8,962,026 | B2 * | 2/2015 | Baker et al. .................. 424/489 |
| 2002/0045667 | A1 | 4/2002 | Baker, Jr. et al. |
| 2002/0119207 | A1 | 8/2002 | Baker, Jr. et al. |
| 2002/0155084 | A1 | 10/2002 | Roessler et al. |
| 2004/0043041 | A1 | 3/2004 | Baker, Jr. et al. |
| 2005/0208083 | A1 | 9/2005 | Annis |
| 2005/0238660 | A1 | 10/2005 | Babiuk |
| 2005/0281843 | A1 | 12/2005 | Singh |
| 2006/0051385 | A1 | 3/2006 | Scholz |
| 2006/0058238 | A1 | 3/2006 | Laurent-Applegate et al. |
| 2006/0134186 | A1 | 6/2006 | Carlton et al. |
| 2006/0204469 | A1 | 9/2006 | Spengler et al. |
| 2006/0233721 | A1 | 10/2006 | Tamarkin et al. |
| 2006/0251684 | A1 | 11/2006 | Annis et al. |
| 2006/0269485 | A1 | 11/2006 | Friedman et al. |
| 2007/0036831 | A1 | 2/2007 | Baker, Jr. et al. |
| 2007/0072793 | A1 | 3/2007 | Chung |
| 2007/0105754 | A1 | 5/2007 | Pinto Da Silva et al. |
| 2007/0116709 | A1 | 5/2007 | O'Hagan |
| 2007/0269526 | A1 | 11/2007 | Bos et al. |
| 2007/0281904 | A1 | 12/2007 | Baker et al. |
| 2007/0292688 | A1 | 12/2007 | Bringley et al. |
| 2008/0038298 | A1 | 2/2008 | Barnikol-Keuten et al. |
| 2008/0044444 | A1 * | 2/2008 | Tamarkin .............. A61K 8/362 424/401 |
| 2008/0138296 | A1 | 6/2008 | Tamarkin et al. |
| 2008/0181905 | A1 | 7/2008 | Baker, Jr. et al. |
| 2008/0181941 | A1 | 7/2008 | Oshlack et al. |
| 2008/0200400 | A1 | 8/2008 | Lersch et al. |
| 2008/0206155 | A1 | 8/2008 | Tamarkin et al. |
| 2008/0317799 | A1 | 12/2008 | Baker, Jr. et al. |
| 2009/0169632 | A1 | 7/2009 | Lu et al. |
| 2009/0258070 | A1 * | 10/2009 | Burnier ................ A61K 9/0014 424/489 |
| 2009/0258841 | A1 | 10/2009 | Murphy et al. |
| 2009/0269380 | A1 | 10/2009 | Baker, Jr. et al. |
| 2009/0291095 | A1 | 11/2009 | Baker et al. |
| 2009/0304799 | A1 | 12/2009 | Baker, Jr. et al. |
| 2010/0003330 | A1 | 1/2010 | Baker, Jr. et al. |
| 2010/0068162 | A1 | 3/2010 | Greenberg et al. |
| 2010/0092526 | A1 | 4/2010 | Baker, Jr. et al. |
| 2011/0070306 | A1 | 3/2011 | Baker, Jr. et al. |
| 2011/0091556 | A1 | 4/2011 | Baker, Jr. et al. |
| 2011/0200657 | A1 * | 8/2011 | Baker .......................... 424/405 |

FOREIGN PATENT DOCUMENTS

| | | |
|---|---|---|
| EP | 0549074 | 6/1993 |
| GB | 2122204 | 1/1984 |
| JP | H10-500686 | 1/1998 |
| WO | 88/09336 | 12/1988 |
| WO | 92/19265 | 11/1992 |
| WO | 93/13202 | 7/1993 |
| WO | 94/00153 | 1/1994 |
| WO | 94/21292 | 9/1994 |
| WO | 95-11700 | 5/1995 |
| WO | 95/14026 | 5/1995 |
| WO | 95/17210 | 6/1995 |
| WO | 96/02555 | 2/1996 |
| WO | 96/11711 | 4/1996 |
| WO | 96/33739 | 10/1996 |
| WO | 97-29773 | 8/1997 |
| WO | 97/48440 | 12/1997 |
| WO | 98/16247 | 4/1998 |
| WO | 98/20734 | 5/1998 |
| WO | 98/28037 | 7/1998 |
| WO | 98/56414 | 12/1998 |
| WO | 99/10008 | 3/1999 |
| WO | 99/11241 | 3/1999 |
| WO | 99/12565 | 3/1999 |
| WO | 99/27961 | 6/1999 |
| WO | 99-33459 | 7/1999 |
| WO | 00/37105 | 6/2000 |
| WO | 00/39299 | 7/2000 |
| WO | 00-50006 | 8/2000 |
| WO | 01/49296 | 7/2001 |
| WO | 01/98334 | 12/2001 |
| WO | 03/000243 | 1/2003 |
| WO | 2004-030608 | 4/2004 |
| WO | 2005/027872 | 3/2005 |
| WO | 2006/110699 | 10/2006 |
| WO | 2008/087410 | 7/2008 |
| WO | 2008/137747 | 11/2008 |
| WO | 2009/143524 | 11/2009 |

OTHER PUBLICATIONS

Meyers, Surfactant Science and Technology, VCH Publishers Inc., New York, pp. 231-245 (1992) (book).

Nelson et al., Serum IgG and sputum IgA antibody to core lipopolysaccharide antigen from Pseudomonas cepacia in patients with cystic fibrosis, J Med Microbiol. Jul. 1993;39(1):39-47.

O'Hagan, D. Recent advances in Vaccine adjuvants for systemic and mucosal administration. J. Pharm. Pharmacol., 1997, vol. 49, 1-10.

Ortega et al., Reconstitution of O-specific lipopolysaccharide expression in Burkholderia cenocepacia strain J2315, which is associated with transmissible infections in patients with cystic fibrosis, J Bacteriol. Feb. 2005;187(4):1324-33.

Piccolo et al., Role of chemotactic factors in neutrophil activation after thermal injury in rats, Inflammation. Aug. 1999;23(4):371-85.

Plesa et al., Conservation of the opcL gene encoding the peptidoglycan-associated outer-membrane lipoprotein among representatives of the Burkholderia cepacia complex, J Med Microbiol. May 2004;53(Pt 5):389-98.

(56) References Cited

OTHER PUBLICATIONS

Rabinovich-Guilatt et al., Cationic vectors in ocular drug delivery, J Drug Target. 2004;12(9-10):623-33.
Reik, Distribution of Burkholderia cepacia complex species among isolates recovered from persons with or without cystic fibrosis, J Clin Microbiol. Jun. 2005;43(6):2926-8.
Salman and Seigel, Infection control recommendations for patients with cystic fibrosis: microbiology, important pathogens, and infection control practices to prevent patient-to-patient transmission, Infect Control Hosp Epidemiol. May 2003;24(5 Suppl):S6-52.
Silver et al., Silver as biocides in burn and wound dressings and bacterial resistance to silver compounds, J Ind Microbiol Biotechnol. Jul. 2006;33(7):627-34. Epub May 25, 2006.
Smith et al., Pulmonary deposition and clearance of aerosolized alpha-1-proteinase inhibitor administered to dogs and to sheep, J Clin Invest. 1989; 84(4):1145-1154.
Steinstraesser et al., Activity of novispirin G10 against Pseudomonas aeruginosa in vitro and in infected burns, Antimicrob Agents Chemother. Jun. 2002;46(6):1837-44.
Steinstraesser et al., Protegrin-1 enhances bacterial killing in thermally injured skin, Crit Care Med. Jul. 2001;29 (7):1431-7.
Till et al., Intravascular activation of complement and acute lung injury. Dependency on neutrophils and toxic oxygen metabolites, J Clin Invest. May 1982;69(5):1126-35.
Tomlin et al., Green and red fluorescent protein vectors for use in biofilm studies of the intrinsically resistant Burkholderia cepacia complex, J Microbiol Methods. Apr. 2004;57(1):95-106.
Tomlin et al., Interspecies biofilms of Pseudomonas aeruginosa and Burkholderia cepacia, Can J Microbiol. Oct. 2001;47(10):949-54.
Triantafilou & Triantafilou, Lipopolysaccharide recognition: CD14, TLRs and the LPS-activation cluster, Trends Immunol. Jun. 2002;23(6):301-4.
UniprotKB entry A2WCE)_9BURK. Mar. 20, 2007 [Retrieved from the internet on Mar. 7, 2010: <www.uniprot.org/uniprot/AA2WCE0.txt?version=1>].
UniprotKB entry Q83ZW Jun. 1, 2003 [Retrieved from the internet on Mar. 7, 2010: www.uniprot.org/uniprot/Q83XW1.txt?version=1>].
Vaara, Agents that increase the permeability of the outer membrane, Microbiol Rev. Sep. 1992;56(3):395-411.
Varedi et al., Serum TGF-beta in thermally injured rats, Shock. Nov. 2001;16(5):380-2.
Adjei, et al., Pulmonary delivery of peptide drugs: effect of particle size on bioavailability of leuprolide acetate in healthy male volunteers, Pharm Res. Jun. 1990;7(6):565-9.
Al Bakri et al., Immigration and emigration of Burkholderia cepacia and Pseudomonas aeruginosa between and within mixed biofilm communities, J Appl Microbiol. 2004;96(3):455-63.
Albrecht et al., Journal of American College of Surgery, Impact of Acinetobacter Infection on the Mortality of Burn Patients, vol. 203(4), Oct. 2006, pp. 546-550.
Baker, Jr. et al., Nasal immunization with a novel nanoemulsion adjuvant modifies Th2-polarized immune responses, Journal of Allergy and Clinical Immunology, vol. 121, No. 3, Mar. 2008, p. 796 & 64th Annual Meeting of the American-Academy-of-Allergy-Asthma-and-Immunology, Philadelphia, PA, USA, Mar. 14-18, 2008.
Baldwin et al., Elucidating global epidemiology of Burkholderia multivorans in cases of cystic fibrosis by multilocus sequence typing, J Clin Microbiol. Jan. 2008;46(1):290-5. Epub Nov. 21, 2007 .
Barton et al., Resuscitation of thermally injured patients with oxygen transport criteria as goals of therapy, J Burn Care Rehabil. Jan.-Feb. 1997;18(1 Pt 1):1-9.
Beg, Endogenous ligands of Toll-like receptors: implications for regulating inflammatory and immune responses, Trends Immunol. Nov. 2002;23(11):509-12.
Benko et al., The microbial and danger signals that activate Nod-like receptors, Cytokine. Sep. 2008;43(3):368-73. Epub Aug. 19, 2008.
Bertot et al., Nasal immunization with Burkholderia multivorans outer membrane proteins and the mucosal adjuvant adamantylamide dipeptide confers efficient protection against experimental lung infections with B. multivorans and B. cenocepacia, Infection and Immunity Feb. 12, 2007, 75:2740-2752.
Bessey, Wound care. In Herndon DN, ed: Total Burn Care 3rd edition. Philadelphia, PA: Elsevier Inc., 2007, pp. 127-135.
Bielinska et al., Mucosal immunization with a novel nanoemulsion-based recombinant anthrax protective antigen vaccine protects against *Bacillus anthracis* spore challenge. Infection and Immunity. Aug. 2007, vol. 75, No. 8, 4020-4029.
Bielinska et al., Nasal Immunization with a Recombinant HIV gp 120 and Nanoemulsion Adjuvant Produces Th1 Polarized Responses and neutralizing Antibodies to Primary HIV Type I Isolates. AIDS Research and Human Retroviruses, Feb. 2008, vol. 24(2), pp. 271-281; Abstract, Fig. 1E; p. 272, para 5; p. 275, para 3, 5; p. 278, para 3; p. 279, para 1.
Braquet, et al., Effect of endothelin-1 on blood pressure and bronchopulmonary system of the guinea pig, J Cardiovasc Pharmacol. 1989;13 Suppl 5:S143-6; discussion S150.
Brazolot-Millan et al., CpG DNA can induce strong Th1 humoral and cell-mediated immune responses against hepatitis B surface antigen in young mice, Proc Natl Acad Sci U S A. Dec. 22, 1998;95(26):15553-8.
Chen, H., Recent advances in mucosal vaccine development, J Control Release. Jul. 3, 2000;67(2-3):117-28.
Chu et al., Differential persistence among genomovars of the Burkholderia cepacia complex in a murine model of pulmonary infection, Infect Immun. May 2002;70(5):2715-20.
Chu et al., Persistence of Burkholderia multivorans within the pulmonary macrophage in the murine lung, Infect Immun. Oct. 2004;72(10):6142-7.
Church et al., Burn wound infections, Clin Microbiol Rev. Apr. 2006;19(2):403-34.
Costigan, The Toxicology of Nanoparticles Used in Healthcare Products, Reprot for the Committee on Human medicine, Sep. 2006, Retrieved from the Internet.
Davis et al., CpG DNA is a potent enhancer of specific immunity in mice immunized with recombinant hepatitis B surface antigen, J Immunol. Jan. 15, 1998;160(2):870-6.
Davis, 2001, Nasal vaccines, Adv Drug Deliv Rev. Sep. 23, 2001;51(1-3):21-42.
Debs et al., Lung-specific delivery of cytokines induces sustained pulmonary and systemic immunomodulation in rats, J Immunol. May 15, 1988;140(10):3482-8.
Eberl and Tummler, Pseudomonas aeruginosa and Burkholderia cepacia in cystic fibrosis: genome evolution, interactions and adaptation, Int J Med Microbiol. Sep. 2004;294(2-3):123-31.
Eldad, A et al., Journal of Burn Care Rehabilitation, May-Jun. 2003, vol. 24(3), pp. 154-157, Abstract Only, Silver-sulfadiazine eschar pigmentation mimics invsive wound infection: a case report.
Graham BS (2006) New Approaches to Vaccine Adjuvants: Inhibiting the Inhibitor. PLoS Med 3(1): e57. Epub Jan. 3, 2006.
Grebski et al., Effect of physical and chemical methods of homogenization on inflammatory mediators in sputum of asthma patients, Chest. May 2001;119(5):1521-5.
Hamouda and Baker, Antimicrobial mechanism of action of surfactant lipid preparations in enteric Gram-negative bacilli, J Appl Microbiol. Sep. 2000;89(3):397-403.
Hamouda et al., A Novel Surfactant nanoemulsion with Broad-Spectrum Sporicidal Activity against *Bacillus* Species, J. Infect Dis., 180:1939-1949 (1999).
Hamouda T Et al: "A Novel Surfactant Nanoemulsion with a unique non-irritant topical antimicrobial activity against bacteria, enveloped viruses and fungi" Microbiological Research vol. 156, No. 1, Jan. 1, 2001, pp. 1-07.
Hamouda, N. Mytle, A. Chepurnov, N. Mank, J. Knowlton, J. Sutcliffe, and J.R. Baker, Jr.: "A Novel Nanoemulsion Adjuvant Enhancing the Immune Response to beta-propiolactone Inactivated Influenza Virus Using a Nasal Route in a Ferret Model", Presented at 48th ICAAC / 46th IDSA Conference Oct. 25-28, 2008; Washington, DC , Oct. 25, 2008, XP007921413, Retrieved from the Internet: www.nanobio.com/documents/Web_Flu_Immune_Resp_G1194.pdf.

(56) References Cited

OTHER PUBLICATIONS

Hansbrough et al., Neutrophil activation and tissue neutrophil sequestration in a rat model of thermal injury, J Surg Res. Feb. 15, 1996;61(1):17-22.

Hershey, IL-13 receptors and signaling pathways: an evolving web, J Allergy Clin Immunol. Apr. 2003;111(4):677-90; quiz 691.

Hilgers et al., Synergistic effects of synthetic adjuvants on the humoral immune response, Int Arch Allergy Appl Immunol. 1986;79(4):392-6.

Hilgers et al., Synthetic sulpholipopolysaccharides: novel adjuvants for humoral immune responses, Immunology. Jan. 1987;60(1):141-6.

Horowitz et al., Solvent/Detergent-Treated Plasma: A Virus-Inactivated Substitute for Fresh Frozen Plasma, Blood 79:826-831 (1992).

Huang et al., Effect of transforming growth factor-beta neutralization on survival and bacterial clearance in a murine model of Pseudomonas aeruginosa burn wound infection, J Burn Care Res. Sep.-Oct. 2006;27(5):682-7.

Hubbard, et al. (1989) Annals of Internal Medicine, vol. III, pp. 206-212.

Hunt et al., Macromolecular mechanisms of sputum inhibition of tobramycin activity, Antimicrob Agents Chemother. Jan. 1995;39(1):34-9.

Illum et al., Hyaluronic acid ester microspheres as a nasal delivery system for insulin, Journal of Controlled Release, vol. 29, Issues 1-2, Feb. 1994, pp. 133-141.

Ipaktchi et al., Topical p38MAPK inhibition reduces dermal inflammation and epithelial apoptosis in burn wounds, Shock. Aug. 2006;26(2):201-9.

Jones et al., Different Toll-like receptor agonists induce distinct macrophage responses, J Leukoc Biol. Jun. 2001;69(6):1036-44.

Kensil et al., Separation and characterization of saponins with adjuvant activity from Quillaja saponaria Molina cortex, J Immunol. Jan. 15, 1991;146(2):431-7.

Kensil, Saponins as vaccine adjuvants, Crit Rev Ther Drug Carrier Syst. 1996;13(1-2):1-55.

Lacaille-Dubois and Wagner (1996) Phytomedicine vol. 2 pp. 363-386.

LiPuma et al, Update on the Burkholderia cepacia complex, Curr Opin Pulm Med. Nov. 2005;11(6):528-33.

LiPuma et al., "In vitro activities of a novel nanoemulsion against Burkholderia and other multidrug-resistant cystic fibrosis-associated bacterial species," Antimicrob. Agents Chemother., 53:249-255 (2009).

Lyons et al., Protective effects of early interleukin 10 antagonism on injury-induced immune dysfunction, Arch Surg. Dec. 1999;134(12):1317-23; discussion 1324.

Mahy, Strategies of virus persistence, Br Med Bull. Jan. 1985;41(1):50-5.

Makidon et al., Pre-clinical evaluation of a novel nanoemulsion-based hepatitis B mucosal vaccine, PLoS One. Aug. 13, 2008;3(8):e2954.

McCluskie and Davis, CpG DNA is a potent enhancer of systemic and mucosal immune responses against hepatitis B surface antigen with intranasal administration to mice, J Immunol. Nov. 1, 1998;161(9):4463-6.

* cited by examiner

| 10 min EXPT 1 | Total Colonies /ml | Log Killing |
|---|---|---|
| Start | 13800000 | 0.00 |
| NE+EDTA | 450 | 4.49 |
| NE | 22510 | 2.79 |
| 10% BLEACH | 0 | 7.14 |
| EDTA | 1420000 | 0.99 |
| PBS | 5600000 | 0.39 |

| 20 min EXPT 1 | Total Colonies /ml | Log Killing |
|---|---|---|
| Start | 4608000 | 0.00 |
| NE+EDTA | 1300 | 3.55 |
| NE | 130 | 4.55 |
| 10% BLEACH | 0 | 6.66 |
| EDTA | 710000 | 0.81 |
| PBS | 2380000 | 0.29 |

| 40min EXPT 2 | Total colonies/ml | LOG Killing |
|---|---|---|
| Start | 1800000 | 0.00 |
| NE+EDTA | 10 | 5.26 |
| NE | 10 | 5.26 |
| 10% BLEACH | 0 | 6.26 |
| EDTA | 140000 | 1.11 |
| PBS | 460000 | 0.59 |

| 40min | Total colonies /ml | Log Killing |
|---|---|---|
| Start | 8000000 | 0.00 |
| NE+EDTA | 150 | 4.74 |
| NE | 100 | 4.90 |
| BLEACH | 0 | 6.91 |
| EDTA | 940000 | 0.93 |
| PBS | 3040000 | 0.42 |

| 60min | Total colonies/ml | Log Killing |
| --- | --- | --- |
| Start | 8575000 | 0 |
| NE | 0 | 6.93 |
| NE + EDTA | 0 | 6.93 |
| Bleach | 0 | 6.93 |
| PBS | 3230000 | 0.42 |
| EDTA | 3940000 | 0.34 |

| 60 min | Colonies/ml | Log Killing |
|---|---|---|
| Start | 12500000 | 0.00 |
| NE | 0 | 7.10 |
| NE + EDTA | 0 | 7.10 |
| 10% Bleach | 0 | 7.10 |
| EDTA | 2420000 | 0.71 |
| NS | 3580000 | 0.54 |

| | 15 Minutes | | 30 Minutes | |
|---|---|---|---|---|
| | Colonies/ml | Log Killing | Colonies/ml | Log Killing |
| Start | 3900000 | 0 | | |
| NE | 120000 | 1.51 | 3830 | 3.01 |
| NE + 2.5mM EDTA | 1350 | 3.46 | 0 | 6.59 |
| NE + 5mM EDTA | 630 | 3.79 | 0 | 6.59 |
| NE + 10mM EDTA | 80 | 4.69 | 0 | 6.59 |
| NE + 15mM EDTA | 40 | 4.99 | 0 | 6.59 |
| NE + 20mM EDTA | 0 | 6.59 | 0 | 6.59 |
| 10% Bleach | 0 | 6.59 | 0 | 6.59 |

| Individual Cultures | Start | | NE ALONE | | NE + EDTA | | EDTA | | BLEACH | |
|---|---|---|---|---|---|---|---|---|---|---|
| | Log Killing | colonics/ml | Log Killing | Colonics/ml | Log Killing | Colonics/ml | Log Killing | Colonics/ml | Log Killing | Colonics/ml |
| *B cepacia* (HI 3802) | 0 | 4800000 | 1.60 | 120000 | 6.68 | 0 | 0.27 | 2560000 | 6.68 | 0 |
| *P. aeruginosa* (PA 01) | 0 | 375000 | 2.57 | 1000 | 5.57 | 0 | 5.57 | 0 | 5.57 | 0 |

| Co-Culture | Start | | NE ALONE | | NE + EDTA | | EDTA | | BLEACH | |
|---|---|---|---|---|---|---|---|---|---|---|
| | Log Killing | Colonies/ ml | Log Killing | Colonies/ ml | Log Killing | Colonies/ ml | Log Killing | Colonies/ ml | Log Killing | Colonies/ ml |
| *B. cepacia* (HI 3802) | 0 | 2400000 | 1.38 | 70000 | 6.38 | 0 | 0.66 | 530000 | 6.38 | 0 |
| *P. aeruginosa* (PA 01) | 0 | 187500 | 1.56 | 0 | 5.27 | 0 | 5.27 | 0 | 5.27 | 0 |

FIG. 11

| Species (no. tested) | MIC (μg/ml CPC) 50% | 90% | Range |
|---|---|---|---|
| *Burkholderia* species | | | |
| *B. cepacia* (5) | | | 31.2 – 125 |
| *B. multivorans* (10) | 62.5 | 125 | 31.2 – 125 |
| *B. cenocepacia* (20) | 62.5 | 125 | ≤ 15.6 – 500 |
| *B. stabilis* (5) | | | ≤ 15.6 – 125 |
| *B. vietnamiensis* (5) | | | ≤ 15.6 – 62.5 |
| *B. dolosa* (5) | | | 62.5 – 125 |
| *B. ambifaria* (5) | | | 31.2 – 62.5 |
| *B. anthina* (5) | | | 31.2 – 62.5 |
| *B. pyrrocinia* (5) | | | 31.2 – 125 |
| *B. gladioli* (10) | 31.2 | 125 | ≤ 15.6 – 125 |
| *P. aeruginosa* (20) | 31.2 | 62.5 | ≤ 15.6 – 62.5 |
| *A. xylosoxidans* (10) | 31.2 | 62.5 | 31.2 – 62.5 |
| *S. maltophilia* (15) | ≤ 15.6 | 31.2 | ≤ 15.6 – 62.5 |
| *Acinetobacter* (10) | ≤ 15.6 | 125 | ≤ 15.6 – 125 |
| *Pandoraea* species | | | |
| *P. apista* (2) | | | 31.2 |
| *P. norimbergensis* (2) | | | 31.2 |
| *P. pnomenusa* (2) | | | 31.2 |
| *P. pulmonicola* (2) | | | 31.2 – 62.5 |
| *P. sputorum* (2) | | | 31.2 – 62.5 |
| *Ralstonia* species | | | |
| *R. mannitolilytica* (5) | | | ≤ 15.6 – 31.2 |
| *R. pickettii* (5) | | | ≤ 15.6 |
| Total (150) | 31.2 | 125 | ≤ 15.6 - 500 |

FIG. 12

| Strain | Species | MIC | MBC | MBIC | MBEC | SMBC |
|---|---|---|---|---|---|---|
| AU8042 | *B. multivorans* | 125 | 125 | 1000 | 1000 | 1000 |
| AU10398b | *B. multivorans* | 62.5 | 62.5 | 500 | 500 | 250 |
| ATCC 17616 | *B. multivorans* | 62.5 | 62.5 | 1000 | 1000 | 1000 |
| AU10321 | *B. cenocepacia* | 31.2 | 31.2 | 1000 | 1000 | 1000 |
| J2315 | *B. cenocepacia* | 62.5 | 125 | 500 | 1000 | 1000 |
| AU4757 | *B. stabilis* | 125 | 125 | 500 | 500 | 500 |
| AU10529 | *B. gladioli* | ≤15.6 | ≤15.6 | 62.5 | 62.5 | 31.2 |
| AU13206 | *A.* xylosoxidans | 62.5 | 125 | 500 | 2000 | 1000 |
| AU12828 | *P.* aeruginosa | 31.2 | 31.2 | 1000 | 1000 | 500 |
| AU8215a | *P.* aeruginosa | 31.2 | 31.2 | 31.2 | 31.2 | 62.5 |
| AU12914 | *R. pickettii* | ≤15.6 | ≤15.6 | ≤15.6 | ≤15.6 | 31.2 |
| AU4194 | *S. maltophilia* | ≤15.6 | ≤15.6 | 31.2 | 31.2 | 31.2 |

Values represent μg/ml CPC. SMBC is MBC in the presence of 43% CF sputum.

| | Total colonies/10ml | Colonies/10 ml after Rx | Log Killing |
|---|---|---|---|
| *B. cepacia* | 600333333 | 0 | 8.78 |
| *E. coli* | 140333333 | 3250 | 4.64 |
| *P. aeruginosa* (3ul on Membrane) | 4500000 | 0 | 6.65 |

| Mixed Biofilm | Start Total Colonies/10ml | Total colonies after treatment/10ml | Log Killing |
|---|---|---|---|
| *B. cepacia* | 810000000 | 1250 | 5.81 |
| *E. coli* | 3000000 | 0 | 6.48 |

| | Total colonies/10ml | Colonies/10ml After Rx | Log Killing |
|---|---|---|---|
| *E. coli* | 6000000 | 0 | 6.78 |
| *B. cep* | 654000000 | 0 | 8.82 |

| Biofilm Details | Start Total Colonies (10ml) | Total Colonies After Treatment (10ml) | Log Killing |
|---|---|---|---|
| Biofilm from escape colonies | 2468000000 | 300 | 6.92 |
| Biofilm from frozen stock | 1686000000 | 700 | 6.38 |

FIG. 17

| CPC conc. | (CPC %) | Soybean oil | Poloxomer 407 | Ethanol | CPC% | EDTA | H2O | EDTA mM | CPC mg/ml |
|---|---|---|---|---|---|---|---|---|---|
| 10mg | 1% | 62.7900 | 5.9200 | 6.7300 | 1.0680 | 0.074500 | 23.4175 | 2.0000 | 10.0000 |
| 5 mg | 0.50% | 31.4000 | 2.9600 | 3.3700 | 0.5300 | 0.037000 | 61.7030 | 1.0000 | 5.0000 |
| 3 mg | 0.3 | 18.8370 | 1.7760 | 2.0190 | 0.3204 | 0.022350 | 77.0253 | 0.6000 | 3.0000 |
| 2.5 mg | 0.25% | 15.7000 | 1.4800 | 1.6800 | 0.2700 | 0.019000 | 80.8510 | 0.5000 | 2.5000 |
| 1000ug | 0.1 | 6.2790 | 0.5920 | 0.6730 | 0.1068 | 0.007450 | 92.3418 | 0.2000 | 1.0000 |
| 500ug | 0.05 | 3.1395 | 0.2960 | 0.3365 | 0.0534 | 0.003725 | 96.1709 | 0.1000 | 0.5000 |
| 250ug | 0.025 | 1.5698 | 0.1480 | 0.1683 | 0.0267 | 0.001863 | 98.0854 | 0.0500 | 0.2500 |
| 10 ug | 0.001 | 0.0628 | 0.0059 | 0.0067 | 0.0011 | 0.000075 | 99.9234 | 0.0020 | 0.0100 |
| 3ug | 0.003 | 0.1884 | 0.0178 | 0.0202 | 0.0032 | 0.000224 | 99.7703 | 0.0060 | 0.0300 |
| 1ug | 0.0001 | 0.0063 | 0.0006 | 0.0007 | 0.0001 | 0.000007 | 99.9923 | 0.0002 | 0.0010 |
| 0.1 ug | 0.00001 | 0.0006 | 0.0001 | 0.0001 | 0.0000 | 0.000001 | 99.9992 | 0.0000 | 0.0001 |

Age Specific Prevalence of Respiratory Infections in CF Patients, 2006

FIG. 19A The Fractional Inhibitory Concentration (FIC) Index

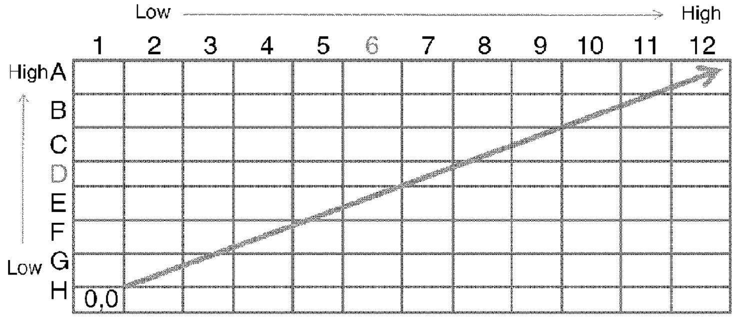

The previously determined MIC used to choose the flanking concentrations of the two drugs being combined is represented by region 6, D

FIG. 19B

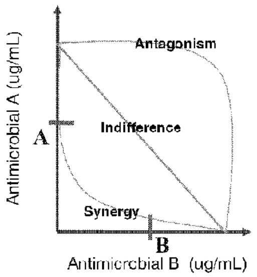

Hash marks A & B indicate typical MIC concentration of each drug alone

The FIC (fractional inhibitory concentration) index examines the ratio of the MIC of a single drug when in combination with another to the MIC of that drug alone. The reduction of the MIC when a drug is in combination results in a fraction that is less than one.

$$X = \frac{\text{MIC of Drug in combination}}{\text{MIC of Drug alone}}$$

This ratio is calculated for both drug A and drug B.
The fractions are added together.
The summation is compared to the following ranges:

Synergism: Sum of FIC for the two drugs ≤ 0.5
Indifference: Sum of FIC for the two drugs > 0.5 to ≤ 4
Antagonism: Sum of FIC for the two drugs > 4

Top graph = FIG. 19A
Bottom graph = FIG. 19B 0 min, no treatment control.

10 minutes after treatment.

20 minutes after treatment 30 minutes after treatment

FIG. 34
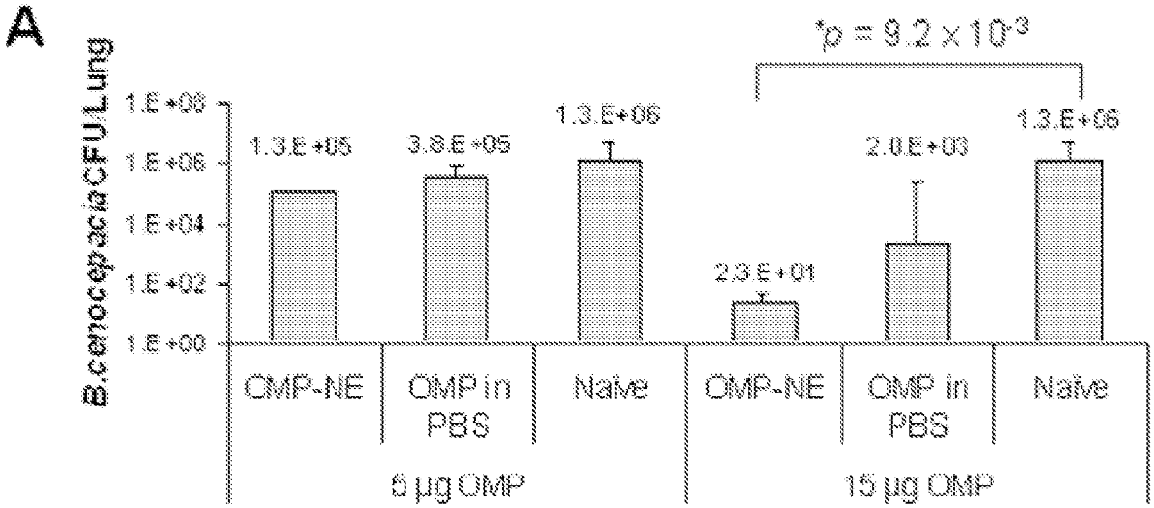
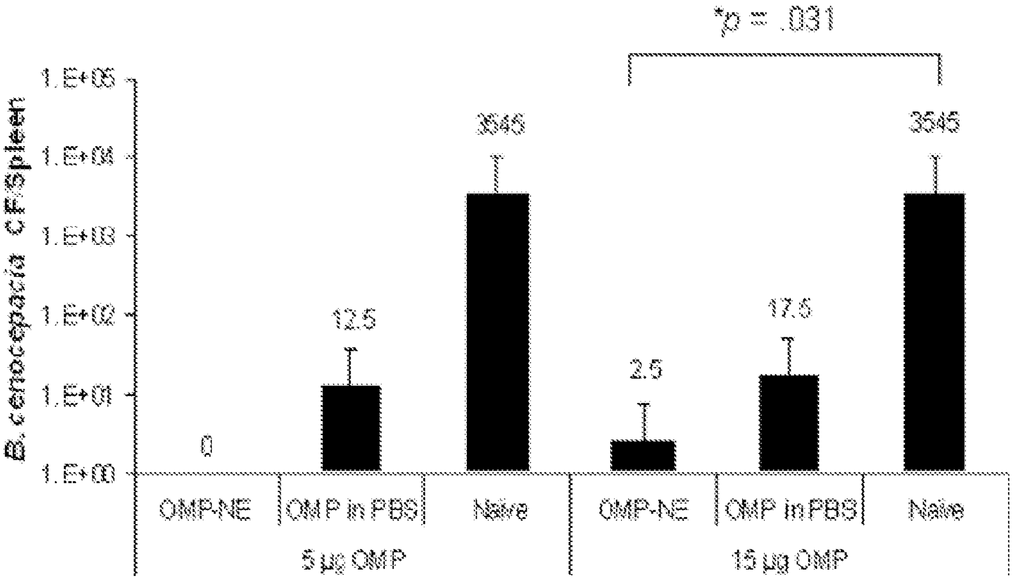

SEQUENCE LISTING

```
<160> NUMBER OF SEQ ID NOS: 16

<210> SEQ ID NO 1
<211> LENGTH: 142
<212> TYPE: PRT
<213> ORGANISM: Burkholderia cenocepacia

<400> SEQUENCE: 1

Leu Asp Asp Lys Ala Asn Ala Gly Ala Val Ser Thr Gln Pro Ser Ala
1               5                   10                  15

Asp Asn Val Ala Gln Val Asn Val Asp Pro Leu Asn Asp Pro Asn Ser
            20                  25                  30

Pro Leu Ala Lys Arg Ser Ile Tyr Phe Asp Phe Asp Ser Tyr Ser Val
        35                  40                  45

Lys Asp Glu Tyr Gln Pro Leu Leu Gln Gln His Ala Gln Tyr Leu Lys
    50                  55                  60

Ser His Pro Gln Arg His Val Leu Ile Gln Gly Asn Thr Asp Glu Arg
65                  70                  75                  80

Gly Thr Ser Glu Tyr Asn Leu Ala Leu Gly Gln Lys Arg Ala Glu Ala
                85                  90                  95

Val Arg Arg Ala Leu Ala Leu Leu Gly Val Ala Asp Ser Gln Met Glu
            100                 105                 110

Ala Val Ser Leu Gly Lys Glu Lys Pro Leu Ala Thr Gly His Asp Ala
        115                 120                 125

Ser Trp Ala Gln Asn Arg Arg Ala Asp Leu Val Tyr Gln Gln
    130                 135                 140


<210> SEQ ID NO 2
<211> LENGTH: 142
<212> TYPE: PRT
<213> ORGANISM: Burkholderia dolosa
```

<400> SEQUENCE: 2

Leu Asp Asp Lys Ala Asn Ala Gly Ala Val Ser Thr Gln Pro Ser Ala
1 5 10 15

Asp Asn Val Ala Gln Val Asn Val Asp Pro Leu Asn Asp Pro Asn Ser
20 25 30

Pro Leu Ala Lys Arg Ser Ile Tyr Phe Asp Phe Asp Ser Tyr Ser Val
35 40 45

Lys Asp Glu Tyr Gln Pro Leu Leu Gln Gln His Ala Gln Tyr Leu Lys
50 55 60

Ser His Pro Gln Arg His Val Leu Ile Gln Gly Asn Thr Asp Glu Arg
65 70 75 80

Gly Thr Ser Glu Tyr Asn Leu Ala Leu Gly Gln Lys Arg Ala Glu Ala
85 90 95

Val Arg Arg Ala Leu Ala Leu Leu Gly Val Ala Asp Ser Gln Met Glu
100 105 110

Ala Val Ser Leu Gly Lys Glu Lys Pro Leu Ala Thr Gly His Asp Ala
115 120 125

Ser Trp Ala Gln Asn Arg Arg Ala Asp Leu Val Tyr Gln Gln
130 135 140

<210> SEQ ID NO 3
<211> LENGTH: 141
<212> TYPE: PRT
<213> ORGANISM: Burkholderia multivorans

<400> SEQUENCE: 3

Leu Asp Asp Lys Ala Asn Ala Gly Ala Ser Thr Gln Pro Ser Ala Asp
1 5 10 15

Asn Val Ala Gln Val Asn Val Asp Pro Leu Asn Asp Pro Asn Ser Pro
20 25 30

Leu Ala Lys Arg Ser Ile Tyr Phe Asp Phe Asp Ser Tyr Ser Val Lys
35 40 45

Asp Glu Tyr Gln Pro Leu Leu Gln Gln His Ala Gln Tyr Leu Lys Ser
50 55 60

His Pro Gln Arg His Val Leu Ile Gln Gly Asn Thr Asp Glu Arg Gly
65 70 75 80

Thr Ser Glu Tyr Asn Leu Ala Leu Gly Gln Lys Arg Ala Glu Ala Val
85 90 95

Arg Arg Ala Leu Ala Leu Leu Gly Val Ala Asp Ser Gln Met Glu Ala
100 105 110

Val Ser Leu Gly Lys Glu Lys Pro Ala Thr Gly His Asp Glu Ala Ser
115 120 125

Trp Ala Gln Asn Arg Arg Ala Asp Leu Val Tyr Gln Gln
130 135 140

<210> SEQ ID NO 4
<211> LENGTH: 138
<212> TYPE: PRT
<213> ORGANISM: Burkholderia ambifaria

<400> SEQUENCE: 4

Leu Asp Asp Lys Ala Asn Ala Gly Ala Val Ser Thr Gln Pro Ser Ala
1 5 10 15

Asp Asn Val Ala Gln Val Asn Val Asp Pro Leu Asn Asp Pro Asn Ser
20 25 30

-continued

```
Pro Leu Ala Lys Arg Ser Ile Tyr Phe Asp Phe Asp Ser Tyr Ser Val
        35                  40                  45

Lys Asp Glu Tyr Gln Pro Leu Gln Gln His Ala Gln Tyr Leu Lys Ser
    50                  55                  60

His Pro Gln Arg His Val Leu Ile Gln Gly Asn Thr Asp Glu Arg Gly
65                  70                  75                  80

Thr Ser Glu Tyr Asn Leu Ala Leu Gly Gln Lys Arg Ala Glu Ala Val
                85                  90                  95

Arg Arg Ala Ala Leu Leu Gly Val Asp Ser Gln Met Glu Ala Val Ser
            100                 105                 110

Leu Gly Lys Glu Lys Pro Ala Gly His Asp Glu Ala Ser Trp Ala Gln
        115                 120                 125

Asn Arg Arg Ala Asp Leu Val Tyr Gln Gln
    130                 135


<210> SEQ ID NO 5
<211> LENGTH: 140
<212> TYPE: PRT
<213> ORGANISM: Burkholderia vietnamiensis

<400> SEQUENCE: 5

Leu Asp Asp Lys Ala Asn Ala Gly Ala Val Ser Thr Gln Pro Ser Ala
1               5                   10                  15

Asp Asn Val Ala Gln Val Asn Val Asp Pro Leu Asn Asp Pro Asn Ser
            20                  25                  30

Pro Leu Ala Lys Arg Ser Ile Tyr Phe Asp Phe Asp Ser Tyr Ser Val
        35                  40                  45

Lys Asp Glu Tyr Gln Pro Leu Leu Gln Gln His Ala Gln Tyr Leu Lys
    50                  55                  60

Ser His Pro Gln Arg His Val Leu Ile Gln Gly Asn Thr Asp Glu Arg
65                  70                  75                  80

Gly Thr Ser Glu Tyr Asn Leu Ala Leu Gly Gln Lys Arg Ala Glu Ala
                85                  90                  95

Val Arg Arg Ala Ala Leu Leu Gly Val Asp Ser Gln Met Glu Ala Val
            100                 105                 110

Ser Leu Gly Lys Glu Lys Pro Ala Thr Gly His Asp Glu Ala Ser Trp
        115                 120                 125

Ala Gln Asn Arg Arg Ala Asp Leu Val Tyr Gln Gln
    130                 135                 140


<210> SEQ ID NO 6
<211> LENGTH: 132
<212> TYPE: PRT
<213> ORGANISM: Burkholderia ubonensis

<400> SEQUENCE: 6

Leu Asp Lys Ala Asn Ala Gly Ala Ser Thr Gln Pro Asn Val Ala Gln
1               5                   10                  15

Val Val Asp Pro Leu Asn Asp Pro Asn Ser Pro Leu Ala Lys Arg Ser
            20                  25                  30

Ile Tyr Phe Asp Phe Asp Ser Tyr Ser Val Lys Asp Glu Tyr Gln Pro
        35                  40                  45

Leu Gln Gln His Ala Gln Tyr Leu Lys Ser His Pro Gln Arg His Val
    50                  55                  60

Leu Ile Gln Gly Asn Thr Asp Glu Arg Gly Thr Ser Glu Tyr Asn Leu
65                  70                  75                  80
```

```
Ala Leu Gly Gln Lys Arg Ala Glu Ala Val Arg Arg Ala Ala Leu Leu
                85                  90                  95

Gly Val Ala Asp Ser Gln Met Glu Ala Val Ser Leu Gly Lys Glu Lys
            100                 105                 110

Pro Ala Gly His Asp Glu Ala Ser Trp Ala Gln Asn Arg Arg Asp Leu
        115                 120                 125

Val Tyr Gln Gln
    130


<210> SEQ ID NO 7
<211> LENGTH: 127
<212> TYPE: PRT
<213> ORGANISM: Burkholderia thailandensis

<400> SEQUENCE: 7

Leu Asp Ala Asn Gly Ala Val Ser Thr Gln Pro Asn Ala Gln Val Val
1               5                   10                  15

Asp Pro Leu Asn Asp Pro Asn Ser Pro Leu Ala Lys Arg Ser Tyr Phe
            20                  25                  30

Asp Phe Asp Ser Tyr Ser Val Asp Tyr Gln Pro Leu Leu Gln Gln His
        35                  40                  45

Ala Gln Tyr Leu Lys Ser His Pro Gln Arg His Leu Ile Gln Gly Asn
    50                  55                  60

Thr Asp Glu Arg Gly Thr Ser Glu Tyr Asn Leu Ala Leu Gly Gln Lys
65                  70                  75                  80

Arg Ala Glu Ala Val Arg Arg Ala Leu Leu Leu Gly Val Asp Ser Gln
                85                  90                  95

Met Glu Ala Val Ser Leu Gly Lys Glu Lys Pro Ala Gly His Asp Glu
            100                 105                 110

Ala Ser Trp Ala Gln Asn Arg Arg Ala Asp Leu Val Tyr Gln Gln
        115                 120                 125


<210> SEQ ID NO 8
<211> LENGTH: 127
<212> TYPE: PRT
<213> ORGANISM: Burkholderia graminis

<400> SEQUENCE: 8

Leu Asp Ala Asn Gly Ala Val Ser Thr Gln Pro Val Ala Gln Val Asn
1               5                   10                  15

Val Asp Pro Leu Asn Asp Pro Asn Ser Pro Leu Ala Lys Arg Ser Ile
            20                  25                  30

Tyr Phe Asp Phe Asp Ser Tyr Ser Val Lys Asp Tyr Gln Leu Leu Gln
        35                  40                  45

Gln His Gln Tyr Leu Lys Ser His Pro Gln Arg His Val Leu Ile Gln
    50                  55                  60

Gly Asn Thr Asp Glu Arg Gly Thr Ser Glu Tyr Asn Leu Ala Leu Gly
65                  70                  75                  80

Gln Lys Arg Ala Glu Ala Val Arg Arg Leu Leu Gly Val Asp Ser Gln
                85                  90                  95

Met Glu Ala Val Ser Leu Gly Lys Glu Lys Pro Ala Thr Gly His Asp
            100                 105                 110

Glu Ser Trp Ala Gln Asn Arg Arg Ala Asp Leu Val Tyr Gln Gln
        115                 120                 125


<210> SEQ ID NO 9
<211> LENGTH: 126
```

<212> TYPE: PRT
<213> ORGANISM: Burkholderia oklahomensis

<400> SEQUENCE: 9

```
Leu Asp Ala Asn Gly Ala Val Ser Thr Gln Pro Asn Val Ala Gln Val
1               5                   10                  15

Val Asp Pro Leu Asn Asp Pro Asn Ser Pro Leu Ala Lys Arg Ser Tyr
            20                  25                  30

Phe Asp Phe Asp Ser Tyr Ser Val Asp Tyr Gln Leu Leu Gln Gln His
        35                  40                  45

Ala Gln Tyr Leu Lys His Pro Gln Arg His Leu Ile Gln Gly Asn Thr
    50                  55                  60

Asp Glu Arg Gly Thr Ser Glu Tyr Asn Leu Ala Leu Gly Gln Lys Arg
65                  70                  75                  80

Ala Glu Ala Val Arg Arg Ala Leu Leu Leu Gly Val Asp Ser Gln Met
                85                  90                  95

Glu Ala Val Ser Leu Gly Lys Glu Lys Pro Ala Gly His Asp Glu Ala
            100                 105                 110

Ser Trp Ala Gln Asn Arg Arg Ala Asp Leu Val Tyr Gln Gln
        115                 120                 125
```

<210> SEQ ID NO 10
<211> LENGTH: 126
<212> TYPE: PRT
<213> ORGANISM: Burkholderia pseudomallei

<400> SEQUENCE: 10

```
Leu Asp Ala Asn Gly Ala Val Ser Thr Gln Pro Asn Val Ala Gln Val
1               5                   10                  15

Val Asp Pro Leu Asn Asp Pro Asn Ser Pro Leu Ala Lys Arg Ser Tyr
            20                  25                  30

Phe Asp Phe Asp Ser Tyr Ser Val Asp Tyr Gln Leu Leu Gln Gln His
        35                  40                  45

Ala Gln Tyr Leu Lys Ser His Pro Gln Arg His Leu Ile Gln Gly Asn
    50                  55                  60

Thr Asp Glu Arg Gly Thr Ser Glu Tyr Asn Leu Ala Leu Gly Gln Lys
65                  70                  75                  80

Arg Ala Glu Ala Val Arg Arg Ala Leu Leu Leu Gly Val Asp Gln Met
                85                  90                  95

Glu Ala Val Ser Leu Gly Lys Glu Lys Pro Ala Gly His Asp Glu Ala
            100                 105                 110

Ser Trp Ala Gln Asn Arg Arg Ala Asp Leu Val Tyr Gln Gln
        115                 120                 125
```

<210> SEQ ID NO 11
<211> LENGTH: 123
<212> TYPE: PRT
<213> ORGANISM: Burkholderia xenovorans

<400> SEQUENCE: 11

```
Leu Asp Ala Asn Gly Val Ser Gln Pro Val Ala Val Val Asp Pro Leu
1               5                   10                  15

Asn Asp Pro Asn Ser Pro Leu Ala Lys Arg Ser Ile Tyr Phe Asp Phe
            20                  25                  30

Asp Ser Tyr Ser Val Lys Asp Tyr Gln Leu Leu Gln Gln His Ala Gln
        35                  40                  45

Tyr Leu Lys Ser His Pro Gln Arg His Leu Ile Gln Gly Asn Thr Asp
```

```
    50                  55                  60

Glu Arg Gly Thr Ser Glu Tyr Asn Leu Ala Leu Gly Gln Lys Arg Ala
65                  70                  75                  80

Glu Ala Val Arg Arg Leu Leu Gly Val Asp Ser Gln Met Glu Ala Val
                85                  90                  95

Ser Leu Gly Lys Glu Lys Pro Ala Thr Gly His Asp Glu Ser Trp Ala
            100                 105                 110

Gln Asn Arg Arg Ala Asp Leu Val Tyr Gln Gln
        115                 120


<210> SEQ ID NO 12
<211> LENGTH: 125
<212> TYPE: PRT
<213> ORGANISM: Burkholderia phytofirmans

<400> SEQUENCE: 12

Leu Asp Ala Asn Gly Val Ser Gln Pro Val Ala Val Asn Val Asp Pro
1               5                   10                  15

Leu Asn Asp Pro Asn Ser Pro Leu Ala Lys Arg Ser Ile Tyr Phe Asp
            20                  25                  30

Phe Asp Ser Tyr Ser Val Lys Asp Tyr Gln Leu Leu Gln Gln His Ala
        35                  40                  45

Gln Tyr Leu Lys Ser His Pro Gln Arg His Val Leu Ile Gln Gly Asn
    50                  55                  60

Thr Asp Glu Arg Gly Thr Ser Glu Tyr Asn Leu Ala Leu Gly Gln Lys
65                  70                  75                  80

Arg Ala Glu Ala Val Arg Arg Leu Leu Gly Val Asp Ser Gln Met Glu
                85                  90                  95

Ala Val Ser Leu Gly Lys Glu Lys Pro Ala Thr Gly His Asp Glu Ser
            100                 105                 110

Trp Ala Gln Asn Arg Arg Ala Asp Leu Val Tyr Gln Gln
        115                 120                 125


<210> SEQ ID NO 13
<211> LENGTH: 125
<212> TYPE: PRT
<213> ORGANISM: Burkholderia phymatum

<400> SEQUENCE: 13

Leu Asp Ala Gly Ala Gln Pro Val Ala Val Asn Val Asp Pro Leu Asn
1               5                   10                  15

Asp Pro Asn Ser Pro Leu Ala Lys Arg Ser Ile Tyr Phe Asp Phe Asp
            20                  25                  30

Ser Tyr Ser Val Lys Asp Tyr Gln Pro Leu Leu Gln Gln His Ala Gln
        35                  40                  45

Tyr Leu Lys Ser His Pro Gln Arg His Val Leu Ile Gln Gly Asn Thr
    50                  55                  60

Asp Glu Arg Gly Thr Ser Glu Tyr Asn Leu Ala Leu Gly Gln Lys Arg
65                  70                  75                  80

Ala Glu Ala Val Arg Arg Leu Leu Leu Gly Val Asp Ser Met Glu Ala
                85                  90                  95

Val Ser Leu Gly Lys Glu Lys Pro Ala Thr Gly His Asp Glu Ala Ser
            100                 105                 110

Trp Ala Gln Asn Arg Arg Ala Asp Leu Val Tyr Gln Gln
        115                 120                 125
```

<210> SEQ ID NO 14
<211> LENGTH: 106
<212> TYPE: PRT
<213> ORGANISM: Ralstonia metallidurans

<400> SEQUENCE: 14

```
Leu Asp Asp Gly Ala Ala Asn Val Ala Val Val Asp Pro Leu Asn Asp
1               5                   10                  15

Pro Asn Pro Leu Ala Lys Arg Ser Tyr Phe Asp Phe Asp Ser Tyr Ser
            20                  25                  30

Val Lys Tyr Gln Leu Gln His Gln Tyr Leu Ser Arg Leu Ile Gln Gly
        35                  40                  45

Asn Thr Asp Glu Arg Gly Thr Ser Glu Tyr Asn Leu Ala Leu Gly Gln
    50                  55                  60

Lys Arg Ala Glu Ala Val Arg Arg Leu Ala Gly Val Asp Ser Gln Met
65                  70                  75                  80

Glu Ala Val Ser Leu Gly Lys Glu Lys Pro Ala Thr Gly His Asp Ala
                85                  90                  95

Ser Trp Ala Asn Arg Arg Ala Asp Val Tyr
            100                 105
```

<210> SEQ ID NO 15
<211> LENGTH: 107
<212> TYPE: PRT
<213> ORGANISM: Ralstonia eutropha

<400> SEQUENCE: 15

```
Leu Asp Asp Ala Asn Ala Gly Ala Ala Asp Val Val Val Asp Pro Leu
1               5                   10                  15

Asn Asp Pro Asn Ser Pro Leu Ala Lys Arg Ser Tyr Phe Asp Phe Asp
            20                  25                  30

Ser Tyr Ser Val Lys Glu Tyr Gln Leu His Ala Tyr Leu Ser Arg Leu
        35                  40                  45

Ile Gln Gly Asn Thr Asp Glu Arg Gly Thr Ser Glu Tyr Asn Leu Ala
    50                  55                  60

Leu Gly Gln Lys Arg Ala Glu Ala Val Arg Arg Leu Ala Gly Val Asp
65                  70                  75                  80

Ser Gln Met Glu Ala Val Ser Leu Gly Lys Glu Lys Pro Thr Gly His
                85                  90                  95

Asp Glu Ala Trp Ala Asn Arg Arg Ala Asp Tyr
            100                 105
```

<210> SEQ ID NO 16
<211> LENGTH: 108
<212> TYPE: PRT
<213> ORGANISM: Ralstonia solanacearum

<400> SEQUENCE: 16

```
Leu Asp Asp Lys Gly Thr Asn Val Val Val Asp Leu Asp Pro Asn Ser
1               5                   10                  15

Pro Leu Ala Lys Arg Ser Tyr Phe Asp Phe Asp Ser Tyr Val Lys Glu
            20                  25                  30

Tyr Gln Leu Leu Gln His Ala Tyr Leu Ser His Gln Arg Val Leu Ile
        35                  40                  45

Gln Gly Asn Thr Asp Glu Arg Gly Thr Ser Glu Tyr Asn Leu Ala Leu
    50                  55                  60

Gly Gln Lys Arg Ala Glu Ala Val Arg Arg Ala Leu Gly Val Asp Ser
65                  70                  75                  80
```

-continued

```
Gln Met Glu Ala Val Ser Leu Gly Lys Glu Lys Pro Ala Thr Gly His
                85                  90                  95

Asp Glu Ser Trp Ala Gln Asn Arg Arg Asp Val Tyr
            100                 105
```

NANOEMULSION THERAPEUTIC COMPOSITIONS AND METHODS OF USING THE SAME

CROSS-REFERENCE TO RELATED APPLICATIONS

The present application is a continuation of U.S. patent application Ser. No. 12/567,571, filed Sep. 25, 2009, now U.S. Pat. No. 8,962,026, issued Feb. 24, 2015, which claims the benefit of Provisional Patent Application No. 61/100,559, filed Sep. 26, 2008, each of which are hereby incorporated by reference in its entirety.

STATEMENT REGARDING FEDERALLY SPONSORED RESEARCH OR DEVELOPMENT

None.

FIELD OF THE INVENTION

The present invention relates to therapeutic nanoemulsion compositions and to methods of utilizing the same. In particular, nanoemulsion compositions are described herein that find use in the treatment and/or prevention of infection (e.g., respiratory infection (e.g., associated with cystic fibrosis)), in burn wound management, and in immunogenic compositions (e.g., comprising a *Burkholderia* antigen) that generate an effective immune response (e.g., against a bacterial species of the genus *Burkholderia*) in a subject administered the immunogenic composition. Compositions and methods of the present invention find use in, among other things, clinical (e.g. therapeutic and preventative medicine), industrial, and research applications.

BACKGROUND OF THE INVENTION

Bacterial infection caused by opportunistic and/or pathogenic bacteria (e.g., *Burkholderia cepacia, Staphylococcus aureus* and *Pseudomonas aeruginosa*) is a major problem in both the developed and undeveloped portions of the world. For example, certain types of individuals are prone to respiratory infection (e.g., by bacteria (e.g., opportunistic bacteria), viruses, fungi and/or parasites) including the immunocompromised, elderly, cancer chemotherapy patients, individuals suffering from asthma, individual suffering from genetically inherited disease (e.g., cystic fibrosis) and virally infected individuals (e.g., infected with influenza virus, respiratory syncytial virus (RSV), adenovirus and/or human immunodeficiency virus). Similarly, wounds (e.g., burn wounds) present on a subject provide an ideal location for bacterial growth and survival.

As the use of conventional pharmaceutical antibiotics has increased for medical, veterinary and agricultural purposes, there has been a concurrent emergence of antibiotic-resistant strains of pathogenic bacteria.

A need exists to develop alternative strategies of antibacterial treatment. For example, there exists a need for new compositions and methods of treating or preventing bacterial infection (e.g., bacteremia) caused by strains of bacteria unsusceptible to current forms of antibacterial treatments.

SUMMARY OF THE INVENTION

The present invention relates to therapeutic nanoemulsion compositions and to methods of utilizing the same. In particular, nanoemulsion compositions are described herein that find use in the treatment and/or prevention of infection (e.g., respiratory infection (e.g., associated with cystic fibrosis)), in burn wound management, and in immunogenic compositions (e.g., comprising a *Burkholderia* antigen) that generate an effective immune response (e.g., against a bacterial species of the genus *Burkholderia*) in a subject administered the immunogenic composition. Compositions and methods of the present invention find use in, among other things, clinical (e.g. therapeutic and preventative medicine), industrial, and research applications.

Accordingly, in some embodiments, the present invention provides an immunogenic composition comprising a nanoemulsion and one or more *Burkholderia* antigens (e.g., *Burkholderia cenocepacia* antigens). In some embodiments, the nanoemulsion comprises an aqueous phase, an oil phase, and a solvent. The present invention is not limited by the type of nanoemulsion composition. Indeed, a variety of nanoemulsion compositions find use in the present invention including, but not limited to, those described herein. The present invention is not limited by the one or more *Burkholderia* antigens utilized in the immunogenic compositions and methods of the invention. Indeed, a variety of *Burkholderia* antigens may be utilized including, but not limited to, *Burkholderia* bacteria inactivated and/or killed by nanoemulsion (NE), killed and/or inactivated *Burkholderia* bacteria (e.g., via mixing with alcohol (e.g., ethanol)), whole cell lysates of a *Burkholderia* bacteria, one or more isolated, purified and/or recombinant *Burkholderia* proteins and/or protein fragments, or other type of *Burkholderia* antigen described herein. In a preferred embodiment, the *Burkholderia* antigen comprises outer membrane lipoprotein A (OmpA). In some embodiments, the OmpA protein comprises the amino acid sequence of SEQ ID NO: 1. In some embodiments, the OmpA protein comprises an amino acid sequence comprising an amino acid sequence of SEQ ID NOS:2-16. In some embodiments, the OmpA protein is from *Burkholderia cepacia*. However, the present invention is not so limited. Indeed, a *Burkholderia* antigen for use in an immunogenic composition of the invention may be from any number of *Burkholderia* species or related species including, but not limited to, *B. cenocepacia, B. dolosa, B. multivorans, B. ambifaria, B. vietnamiensis, B. ubonensis, B. thailandensis, B. graminis, B. oklahomensis, B. pseudomallei, B. xenovorans, B. phytofirmans, B. phymatum, R. metallidurans, R. eutropha, R. solanacearum*. In some embodiments, an immunogenic composition comprising a *Burkholderia* antigen comprises one or more adjuvants (e.g., cholera toxin (CT)). The present invention is not limited to any particular adjuvant and any one or more adjuvants described herein find use in a composition of the invention including but not limited to adjuvants that skew toward a Th1 and/or Th2 type immune responses described herein. In some embodiments, the nanoemulsion is $W_{80}5EC$, although the present invention is not so limited. For example, in some embodiments, the nanoemulsion is selected from one of the nanoemulsion formulations described herein. In some embodiments, the composition comprises between 1-50% nanoemulsion solution, although greater and lesser amounts also find use in the invention. For example, in some embodiments, the immunogenic composition comprises about 1.0%-10%, about 10%-20%, about 20%-30%, about 30%-40%, about 40%-50%, about 50%-60% or more nanoemulsion solution. In some embodiments, the immunogenic composition comprises about 10% nanoemulsion solution. In some embodiments, the immunogenic composition comprises about 15% nanoemulsion solution. In some embodiments, the immunogenic composition comprises about 20% nanoemulsion solution. In some embodiments, the immunogenic composition comprises about 12% nanoemulsion solution. In some embodiments, the immunogenic composition comprises about 8% nanoemulsion solution. In some embodiments, the immunogenic composition comprises about 5% nanoemulsion solution. In some embodiments, the immunogenic composition comprises about 2% nanoemulsion solution. In some embodiments, the immunogenic composition comprises about 1% nanoemulsion solution. In some embodiments, an immunogenic composition (e.g., that is administered to a subject in order to generate a *Burkholderia* specific immune response in the subject) comprises about 0.05-5000 μg of immunogen (e.g., recombinant and/or purified *Burkholderia* OmpA protein). In some embodiments, each dose (e.g., of a composition comprising a NE and an immunogen (e.g., administered to a subject to induce an immune response (e.g., a protective immune response (e.g., protective immunity))) comprises about 0.05-5000 μg of the immunogen (e.g., recombinant and/or purified *Burkholderia* OmpA protein) and comprises about 0.05-5000 μg of another immunogen (e.g., recombinant and/or purified protein, adjuvant (e.g., cholera toxin), etc.). In some embodiments, each dose will comprise 1-500 μg, in some embodiments, each dose will comprise 350-750 μg, in some embodiments, each dose will comprise 50-200 μg, in some embodiments, each dose will comprise 25-75 μg of immunogen (e.g., recombinant and/or purified protein (e.g., *Burkholderia* antigen). In some embodiments, each dose comprises an amount of the immunogen sufficient to generate an immune response. An effective amount of the immunogen in a dose need not be quantified, as long as the amount of immunogen generates an immune response in a subject when administered to the subject. In some embodiments, the composition is stable (e.g., at room temperature (e.g., for 12 hours, one day, two days, three days, four days, a week, two weeks, three weeks, a month, two months, three months, four months, five months, six months, 9 months, a year or more). In some embodiments, the immunogenic composition comprises a pharmaceutically acceptable carrier. The present invention is not limited to any particular pharmaceutically acceptable carrier. Indeed, any suitable carrier may be utilized including but not limited to those described herein. In some embodiments, the immunogen comprises a *Burkholderia* product (e.g., including, but not limited to, a protein, peptide, polypeptide, nucleic acid, polysaccharide, or a membrane component derived from the *Burkholderia*). In some embodiments, the immunogen and the nanoemulsion are combined in a single vessel.

In some embodiments, the present invention provides a method of inducing an immune response to *Burkholderia* (e.g., *Burkholderia cepacia*) in a subject comprising: providing a subject and an immunogenic composition comprising a nanoemulsion and an immunogen, wherein the immunogen comprises a *Burkholderia* antigen and administering the composition to the subject under conditions such that the subject generates a *Burkholderia* specific immune response. The present invention is not limited by the route chosen for administration of a composition of the present invention. In some preferred embodiments, administering the immunogenic composition comprises contacting a mucosal surface of the subject with the composition. In some embodiments, the mucosal surface comprises nasal mucosa. In some embodiments, inducing an immune response induces immunity to *Burkholderia* in the subject. In some embodiments, the immunity comprises systemic immunity. In some embodiments, the immunity comprises mucosal immunity. In some embodiments, the immune response comprises altered (e.g., enhanced) cytokine expression in the subject. In some embodiments, the immune response comprises an IgG response (e.g., a systemic IgG response) to *Burkholderia* in the subject. In some embodiments, the immunity protects the subject from displaying signs or symptoms of disease caused by *Burkholderia*. In some embodiments, the immunity protects the subject from challenge with a subsequent exposure to live *Burkholderia*. In some embodiments, the composition further comprises an adjuvant. In some embodiments, the subject is a human. In some embodiments, inducing an immune response induces immunity to one or more species of *Burkholderia* in the subject. In some embodiments, inducing an immune response induces immunity to two or more species of *Burkholderia* in the subject. In some embodiments, inducing immunity to *Burkholderia* comprises systemic immunity. In some embodiments, immunity comprises mucosal immunity. In some embodiments, the immune response comprises altered (e.g., increased) cytokine expression in the subject. In some embodiments, the immune response comprises a systemic IgG response to the immunogen. In some embodiments, the immune response comprises a mucosal IgA response to the immunogen. In some embodiments, each dose comprises an amount of *Burkholderia* antigen sufficient to generate an immune response to *Burkholderia*. An effective amount of the *Burkholderia* antigen is a dose that need not be quantified, as long as the amount of *Burkholderia* antigen generates an immune response in a subject when administered to the subject.

Thus, in some embodiments, the present invention provides an immunogenic composition comprising a nanoemulsion and a *Burkholderia* antigen (e.g., wherein the *Burkholderia* antigen comprises outer membrane lipoprotein A (OmpA)). In some embodiments, the OmpA protein comprises the amino acid sequence of SEQ ID NO: 1. In some embodiments, the OmpA protein comprises an amino acid sequence selected from the group consisting of SEQ ID NOS: 2-16. In some embodiment, the OmpA protein is from *Burkholderia cepacia*. In some embodiments, the present invention provides a method of making a vaccine comprising the steps of mixing antigens to make an immunogenic composition comprising a nanoemulsion and a *Burkholderia* antigen (e.g., wherein the *Burkholderia* antigen comprises outer membrane lipoprotein A (OmpA)) and adding a pharmaceutically acceptable excipient. The present invention also provides a use of the immunogenic composition comprising a nanoemulsion and a *Burkholderia* antigen (e.g., wherein the *Burkholderia* antigen comprises outer membrane lipoprotein A (OmpA)) in the manufacture of a vaccine for treatment or prevention of *Burkholderia* infection. In some embodiments, the present invention provides a use of the immunogenic composition comprising a nanoemulsion and a *Burkholderia* antigen (e.g., wherein the *Burkholderia* antigen comprises outer membrane lipoprotein A (OmpA)) in the treatment or prevention of *Burkholderia* infection. The present invention also provides a method of preparing an immune globulin for use in prevention or treatment of *Burkholderia* infection comprising the steps of immunizing a recipient with an immunogenic composition comprising a nanoemulsion and a *Burkholderia* antigen (e.g., wherein the *Burkholderia* antigen comprises outer membrane lipoprotein A (OmpA) e.g., a *Burkholderia* vaccine) and isolating immune globulin from the recipient.

The present invention also provides compositions and methods for treating burn wounds. For example, in some embodiments, the present invention provides a method of treating a burn wound comprising: providing a subject harboring a burn wound; and a composition comprising a nanoemulsion; and administering the composition comprising a nanoemulsion to the burn wound, wherein the administering reduces inflammation at the site of the burn wound. In some embodiments, administering the composition comprising a nanoemulsion reduces, attenuates and/or prevents bacterial growth in the burn wound. In some embodiments, administering the composition comprising a nanoemulsion reduces tissue edema at the site of the burn wound. In some embodiments, administering the composition comprising a nanoemulsion reduces intravascular hypovolemia at the site of the burn wound. The present invention is not limited by the type of nanoemulsion utilized for administration to a burn wound. For example, in some embodiments, a nanoemulsion comprising distilled water; polysorbate (Tween) 20; glycerine; soybean oil; either cetylpyridinium chloride (CPC) or benzalkonium chloride or alkyl dimethyl benzyl ammonium chloride (BTC 824), or a combination thereof; and ethylenediaminetetraacetic acid (EDTA) is administered to a burn wound. In some embodiments, administering the composition comprising a nanoemulsion reduces the occurrence of shock, pulmonary dysfunction, abdominal or extremity compartment syndrome, or cardiac failure in the subject. In some embodiments, the composition is co-administered with an antimicrobial agent or an anti-inflammatory agent. The present invention is not limited by the type of antimicrobial agent or anti-inflammatory agent utilized. Indeed, a variety of antimicrobial agents or an anti-inflammatory agents may be co-administered with the composition comprising a nanoemulsion including but not limited to those described herein. In some embodiments, the antimicrobial agent is an antibiotic. In some embodiments, the anti-inflammatory agent is silver nitrate ($AgNO_3$), silver sulfadiazine, mafenide acetate, nanocrystalline impregnated silver dressings, a p38 MAPK inhibitor or other anti-inflammatory agent.

In some embodiments, the present invention provide a composition comprising a nanoemulsion, wherein the nanoemulsion comprises: about 19% by volume distilled water; about 5% by volume polysorbate (Tween) 20; about 8% by volume glycerine; about 64% by volume soybean oil; about 4% by volume of either cetylpyridinium chloride (CPC) or benzalkonium chloride or alkyl dimethyl benzyl ammonium chloride, or a combination thereof; and about 0.07% by volume ethylenediaminetetraacetic acid (EDTA). In some embodiments, the composition comprises a nanoemulsion comprising droplets the have an average diameter selected from the group comprising less than about 1000 nm, less than about 950 nm, less than about 900 nm, less than about 850 nm, less than about 800 nm, less than about 750 nm, less than about 700 nm, less than about 650 nm, less than about 600 nm, less than about 550 nm, less than about 500 nm, less than about 450 nm, less than about 400 nm, less than about 350 nm, less than about 300 nm, less than about 250 nm, less than about 200 nm, less than about 150 nm, less than about 100 nm, greater than about 50 nm, greater than about 70 nm, greater than about 125 nm, and any combination thereof.

In some embodiments, the composition further comprises an antimicrobial agent or anti-inflammatory agent. The present invention is not limited by the type of antimicrobial agent or anti-inflammatory agent utilized. Indeed, a variety of antimicrobial agents or an anti-inflammatory agents may be co-administered with the composition comprising a nanoemulsion including but not limited to those described herein. In some embodiments, the antimicrobial agent is an antibiotic. In some embodiments, the anti-inflammatory agent is silver nitrate ($AgNO_3$), silver sulfadiazine, mafenide acetate, nanocrystalline impregnated silver dressings, a p38 MAPK inhibitor or other anti-inflammatory agent. In some embodiments, the present invention provides a method of treating an infection present on and/or within a burn wound comprising administering the composition to the infection under conditions such that the composition kills, attenuates growth of and/or eliminates bacteria associated with the infection. The present invention is not limited by the type of bacteria associated with infection of a burn wound treated with a nanoemulsion of the invention. In some embodiments, bacteria associated with infection comprise *Staphylococcus aureus*. In some embodiments, the *Staphylococcus aureus* are antibiotic resistant. In some embodiments, the bacteria associated with the infection comprise *Pseudomonas aeruginosa*. The present invention is not limited by the type of burn wound treated. In some embodiments, the burn wound is a superficial burn wound, a partial thickness burn wound, or other type of burn wound.

The present invention is not limited by the type of nanoemulsion utilized. Indeed, a variety of nanoemulsions are contemplated to be useful in the present invention. For example, in some preferred embodiments, the nanoemulsion (e.g., for pulmonary administration (e.g., to treat or prevent respiratory infection) or for burn wound treatment) comprises an oil-in-water emulsion, the oil-in-water emulsion comprising a discontinuous oil phase distributed in an aqueous phase, a first component comprising a solvent (e.g., an alcohol or glycerol), and a second component comprising a surfactant or a halogen-containing compound. The aqueous phase can comprise any type of aqueous phase including, but not limited to, water (e.g., $diH_2O$, distilled water, tap water) and solutions (e.g., phosphate buffered saline solution). The oil phase can comprise any type of oil including, but not limited to, plant oils (e.g., soybean oil, avocado oil, flaxseed oil, coconut oil, cottonseed oil, squalene oil, olive oil, canola oil, corn oil, rapeseed oil, safflower oil, and sunflower oil), animal oils (e.g., fish oil), flavor oil, water insoluble vitamins, mineral oil, and motor oil. In some preferred embodiments, the oil phase comprises 30-90 vol % of the oil-in-water emulsion (i.e., constitutes 30-90% of the total volume of the final emulsion), more preferably 50-80%. While the present invention in not limited by the nature of the alcohol component, in some preferred embodiments, the alcohol is ethanol or methanol. Furthermore, while the present invention is not limited by the nature of the surfactant, in some preferred embodiments, the surfactant is a polysorbate surfactant (e.g., TWEEN 20, TWEEN 40, TWEEN 60, and TWEEN 80), a pheoxypolyethoxyethanol (e.g., TRITON X-100, X-301, X-165, X-102, and X-200, and TYLOXAPOL) or sodium dodecyl sulfate. Likewise, while the present invention is not limited by the nature of the halogen-containing compound, in some preferred embodiments, the halogen-containing compound comprises a cetylpyridinium halides, cetyltrimethylammonium halides, cetyldimethylethylammonium halides, cetyldimethylbenzylammonium halides, cetyltributylphosphonium halides, dodecyltrimethylammonium halides, tetradecyltrimethylammonium halides, cetylpyridinium chloride, cetyltrimethylammonium chloride, cetylbenzyldimethylammonium chloride, cetylpyridinium bromide, cetyltrimethylammonium bromide, cetyidimethylethylammonium bromide, cetyltributylphosphonium bromide, dodecyltrimethylammonium bromide, or tetrad ecyltrimethylammonium bromide. Nanoemulsions of the present invention may further comprise third, fourth, fifth, etc. components. In some preferred embodiments, an additional component is a surfactant (e.g., a second surfactant), a germination enhancer, a phosphate based solvent (e.g., tributyl phosphate), a neutramingen, L-alanine, ammonium chloride, trypticase soy broth, yeast extract, L-ascorbic acid, lecithin, p-hyroxybenzoic acid methyl ester, sodium thiosulate, sodium citrate, inosine, sodium hyroxide, dextrose, and polyethylene glycol (e.g., PEG 200, PEG 2000, etc.). In some embodiments, the oil-in-water emulsion comprises a quaternary ammonium compound. In some preferred embodiments, the oil-in-water emulsion has no detectable toxicity to plants or animals (e.g., to humans). In other preferred embodiments, the oil-in-water emulsion causes no detectable irritation to plants or animals (e.g., to humans). In some embodiments, the oil-in-water emulsion further comprises any of the components described above. Quaternary ammonium compounds include, but are not limited to, N-alkyldimethyl benzyl ammonium saccharinate, 1,3,5-Triazine-1,3,5(2H,4H,6H)-triethanol; 1-Decanaminium, N-decyl-N, N-dimethyl-, chloride (or) Didecyl dimethyl ammonium chloride; 2-(2-(p-(Diisobuyl)cresosxy) ethoxy)ehyl dimethyl benzyl ammonium chloride; 2-(2-(p-(Diisobutyl)phenoxy)ethoxy)ethyl dimethyl benzyl ammonium chloride; alkyl 1 or 3 benzyl-1-(2-hydroxethyl)-2-imidazolinium chloride; alkyl bis(2-hydroxyethyl) benzyl ammonium chloride; alkyl demethyl benzyl ammonium chloride; alkyl dimethyl 3,4-dichlorobenzyl ammonium chloride (100% C12); alkyl dimethyl 3,4-dichlorobenzyl ammonium chloride (50% C14, 40% C12, 10% C16); alkyl dimethyl 3,4-dichlorobenzyl ammonium chloride (55% C14, 23% C12, 20% C16); alkyl dimethyl benzyl ammonium chloride; alkyl dimethyl benzyl ammonium chloride (100% C14); alkyl dimethyl benzyl ammonium chloride (100% C16); alkyl dimethyl benzyl ammonium chloride (41% C14, 28% C12); alkyl dimethyl benzyl ammonium chloride (47% C12, 18% C14); alkyl dimethyl benzyl ammonium chloride (55% C16, 20% C14); alkyl dimethyl benzyl ammonium chloride (58% C14, 28% C16); alkyl dimethyl benzyl ammonium chloride (60% C14, 25% C12); alkyl dimethyl benzyl ammonium chloride (61% C11, 23% C14); alkyl dimethyl benzyl ammonium chloride (61% C12, 23% C14); alkyl dimethyl benzyl ammonium chloride (65% C12, 25% C14); alkyl dimethyl benzyl ammonium chloride (67% C12, 24% C14); alkyl dimethyl benzyl ammonium chloride (67% C12, 25% C14); alkyl dimethyl benzyl ammonium chloride (90% C14, 5% C12); alkyl dimethyl benzyl ammonium chloride (93% C14, 4% C12); alkyl dimethyl benzyl ammonium chloride (95% C16, 5% C18); alkyl dimethyl benzyl ammonium chloride (and) didecyl dimethyl ammonium chloride; alkyl dimethyl benzyl ammonium chloride (as in fatty acids); alkyl dimethyl benzyl ammonium chloride (C12-C16); alkyl dimethyl benzyl ammonium chloride (C12-C18); alkyl dimethyl benzyl and dialkyl dimethyl ammonium chloride; alkyl dimethyl dimethybenzyl ammonium chloride; alkyl dimethyl ethyl ammonium bromide (90% C14, 5% C16, 5% C12); alkyl dimethyl ethyl ammonium bromide (mixed alkyl and alkenyl groups as in the fatty acids of soybean oil); alkyl dimethyl ethylbenzyl ammonium chloride; alkyl dimethyl ethylbenzyl ammonium chloride (60% C14); alkyl dimethyl isoproylbenzyl ammonium chloride (50% C12, 30% C14, 17% C16, 3% C18); alkyl trimethyl ammonium chloride (58% C18, 40% C16, 1% C14, 1% C12); alkyl trimethyl ammonium chloride (90% C18, 10% C16); alkyldimethyl(ethylbenzyl) ammonium chloride (C12-18); Di-(C8-10)-alkyl dimethyl ammonium chlorides; dialkyl dimethyl ammonium chloride; dialkyl dimethyl ammonium chloride; dialkyl dimethyl ammonium chloride; dialkyl methyl benzyl ammonium chloride; didecyl dimethyl ammonium chloride; diisodecyl dimethyl ammonium chloride; dioctyl dimethyl ammonium chloride; dodecyl bis (2-hydroxyethyl) octyl hydrogen ammonium chloride; dodecyl dimethyl benzyl ammonium chloride; dodecylcarbamoyl methyl dinethyl benzyl ammonium chloride; heptadecyl hydroxyethylimidazolinium chloride; hexahydro-1,3,5-thris(2-hydroxyethyl)-s-triazine; myristalkonium chloride (and) Quat RNIUM 14; N,N-Dimethyl-2-hydroxypropylammonium chloride polymer; n-alkyl dimethyl benzyl ammonium chloride; n-alkyl dimethyl ethylbenzyl ammonium chloride; n-tetradecyl dimethyl benzyl ammonium chloride monohydrate; octyl decyl dimethyl ammonium chloride; octyl dodecyl dimethyl ammonium chloride; octyphenoxyethoxyethyl dimethyl benzyl ammonium chloride; oxydiethylenebis (alkyl dimethyl ammonium chloride); quaternary ammonium compounds, dicoco alkyldimethyl, chloride; trimethoxysily propyl dimethyl octadecyl ammonium chloride; trimethoxysilyl quats, trimethyl dodecylbenzyl ammonium chloride; n-dodecyl dimethyl ethylbenzyl ammonium chloride; n-hexadecyl dimethyl benzyl ammonium chloride; n-tetradecyl dimethyl benzyl ammonium chloride; n-tetradecyl dimethyl ethyylbenzyl ammonium chloride; and n-octadecyl dimethyl benzyl ammonium chloride. In some embodiments, the emulsion lacks any antimicrobial substances (i.e., the only antimicrobial composition is the emulsion itself). In some embodiments, the nanoemulsion is X8P. In some embodiments, the nanoemulsion is $P_{407}$5EC. In some embodiments, administration of a nanoemulsion of the present invention protects the subject from displaying signs or symptoms of disease or infection (e.g., caused by one or microbes and/or pathogens (e.g., pathogenic bacteria)) residing in the pulmonary system (e.g., *Burkhoderia cepacia* and *Pseudomonas aeruginosa*)). In some embodiments, administration of a nanoemulsion (e.g., pulmonary administration (e.g., to treat or prevent pulmonary infection)) protects a subject from morbidity and/or mortality associated with respiratory infection. In some embodiments, the subject is a human.

BRIEF DESCRIPTION OF THE DRAWINGS

FIG. 11 shows in vitro activity of $P_{407}$5EC.

FIG. 12 shows in vitro activity of $P_{407}$5EC against biofilm bacteria and in the presence of CF sputum.

FIG. 17 shows serial, two-fold dilutions of $P_{407}$5EC in one embodiment of the invention.

FIG. 19A shows a Fractional Inhibitory Concentration Index;

FIG. 19B shows a graph demonstrating the relationship between antagonism, indifference, and synergy for Antimicrobial A (micrograms/mL) and Antimicrobial B (micrograms/mL);

FIG. 20A shows 0 min, no treatment control; FIG. 20B shows 10 minutes after treatment; FIG. 20C shows 20 minutes after treatment; and FIG. 20D shows 30 minutes after treatment.

FIG. 34 shows pulmonary and splenic colonization assay. A) Pulmonary tissue associated and B) Splenic tissue associated cfu determined at six days following intratracheal challenge of $5\times10^7$ cfu of *B. cenocepacia.*

DEFINITIONS

Figure 1:
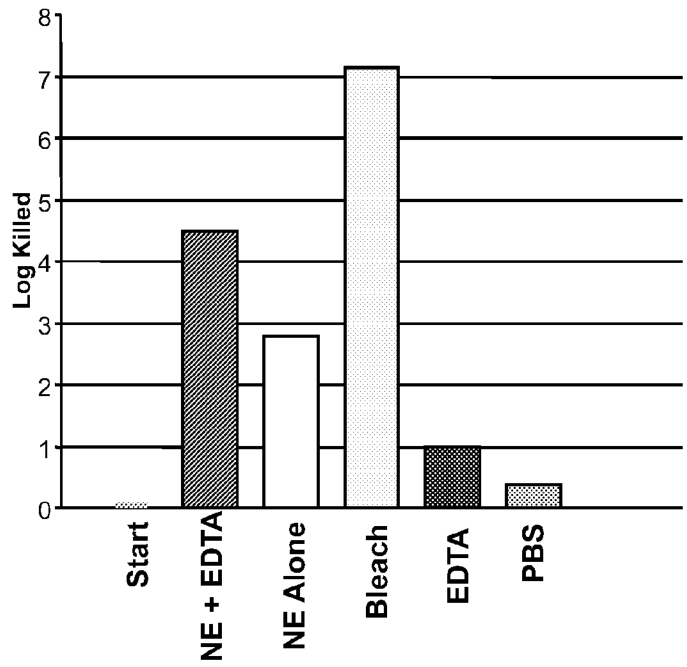
FIG. 1 shows killing of *Burkholderia cepacia* in PBS by 20% Nanemulsion (NE) alone or with 20 mM EDTA in 10 minutes.

To facilitate an understanding of the present invention, a number of terms and phrases are defined below:

As used herein, the term "microorganism" refers to any species or type of microorganism, including but not limited to, bacteria, viruses, archaea, fungi, protozoans, mycoplasma, prions, and parasitic organisms. The term microorganism encompasses both those organisms that are in and of themselves pathogenic to another organism (e.g., animals, including humans, and plants) and those organisms that produce agents that are pathogenic to another organism, while the organism itself is not directly pathogenic or infective to the other organism.

As used herein, the term "pathogen" refers a biological agent that causes a disease state (e.g., infection, sepsis, etc.) in a host. "Pathogens" include, but are not limited to, viruses, bacteria, archaea, fungi, protozoans, mycoplasma, prions, and parasitic organisms.

The terms "bacteria" and "bacterium" refer to all prokaryotic organisms, including those within all of the phyla in the Kingdom Procaryotae. It is intended that the term encompass all microorganisms considered to be bacteria including *Mycoplasma, Chlamydia, Actinomyces, Streptomyces*, and *Rickettsia*. All forms of bacteria are included within this definition including cocci, bacilli, spirochetes, spheroplasts, protoplasts, etc. Also included within this term are prokaryotic organisms that are Gram-negative or Gram-positive. "Gram-negative" and "Gram-positive" refer to staining patterns with the Gram-staining process, which is well known in the art. (See e.g., Finegold and Martin, Diagnostic Microbiology, 6th Ed., CV Mosby St. Louis, pp. 13-15 (1982)). "Gram-positive bacteria" are bacteria that retain the primary dye used in the Gram stain, causing the stained cells to generally appear dark blue to purple under the microscope. "Gram-negative bacteria" do not retain the primary dye used in the Gram stain, but are stained by the counterstain. Thus, Gram-negative bacteria generally appear red. In some embodiments, bacteria are continuously cultured. In some embodiments, bacteria are uncultured and existing in their natural environment (e.g., at the site of a wound or infection) or obtained from patient tissues (e.g., via a biopsy). Bacteria may exhibit pathological growth or proliferation. Examples of bacteria include, but are not limited to, bacterial cells of a genus of bacteria selected from the group comprising *Salmonella, Shigella, Escherichia, Enterobacter, Serratia, Proteus, Yersinia, Citrobacter, Edwardsiella, Providencia, Klebsiella, Hafnia, Ewingella, Kluyvera, Morganella, Planococcus, Stomatococcus, Micrococcus, Staphylococcus, Vibrio, Aeromonas, Plessiomonas, Haemophilus, Actinobacillus, Pasteurella, Mycoplasma, Ureaplasma, Rickettsia, Coxiella, Rochalimaea, Ehrlichia, Streptococcus, Enterococcus, Aerococcus, Gemella, Lactococcus, Leuconostoc, Pedicoccus, Bacillus, Corynebacterium, Arcanobacterium, Actinomyces, Rhodococcus, Listeria, Erysipelothrix, Gardnerella, Neisseria, Campylobacter, Arcobacter, Wolinella, Helicobacter, Achromobacter, Acinetobacter, Agrobacterium, Alcaligenes, Chryseomonas, Comamonas, Eikenella, Flavimonas, Flavobacterium, Moraxella, Oligella, Pseudomonas, Shewanella, Weeksella, Xanthomonas, Bordetella, Franciesella, Brucella, Legionella, Afipia, Bartonella, Calymmatobacterium, Cardiobacterium, Streptobacillus, Spirillum, Peptostreptococcus, Peptococcus, Sarcinia, Coprococcus, Ruminococcus, Propionibacterium, Mobiluncus, Bifidobacterium, Eubacterium, Lactobacillus, Rothia, Clostridium, Bacteroides, Porphyromonas, Prevotella, Fusobacterium, Bilophila, Leptotrichia, Wolinella, Acidaminococcus, Megasphaera, Veilonella, Norcardia, Actinomadura, Norcardiopsis, Streptomyces, Micropolysporas, Thermoactinomycetes, Mycobacterium, Treponema, Borrelia, Leptospira*, and *Chlamydiae.*

As used herein, the terms "microorganism" and "microbe" refer to any species or type of microorganism, including but not limited to, bacteria, archaea, fungi, protozoans, mycoplasma, and parasitic organisms.

As used herein, the term "fungi" is used in reference to eukaryotic organisms such as molds and yeasts, including dimorphic fungi.

As used herein the terms "disease" and "pathologic condition" are used interchangeably, unless indicated otherwise herein, to describe a deviation from the condition regarded as normal or average for members of a species or group (e.g., humans), and which is detrimental to an affected individual under conditions that are not inimical to the majority of individuals of that species or group. Such a deviation can manifest as a state, signs, and/or symptoms (e.g., diarrhea, nausea, fever, pain, blisters, boils, rash, immune suppression, inflammation, etc.) that are associated with any impairment of the normal state of a subject or of any of its organs or tissues that interrupts or modifies the performance of normal functions. A disease or pathological condition may be caused by or result from contact with a microorganism (e.g., a pathogen or other infective agent (e.g., a virus or bacteria)), may be responsive to environmental factors (e.g., malnutrition, industrial hazards, and/or climate), may be responsive to an inherent defect of the organism (e.g., genetic anomalies) or to combinations of these and other factors.

"Respiratory" and "respiration" refer to the process by which oxygen is taken into the body and carbon dioxide is discharged, through the bodily system including the nose, throat, larynx, trachea, bronchi and lungs.

"Respiratory infection" and "pulmonary infection" refer to an infection (e.g., bacterial, viral, fungal, etc.) of the respiratory tract. In humans, the respiratory tract comprises the upper respiratory tract (e.g., nose, throat or pharynx, and larynx); the airways (e.g.,: voice box or larynx, windpipe or trachea, and bronchi); and the lungs (e.g., bronchi, bronchioles, alveolar ducts, alveolar sacs, and alveoli).

"Respiratory disease", "pulmonary disease," "respiratory disorder", "pulmonary disorder," "respiratory condition", "pulmonary condition," "pulmonary syndrome," and "respiratory syndrome" refer to any one of several ailments that involve inflammation and affect a component of the respiratory system including especially the trachea, bronchi and lungs. Examples of such ailments include acute alveolar disease, obstructive respiratory disease (e.g., asthma; bronchitis; and chronic obstructive pulmonary disease, referred to as COPD), upper airway disease (e.g., such as otitis media, and rhinitis/sinusitis), insterstitial lung disease, allergy, and respiratory infection (e.g., pneumonia, pneyumocystis carinii, and respiratory syncitial virus (RSV)).

Specific examples of acute alveolar disease include acute lung injury (ALI), acute respiratory distress syndrome (ARDS), meconium aspiration syndrome (MAS) and respiratory distress syndrome (RDS). ALI is associated with conditions that either directly or indirectly injure the air sacs of the lung, the alveoli. ALI is a syndrome of inflammation and increased permeability of the lungs with an associated breakdown of the lungs' surfactant layer. The most serious manifestation of ALI is ARDS. Among the causes of ALI are complications typically associated with certain major surgeries, mechanical ventilator induced lung injury (often referred to as VILI), smoke inhalation, pneumonia, and sepsis.

The term "subject" as used herein refers to organisms to be treated by the compositions of the present invention. Such organisms include animals (domesticated animal species, wild animals), and humans.

As used herein, the terms "inactivating," "inactivation" and grammatical equivalents, when used in reference to a microorganism refer to the killing, elimination, neutralization and/or reducing the capacity of the microorganism to infect and/or cause a pathological response and/or disease in a host.

As used herein, the term "fusigenic" is intended to refer to an emulsion that is capable of fusing with the membrane of a microbial agent (e.g., a bacterium or bacterial spore). Specific examples of fusigenic emulsions are described herein.

As used herein, the term "lysogenic" refers to an emulsion (e.g., a nanoemulsion) that is capable of disrupting the membrane of a microbial agent (e.g., a virus (e.g., viral envelope) or a bacterium, bacterial spore, or bacterial biofilm). In preferred embodiments of the present invention, the presence of a lysogenic and a fusigenic agent in the same composition produces an enhanced inactivating effect compared to either agent alone. Methods and compositions using this improved antimicrobial composition are described in detail herein.

The term "nanoemulsion," as used herein, includes dispersions or droplets, as well as other lipid structures that can form as a result of hydrophobic forces that drive apolar residues (i.e., long hydrocarbon chains) away from water and drive polar head groups toward water, when a water immiscible oily phase is mixed with an aqueous phase. These other lipid structures include, but are not limited to, unilamellar, paucilamellar, and multilamellar lipid vesicles, micelles, and lamellar phases.

As used herein, the terms "contact," "contacted," "expose," and "exposed," when used in reference to a nanoemulsion and a live microorganism, refer to bringing one or more nanoemulsions into contact with a microorganism (e.g., a pathogen) such that the nanoemulsion kill and/or attenuate growth of the microorganism or pathogenic agent, if present. The present invention is not limited by the amount or type of nanoemulsion used for microorganism killing and/or growth attenuation. A variety of nanoemulsion that find use in the present invention are described herein and elsewhere (e.g., nanoemulsions described in U.S. Pat. Apps. 20020045667 and 20040043041, and U.S. Pat. Nos. 6,015,832, 6,506,803, 6,635,676, and 6,559,189, each of which is incorporated herein by reference in its entirety for all purposes). Ratios and amounts of nanoemulsion are contemplated in the present invention including, but not limited to, those described herein (e.g., in Examples 1-4, the Figures associated therewith and FIG. 17).

As used herein, "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

The term "surfactant" refers to any molecule having both a polar head group, which energetically prefers solvation by water, and a hydrophobic tail which is not well solvated by water. The term "cationic surfactant" refers to a surfactant with a cationic head group. The term "anionic surfactant" refers to a surfactant with an anionic head group.

The terms "Hydrophile-Lipophile Balance Index Number" and "HLB Index Number" refer to an index for correlating the chemical structure of surfactant molecules with their surface activity. The HLB Index Number may be calculated by a variety of empirical formulas as described by Meyers, (Meyers, Surfactant Science and Technology, VCH Publishers Inc., New York, pp. 231-245 [1992]), incorporated herein by reference. As used herein, the HLB Index Number of a surfactant is the HLB Index Number assigned to that surfactant in McCutcheon's Volume 1: Emulsifiers and Detergents North American Edition, 1996 (incorporated herein by reference). The HLB Index Number ranges from 0 to about 70 or more for commercial surfactants. Hydrophilic surfactants with high solubility in water and solubilizing properties are at the high end of the scale, while surfactants with low solubility in water which are good solubilizers of water in oils are at the low end of the scale.

As used herein the term “interaction enhancers” refers to compounds that act to enhance the interaction of an emulsion with a microorganism (e.g., with a cell wall of a bacteria (e.g., a Gram negative bacteria) or with a viral envelope. Contemplated interaction enhancers include, but are not limited to, chelating agents (e.g., ethylenediaminetetraacetic acid (EDTA), ethylenebis(oxyethylenenitrilo)tetraacetic acid (EGTA), and the like) and certain biological agents (e.g., bovine serum abulmin (BSA) and the like).

The terms “buffer” or “buffering agents” refer to materials which when added to a solution, cause the solution to resist changes in pH.

The terms “reducing agent” and “electron donor” refer to a material that donates electrons to a second material to reduce the oxidation state of one or more of the second material’s atoms.

The term “monovalent salt” refers to any salt in which the metal (e.g., Na, K, or Li) has a net 1+ charge in solution (i.e., one more proton than electron).

The term “divalent salt” refers to any salt in which a metal (e.g., Mg, Ca, or Sr) has a net 2+ charge in solution.

The terms “chelator” or “chelating agent” refer to any materials having more than one atom with a lone pair of electrons that are available to bond to a metal ion.

The term “solution” refers to an aqueous or non-aqueous mixture.

As used herein, the term “effective amount” refers to the amount of a composition (e.g., a composition comprising a nanoemulsion) sufficient to effect a beneficial or desired result (e.g., to treat and/or prevent infection (e.g., through bacterial cell killing and/or prevention of bacterial cell growth). An effective amount can be administered in one or more administrations, applications or dosages and is not intended to be limited to a particular formulation or administration route.

As used herein, the term “a composition for inducing an immune response” refers to a composition that, when administered to a subject (e.g., once, twice, three times or more (e.g., separated by weeks, months or years)), stimulates, generates and/or elicits an immune response in the subject (e.g., resulting in total or partial immunity to a microorganism (e.g., pathogen) capable of causing disease). In preferred embodiments of the invention, the composition comprises a nanoemulsion and an immunogen. In further preferred embodiments, the composition comprising a nanoemulsion and an immunogen comprises one or more other compounds or agents including, but not limited to, therapeutic agents, physiologically tolerable liquids, gels, carriers, diluents, adjuvants, excipients, salicylates, steroids, immunosuppressants, immunostimulants, antibodies, cytokines, antibiotics, binders, fillers, preservatives, stabilizing agents, emulsifiers, and/or buffers. An immune response may be an innate (e.g., a non-specific) immune response or a learned (e.g., acquired) immune response (e.g. that decreases the infectivity, morbidity, or onset of mortality in a subject (e.g., caused by exposure to a pathogenic microorganism) or that prevents infectivity, morbidity, or onset of mortality in a subject (e.g., caused by exposure to a pathogenic microorganism)). Thus, in some preferred embodiments, a composition comprising a nanoemulsion and an immunogen is administered to a subject as a vaccine (e.g., to prevent or attenuate a disease (e.g., by providing to the subject total or partial immunity against the disease or the total or partial attenuation (e.g., suppression) of a sign, symptom or condition of the disease.

As used herein, the term “adjuvant” refers to any substance that can stimulate an immune response (e.g., a mucosal immune response). Some adjuvants cause activation of a cell of the immune system (e.g., an adjuvant can cause an immune cell to produce and secrete a cytokine) Examples of adjuvants that can cause activation of a cell of the immune system include, but are not limited to, the nanoemulsion formulations described herein, saponins purified from the bark of the *Q. saponaria* tree, such as QS21 (a glycolipid that elutes in the 21st peak with HPLC fractionation; Aquila Biopharmaceuticals, Inc., Worcester, Mass.); poly(di(carboxylatophenoxy) phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); cholera toxin (CT), and Leishmania elongation factor (a purified Leishmania protein; Corixa Corporation, Seattle, Wash.). Traditional adjuvants are well known in the art and include, for example, aluminum phosphate or hydroxide salts (“alum”). In some embodiments, immunogenic compositions described herein are administered with one or more adjuvants (e.g., to skew the immune response towards a Th1 and/or Th2 type response).

As used herein, the term “an amount effective to induce an immune response” (e.g., of a composition for inducing an immune response), refers to the dosage level required (e.g., when administered to a subject) to stimulate, generate and/or elicit an immune response in the subject. An effective amount can be administered in one or more administrations (e.g., via the same or different route), applications or dosages and is not intended to be limited to a particular formulation or administration route.

As used herein, the term “under conditions such that said subject generates an immune response” refers to any qualitative or quantitative induction, generation, and/or stimulation of an immune response (e.g., innate or acquired).

As used herein, the term “immune response” refers to any detectable response by the immune system of a subject. For example, immune responses include, but are not limited to, an alteration (e.g., increase) in Toll receptor activation, lymphokine (e.g., cytokine (e.g., Th1 or Th2 type cytokines) or chemokine) expression and/or secretion, macrophage activation, dendritic cell activation, T cell (e.g., CD4+ or CD8+ T cell) activation, NK cell activation, and/or B cell activation (e.g., antibody generation and/or secretion). Additional examples of immune responses include binding of an immunogen (e.g., antigen (e.g., immunogenic polypeptide)) to an MHC molecule and induction of a cytotoxic T lymphocyte (“CTL”) response, induction of a B cell response (e.g., antibody production), and/or T-helper lymphocyte response, and/or a delayed type hypersensitivity (DTH) response (e.g., against the antigen from which an immunogenic polypeptide is derived), expansion (e.g., growth of a population of cells) of cells of the immune system (e.g., T cells, B cells (e.g., of any stage of development (e.g., plasma cells), and increased processing and presentation of antigen by antigen presenting cells. An immune response may be to immunogens that the subject’s immune system recognizes as foreign (e.g., non-self antigens from microorganisms (e.g., pathogens), or self-antigens recognized as foreign). Thus, it is to be understood that, as used herein, “immune response” refers to any type of immune response, including, but not limited to, innate immune responses (e.g., activation of Toll receptor signaling cascade) cell-mediated immune responses (e.g., responses mediated by T cells (e.g., antigen-specific T cells) and non-specific cells of the immune system) and humoral immune responses (e.g., responses mediated by B cells (e.g., via generation and secretion of antibodies into the plasma, lymph, and/or tissue fluids). The term "immune response" is meant to encompass all aspects of the capability of a subject's immune system to respond to an antigen and/or immunogen (e.g., both the initial response to an immunogen (e.g., a pathogen) as well as acquired (e.g., memory) responses that are a result of an adaptive immune response).

As used herein, the term "immunity" refers to protection from disease (e.g., preventing or attenuating (e.g., suppression of) a sign, symptom or condition of the disease) upon exposure to a microorganism (e.g., pathogen) capable of causing the disease. Immunity can be innate (e.g., non-adaptive (e.g., non-acquired) immune responses that exist in the absence of a previous exposure to an antigen) and/or acquired (e.g., immune responses that are mediated by B and T cells following a previous exposure to antigen (e.g., that exhibit increased specificity and reactivity to the antigen)).

As used herein, the terms "immunogen" and "antigen" are used interchangeably to refer to an agent (e.g., a microorganism (e.g., bacterium, virus or fungus) and/or portion or component thereof (e.g., a protein antigen)) that is capable of eliciting an immune response in a subject. In preferred embodiments, immunogens elicit immunity against the immunogen (e.g., microorganism (e.g., pathogen or a pathogen product)) when administered in combination with a nanoemulsion of the present invention. As used herein, the term *Burkholderia* antigen refers to a component or product of a bacteria of the genus *Burkholderia* that elicits an immune response when administered to a subject. An antigen may be a component or product derived from an organism (e.g., bacteria of the genus *Burkholderia*) including, but not limited to, polypeptides, peptides, proteins, nucleic acids, membrane fractions, and polysaccharides.

As used herein, the term "enhanced immunity" refers to an increase in the level of adaptive and/or acquired immunity in a subject to a given immunogen (e.g., microorganism (e.g., pathogen)) following administration of a composition relative to the level of adaptive and/or acquired immunity in a subject that has not been administered the composition.

As used herein, the terms "purified" or "to purify" refer to the removal of contaminants or undesired compounds from a sample or composition. As used herein, the term "substantially purified" refers to the removal of from about 70 to 90%, up to 100%, of the contaminants or undesired compounds from a sample or composition.

As used herein, the terms "administration" and "administering" refer to the act of giving a drug, prodrug, or other agent, or therapeutic treatment (e.g., a composition of the present invention) to a physiological system (e.g., a subject or in vivo, in vitro, or ex vivo cells, tissues, and organs).

As used herein, the terms "co-administration" and "co-administering" refer to the administration of at least two agent(s) (e.g., a nanoemulsion and one or more other pharmaceutically acceptable substances (e.g., a second nanoemulsion)) or therapies to a subject. In some embodiments, the co-administration of two or more agents or therapies is concurrent. In other embodiments, a first agent/therapy is administered prior to a second agent/therapy. In some embodiments, co-administration can be via the same or different route of administration. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent. In other embodiments, co-administration is preferable to treat and/or prevent infection by more than one type of infectious agent (e.g., bacteria and/or viruses).

As used herein, the term "topically" refers to application of a compositions of the present invention (e.g., a composition comprising a nanoemulsion) to the surface of the skin and/or mucosal cells and tissues (e.g., alveolar, buccal, lingual, masticatory, vaginal or nasal mucosa, and other tissues and cells which line hollow organs or body cavities). Compositions described herein can be applied using any pharmaceutically acceptable method, such as for example, intranasal, buccal, sublingual, oral, rectal, ocular, parenteral (intravenously, intradermally, intramuscularly, subcutaneously, intracisternally, intraperitoneally), pulmonary, intravaginal, locally administered, topically administered, mucosally administered, via an aerosol, or via a buccal or nasal spray formulation. Further, the nanoemulsion vaccines described herein can be formulated into any pharmaceutically acceptable dosage form, such as a liquid dispersion, gel, aerosol, pulmonary aerosol, nasal aerosol, ointment, cream, semi-solid dosage form, and a suspension. Further, the composition may be a controlled release formulation, sustained release formulation, immediate release formulation, or any combination thereof.

The terms "pharmaceutically acceptable" or "pharmacologically acceptable," as used herein, refer to compositions that do not substantially produce adverse allergic or immunological reactions when administered to a host (e.g., an animal or a human). Such formulations include dips, sprays, seed dressings, stem injections, sprays, and mists. As used herein, "pharmaceutically acceptable carrier" includes any and all solvents, dispersion media, coatings, wetting agents (e.g., sodium lauryl sulfate), isotonic and absorption delaying agents, disintegrants (e.g., potato starch or sodium starch glycolate), and the like. Examples of carriers, stabilizers and adjuvants have been described and are known in the art (See e.g., Martin, Remington's Pharmaceutical Sciences, 15th Ed., Mack Publ. Co., Easton, Pa. (1975), incorporated herein by reference).

As used herein, the term "pharmaceutically acceptable salt" refers to any salt (e.g., obtained by reaction with an acid or a base) of a composition of the present invention that is physiologically tolerated in the target subject. "Salts" of the compositions of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compositions of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

For therapeutic use, salts of the compositions of the present invention are contemplated as being pharmaceutically acceptable. However, salts of acids and bases that are non-pharmaceutically acceptable may also find use, for example, in the preparation or purification of a pharmaceutically acceptable composition.

As used herein, the terms "at risk for disease" and "at risk for infection" refer to a subject that is predisposed to experiencing a particular disease and/or infection. This predisposition may be genetic (e.g., a particular genetic tendency to experience the disease, such as heritable disorders), or due to other factors (e.g., environmental conditions, exposures to detrimental compounds present in the environment, etc.). Thus, it is not intended that the present invention be limited to any particular risk (e.g., a subject may be "at risk for disease" simply by being exposed to and interacting with other people that carry a risk of transmitting a pathogen), nor is it intended that the present invention be limited to any particular disease and/or infection.

"Nasal application", as used herein, means applied through the nose into the nasal or sinus passages or both. The application may, for example, be done by drops, sprays, mists, coatings or mixtures thereof applied to the nasal and sinus passages.

"Pulmonary application" and "pulmonary administration" refers to any means of applying a composition of the present invention to the pulmonary system of a subject. The present invention is not limited to any particular means of administration. Indeed, a variety of means are contemplated to be useful for pulmonary administration including those described herein.

As used herein, the term "kit" refers to any delivery system for delivering materials. In the context of the nanoemulsion compositions of the present invention, such delivery systems include systems that allow for the storage, transport, or delivery of the compositions and/or supporting materials (e.g., written instructions for using the materials, etc.) from one location to another. For example, kits include one or more enclosures (e.g., boxes) containing the relevant nanoemulsions and/or supporting materials. As used herein, the term "fragmented kit" refers to delivery systems comprising two or more separate containers that each contain a subportion of the total kit components. The containers may be delivered to the intended recipient together or separately. For example, a first container may contain a composition comprising a nanoemulsion for a particular use, while a second container contains a second agent (e.g., an antibiotic or spray applicator). Indeed, any delivery system comprising two or more separate containers that each contains a subportion of the total kit components are included in the term "fragmented kit." In contrast, a "combined kit" refers to a delivery system containing all of the components of a composition needed for a particular use in a single container (e.g., in a single box housing each of the desired components). The term "kit" includes both fragmented and combined kits.

DETAILED DESCRIPTION OF THE INVENTION

The present invention relates to methods and compositions useful for treating pulmonary infection. In particular, the present invention provides nanoemulsion compositions and methods of using the same to treat bacteria associated with biofilms (e.g., found in pulmonary infections). Compositions and methods of the present invention find use in, among other things, clinical (e.g. therapeutic and preventative medicine), industrial, and research applications.

Several pathogenic microorganisms initiate infection by attaching to mucosal epithelial cells lining the gastro-intestinal, oropharyngeal, respiratory or genito-urinacy tracts. Some pathogens, such as influenza virus, *Bordetella pertussis*, or *Vibrio cholerae*, remain at or within the mucosal tissue, while others, such as *Salmonella typhi* or hepatitis A virus, possess mechanisms permitting penetration into deeper tissues and spread systemically. Specific and non-specific defense mechanisms of the mucous membranes provide first line protection against both types of pathogen. Non-specific effectors include resident macrophages, antimicrobial peptides, lactoferrin and lysozyme, extremes of pH, bile acids, digestive enzymes, mucus, shedding of epithelial cells, flushing mechanisms (peristalsis, ciliary beating, micturation, etc.) and competition from local flora. However, successful pathogens have generally evolved means to survive the non-specific defenses present at the site they infect and it is the secretory immune system which plays a major role in protecting against diseases caused by a number of bacterial and viral pathogens, and is probably a major effector against pathogens that are restricted to mucosal surfaces. For organisms that spread systemically, both local and systemic immune responses are desirable for optimum immunity.

As described herein, certain microbes (e.g., bacteria) are able to thrive when a normal and/or healthy immune system does not function properly for one reason or another. Cystic fibrosis (CF), asthma, HIV infection, chemotherapeutic therapy and a host of other conditions lead to malfunctioning and/or attenuation of immune responses that would normally function to protect against and clear microbes capable of causing pathology in a healthy subject.

For example, *Pseudomonas aeruginosa* is an opportunistic pathogen that infects the immunocompromised, elderly, cancer chemotherapy patients, and individual suffering from CF. In CF lung disease, *P. aeruginosa* is trapped in thickened, dehydrated, hypoxic mucus lining in airway epithelia. Morphologic data suggests that the airway lumen of CF patients harbor *P. aeruginosa* biofilms that are characterized as spherical microcolonies.

Other types of microbes can cause pathology in an otherwise healthy host subject. For example, colonization of the respiratory tract by the Gram-negative coccobacillus *Bordetella pertussis* results in whooping cough, also called pertussis, a significant cause of morbidity and mortality of human infants. Two other closely-related isolates of *Bordetella* have also been found in humans: *B. parapertussis* and *B. bronchiseptica*. Molecular genetic analyses suggest that these three isolates are too closely related to be classified as separate species. (See Gilchrist. M. J. R., 1991, *"Bordetella"*, in Manual of Clinical Microbiology, 5th ed., Balows, A. et al., eds., American Society for Microbiology, Washington, D.C.). While *B. pertussis* differs from *B. bronchiseptica* and *B. parapertussis* in the nature of the toxins it produces, *B. bronchiseptica* and *B. parapertussis* do produce active toxins (See Hausman, S. Z. et al., 1996, Infect. Immun. 64: 4020-4026), and there is some evidence to indicate that *B. pertussis* organisms can covert to the *B. parapertussis* phenotype (Gilchrist, M. J. R., 1991, *"Bordetella"*, in Manual of Clinical Microbiology, 5th ed., Balows, A. et al., eds., American Society for Microbiology, Washington, D.C.).

Thus, the present invention provides compositions and methods for the treatment of respiratory infections. Compositions and methods of the present invention may be used to treat and/or prevent respiratory infection (e.g., in cystic fibrosis patients) caused by one or more of *pseudomonas* (e.g., *P. aeruginosa, P. paucimobilis, P. putida, P. fluorescens*, and *P. acidovorans*), staphylococci, Methicillin-resistant *Staphylococcus aureus* (MRSA), streptococci (including *Streptococcus pneumoniae*), *Escherichia coli, Klebsiella, Enterobacter, Serratia, Haemophilus, Yersinia pestis, Burkholderia pseudomallei, B. cepacia, B. gladioli, B. multivorans, B. vietnamiensis, Mycobacterium tuberculosis, M. avium* complex (MAC)(*M. avium* and *M. intracellulare*), *M. kansasii, M. xenopi, M. marinum, M. ulcerans*, or *M. fortuitum* complex (*M. fortuitum* and *M. chelonei*), *Bordetella pertussis, B. parapertussis* and *B. bronchiseptica*. Furthermore, compositions and methods of the present invention find use in the treatment and/or prevention of a host of respiratory infections (e.g., respiratory infections of the upper respiratory tract (e.g., nose, ears, sinuses, and throat) and the lower respiratory tract (e.g., trachea, bronchial tubes, and lungs)). Several examples of microbes that may be treated (e.g., killed and/or attenuated in growth (e.g., within the respiratory tract of a subject)) are provided below.

Accordingly, in some embodiments, the present invention provides a composition comprising a nanoemulsion, and methods of pulmonary administration of the same to prevent and/or treat respiratory infection. In some embodiments, the nanoemulsion comprises ethylenediaminetetraacetic acid (EDTA). The present invention is not limited by the amount of EDTA utilized. In some embodiments, 0.01-0.1 mM, 0.1-1.0 mM, 1.0-1.5 mM, 1.5-2.5 mM, 2.5-5.0 mM, 5.0-10.0 mM, 10-20 mM, 20-30 mM, or 30-50 mM EDTA is used. However, the present invention is not limited to this amount of EDTA. In some embodiments, less than 0.01 mM or more than 50 mM EDTA is utilized. In some embodiments, the composition is co-administered with a hypertonic salt (e.g., sodium chloride) solution (e.g., a 6-7%, 1-3%, 3-6%, 0.1-1%, or more than 7% salt solution (e.g., NaCl solution)). In some embodiments, the composition comprises a 20% nanoemulsion solution. In some embodiments, the composition comprises greater than 20% (e.g., 25%, 30%, or more) nanoemulsion solution. In some embodiments, the composition comprises less than 20% (e.g., 15%, 10% or less) nanoemulsion solution. However, the present invention is not limited to this amount (e.g., percentage) of nanoemusion. For example, in some embodiments, a composition comprises less than 10% nanoemulsion. In some embodiments, a composition comprises more than 20% nanoemulsion. In some embodiments, the composition comprises 10 mM EDTA. In some embodiments, the composition comprises 20 mM EDTA. In some embodiments, a composition of the present invention comprises any of the nanoemulsions described herein. In some embodiments, a composition comprising a nanoemulsion utilized to treat bacteria (e.g., present in pulmonary space of a subject (e.g., biofilm forming bacteria)) comprises $P_{407}$5EC. In some embodiments, a composition comprising a nanoemulsion comprises $W_{80}$5EC.

Administration of nanoemulsion alone or in combination with EDTA (e.g., 10-20 mM EDTA) was able to achieve complete killing of $10^6$ bacteria in PBS in 60 minutes (See Examples 2-4). In the presence of hypertonic saline (e.g., 6-7% NaCl), the killing ability of the nanoemulsion was surprisingly and strikingly enhanced, achieving complete killing within 15 minutes while in the presence of 20 mM EDTA (See Example 2). Also, nanoemulsions comprising a lower concentration of EDTA were able to achieve complete killing of bacteria in 30 minutes in the presence of hypertonic saline.

Thus, in some embodiments, the present invention provides that a nanoemulsion composition can be used to kill (e.g., completely) bacteria over a short time period (e.g., less than 60 minutes, less than 30 minutes, or less than 15 minutes).

The present invention also demonstrates that compositions of the present invention are able to eradicate a mixed population of bacteria. Moreover, toxicity studies performed during the development of embodiments of the present invention characterized the nanoemulsion compositions as being safe and causing no detectable harm to a subject (e.g., no histological changes and/or detectable pathology (See, e.g., Example 1)).

As described in Examples 3 and 4, compositions comprising nanoemulsions of the present invention are able to treat (e.g., kill and/or inhibit growth of) bacterial species that are generally not virulent in healthy persons, but that are opportunists that cause severe and chronic respiratory tract infections (e.g., in individuals with cystic fibrosis (CF)). Unremitting infection with these species results in inflammation and progressive lung disease that culminates in pulmonary failure, the leading cause of death for CF patients. Effective therapy of pulmonary infection in CF to date has been severely limited by the broad spectrum antimicrobial resistance exhibited by these species, which are among the most drug-resistant bacteria encountered in human infection. The site of infection in CF presents another important obstacle to effective therapy. Infecting bacteria primarily reside within the airway lumen in sputum, airway epithelial surface fluid, and the bronchial mucosa (ref). The penetration of systemically delivered antimicrobials to this infected site is generally poor. Treatment is further hampered by bacterial biofilm formation, which is believed to occur in the airways of infected patients, and by the exceptionally viscous secretions that characterize the CF respiratory tract.

Although an understanding of a mechanism is not necessary to practice the present invention, and the present invention is not limited to any particular mechanism of action, in some embodiments, a mechanism of bacterial and/or viral killing utilizing compositions comprising nanoemulsions of the present invention involves fusion of the emulsion with microorganism lipid membranes, leading to rapid osmotic disruption and cell lysis (See, e.g., Hamouda and Baker, J Appl Microbiol. 2000 September; 89(3):397-403). Additionally, in some embodiments, electrostatic attraction (e.g., provided by cationic surface charge of CPC) overcomes the LPS-mediated resistance of gram-negative bacteria to neutral and anionic detergents (See, e.g., Hamouda and Baker, J Appl Microbiol. 2000 September; 89(3):397-403). In some embodiments, bactericidal activity of a composition comprising a nanoemulsion (e.g., $P_{407}$5EC (e.g., against gram-negative and/or gram-positive bacteria)) is enhanced by the addition of EDTA. Although an understanding of a mechanism is not necessary to practice the present invention, and the present invention is not limited to any particular mechanism of action, in some embodiments, EDTA chelates divalent cations that stabilize outer membrane LPS thereby facilitating interactions with the cationic emulsion, an interaction that leads to membrane permeabilization and lysis as well as augmenting transmembrane diffusion of macromolecules (See, e.g., Rabinovich-Guilatt et al., J Drug Target. 2004; 12(9-10):623-33, Vaara, Microbiol Rev. 1992 September; 56(3):395-411).

Experiments conducted during development of embodiments of the present invention identified $P_{407}$5EC to be stable after nebulization in 7% saline using the PARI LC Plus nebulizer Inhalation of a single dose of $P_{407}$5EC nebulized in 7% saline was well tolerated by animals. Thus, in some embodiments, the present invention provides compositions comprising $P_{407}$5EC and hypertonic saline, and methods of using the same (e.g., via inhalation (e.g., post nebulizing the solution)) for treating one or more types of pulmonary bacterial infections (e.g., to treat bacteria and/or bacterial biofilms (e.g., that possess resistance to conventional treatments) without increasing the already high treatment burden for CF patients).

For example, experiments conducted during development of embodiments of the invention show that compositions comprising nanoemulsions (e.g., $P_{407}$5EC and saline solution) were effective to treat (e.g., kill and/or inhibit growth of) species within the *Burkholderia cepacia* complex (Bcc) (See, e.g., Example 3). Infection with *Burkholderia cepacia* species is particularly refractory to antimicrobial therapy and associated with increased rates of morbidity and mortality in CF. Infection with Bcc is also regarded by many CF care centers as an absolute contraindication to lung transplantation. Compositions comprising nanoemulsions (e.g., $P_{407}$5EC and saline solution) were effective to treat (e.g., kill and/or inhibit growth of) *B. multivorans* and *B. cenocepacia* which account for the majority of Bcc infection in CF (See, e.g., Reik J Clin Microbiol. 2005 June; 43(6):2926-8). Compositions comprising nanoemulsions (e.g., $P_{407}$5EC and saline solution) were effective to treat (e.g., kill and/or inhibit growth of) *B. gladioli*, which although not a member of the Bcc, is being recovered with increasing frequency from CF patients. Also shown in Example 3, compositions comprising nanoemulsions (e.g., $P_{407}$5EC) were effective to treat (e.g., kill and/or inhibit growth of) *Acinetobacter*, which although currently infrequently recovered in CF, appears to be an emerging pathogen in this patient population. The great majority (94%) of isolates tested in Example 3 were recovered from cultures of respiratory specimens from persons with CF. The panel also included one representative isolate from each of five previously described so-called epidemic lineages, each of which has been identified as infecting multiple CF patients. These included the *B. cenocepacia* ET12 (Johnson et al., *J Clin Microbiol* 1994; 32:924-30.), PHDC (Chen et al., *J Pediatr* 2001; 139:643-9), and Midwest (Coenye and LiPuma, J. Infect. Dis. 185:1454-1462) lineages, as well as the *B. multivorans* OHBM lineage (Biddick et al., *FEMS Microbiol Lett* 2003; 228:57-62) and the *B. dolosa* SLC6 lineage (Biddick et al., *FEMS Microbiol Lett* 2003; 228:57-62). Compositions comprising nanoemulsions (e.g., $P_{407}$5EC and saline solution) effectively treated (e.g., killed and/or inhibited growth of) each of these different species. Moreover, compositions comprising nanoemulsions (e.g., $P_{407}$5EC) were effective to treat (e.g., kill and/or inhibit growth of) strains that were found in previous susceptibility testing to be multi-drug resistant (e.g., defined as resistant to all antibiotics tested in two of three antibiotic classes: lactams (including carbapenems), aminoglycosides, and quinolones) as well as panresistant strains (See Example 3). Genotyping analyses of all isolates was performed to confirm that each sample treated was a distinct strain.

As shown in Example 3, $P_{407}$5EC showed very good activity against the strains tested. With the exception of two *B. cenocepacia* strains, all strains in the test panel were inhibited by a $P_{407}$5EC concentration of ≤125 μg/ml, or a 1:16 dilution of the starting material; 59% of strains were inhibited by a concentration of ≤31.2 μg/ml, a 1:64 dilution of $P_{407}$5EC. Multi-drug resistant or panresistant strains did not show decreased susceptibility to $P_{407}$5EC, demonstrating $MIC_{90}$s of 125 μg/ml and 62.5 μg/ml, respectively. In general, *Burkholderia* species tended to be slightly less susceptible to $P_{407}$5EC than the other species examined. Sixteen of the 18 strains requiring the highest MICs were *Burkholderia*. Conversely, 33 of the 38 strains with the lowest tested MIC (15.6 μg/ml) were non-*Burkholderia* species. No striking differences in $P_{407}$5EC activity was observed among the 10 *Burkholderia* species examined, although the two strains requiring the highest MICs (250 μg/ml and 500 μg/ml) were both *B. cenocepacia*. Among the non-*Burkholderia* species, *Ralstonia* strains were most susceptible ($MIC_{90}$≤15.6 μg/ml) while *Acinetobacter* strains were relatively less susceptible ($MIC_{90}$=125 μg/ml). No evidence was found of tolerance to $P_{407}$5EC among a subset of 34 strains for which both MIC and MBC were determined. $P_{407}$5EC killing of planktonically grown bacteria was time- and concentration-dependent; at a concentration 16 times greater than the MIC, complete killing was achieved within 30 min. Thus, the present invention provides that relatively brief exposure of bacteria to $P_{407}$5EC can be utilized to effect several log decreases in viable bacteria. Thus, a composition comprising a nanoemulsion (e.g., $P_{407}$5EC) of the present invention can be utilized individually, or in combination with other antimicrobials, to kill and/or inhibit growth of bacteria.

Experiments were conducted during development of embodiments of the invention to assess the activity of $P_{407}$5EC against bacteria grown in vitro as biofims. A relatively strict definition of in vitro biofilm formation was employed, as described in Example 3, in an effort to provide a stringent test of $P_{407}$5EC activity. 12 strains that met the definition were tested. As shown in Example 3, the strains represented several species and a range of susceptibility to $P_{407}$5EC based on standard MIC/MBC testing. Although the MBIC and MBEC of $P_{407}$5EC were increased compared to the respective MIC and MBC for each strain tested (median four-fold increase in MBIC compared to MIC), all 12 strains were inhibited or killed by $P_{407}$5EC when grown as biofilms. Only a single strain required undiluted $P_{407}$5EC (2000 μg/ml) for eradication of viable biofilm bacteria. Relative biomass was assessed among the biofilm forming strains spectrophotometrically with crystal violet staining and no correlation was observed between biomass and MBIC/MBEC. In fact, although *B. gladioli* strain AU10529 produced the greatest biomass among the 12 strains tested, the MBIC and MBEC of $P_{407}$5EC for this strain were relatively low (both 62.5 μg/ml). Conversely, *B. cenocepacia* strain J2315 produced relatively little biomass, yet required a $P_{407}$5EC MBEC of 1000 μg/ml.

Figure 10:
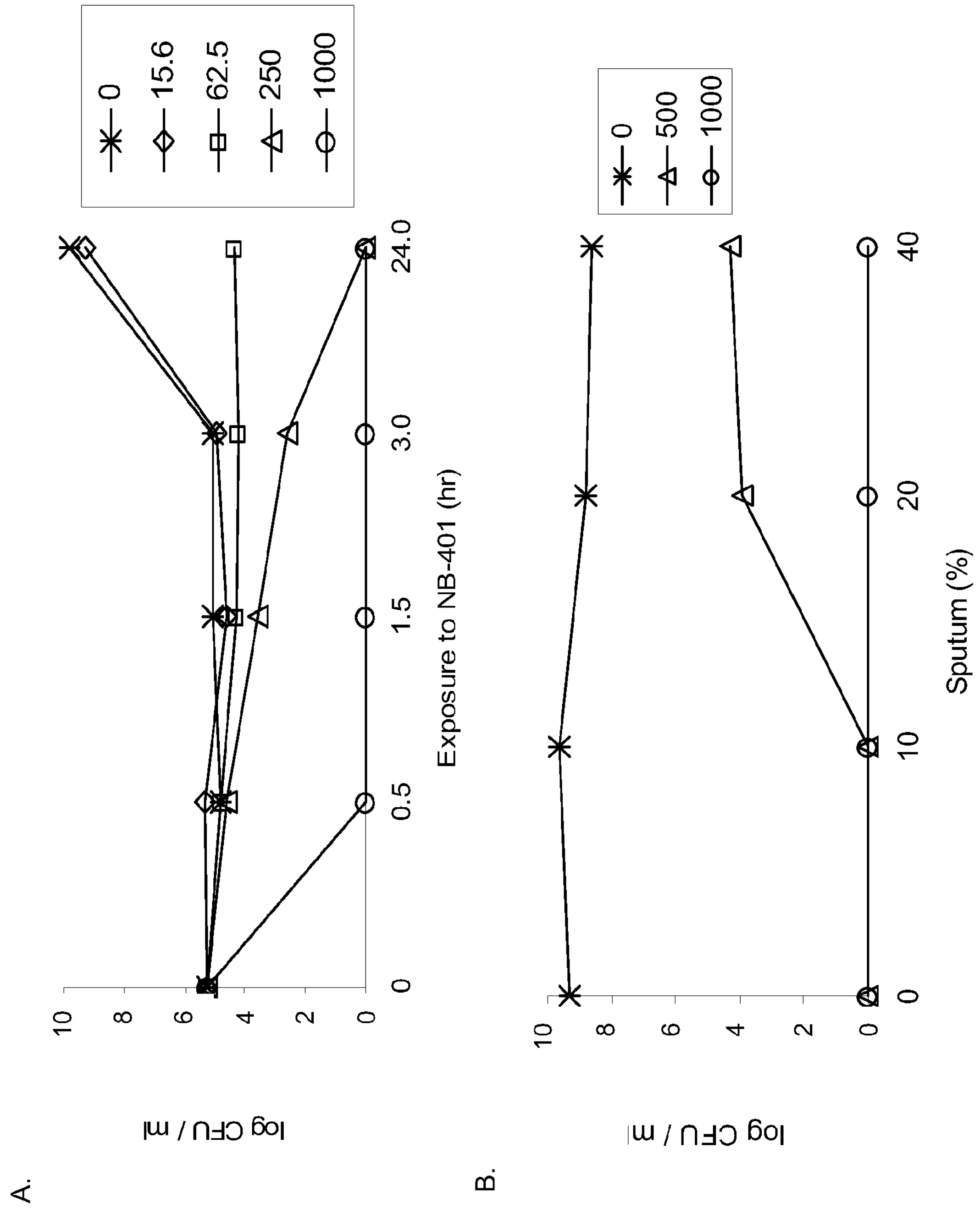
FIG. 10 shows a time-kill study of $P_{407}$5EC activity and concentration-dependent inhibition of $P_{407}$5EC activity by CF sputum. (A) $10^5$ CFU/ml of *B. multivorans* ATCC 17616 were exposed to various concentrations of $P_{407}$5EC around the MIC (62.5 μg/ml) and viable bacterial counts were determined at the times indicated. (B) $10^5$ CFU/ml of *B. multivorans* ATCC 17616 were exposed to various concentrations of $P_{407}$5EC in the presence of three concentrations of CF sputum for 24 hr before viable bacterial counts were determined. Numbers and symbols in inset boxes indicate concentrations of $P_{407}$5EC (μg/ml CPC) used.

CF sputum, like biofilm, is reported to antagonize the activity of antibacterial drugs (See, e.g., Hunt et al., Antimicrob Agents Chemother. 1995 January; 39(1):34-9). Glycoproteins such as mucin, which compose 2-3% of the dry weight of sputum, and high molecular weight DNA are present in elevated levels resulting in exceptionally viscous sputum that provides a physical barrier protecting bacteria. In addition, these macromolecules bind and sequester antibiotics while small cationic molecules and the decreased pH of CF sputum block drug penetration into bacteria and reduce drug bioactivity. The strategy of increasing drug dosing to overcome these obstacles is limited by drug toxicity. To assess the impact of sputum on the antibacterial activity of $P_{407}$5EC, standard planktonic susceptibility testing was repeated for the 12 biofilm-forming strains in the presence of CF sputum. A mixture of sputum from 15 CF patients was used to avoid inter-patient variation in macromolecule and high molecular weight DNA composition, and ionic conditions, and only mechanical shearing was applied to minimize changes to the native microenvironment (See, e.g., Grebski et al., Chest. 2001 May; 119(5): 1521-5). The activity of $P_{407}$5EC against bacteria suspended in media containing 43% sputum (the maximum sputum concentration achieved in the test system) was decreased with bactericidal concentrations 2- to 32-fold greater than the respective planktonic MBCs without sputum. The sputum-MBCs were identical to (6 of 12) or within one dilution of (6 of 12) the MBECs obtained with biofilm grown bacteria. Although the activity of $P_{407}$5EC was similarly antagonized by both CF sputum and biofilm growth, it remained bactericidal for all the strains tested under both test conditions (See FIG. 10).

Thus, in some embodiments, the present invention provides compositions comprising nanoemulsions (e.g., $P_{407}$5EC) and methods of using the same for antimicrobial treatment for infection due to CF-related opportunistic pathogens. In particular, nanoemulsion compositions of the present invention are rapidly bactericidal, and active against bacteria whether grown planktonically or as a biofilm, or in the presence of CF sputum. Moreover, compositions comprising nanoemulsions of the present invention are exceptionally stable, unchanged after nebulization, and broadly microbicidal. Importantly, the development of resistance to a nanemulsion composition of the present invention has not been observed by any bacterial species examined to date. Thus, the present invention provides that $P_{407}$5EC can be used effectively as an inhaled antimicrobial.

The present invention is not limited to treatment of bacterial biofilms the reside in pulmonary spaces (e.g., within a subject with CF). Indeed, compositions comprising a nanoemulsion of the present invention can be utilized as a therapeutic and/or antimicrobial agent (e.g., to kill and/or inhibit growth of) bacterial biofilms in any clinical and/or industrial setting.

Multiple species of bacteria exist that are able to form biofilms. For example, bacteria that adhere to implanted medical devices or damaged tissue often encase themselves in a hydrated matrix of polysaccharide and protein to form biofilm. Biofilms pose a serious problem for public health because of the increased resistance of biofilm-associated organisms to antimicrobial agents and the association of infections with these organisms in patients with indwelling medical devices or damaged tissue. Antibiotic resistance of bacteria growing in biofilms contributes to the persistence and chronic nature of infections such as those associated with implanted medical devices. The mechanisms of resistance in biofilms are different from the now familiar plasmids, transposons, and mutations that confer innate resistance to individual bacterial cells. In biofilms, resistance seems to depend on multicellular strategies.

Biofilms are complex communities of microorganisms attached to surfaces or associated with interfaces or damaged tissue. Despite the focus of modern microbiology research on pure culture, planktonic (free-swimming) bacteria, it is now widely recognized that most bacteria found in natural, clinical, and industrial settings persist in association with surfaces as biofilms. Furthermore, these microbial communities are often composed of multiple species that interact with each other and their environment. The determination of biofilm architecture, particularly the spatial arrangement of microcolonies (clusters of cells) relative to one another, has profound implications for the function of these complex communities.

The biofilm matrix is a dynamic environment in which the component microbial cells appear to reach homeostasis and are optimally organized to make use of all available nutrients. The matrix therefore shows great microheterogeneity, within which numerous microenvironments can exist. Biofilm formation is believed to be a two-step process in which the attachment of bacterial cells to a surface is followed by growth dependent accumulation of bacteria in multilayered cell clusters. Although exopolysaccharides provide the matrix framework, a wide range of enzyme activities can be found within the biofilm, some of which greatly affect structural integrity and stability.

More specifically, during the first phase of formation, it is hypothesized that the fibrinogen and fibronectin of host plasma cover the surface of a medical implant or damaged tissue and are identified by constitutively expressed microbial surface components, which mediate the initial attachment of bacteria to the surface of the biomaterial or damaged tissue. In the second step, a specific gene locus in the bacteria cells, called the intracellular adhesion (ica) locus, activates the adhesion of bacteria cells to each other, forming the secondary layers of the biofilm. The ica locus is responsible for the expression of the capsular polysaccharide operon, which in turn activates polysaccharide intercellular adhesion (PIA), via the sugar poly-N-succinylglucosamine (PNSG), a-1,6-linked glucosaminoglycan. The production of this polysaccharide layer gives the biofilm its slimy appearance when viewed using electron microscopy.

*Staphylococcus aureus* is a highly virulent human pathogen. Both *S. aureus* and coagulase-negative staphylococci have emerged as major nosocomial pathogens associated with biofilm formation on implanted medical devices and damaged tissue. These organisms are among the normal carriage flora of human skin and mucous membranes, making them prevalent complications during and after invasive surgery or prolonged hospital stays. As bacteria carried on both healthy and sick people, staphylococci are considered opportunistic pathogens that invade patients via open wounds and via biomaterial implants.

Biofilm infections associated with *S. aureus* are a significant cause of morbidity and mortality, particularly in settings such as hospitals, nursing homes and infirmaries. Patients at risk include infants, the elderly, the immuno-compromised, the immuno-suppressed, and those with chronic conditions requiring frequent hospital stays. Patients with intravascular and other implanted prosthetic devices are at even greater risk from staphylococcal infections because of compromised immune systems and the introduction of foreign bodies, which serve to damage tissue and/or act as a surface for the formation of biofilms. Such infections can have chronic, if not fatal, implications.

The causes of biofilm resistance to antibiotics include the failure of some antimicrobial agents to penetrate all the layers of a biofilm, the slow-growth rate of certain biofilm cells that make them less susceptible to antimicrobial agents requiring active bacterial growth, and the expression of gene patterns by the bacterial cells embedded in the biofilm that differ from the genes expressed in their planktonic (free-swimming) state. These differences in biofilm-associated bacteria render antimicrobial agents that work effectively to kill planktonic bacteria ineffective in killing biofilm-associated bacteria. Often the only way to treat biofilms (e.g., associated with catheters or prosthetic devices) is the removal of the contaminated device, which may require additional surgery and present further risks to patients.

Thus, as used herein, biofilms refer to an aggregate of microorganisms with an extracellular matrix that facilitates adhesion to, and colonization and growth of the aggregate on a surface, such as an internal or external tissue or organ. Biofilms can be comprised of bacteria, fungi, yeast, protozoa, or other microorganisms. Bacterial biofilms typically display high resistance to antibiotics, often up to 1,000-times greater resistance than the same bacteria not growing in a biofilm.

In some embodiments, compositions and methods of the invention are utilized to treat (e.g., kill and/or inhibit growth of) and/or prevent biofilms on and/or within a subject (e.g., within the pulmonary system, on internal organs or tissue (e.g., the bladder, kidney, heart, middle ear, sinuses, a joint, the eye), on an external tissue (e.g., the skin), and/or oral surfaces such as teeth, tongue, oral mucosa, or gums. Compositions and methods of the invention may be used to treat a biofilm-associated condition such as a soft-tissue infection, chronic sinusitis, endocarditis, osteomyelitis, urinary tract infection, chronic bacterial vaginosis, dental plaque or halitosis, infection of prosthetic device and/or catheter, bacterial keratitis, or prostatitis.

As described in Examples 3 and 4, compositions of the present invention can be utilized to treat (e.g., kill and/or inhibit growth of) any one or more Gram-positive and Gram-negative bacterial species. Indeed, compositions and methods of the present invention can be utilized to kill and/or inhibit growth of a number of bacterial species including, but not limited to, *Staphylococcus aureus*, coagulase negative staphylococci such as *Staphylococcus epidermis, Streptococcus pyogenes* (Group A), *Streptococcus* species (viridans group), *Streptococcus agalactiae* (group B), *S. bovis, Streptococcus* (anaerobic species), *Streptococcus pneumoniae, Enterococcus* species, *Bacillus anthracis, Corynebacterium diptheriae*, and *Corynebacterium* species which are diptheroids (aerobic and anaerobic), *Listeria monocytogenes, Clostridium tetani*, and *Clostridium difficile, Escherichia coli, Enterobacter* species, *Proteus mirablis, Pseudomonas aeruginosa, Klebsiella pneumoniae, Salmonella, Shigella, Serratia, Campylobacterjejuni, Neisseria, Branhamella catarrhalis*, and *Pasteurella.*

Compositions and methods of the present invention can be utilized to treat (e.g., kill and/or inhibit growth of) organisms capable of forming biofilms including, but not limited to, dermatophytes (e.g, *Microsporum* species such as *Microsporum canis, Trichophyton* species such as *Trichophyton rubrum* and *Trichophyton mentagrophytes*), yeasts (e.g., *Candida albicans, Candidaparapsilosis, Candida glabrata, Candida tropicalis*, and other *Candida* species including drug resistant *Candida* species), Epidermophytonfloccosum, Malasseziafuurfur (*Pityropsporon orbiculare, Pityropsporon ovale*) *Cryptococcus neoformans, Aspergillusfumigatus* and other *Aspergillus* species, *Zygomycetes* (*Rizopus, Mucor*), hyalohyphomycosis (*Fusarium* species), *Paracoccidioides brasiliensis, Blastmyces dermatitides, Histoplasma capsulatum, Coccidiodes immitis, Sporothrix schenckii*, and *Blastomyces.*

Thus, in some embodiments, the present invention provides a method for treating a subject possessing a biofilm (e.g., possessing an indwelling prosthetic device or catheter, wherein the indwelling prosthetic device or catheter is in contact with a biofilm, or wherein the subject has an infection (e.g., respiratory infection) within which a biofilm resides) comprising administering to the subject a composition comprising a nanoemulsion (e.g., $P_{407}5EC$) under conditions such that the biofilm is altered and/or bacteria residing within the biofilm are killed and/or their growth is inhibited. In some embodiments, altering the biofilm comprises eradicating the biofilm. In some embodiments, altering the biofilm comprises killing bacteria involved in forming the biofilm. In some embodiments, the bacteria comprise *S. aureus, S. epidermidis*, antibiotic resistant bacteria (e.g., methicillin resistant, vancomycin resistant, etc.), and/or other type of bacteria described herein. In some embodiments, the composition comprising a nanoemulsion (e.g., $P_{407}5EC$) is co-administered with one or more antibacterial agents. In some embodiments, the antibacterial agents are selected from the group comprising, but not limited to, antibiotics, antibodies, antibacterial enzymes, peptides, and lanthione-containing molecules. In some embodiments, the antibiotic interferes with or inhibits cell wall synthesis. In some embodiments, the antibiotic is selected from the group including, but not limited to, β-lactams, cephalosporins, glycopeptides, aminoglycosides, sulfonomides, macrolides, folates, polypeptides and combinations thereof. In some embodiments, the antibiotic interferes with protein synthesis (e.g., glycosides, tetracyclines and streptogramins). The present invention is not limited by the number of doses of composition comprising nanoemulsion administered. In some embodiments, multiple doses are administered on separate days. In some embodiments, the multiple doses are administered on the same day. In some embodiments, a composition comprising a nanoemulsion described herein is administered continuously. In some embodiments, co-administration with a composition comprising a nanoemulsion permits administering a lower dose of an antibacterial agent than would be administered without co-administration of a composition comprising a nanoemulsion. In some embodiments, the composition comprising a nanoemulsion described herein is administered using a nebulizer. In some embodiments, administration is intramuscularly, subcutaneously, locally, directly into an infected site, directly onto an indwelling prosthetic device (e.g., a shunt, stent, scaffold for tissue construction, feeding tube, punctual plug, artificial joint, pacemaker, artificial valve, etc.) or catheter. In some embodiments, administration is directly through a catheter.

The present invention is not limited by the type of microbe treated. Indeed a variety of microbial pathogens can be treated (e.g, killed (e.g., completely killed)) and/or the growth thereof prevented and/or attenuated in a subject using the compositions and methods of the present invention including, but not limited to, bacteria, viruses, and fungi described herein.

The present invention also provides compositions and methods for treating (e.g., killing and/or inhibiting growth of) organisms that heretofore display resistance to a broad spectrum of antibiotics (e.g., species of the genus *Acinetobacter*).

*Acinetobacter* species are generally considered nonpathogenic to healthy individuals. However, several species persist in hospital environments and cause severe, life-threatening infections in compromised patients (See, e.g., Gerischer U (editor). (2008). *Acinetobacter Molecular Biology,* 1st ed., Caister Academic Press). The spectrum of antibiotic resistances of these organisms together with their survival capabilities make them a threat to hospitals as documented by recurring outbreaks both in highly developed countries and elsewhere. Infections occur in immunocompromised individuals, and the strain *A. baumannii* is the second most commonly isolated nonfermenting bacteria in human specimens. *Acinetobacter* is frequently isolated in nosocomial infections and is especially prevalent in intensive care units, where both sporadic cases as well as epidemic and endemic occurrence is common. *A. baumannii* is a frequent cause of nosocomial pneumonia, especially of late-onset ventilator associated pneumonia. It can cause various other infections including skin and wound infections, bacteremia, and meningitis. *A. lwoffi* is also causative of meningitis. *A. baumannii* can survive on the human skin or dry surfaces for weeks.

Since the start of the Iraq War, over 700 U.S. soldiers have been infected or colonized by *A. baumannii*. Four civilians undergoing treatment for serious illnesses at Walter Reed Army Medical Center in Washington, D.C., contracted *A. baumannii* infections and died. At Landstuhl Regional Medical Center, a U.S. military hospital in Germany, another civilian under treatment, a 63-year-old German woman, contracted the same strain of *A. baumannii* infecting troops in the facility and also died.

*Acinetobacter* species are innately resistant to many classes of antibiotics, including penicillin, chloramphenicol, and often aminoglycosides. Resistance to fluoroquinolones has been reported during therapy and this has also resulted in increased resistance to other drug classes mediated through active drug efflux. A dramatic increase in antibiotic resistance in *Acinetobacter* strains has been reported by the CDC and the carbapenems are recognized as the gold-standard and/or treatment of last resort. An increase in resistance to the carbapenems leaves very little treatment option although there has been some success reported with polymyxin *B. Acinetobacter* species are unusual in that they are sensitive to sulbactam; sulbactam is most commonly used to inhibit bacterial beta-lactamase, but this is an example of the antibacterial property of sulbactam itself.

Thus, in some embodiments, compositions and methods of the present invention are utilized to treat (e.g., kill and/or inhibit growth of) bacteria of the *Acinetobacter* species (e.g., individually or in combination with other treatments (e.g., carbapenems, polymyxin B, and/or sulbactam)).

Cystic Fibrosis

Cystic fibrosis (CF) is a life-threatening disorder that causes severe lung damage due to a defective transmembrane protein called CFTR responsible for the balance of electrolytes. Thick mucus forms plugging the tubes, ducts and passageways in the lungs. This environment is ideal for opportunistic bacteria to establish biofilm communities, leading to respiratory infections. Systemically-administered antibiotics can decrease the frequency and severity of exacerbations; however, the bacteria are never be completely eradicated from the airways and the lungs. Nebulized antibiotics are used, but resistance emergence and/or colonization of different resistant species is a major concern. Cystic fibrosis (CF) results in the functional impairment of innate respiratory defense mechanisms, providing an environment for colonization of pathogenic bacterial species such as *Staphylococcus aureus* and *Haemophilus influenzae*, and a number of opportunistic species such as *Pseudomonas aeruginosa, Achromobacter xylosoxidans, Stenotrophomonas maltophilia, Ralstonia* spp., *Pandoraea* spp., and the *Burkholderia cepacia* complex (Bcc) species (See, e.g., LiPuma et al., (2009) Antimicrob Agents Chemother 53, 249-255). The Bcc comprises a group of at least 17 phylogenetically related saprophytic gram-negative bacilli, most of which can form biofilm (See, e.g., Al Bakri et al., 2004, Journal of Applied Microbiology 96, 455-463; Eberl and Tummler, 2004, International Journal of Medical Microbiology 294, 123-131; LiPuma et al., (2009) Antimicrob Agents Chemother 53, 249-255; and Tomlin et al., 2004, Journal of Microbiological Methods 57, 95-106). They are particularly difficult to treat and are associated with increased rates of morbidity and mortality in CF patients. They also are among the most antimicrobial-resistant bacterial species encountered in human infections (See, e.g., LiPuma et al, 2005, Curr Opin Pulm Med 11, 528-533; LiPuma et al., (2009) Antimicrob Agents Chemother 53, 249-255). Once established, the infection and associated inflammation are rarely eliminated, resulting in progressive lung disease ending in pulmonary failure and death (See, e.g., LiPuma et al., (2009) Antimicrob Agents Chemother 53, 249-255; Saiman and Seigel, 2003, Infect Control Hosp Epidemiol 24, S6-S52).

The present invention is directed to a novel broad-spectrum antimicrobial nanoemulsion (NE) and uses thereof. The NE kills pathogens by interacting with their membranes. This physical kill-on-contact mechanism significantly reduces any concerns about resistance. The NE is formulated from pharmaceutically approved safe ingredients.

In Example 8 below, the minimum inhibitory concentration (MIC) and minimum bactericidal concentration (MBC) of a against four genera of problematic bacteria in CF patients was evaluated: *Pseudomonas, Burkholderia, Acinetobacter* and *Stenotrophomonas*. Example 8 also describes evaluating potential synergy between the NE and other antimicrobials. *P. aeruginosa, B. cenocepacia, A. baumannii* and *S. maltophilia*, which were evaluated in Example 8, are important respiratory pathogens implicated in acute exacerbations of cystic fibrosis patients. In one aspect of the invention, the activity of a nanoemulsion is defined herein in terms of its minimum inhibitory concentration (MIC), and/or minimum bactericidal concentration (MBC), both in comparison to traditionally used antimicrobial medicines The results described in Example 8 show that the $MIC_{90}$/$MBC_{90}$ values for the NE tested were 8/64 μg/ml for *P. aeruginosa*, 64/>514 μg/ml for *B. cenocepacia*, 8/64 μg/ml for *A. baumannii* and 8/32 μg/ml for *S. maltophilia*. Colistin had $MIC_{90}$/$MBC_{90}$ values of 2/8, >32/>32, 1/>16 and >32/>32 for *P. aeruginosa, B. cenocepacia, A. baumannii* and *S. maltophilia*, respectively. Cefepime, imipenem, levofloxacin and tobramycin had $MIC_{90}$/$MBC_{90}$ values of ≥32/>32, ≥32/>32, 16/16 and >32/>32 μg/ml, respectively, against all strains. These results are significant as in contrast to conventional drugs such as colistin, cefepime, imipenem, levofloxacin and tobramycin used to treat CF and which can exhibit significant side effects and potential toxicity with increasing dosage, NE are completely non-toxic.

Also evaluated in Example 8 below was synergy data. Specifically, also evaluated was the fractional inhibitory concentration (FIC) index when in combination with another antimicrobial and the fractional bactericidal concentration (FBC) index when in combination with another antimicrobial. The FIC and the FBC are calculated to make the judgment on synergy, antagonism or indifference of the nanoemulsion in combination. For this determination, ten strains of *Burkholderia, Stenotrophomonas* and 10 strains of *Acinetobacter* were tested to determine a shift in MIC when $P_{407}$5EC+EDTA was in combination with either colistin or tobramycin, two traditional antimicrobials used in the lungs of CF patients to treat chronic lung infections. The results showed that the NE texted ($P_{407}$5EC+EDTA) in combination with colistin was found to be synergistic for 90% (in terms of the FIC) and 70% (in terms of the FBC) of the *Stenotrophomonas* strains, but indifferent, only 20% synergy in by the FIC and 0% by the FBC, when in combination with tobramycin. For the *Acinetobacter* strains, $P_{407}$5EC+EDTA in combination with colistin was found to be indifferent, only 20% synergy in by the FIC and 0% by the FBC, as well as when in combination with tobramycin, only 10% synergy in by the FIC and 10% by the FBC. For the *Burkholderia* strains, $P_{407}$5EC+EDTA in combination with colistin was found to be indifferent, only 30% synergy in by the FIC and 10% by the FBC, but when in combination with tobramycin, 50% synergy in by the FIC and 20% by the FBC.

Finally, Example 8 generated a short time-kill curve to produce samples to be used in pictures using electron microscopy for a strain of *Burkholderia* to demonstrate the physical kill-on-contact mechanism of action. Time-kill resulted in an overall 4.44 log reduction in cfu/ml from the untreated beginning to the 30 minute time point. Each 10 minute time point had between 1-2 log reduction as follows: from the untreated to the 10 minute point there was a 1.40 log reduction, from the 10 to 20 minute time points there was a 1.91 log reduction and from the 20 to 30 minute time points there was a 1.13 log reduction. See FIGS. 2A-2D.

The data herein, such as that presented in Example 8, demonstrates that nanoemulsions, such as the tested $P_{407}$5EC, are effective against strains that are multidrug-resistant, including colistin-resistant isolates of *Burkholderia* and *Stenotrophomonas*. None of the described lipid A modifications in *Pseudomonas* species impacted the MIC/MBCs with $P_{407}$5EC. No evidence of antagonism with two major antibiotics, colistin and tobramycin, was observed and in the case of the *Stenotrophomonas*, synergy was evident. This is valuable because the treatment of patients with CF should not need their normal antibiotic regime suspended in order to use the nanoemulsion, complicating their treatment programs. The SEM images demonstrate the kill on contact mechanism, here in this case a Gram negative bacterium with a reputation of having a tough outer membrane. Further studies are ongoing to investigate the nebulization of $P_{407}$5EC for the treatment of pulmonary infection in cystic fibrosis patients.

While therapeutic progress has been made in preserving functional pulmonary physiology in CF patients by managing nutrition and mucosal secretions, little progress has been made in therapeutic interventions for the prevention and management of Bcc infections. For example, at present, no effective vaccines against Bcc are available. Mucosal vaccine development for Bcc has been limited in part due to the lack of an identified protective antigen and the lack of effective mucosal adjuvants (See, e.g., Davis, 2001, Advanced Drug Delivery Reviews 51, 21-42).

As shown in Example 10 below, the present invention provides immunogenic compositions comprising a nanoemulsion and *Burkholderia* antigen (e.g., *Burkholderia* outer membrane protein (OMP)) that, when administered to a subject, induces immunity (e.g., protective immunity) in the subject against bacteria from the genus *Burkholderia* (e.g., *B. cenocepacia, B. multivorans* or others species associated with respiratory infection). In some embodiments, the present invention provides all or a portion of an OMP (e.g., isolated, purified, and/or recombinant OMPs)) from a bacteria of the genus *Burkholderia* (See, e.g., Example 10, Table 25) that is utilized in an immunogenic composition comprising a nanoemulsion (e.g., for administration to a subject (e.g., to induce immunity to a bacteria of the genus *Burkholderia* in the subject)). As shown in Example 10, the present invention provides that when administered to a subject, an immunogenic composition comprising a nanoemulsion and *Burkholderia* OMP induces both mucosal and systemic anti-OMP antibodies. Also shown in Example 10, the present invention provides that when administered to a subject, an immunogenic composition comprising a nanoemulsion and an OMP from a specific strain of *Burkholderia* (e.g., *B. cenocepacia*) induces both mucosal and systemic anti-OMP antibodies that neutralize bacteria of the specific species from which the OMP is derived (e.g., *B. cenocepacia*) and cross-neutralize bacteria from one or more other species of bacteria (e.g., of the genus *Burkholderia*).

Example 10 shows that a single nasal immunization with OMP-NE produces a robust immune response characterized by rapid induction of antigen-specific T cell responses and secretory antibody responses, as documented by induction of IFN-γ, IL-2 and mucosal sIgA and IgG, and that the immune response can be subsequently boosted. Mice immunized with OMP-NE displayed a dramatic decrease in K56-1 colony forming units (cfu) in the lungs when compared with non-immunized controls. Pulmonary bacterial clearance was significantly enhanced in OMP-NE vaccinated mice which showed fewer *B. cenocepacia* organisms in the spleens as compared to non-vaccinated groups. Thus, the present invention provides that mucosal OMP-NE administration produced protective immunity and reduced the likelihood of sepsis in subjects.

Example 10 also provides data identifying a 17 KDa OmpA-like protein and immune responses associated with exposure to the protein. The 17 KDa lipoprotein fractions were better recognized by antibodies contained in serum from OMP-NE vaccinated mice (See, e.g., Example 10, FIG. 29C). Thus, the present invention provides that immunogenic compositions comprising epitopes contained within the 17KDa OmpA-like proteins generate protective antibodies (e.g., against one or more species of *Burkholderia*) in a subject administered the immunogenic composition.

Significant differences between OMP-NE and OMP in PBS responses were observed. For example, immunization with OMP in the absence of nanoemulsion resulted in relatively high titers of IgG, but were consistently lower (13 to 30 fold) than those induced by OMP-NE immunogenic compositions. Immunization with OMP in the absence of nanoemulsion failed to respond to a booster immunization. The response induced with OMP plus nanoemulsion was primarily directed toward specific proteins contained within the preparation, whereas OMP in the absence of nanoemulsion appears to have elicited immune responses to the intrinsic endotoxin content.

Accordingly, the present invention provides methods and compositions for the stimulation of immune responses. In particular, the present invention provides immunogenic nanoemulsion compositions and methods of using the same for the induction of immune responses (e.g., innate and/or adaptive immune responses (e.g., for generation of host immunity against a bacterial species of the genus *Burkholderia* (e.g., *B. cenocepacia, B. multivorans*, etc.))). Compositions and methods of the present invention find use in, among other things, clinical (e.g. therapeutic and preventative medicine (e.g., vaccination)) and research applications.

In some embodiments, the present invention provides nanoemulsion adjuvants and compositions comprising the same (e.g., vaccines) for the stimulation of immune responses (e.g., immunity) against a bacterial species of the genus *Burkholderia* (e.g., *B. cenocepacia, B. multivorans*, etc.). In some embodiments, the present invention provides nanoemulsion adjuvant compositions that stimulate and/or elicit immune responses (e.g., innate immune responses and/or adaptive/acquired immune responses) when administered to a subject (e.g., a human or other mammalian subject)). In some embodiments, the present invention provides nanoemulsion adjuvant compositions comprising one or a plurality of *Burkholderia* (e.g., *B. cenocepacia, B. multivorans*, etc.) antigens (e.g., *Burkholderia* components isolated and/or purified, and/or recombinant *Burkholderia* proteins (e.g., OMPs)). The present invention is not limited to any particular nanoemulsion or *Burkholderia* antigen. Exemplary immunogenic compositions (e.g., vaccine compositions) and methods of administering the compositions are described in more detail below.

In some embodiments, the present invention provides an immunogenic composition comprising a nanoemulsion and one or more *Burkholderia* antigens (e.g., *B. cepacia* antigens). In some embodiments, the present invention provides a method of inducing an immune response to *Burkholderia* (e.g., *B. cepacia*) in a subject comprising: providing a subject and an immunogenic composition comprising a nanoemulsion and an immunogen, wherein the immunogen comprises a *Burkholderia* (e.g., *Burkholderia cepacia*) antigen and administering the composition to the subject under conditions such that the subject generates a *Burkholderia* (e.g., *Burkholderia cepacia*) specific immune response. The present invention is not limited by the route chosen for administration of a composition of the present invention. In some preferred embodiments, administering the immunogenic composition comprises contacting a mucosal surface of the subject with the composition. In some embodiments, the mucosal surface comprises nasal mucosa. In some embodiments, inducing an immune response induces immunity to *Burkholderia* (e.g., *Burkholderia cepacia*) in the subject.

Experiments were conducted during development of embodiments of the invention to determine if a composition comprising a nanoemulsion (NE) and *Burkholderia* antigen could be utilized to generate an immune response in a subject. Nasal immunization with a whole cell *Streptococcus pneumoniae* antigen (WCPAg) mixed with nanoemulsion was performed and shown to induce an IgG response in a host subject and the ability to eradicate upper respiratory colonization of *S. pneumoniae.*

In particular, as described in Example 10, the present invention provides immunogenic compositions comprising a nanoemulsion and *Burkholderia* antigen (e.g., *Burkholderia* outer membrane protein (OMP)) that, when administered to a subject, induces immunity (e.g., protective immunity) in the subject against bacteria from the genus *Burkholderia* (e.g., *B. cenocepacia, B. multivorans* or others species associated with respiratory infection). Accordingly, in some embodiments, the present invention provides that administration (e.g., nasal administration) of a composition comprising nanoemulsion and *Burkholderia* antigen (e.g., OMP antigen (e.g., a 17KDa protein comprising an amino acid sequence selected from SEQ ID NOs. 1-16)) to a subject produces immunity toward *Burkholderia* in the subject thereby protecting the subject against *Burkholderia* infection (e.g., associated with a respiratory infection).

The present invention is not limited by the type of bacteria of the genus *Burkholderia* utilized in the immunogenic compositions and methods of using the same of the invention. In some embodiments, the bacteria is a pathogen. In some embodiments, the pathogen is a *Burkholderia* species responsible for respiratory or respiratory associated infection. A variety of *Burkholderia* species find use in the compositions and methods of the invention including, but not limited to, *B. cenocepacia, B. dolosa, B. multivorans, B. ambifaria, B. vietnamiensis, B. ubonensis, B. thailandensis, B. graminis, B. oklahomensis, B. pseudomallei, B. xenovorans, B. phytofirmans, B. phymatum, R. metallidurans, R. eutropha, R. solanacearum.*

In some embodiments, the bacteria of the genus *Burkholderia* is *B. cepecia*. In some embodiments, an immunogenic composition comprising a nanoemulsion and an Omp-A like protein comprises an Omp-A like protein from a *Burkholderia* species including, but not limited to, *B. cenocepacia, B. dolosa, B. multivorans, B. ambifaria, B. vietnamiensis, B. ubonensis, B. thailandensis, B. graminis, B. oklahomensis, B. pseudomallei, B. xenovorans, B. phytofirmans, B. phymatum, R. metallidurans, R. eutropha, R. solanacearum*. In some embodiments, an immunogenic composition comprising a nanoemulsion and an Omp-A like protein comprises an Omp-A like protein (e.g., isolated, purified, and/or recombinant Omp-A like protein) comprising an amino acid sequence identified in SEQ ID NOs.: 1-16. In some embodiments, an immunogenic composition comprising a nanoemulsion and an Omp-A like protein comprises an Omp-A like protein (e.g., isolated, purified, and/or recombinant Omp-A like protein) comprising an amino acid sequence of SEQ ID NO. 1.

In some embodiments, an immunogenic composition comprising a nanoemulsion and *Burkholderia* antigen comprises antigens (e.g., polysaccharide, protein, killed whole cells (e.g., conjugated or non-conjugated antigens)), wherein the antigens are derived from multiple (e.g., at least 2, 3, 5, 7, 10, 15, 20 or more) serotypes of *Burkholderia*. The number of *Burkholderia* antigens utilized can range from 2 different serotypes to about 20 different serotypes. In some embodiments, an immunogenic composition comprising a nanoemulsion and *Burkholderia* antigen may comprise *Burkholderia* antigen (e.g., whole cell, polysaccharide, Omp-A protein, other protein, etc.) from every known and/or isolated *Burkholderia* serotype.

In some embodiments, an immunogenic composition comprising a nanoemulsion and *Burkholderia* (e.g., *B. cepacia*) antigen comprises one, two or more different types of carrier protein (e.g., that act as carriers for proteins, saccharides, etc.). For example, in one embodiment, two or more different saccharides or proteins may be conjugated to the same carrier protein, either to the same molecule of carrier protein or to different molecules of the same carrier protein. Carrier proteins may be TT, DT, CRM197, fragment C of TT, PhtD, PhtBE or PhtDE fusions (particularly those described in WO 01/98334 and WO 03/54007), detoxified pneumolysin and protein D. In some embodiments, a carrier protein present in a composition comprising a nanoemulsion and *Burkholderia* (e.g., *B. cenocepacia*) antigen is a member of the polyhistidine triad family (Pht) proteins, fragments or fusion proteins thereof. The PhtA, PhtB, PhtD or PhtE proteins may have an amino acid sequence sharing 80%, 85%, 90%, 95%, 98%, 99% or 100% identity with a sequence disclosed in WO 00/37105 or WO 00/39299 (e.g. with amino acid sequence 1-838 or 21-838 of SEQ ID NO: 4 of WO 00/37105 for PhtD). For example, fusion proteins are composed of full length or fragments of 2, 3 or 4 of PhtA, PhtB, PhtD, PhtE. Examples of fusion proteins are PhtA/B, PhtA/D, PhtA/E, PhtB/A, PhtB/D, PhtB/E. PhtD/A. PhtD/B, PhtD/E, PhtE/A, PhtE/B and PhtE/D, wherein the proteins are linked with the first mentioned at the N-terminus (see for example WO01/98334). Carriers may comprise histidine triad motif(s) and/or coiled coil regions. A histidine triad motif is the portion of polypeptide that has the sequence HxxHxH where H is histidine and x is an amino acid other than histidine. A coiled coil region is a region predicted by "Coils" algorithm Lupus, A et al (1991) Science 252; 1162-1164.

Examples of carrier proteins which may be used in the present invention are DT (Diphtheria toxoid), TT (tetanus toxoid) or fragment C of TT, DT CRM197 (a DT mutant) other DT point mutants, such as CRM176, CRM228, CRM 45 (Uchida et al J. Biol. Chem. 218; 3838-3844, 1973); CRM 9, CRM 45, CRM102, CRM 103 and CRM107 and other mutations described by Nicholls and Youle in Genetically Engineered Toxins, Ed: Frankel, Maecel Dekker Inc, 1992; deletion or mutation of Glu-148 to Asp, Gln or Ser and/or Ala 158 to Gly and other mutations disclosed in U.S. Pat. Nos. 4,709,017 or 4,950,740; mutation of at least one or more residues Lys 516, Lys 526, Phe 530 and/or Lys 534 and other mutations disclosed in U.S. Pat. Nos. 5,917,017 or 6,455,673; or fragment disclosed in U.S. Pat. No. 5,843,711, pneumococcal pneumolysin (Kuo et al (1995) Infect Immun 63; 2706-13) including ply detoxified in some fashion for example dPLY-GMBS (WO 04081515, PCT/EP2005/010258) or dPLY-formol, PhtX, including PhtA, PhtB, PhtD, PhtE and fusions of Pht proteins for example PhtDE fusions, PhtBE fusions (WO 01/98334 and WO 03/54007), (Pht A-E are described in more detail below) OMPC (meningococcal outer membrane protein—usually extracted from *N. meningitidis* serogroup B—EP0372501), PorB (from *N. meningitidis*), PD (*Haemophilus influenzae* protein D—see, e.g., EP 0 594 610 B), or immunologically functional equivalents thereof, synthetic peptides (EP0378881, EPO427347), heat shock proteins (WO 93/17712, WO 94/03208), pertussis proteins (WO 98/58668, EPO471177), cytokines, lymphokines, growth factors or hormones (WO 91/01146), artificial proteins comprising multiple human CD4+ T cell epitopes from various pathogen derived antigens (Falugi et al (2001) Eur J Immunol 31; 3816-3824) such as N19 protein (Baraldoi et al (2004) Infect Immun 72; 4884-7) pneumococcal surface protein PspA (WO 02/091998), iron uptake proteins (WO 01/72337), toxin A or B of *C. difficile* (WO 00/61761).

Generation of Antibodies

An immunogenic composition comprising a nanoemulsion and *Burkholderia* (e.g., *B. cenocepacia*) antigen can be used to immunize a mammal, such as a mouse, rat, rabbit, guinea pig, monkey, or human, to produce polyclonal antibodies. If desired, a *Burkholderia* (e.g., *B. cenocepacia*) antigen can be conjugated to a carrier protein, such as bovine serum albumin, thyroglobulin, keyhole limpet hemocyanin or other carrier described herein. Depending on the host species, various adjuvants can be used to increase the immunological response. Such adjuvants include, but are not limited to, Freund's adjuvant, mineral gels (e.g., aluminum hydroxide), and surface active substances (e.g. lysolecithin, pluronic polyols, polyanions, peptides, nanoemulsions described herein, keyhole limpet hemocyanin, and dinitrophenol). Among adjuvants used in humans, BCG (bacilli Calmette-Guerin) and *Corynebacterium parvum* are especially useful.

Monoclonal antibodies that specifically bind to a *Burkholderia* (e.g., *B. cepacia*) antigen can be prepared using any technique which provides for the production of antibody molecules by continuous cell lines in culture. These techniques include, but are not limited to, the hybridoma technique, the human B cell hybridoma technique, and the EBV hybridoma technique (See, e.g., Kohler et al., Nature 256, 495 497, 1985; Kozbor et al., J. Immunol. Methods 81, 3142, 1985; Cote et al., Proc. Natl. Acad. Sci. 80, 2026 2030, 1983; Cole et al., Mol. Cell. Biol. 62, 109 120, 1984).

In addition, techniques developed for the production of "chimeric antibodies," the splicing of mouse antibody genes to human antibody genes to obtain a molecule with appropriate antigen specificity and biological activity, can be used (See, e.g., Morrison et al., Proc. Natl. Acad. Sci. 81, 68516855, 1984; Neuberger et al., Nature 312, 604 608, 1984; Takeda et al., Nature 314, 452 454, 1985). Monoclonal and other antibodies also can be "humanized" to prevent a patient from mounting an immune response against the antibody when it is used therapeutically. Such antibodies may be sufficiently similar in sequence to human antibodies to be used directly in therapy or may require alteration of a few key residues. Sequence differences between rodent antibodies and human sequences can be minimized by replacing residues which differ from those in the human sequences by site directed mutagenesis of individual residues or by grating of entire complementarity determining regions.

Alternatively, humanized antibodies can be produced using recombinant methods, as described below. Antibodies which specifically bind to a particular antigen can contain antigen binding sites which are either partially or fully humanized, as disclosed in U.S. Pat. No. 5,565,332.

Alternatively, techniques described for the production of single chain antibodies can be adapted using methods known in the art to produce single chain antibodies which specifically bind to a particular antigen. Antibodies with related specificity, but of distinct idiotypic composition, can be generated by chain shuffling from random combinatorial immunoglobin libraries (See, e.g., Burton, Proc. Natl. Acad. Sci. 88, 11120 23, 1991).

Single-chain antibodies also can be constructed using a DNA amplification method, such as PCR, using hybridoma cDNA as a template (See, e.g., Thirion et al., 1996, Eur. J. Cancer Prev. 5, 507-11). Single-chain antibodies can be mono- or bispecific, and can be bivalent or tetravalent. Construction of tetravalent, bispecific single-chain antibodies is taught, for example, in Coloma & Morrison, 1997, Nat. Biotechnol. 15, 159-63. Construction of bivalent, bispecific single-chain antibodies is taught, for example, in Mallender & Voss, 1994, J. Biol. Chem. 269, 199-206.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology (See, e.g., Verhaar et al., 1995, Int. J. Cancer 61, 497-501; Nicholls et al., 1993, J. Immunol. Meth. 165, 81-91).

Antibodies which specifically bind to a particular antigen also can be produced by inducing in vivo production in the lymphocyte population or by screening immunoglobulin libraries or panels of highly specific binding reagents as disclosed in the literature (See, e.g., Orlandi et al., Proc. Natl. Acad. Sci. 86, 3833 3837, 1989; Winter et al., Nature 349, 293 299, 1991).

Chimeric antibodies can be constructed as disclosed in WO 93/03151. Binding proteins which are derived from immunoglobulins and which are multivalent and multispecific, such as the "diabodies" described in WO 94/13804, also can be prepared. Antibodies can be purified by methods well known in the art. For example, antibodies can be affinity purified by passage over a column to which the relevant antigen is bound. The bound antibodies can then be eluted from the column using a buffer with a high salt concentration.

Burn Wound Management

Contemporary burn wound management involves early debridement and reconstruction of non-viable skin coupled with provision of supportive care and topical antimicrobial dressing changes to partial thickness burn wounds. The goal of modern burn wound care is to provide an optimal environment for epidermal renewal. Restoration of skin integrity takes place via regrowth of keratinocytes from preserved hair follicles or transfer of split thickness skin grafts harvested from non-burn regions. During the period of epidermal renewal it is important to avoid further injury to the skin, abrogate burn wound progression, and minimize secondary complications such as wound infection. Early excision of full-thickness burn eschar, immediate skin grafting, and treatment of remaining open or partial thickness areas of burn wound with topical antimicrobial agents is the most effective way of minimizing burn wound colonization and invasive wound infection. (See, e.g., Bessey, Wound care. In Herndon D N, ed: *Total Burn Care 3rd edition*. Philadelphia, Pa.: Elsevier Inc., 2007, pp 127-135.). Popular topical antimicrobial agents include silver sulfadiazine (SILVADENE), mafenide acetate (SULFAMYLON), and colloidal silver impregnated dressings (ACTICOAT, SILVERLON). Each of these agents has potential limitations such as variable ability to penetrate eschar, uneven efficacy against both Gram-negative and Gram-positive bacteria, and potential toxicity to host immune cells (See, e.g., Steinstraesser et al., Antimicrob Agents Chemother 46(6):1837-1844, 2002).

Accordingly, the present invention provides nanoemulsion compositions and methods of using the same for the treatment of burn wounds. For example, as shown in Example 9, the present invention provides nanoemulsion compositions and methods of using the same to reduce, attenuate and/or prevent bacterial growth in a burn wound. The present invention also provides nanoemulsion compositions that reduce wound inflammation following burn injury. Although an understanding of a mechanism of action is not needed to practice the present invention, and the present invention is not limited to any particular mechanism of action, in some embodiments, a nanoemulsion composition that is applied to a wound following burn injury is able to penetrate more deeply and uniformly into a burn wound (e.g., thereby decreasing and/or inhibiting bacterial growth and/or inflammation at the site of the wound). As shown in Example 9, the present invention provides a method of reducing, inhibiting and/or eliminating bacterial growth in a burn wound comprising providing a burn wound and a nanoemulsion and administering the nanoemulsion to the burn wound under conditions that bacterial growth is reduced, inhibited and/or eliminated. In some embodiments, a nanoemulsion composition described herein is combined with one or more antimicrobial drugs for administration to a burn wound to minimize bacterial growth at the burn wound site. The present invention is not limited to any particular antimicrobial drug. Indeed, any antimicrobial drug that inhibits bacterial growth known to those in the art can be utilized in combination with a nanoemulsion composition described herein.

In addition to local effects, severe dermal burns are known to induce the systemic inflammatory response syndrome (SIRS), which results in a high-risk of end-organ dysfunction (See, e.g., Barton et al., *J Burn Care Rehabil* 18(1):1-9, 1997). Increased vascular permeability and systemic capillary leak as a consequence of SIRS following burn injury creates seepage of plasma into interstitial tissue throughout the body. This tissue edema and intravascular hypovolemia is responsible for a host of undesired clinical problems such as shock, pulmonary dysfunction, abdominal or extremity compartment syndrome, and cardiac failure.

As shown in Example 9 below, nanoemulsion compositions described herein can be administered to a burn wound to treat (e.g., reduce, attenuate and/or prevent) inflammation, tissue edema and/or intravascular hypovolemia at the site of a burn wound. In some embodiments, reducing inflammation, tissue edema and/or intravascular hypovolemia at the site of a burn wound reduces the occurrence of shock, pulmonary dysfunction, abdominal or extremity compartment syndrome, and/or cardiac failure. In some embodiments, a nanoemulsion composition described herein is used in combination with (e.g., is co-administered with) one or more anti-inflammatory drugs to minimize early burn wound inflammation and tissue edema. The present invention is not limited to any particular anti-inflammatory drug. Indeed, any anti-inflammatory drug that minimizes early burn wound inflammation and tissue edema can be utilized in combination with a nanoemulsion composition described herein.

In some embodiments, a nanoemulsion of the invention (e.g., $W_{20}5GBA_2ED$) is administered to a burn wound to prevent, attenuate and/or eradicate bacterial growth (e.g., *Staphylococcus aureus, P. aeruginosa*, or other bacteria) within a partial thickness burn wound. Example 9 shows that reduction in microbial infection was coupled with generation of lower levels of local dermal pro-inflammatory cytokines and evidence of reduced neutrophil sequestration into the burn wound. This decrease in burn wound bacterial growth and inflammation also produced less capillary leak in the early post-thermal injury time-period. Having the ability to clinically reduce capillary leak and tissue edema in the immediate post-burn time-period provides a lesser need for large volume crystalloid fluid resuscitation and a reduction in the associated sequela of physiologic volume overload, pulmonary dysfunction, and abdominal compartment syndrome.

Skin that is damaged by thermal injury loses its ability to protect the host against infection from both the loss of physical barrier function and the secondary immunosuppression caused by the thermal injury. Moreover, increased production of TGF-β and IL-10 during the post-burn period can result in immunosuppression. (See, e.g., Lyons et al., Arch Surg 134 (12):1317-1323, 1999; Varedi et al., Shock 16(5):380-382, 2001). It has been established that treatment of burn injured animals with anti-TGF-β can improve local and systemic clearance of *P. aeruginosa* (See, e.g., Huang et al., J Burn Care Res 27(5):682-687, 2006) Inhibition of TGF-β also results in increased survival following bacterial challenge. As shown in Example 9, a significant elevation of TGF-β, but not IL-10 was observed in the skin following partial thickness burn injury. However, topical nanoemulsion application (e.g., 10% $W_{20}5GBA_2ED$) to the burn wound inoculated with bacteria resulted in a reduction of the level of TGF-β when compared to the untreated burn wound.

Onset of a bacterial infection within a burn wound can delay or even reverse the tissue healing process (See, e.g., Steinstraesser et al., Crit Care Med 29(7):1431-1437, 2001). Topical antimicrobial therapy is used to reduce the microbial load in the burn wound and reduce this risk of infection. Current topical agents include silver nitrate ($AgNO_3$), silver sulfadiazine, mafenide acetate, and nanocrystalline impregnated silver dressings. Silver nitrate is limited in its use because of the problem it creates from contact staining and its limited antifungal activity. Silver sulfadiazine is the mainstay of topical burn antimicrobial treatment. It is bactericidal against *P. aeruginosa* and other Gram-negative enteric bacteria. Resistance to Silvadene by some of these organisms has emerged (See, e.g., Silver et al., J Ind Microbiol Biotechnol 33(7):627-634, 2006). The agent has limited antifungal activity, but can be used in conjunction with nystatin. Silvadene has no real ability to penetrate burn eschar and sometimes leads to leukopenia which requires conversion to another topical agent. The use of mafenide acetate is narrowed by the fact that it is bacteriostatic against select organisms, it has limited activity against Gram-positive bacteria such as *Staphylococcus aureus*, and that its use over a large surface area can lead to a metabolic acidosis because of its metabolism into a carbonic anhydrase inhibitor. The nanocrystalline silver dressings have the broadest activity against burn wound pathogens of the current agents available. They have a modest ability to penetrate eschar and can be left in place for many days (See, e.g., Church et al., Clin Microbiol Rev 19(2):403-434, 2006). SB 202190, an inhibitor of activated p38 MAPK, can substantially reduce the dermal inflammation generated in burn wounds (See, e.g., Arbabi et al., Shock. 26(2):201-209, 2006). Thermal injury initiates dermal inflammatory and pro-apoptotic cell signaling.

As shown in Example 9, topical application of nanoemulsion (e.g., $W_{20}5GBA_2ED$ resulted in reduced hair follicle cell apoptosis within the dermis of burned skin. Thus, in some embodiments, the present invention provides nanoemulsion compositions that can be utilized to reduce, when administered to a burn wound, conversion of the partial thickness burn wound within the "zone of stasis" to regions of full thickness burn.

In patients without evidence of inhalational injury, the burn wound itself is the primary source triggering the systemic inflammatory response via generation of pro-inflammatory cytokines and sequestration of neutrophils into the burn wound (See, e.g., Hansbrough et al., J Surg Res 61(1):17-22, 1996; Piccolo et al., Inflammation 23(4):371-385, 1999; Till et al., J Clin Invest 69(5):1126-1135, 1982). Topical application of a p38 MAPK inhibitor can control the source of inflammation at the level of the dermis, resulting in lower levels of pro-inflammatory mediators, reduced neutrophil sequestration and microvascular damage, and less epithelial apoptosis in burn wound hair follicle cells (See, e.g., Ipaktchi et al., Shock. 26(2):201-209, 2006). Dermal source control of inflammation also reduces bacterial growth and attenuates the systemic inflammatory response resulting in less acute lung injury and cardiac dysfunction following partial thickness burn injury in a rodent model. Accordingly, in some embodiments, a nanoemulsion of the invention is utilized (e.g., administered) alone or in combination with an anti-inflammatory and/or antimicrobial agent to reduce local dermal inflammation and risk of infection within burn wounds (e.g., early burn wounds, partial thickness wounds, full thickness wounds or other burn wounds). The present invention is not limited by the type of anti-inflammatory agent and/or antimicrobial utilized for co-administration with a nanoemulsion described herein. Indeed, a variety of anti-inflammatory agents and/or antimicrobial agents can be used including, but not limited to, silver nitrate ($AgNO_3$), silver sulfadiazine, mafenide acetate, nanocrystalline impregnated silver dressings, p38 MAPK inhibitor (e.g., SB 202190), or another anti-inflammatory or antimicrobial agent described herein.

In some embodiments, when a nanoemulsion of the invention is administered to a burn wound, the nanoemulsion can be administered (e.g., to a subject (e.g., to a burn or wound surface)) by multiple methods, including, but not limited to, direct use or being suspended in a solution (e.g., colloidal solution) and applied to a surface (e.g., a surface comprising bacteria (e.g., pathogenic bacteria) or susceptible to bacterial invasion); being sprayed onto a surface using a spray applicator; being mixed with fibrin glue and applied (e.g., sprayed) onto a surface (e.g., skin burn or wound); being impregnated onto a wound dressing or bandage and applying the bandage to a surface (e.g., an infection or burn wound); being applied by a controlled-release mechanism; or being impregnated on one or both sides of an acellular biological matrix that is then placed on a surface (e.g., skin burn or wound) thereby protecting at both the wound and graft interfaces. In some embodiments, the invention provides a pharmaceutical composition containing (a) a composition comprising a nanoemulsion (e.g., $W_{20}5GBA_2ED$); and (b) one or more other agents (e.g., an antibiotic). Examples of other types of antibiotics include, but are not limited to, almecillin, amdinocillin, amikacin, amoxicillin, amphomycin, amphotericin B, ampicillin, azacitidine, azaserine, azithromycin, azlocillin, aztreonam, bacampicillin, bacitracin, benzyl penicilloyl-polylysine, bleomycin, candicidin, capreomycin, carbenicillin, cefaclor, cefadroxil, cefamandole, cefazoline, cefdinir, cefepime, cefixime, cefinenoxime, cefinetazole, cefodizime, cefonicid, cefoperazone, ceforanide, cefotaxime, cefotetan, cefotiam, cefoxitin, cefpiramide, cefpodoxime, cefprozil, cefsulodin, ceftazidime, ceftibuten, ceftizoxime, ceftriaxone, cefuroxime, cephacetrile, cephalexin, cephaloglycin, cephaloridine, cephalothin, cephapirin, cephradine, chloramphenicol, chlortetracycline, cilastatin, cinnamycin, ciprofloxacin, clarithromycin, clavulanic acid, clindamycin, clioquinol, cloxacillin, colistimethate, colistin, cyclacillin, cycloserine, cyclosporine, cyclo-(Leu-Pro), dactinomycin, dalbavancin, dalfopristin, daptomycin, daunorubicin, demeclocycline, detorubicin, dicloxacillin, dihydrostreptomycin, dirithromycin, doxorubicin, doxycycline, epirubicin, erythromycin, eveminomycin, floxacillin, fosfomycin, fusidic acid, gemifloxacin, gentamycin, gramicidin, griseofulvin, hetacillin, idarubicin, imipenem, iseganan, ivermectin, kanamycin, laspartomycin, linezolid, linocomycin, loracarbef, magainin, meclocycline, meropenem, methacycline, methicillin, mezlocillin, minocycline, mitomycin, moenomycin, moxalactam, moxifloxacin, mycophenolic acid, nafcillin, natamycin, neomycin, netilmicin, niphimycin, nitrofurantoin, novobiocin, oleandomycin, oritavancin, oxacillin, oxytetracycline, paromomycin, penicillamine, penicillin G, penicillin V, phenethicillin, piperacillin, plicamycin, polymyxin B, pristinamycin, quinupristin, rifabutin, rifampin, rifamycin, rolitetracycline, sisomicin, spectrinomycin, streptomycin, streptozocin, sulbactam, sultamicillin, tacrolimus, tazobactam, teicoplanin, telithromycin, tetracycline, ticarcillin, tigecycline, tobramycin, troleandomycin, tunicamycin, tyrthricin, vancomycin, vidarabine, viomycin, virginiamycin, BMS-284,756, L-749,345, ER-35,786, S-4661, L-786, 392, MC-02479, PepS, RP 59500, and TD-6424. In some embodiments, two or more combined agents (e.g., a composition comprising a nanoemulsion and an antibiotic) may be used together or sequentially. In some embodiments, an antibiotic may comprise bacteriocins, type A lantibiotics, type B lantibiotics, liposidomycins, mureidomycins, alanoylcholines, quinolines, eveminomycins, glycylcyclines, carbapenems, cephalosporins, streptogramins, oxazolidonones, tetracyclines, cyclothialidines, bioxalomycins, cationic peptides, and/or protegrins. In some embodiments, the composition comprises lysostaphin.

The present invention is not limited by the type of nanoemulsion utilized (e.g., for respiratory administration, administration to a burn wound and/or for use in an immunogenic composition for induction of protective immune responses). Indeed, a variety of nanoemulsion compositions are contemplated to be useful in the present invention.

For example, in some embodiments, a nanoemulsion comprises (i) an aqueous phase; (ii) an oil phase; and at least one additional compound. In some embodiments of the present invention, these additional compounds are admixed into either the aqueous or oil phases of the composition. In other embodiments, these additional compounds are admixed into a composition of previously emulsified oil and aqueous phases. In certain of these embodiments, one or more additional compounds are admixed into an existing emulsion composition immediately prior to its use. In other embodiments, one or more additional compounds are admixed into an existing emulsion composition prior to the compositions immediate use.

Additional compounds suitable for use in a nanoemulsion of the present invention include, but are not limited to, one or more organic, and more particularly, organic phosphate based solvents, surfactants and detergents, cationic halogen containing compounds, germination enhancers, interaction enhancers, food additives (e.g., flavorings, sweeteners, bulking agents, and the like) and pharmaceutically acceptable compounds. Certain exemplary embodiments of the various compounds contemplated for use in the compositions of the present invention are presented below. Unless described otherwise, nanoemulsions are described in undiluted form.

Stability on Storage and after Application of the Nanoemulsions of the Invention Storage Stability The nanoemulsions of the invention can be stable at about 40° C. and about 75% relative humidity for a time period of at least up to about 1 month, at least up to about 3 months, at least up to about 6 months, at least up to about 12 months, at least up to about 18 months, at least up to about 2 years, at least up to about 2.5 years, or at least up to about 3 years.

In another embodiment of the invention, the nanoemulsions of the invention can be stable at about 25° C. and about 60% relative humidity for a time period of at least up to about 1 month, at least up to about 3 months, at least up to about 6 months, at least up to about 12 months, at least up to about 18 months, at least up to about 2 years, at least up to about 2.5 years, or at least up to about 3 years, at least up to about 3.5 years, at least up to about 4 years, at least up to about 4.5 years, or at least up to about 5 years.

Further, the nanoemulsions of the invention can be stable at about 4° C. for a time period of at least up to about 1 month, at least up to about 3 months, at least up to about 6 months, at least up to about 12 months, at least up to about 18 months, at least up to about 2 years, at least up to about 2.5 years, at least up to about 3 years, at least up to about 3.5 years, at least up to about 4 years, at least up to about 4.5 years, at least up to about 5 years, at least up to about 5.5 years, at least up to about 6 years, at least up to about 6.5 years, or at least up to about 7 years.

Stability Upon Application

The nanoemulsions of the invention are stable upon application, as surprisingly the nanoemulsions do not lose their physical structure upon application. Microscopic examination of skin surface following application of a nanoemulsion according to the invention demonstrates the physical integrity of the nanoemulsions of the invention. This physical integrity may result in the desired absorption observed with the nanoemulsions of the invention.

Nanoemulsions

The term "nanoemulsion", as defined herein, refers to a dispersion or droplet or any other lipid structure. Typical lipid structures contemplated in the invention include, but are not limited to, unilamellar, paucilamellar and multilamellar lipid vesicles, micelles and lamellar phases.

The nanoemulsion of the present invention comprises droplets having an average diameter size of less than about 1,000 nm, less than about 950 nm, less than about 900 nm, less than about 850 nm, less than about 800 nm, less than about 750 nm, less than about 700 nm, less than about 650 nm, less than about 600 nm, less than about 550 nm, less than about 500 nm, less than about 450 nm, less than about 400 nm, less than about 350 nm, less than about 300 nm, less than about 250 nm, less than about 200 nm, less than about 150 nm, or any combination thereof. In one embodiment, the droplets have an average diameter size greater than about 125 nm and less than or equal to about 300 nm. In a different embodiment, the droplets have an average diameter size greater than about 50 nm or greater than about 70 nm, and less than or equal to about 125 nm. In other embodiments of the invention, the nanoemulsion droplets have an average diameter of from about 300 nm to about 600 nm; or the nanoemulsion droplets have an average diameter of from about 150 nm to about 400 nm.

In one embodiment of the invention, the nanoemulsion has a narrow range of MIC (minimum inhibitory concentration) and MBC (minimum bactericidal concentrations) values. In another embodiment, the MIC and MBC for the nanoemulsion differ by less than or equal to four-fold, meaning that the nanoemulsion is bactericidal. In addition, the MIC and MBC for the nanoemulsion may differ by greater than four-fold, meaning that the nanoemulsion is bacteriostatic.

In one embodiment of the invention, the nanoemulsion comprises: (a) an aqueous phase; (b) about 1% oil to about 80% oil; (c) about 0.1% organic solvent to about 50% organic solvent; (d) about 0.001% surfactant or detergent to about 10% surfactant or detergent; (e) about 0.0005% to about 1.0% of a chelating agent; or (e) any combination thereof. In another embodiment of the invention, the nanoemulsion comprises: (a) about 10% oil to about 80% oil; (b) about 1% organic solvent to about 50% organic solvent; (c) at least one non-ionic surfactant present in an amount of about 0.1% to about 10%; (d) at least one cationic agent present in an amount of about 0.01% to about 3%; or any combination thereof.

In another embodiment, the nanoemulsion comprises a cationic surfactant which is either cetylpyridinium chloride (CPC) or benzalkonium chloride, or alkyl dimethyl benzyl ammonium chloride (BTC 824), or combination thereof. The cationic surfactant may have a concentration in the nanoemulsion of less than about 5.0% and greater than about 0.001%, or further, may have a concentration of less than about 5%, less than about 4.5%, less than about 4.0%, less than about 3.5%, less than about 3.0%, less than about 2.5%, less than about 2.0%, less than about 1.5%, less than about 1.0%, less than about 0.90%, less than about 0.80%, less than about 0.70%, less than about 0.60%, less than about 0.50%, less than about 0.40%, less than about 0.30%, less than about 0.20%, less than about 0.10%, greater than about 0.001%, greater than about 0.002%, greater than about 0.003%, greater than about 0.004%, greater than about 0.005%, greater than about 0.006%, greater than about 0.007%, greater than about 0.008%, greater than about 0.009%, and greater than about 0.010%.

In a further embodiment, the nanoemulsion comprises a non-ionic surfactant, and may have a concentration of about 0.01% to about 10.0%, or about 0.1% to about 3% of a non-ionic surfactant, such as a polysorbate.

In yet other embodiments of the invention, the nanoemulsion: (a) comprises at least one cationic surfactant; (b) comprises a cationic surfactant which is either cetylpyridinium chloride or benzalkonium chloride, or alkyl dimethyl benzyl ammonium chloride (BTC 824), or combination thereof; (c) comprises a cationic surfactant, and wherein the concentration of the cationic surfactant is less than about 5.0% and greater than about 0.001%; (d) comprises a cationic surfactant, and wherein the concentration of the cationic surfactant is selected from the group consisting of less than about 5%, less than about 4.5%, less than about 4.0%, less than about 3.5%, less than about 3.0%, less than about 2.5%, less than about 2.0%, less than about 1.5%, less than about 1.0%, less than about 0.90%, less than about 0.80%, less than about 0.70%, less than about 0.60%, less than about 0.50%, less than about 0.40%, less than about 0.30%, less than about 0.20%, less than about 0.10%, greater than about 0.001%, greater than about 0.002%, greater than about 0.003%, greater than about 0.004%, greater than about 0.005%, greater than about 0.006%, greater than about 0.007%, greater than about 0.008%, greater than about 0.009%, and greater than about 0.010%; or (e) any combination thereof. In yet other embodiments, (a) the nanoemulsion comprises at least one cationic surfactant and at least one non-cationic surfactant; (b) the nanoemulsion comprises at least one cationic surfactant and at least one non-cationic surfactant, wherein the non-cationic surfactant is a nonionic surfactant; (c) the nanoemulsion comprises at least one cationic surfactant and at least one non-cationic surfactant, wherein the non-cationic surfactant is a polysorbate nonionic surfactant; (d) the nanoemulsion comprises at least one cationic surfactant and at least one non-cationic surfactant, wherein the non-cationic surfactant is a nonionic surfactant, and the nonionic surfactant is present in a concentration of about 0.05% to about 10%, about 0.05% to about 7.0%, about 0.1% to about 7%, or about 0.5% to about 5%; (e) the nanoemulsion comprises at least one cationic surfactant and at least one a nonionic surfactant, wherein the cationic surfactant is present in a concentration of about 0.05% to about 2% or about 0.01% to about 2%; or (f) any combination thereof.

In other embodiments, the nanoemulsion comprises: (a) water; (b) ethanol or glycerol (glycerine), or a combination thereof; (c) either cetylpyridinium chloride (CPC), or benzalkonium chloride, or alkyl dimethyl benzyl ammonium chloride (BTC 824), or a combination thereof; (c) soybean oil; and (e) Poloxamer 407, Tween 80, or Tween 20. The nanoemulsion can further comprise EDTA.

These quantities of each component present in the nanoemulsion refer to a therapeutic nanoemulsion, and not to a nanoemulsion to be tested in vitro. This is significant, as nanoemulsions tested in vitro generally have lower concentrations of oil, organic solvent, surfactant or detergent, and (if present) chelating agent than that present in a nanoemulsion intended for therapeutic use, e.g., topical use. This is because in vitro studies do not require the nanoemulsion droplets to traverse the skin. For topical, aerosol, intradermal etc. use, the concentrations of the components must be higher to result in a therapeutic nanoemulsion.

However, the relative quantities of each component used in a nanoemulsion tested in vitro are applicable to a nanoemulsion to be used therapeutically and, therefore, in vitro quantities can be scaled up to prepare a therapeutic composition, and in vitro data is predictive of topical application success.

1. Aqueous Phase

The aqueous phase can comprise any type of aqueous phase including, but not limited to, water (e.g., $H_2O$, distilled water, tap water) and solutions (e.g., phosphate buffered saline (PBS) solution). In certain embodiments, the aqueous phase comprises water at a pH of about 4 to 10, preferably about 6 to 8. The water can be deionized (hereinafter "Di$H_2O$"). In some embodiments the aqueous phase comprises phosphate buffered saline (PBS). The aqueous phase may further be sterile and pyrogen free.

2. Organic Solvents

Organic solvents in the nanoemulsions of the invention include, but are not limited to, $C_1$-$C_{12}$ alcohol, diol, triol, dialkyl phosphate, tri-alkyl phosphate, such as tri-n-butyl phosphate, semi-synthetic derivatives thereof, and combinations thereof. In one aspect of the invention, the organic solvent is an alcohol chosen from a nonpolar solvent, a polar solvent, a protic solvent, or an aprotic solvent.

Suitable organic solvents for the nanoemulsion include, but are not limited to, ethanol, methanol, isopropyl alcohol, glycerol, medium chain triglycerides, diethyl ether, ethyl acetate, acetone, dimethyl sulfoxide (DMSO), acetic acid, n-butanol, butylene glycol, perfumers alcohols, isopropanol, n-propanol, formic acid, propylene glycols, glycerol, sorbitol, industrial methylated spirit, triacetin, hexane, benzene, toluene, diethyl ether, chloroform, 1,4-dixoane, tetrahydrofuran, dichloromethane, acetone, acetonitrile, dimethylformamide, dimethyl sulfoxide, formic acid, semi-synthetic derivatives thereof, and any combination thereof.

3. Oil Phase

The oil in the nanoemulsion of the invention can be any cosmetically or pharmaceutically acceptable oil. The oil can be volatile or non-volatile, and may be chosen from animal oil, vegetable oil, natural oil, synthetic oil, hydrocarbon oils, silicone oils, semi-synthetic derivatives thereof, and combinations thereof.

Suitable oils include, but are not limited to, mineral oil, squalene oil, flavor oils, silicon oil, essential oils, water insoluble vitamins, Isopropyl stearate, Butyl stearate, Octyl palmitate, Cetyl palmitate, Tridecyl behenate, Diisopropyl adipate, Dioctyl sebacate, Menthyl anthranhilate, Cetyl octanoate, Octyl salicylate, Isopropyl myristate, neopentyl glycol dicarpate cetols, Ceraphyls®, Decyl oleate, diisopropyl adipate, $C_{12-15}$ alkyl lactates, Cetyl lactate, Lauryl lactate, Isostearyl neopentanoate, Myristyl lactate, Isocetyl stearoyl stearate, Octyldodecyl stearoyl stearate, Hydrocarbon oils, Isoparaffin, Fluid paraffins, Isododecane, Petrolatum, Argan oil, Canola oil, Chile oil, Coconut oil, corn oil, Cottonseed oil, Flaxseed oil, Grape seed oil, Mustard oil, Olive oil, Palm oil, Palm kernel oil, Peanut oil, Pine seed oil, Poppy seed oil, Pumpkin seed oil, Rice bran oil, Safflower oil, Tea oil, Truffle oil, Vegetable oil, Apricot (kernel) oil, Jojoba oil (simmondsia chinensis seed oil), Grapeseed oil, Macadamia oil, Wheat germ oil, Almond oil, Rapeseed oil, Gourd oil, Soybean oil, Sesame oil, Hazelnut oil, Maize oil, Sunflower oil, Hemp oil, Bois oil, Kuki nut oil, Avocado oil, Walnut oil, Fish oil, berry oil, allspice oil, juniper oil, seed oil, almond seed oil, anise seed oil, celery seed oil, cumin seed oil, nutmeg seed oil, leaf oil, basil leaf oil, bay leaf oil, cinnamon leaf oil, common sage leaf oil, eucalyptus leaf oil, lemon grass leaf oil, melaleuca leaf oil, oregano leaf oil, patchouli leaf oil, peppermint leaf oil, pine needle oil, rosemary leaf oil, spearmint leaf oil, tea tree leaf oil, thyme leaf oil, wintergreen leaf oil, flower oil, chamomile oil, clary sage oil, clove oil, geranium flower oil, hyssop flower oil, jasmine flower oil, lavender flower oil, manuka flower oil, Marhoram flower oil, orange flower oil, rose flower oil, ylang-ylang flower oil, Bark oil, cassia Bark oil, cinnamon bark oil, sassafras Bark oil, Wood oil, camphor wood oil, cedar wood oil, rosewood oil, sandalwood oil), rhizome (ginger) wood oil, resin oil, frankincense oil, myrrh oil, peel oil, bergamot peel oil, grapefruit peel oil, lemon peel oil, lime peel oil, orange peel oil, tangerine peel oil, root oil, valerian oil, Oleic acid, Linoleic acid, Oleyl alcohol, Isostearyl alcohol, semi-synthetic derivatives thereof, and any combinations thereof.

The oil may further comprise a silicone component, such as a volatile silicone component, which can be the sole oil in the silicone component or can be combined with other silicone and non-silicone, volatile and non-volatile oils. Suitable silicone components include, but are not limited to, methylphenylpolysiloxane, simethicone, dimethicone, phenyltrimethicone (or an organomodified version thereof), alkylated derivatives of polymeric silicones, cetyl dimethicone, lauryl trimethicone, hydroxylated derivatives of polymeric silicones, such as dimethiconol, volatile silicone oils, cyclic and linear silicones, cyclomethicone, derivatives of cyclomethicone, hexamethylcyclotrisiloxane, octamethylcyclotetrasiloxane, decamethylcyclopentasiloxane, volatile linear dimethylpolysiloxanes, isohexadecane, isoeicosane, isotetracosane, polyisobutene, isooctane, isododecane, semi-synthetic derivatives thereof, and combinations thereof.

The volatile oil can be the organic solvent, or the volatile oil can be present in addition to an organic solvent. Suitable volatile oils include, but are not limited to, a terpene, monoterpene, sesquiterpene, carminative, azulene, menthol, camphor, thujone, thymol, nerol, linalool, limonene, geraniol, perillyl alcohol, nerolidol, farnesol, ylangene, bisabolol, farnesene, ascaridole, chenopodium oil, citronellal, citral, citronellol, chamazulene, yarrow, guaiazulene, chamomile, semi-synthetic derivatives, or combinations thereof In one aspect of the invention, the volatile oil in the silicone component is different than the oil in the oil phase.

4. Surfactants/Detergents

The surfactant or detergent in the nanoemulsion of the invention can be a pharmaceutically acceptable ionic surfactant, a pharmaceutically acceptable nonionic surfactant, a pharmaceutically acceptable cationic surfactant, a pharmaceutically acceptable anionic surfactant, or a pharmaceutically acceptable zwitterionic surfactant.

Exemplary useful surfactants are described in Applied Surfactants: Principles and Applications. Tharwat F. Tadros, Copyright 8 2005 WILEY-VCH Verlag GmbH & Co. KGaA, Weinheim ISBN: 3-527-30629-3), which is specifically incorporated by reference.

Further, the surfactant can be a pharmaceutically acceptable ionic polymeric surfactant, a pharmaceutically acceptable nonionic polymeric surfactant, a pharmaceutically acceptable cationic polymeric surfactant, a pharmaceutically acceptable anionic polymeric surfactant, or a pharmaceutically acceptable zwitterionic polymeric surfactant. Examples of polymeric surfactants include, but are not limited to, a graft copolymer of a poly(methyl methacrylate) backbone with multiple (at least one) polyethylene oxide (PEO) side chain, polyhydroxystearic acid, an alkoxylated alkyl phenol formaldehyde condensate, a polyalkylene glycol modified polyester with fatty acid hydrophobes, a polyester, semi-synthetic derivatives thereof, or combinations thereof.

Surface active agents or surfactants, are amphipathic molecules that consist of a nonpolar hydrophobic portion, usually a straight or branched hydrocarbon or fluorocarbon chain containing 8-18 carbon atoms, attached to a polar or ionic hydrophilic portion. The hydrophilic portion can be nonionic, ionic or zwitterionic. The hydrocarbon chain interacts weakly with the water molecules in an aqueous environment, whereas the polar or ionic head group interacts strongly with water molecules via dipole or ion-dipole interactions. Based on the nature of the hydrophilic group, surfactants are classified into anionic, cationic, zwitterionic, nonionic and polymeric surfactants.

Suitable surfactants include, but are not limited to, ethoxylated nonylphenol comprising 9 to 10 units of ethyleneglycol, ethoxylated undecanol comprising 8 units of ethyleneglycol, polyoxyethylene (20) sorbitan monolaurate, polyoxyethylene (20) sorbitan monopalmitate, polyoxyethylene (20) sorbitan monostearate, polyoxyethylene (20) sorbitan monooleate, sorbitan monolaurate, sorbitan monopalmitate, sorbitan monostearate, sorbitan monooleate, ethoxylated hydrogenated ricin oils, sodium laurylsulfate, a diblock copolymer of ethyleneoxyde and propyleneoxyde, Ethylene Oxide-Propylene Oxide Block Copolymers, and tetra-functional block copolymers based on ethylene oxide and propylene oxide, Glyceryl monoesters, Glyceryl caprate, Glyceryl caprylate, Glyceryl cocate, Glyceryl erucate, Glyceryl hydroxysterate, Glyceryl isostearate, Glyceryl lanolate, Glyceryl laurate, Glyceryl linolate, Glyceryl myristate, Glyceryl oleate, Glyceryl PABA, Glyceryl palmitate, Glyceryl ricinoleate, Glyceryl stearate, Glyceryl thiglycolate, Glyceryl dilaurate, Glyceryl dioleate, Glyceryl dimyristate, Glyceryl disterate, Glyceryl sesuioleate, Glyceryl stearate lactate, Polyoxyethylene cetyl/stearyl ether, Polyoxyethylene cholesterol ether, Polyoxyethylene laurate or dilaurate, Polyoxyethylene stearate or distearate, polyoxyethylene fatty ethers, Polyoxyethylene lauryl ether, Polyoxyethylene stearyl ether, polyoxyethylene myristyl ether, a steroid, Cholesterol, Betasitosterol, Bisabolol, fatty acid esters of alcohols, isopropyl myristate, Aliphati-isopropyl n-butyrate, Isopropyl n-hexanoate, Isopropyl n-decanoate, Isoproppyl palmitate, Octyldodecyl myristate, alkoxylated alcohols, alkoxylated acids, alkoxylated amides, alkoxylated sugar derivatives, alkoxylated derivatives of natural oils and waxes, polyoxyethylene polyoxypropylene block copolymers, nonoxynol-14, PEG-8 laurate, PEG-6 Cocoamide, PEG-20 methylglucose sesquistearate, PEG40 lanolin, PEG-40 castor oil, PEG-40 hydrogenated castor oil, polyoxyethylene fatty ethers, glyceryl diesters, polyoxyethylene stearyl ether, polyoxyethylene myristyl ether, and polyoxyethylene lauryl ether, glyceryl dilaurate, glyceryl dimystate, glyceryl distearate, semi-synthetic derivatives thereof, or mixtures thereof.

Additional suitable surfactants include, but are not limited to, non-ionic lipids, such as glyceryl laurate, glyceryl myristate, glyceryl dilaurate, glyceryl dimyristate, semi-synthetic derivatives thereof, and mixtures thereof.

In additional embodiments, the surfactant is a polyoxyethylene fatty ether having a polyoxyethylene head group ranging from about 2 to about 100 groups, or an alkoxylated alcohol having the structure $R_5$—$(OCH_2\ CH_2)_y$—OH, wherein $R_5$ is a branched or unbranched alkyl group having from about 6 to about 22 carbon atoms and y is between about 4 and about 100, and preferably, between about 10 and about 100. Preferably, the alkoxylated alcohol is the species wherein $R_5$ is a lauryl group and y has an average value of 23.

In a different embodiment, the surfactant is an alkoxylated alcohol which is an ethoxylated derivative of lanolin alcohol. Preferably, the ethoxylated derivative of lanolin alcohol is laneth-10, which is the polyethylene glycol ether of lanolin alcohol with an average ethoxylation value of 10.

Nonionic surfactants include, but are not limited to, an ethoxylated surfactant, an alcohol ethoxylated, an alkyl phenol ethoxylated, a fatty acid ethoxylated, a monoalkaolamide ethoxylated, a sorbitan ester ethoxylated, a fatty amino ethoxylated, an ethylene oxide-propylene oxide copolymer, Bis(polyethylene glycol bis[imidazoyl carbonyl]), nonoxynol-9, Bis(polyethylene glycol bis[imidazoyl carbonyl]), Brij® 35, Brij® 56, Brij® 72, Brij® 76, Brij® 92V, Brij® 97, Brij® 58P, Cremophor® EL, Decaethylene glycol monododecyl ether, N-Decanoyl-N-methylglucamine, n-Decyl alpha-D-glucopyranoside, Decyl beta-D-maltopyranoside, n-Dodecanoyl-N-methylglucamide, n-Dodecyl alpha-D-maltoside, n-Dodecyl beta-D-maltoside, n-Dodecyl beta-D-maltoside, Heptaethylene glycol monodecyl ether, Heptaethylene glycol monododecyl ether, Heptaethylene glycol monotetradecyl ether, n-Hexadecyl beta-D-maltoside, Hexaethylene glycol monododecyl ether, Hexaethylene glycol monohexadecyl ether, Hexaethylene glycol monooctadecyl ether, Hexaethylene glycol monotetradecyl ether, Igepal CA-630, Igepal CA-630, Methyl-6-O-(N-heptylcarbamoyl)-alpha-D-glucopyranoside, Nonaethylene glycol monododecyl ether, N—N-Nonanoyl-N-methylglucamine, Octaethylene glycol monodecyl ether, Octaethylene glycol monododecyl ether, Octaethylene glycol monohexadecyl ether, Octaethylene glycol monooctadecyl ether, Octaethylene glycol monotetradecyl ether, Octyl-beta-D-glucopyranoside, Pentaethylene glycol monodecyl ether, Pentaethylene glycol monododecyl ether, Pentaethylene glycol monohexadecyl ether, Pentaethylene glycol monohexyl ether, Pentaethylene glycol monooctadecyl ether, Pentaethylene glycol monooctyl ether, Polyethylene glycol diglycidyl ether, Polyethylene glycol ether W-1, Polyoxyethylene 10 tridecyl ether, Polyoxyethylene 100 stearate, Polyoxyethylene 20 isohexadecyl ether, Polyoxyethylene 20 oleyl ether, Polyoxyethylene 40 stearate, Polyoxyethylene 50 stearate, Polyoxyethylene 8 stearate, Polyoxyethylene bis(imidazolyl carbonyl), Polyoxyethylene 25 propylene glycol stearate, Saponin from Quillaja bark, Span® 20, Span® 40, Span® 60, Span® 65, Span® 80, Span® 85, Tergitol, Type 15-S-12, Tergitol, Type 15-S-30, Tergitol, Type 15-S-5, Tergitol, Type 15-S-7, Tergitol, Type 15-S-9, Tergitol, Type NP-10, Tergitol, Type NP-4, Tergitol, Type NP-40, Tergitol, Type NP-7, Tergitol, Type NP-9, Tergitol, Tergitol, Type TMN-10, Tergitol, Type TMN-6, Tetradecyl-beta-D-maltoside, Tetraethylene glycol monodecyl ether, Tetraethylene glycol monododecyl ether, Tetraethylene glycol monotetradecyl ether, Triethylene glycol monodecyl ether, Triethylene glycol monododecyl ether, Triethylene glycol monohexadecyl ether, Triethylene glycol monooctyl ether, Triethylene glycol monotetradecyl ether, Triton CF-21, Triton CF-32, Triton DF-12, Triton DF-16, Triton GR-5M, Triton QS-15, Triton QS-44, Triton X-100, Triton X-102, Triton X-15, Triton X-151, Triton X-200, Triton X-207, Triton® X-114, Triton® X-165, Triton® X-305, Triton® X-405, Triton® X-45, Triton® X-705-70, TWEEN® 20, TWEEN® 21, TWEEN® 40, TWEEN® 60, TWEEN® 61, TWEEN® 65, TWEEN® 80, TWEEN® 81, TWEEN® 85, Tyloxapol, n-Undecyl beta-D-glucopyranoside, semi-synthetic derivatives thereof, or combinations thereof.

In addition, the nonionic surfactant can be a poloxamer. Poloxamers are polymers made of a block of polyoxyethylene, followed by a block of polyoxypropylene, followed by a block of polyoxyethylene. The average number of units of polyoxyethylene and polyoxypropylene varies based on the number associated with the polymer. For example, the smallest polymer, Poloxamer 101, consists of a block with an average of 2 units of polyoxyethylene, a block with an average of 16 units of polyoxypropylene, followed by a block with an average of 2 units of polyoxyethylene. Poloxamers range from colorless liquids and pastes to white solids. In cosmetics and personal care products, Poloxamers are used in the formulation of skin cleansers, bath products, shampoos, hair conditioners, mouthwashes, eye makeup remover and other skin and hair products. Examples of Poloxamers include, but are not limited to, Poloxamer 101, Poloxamer 105, Poloxamer 108, Poloxamer 122, Poloxamer 123, Poloxamer 124, Poloxamer 181, Poloxamer 182, Poloxamer 183, Poloxamer 184, Poloxamer 185, Poloxamer 188, Poloxamer 212, Poloxamer 215, Poloxamer 217, Poloxamer 231, Poloxamer 234, Poloxamer 235, Poloxamer 237, Poloxamer 238, Poloxamer 282, Poloxamer 284, Poloxamer 288, Poloxamer 331, Poloxamer 333, Poloxamer 334, Poloxamer 335, Poloxamer 338, Poloxamer 401, Poloxamer 402, Poloxamer 403, Poloxamer 407, Poloxamer 105 Benzoate, and Poloxamer 182 Dibenzoate.

Suitable cationic surfactants include, but are not limited to, a quarternary ammonium compound, an alkyl trimethyl ammonium chloride compound, a dialkyl dimethyl ammonium chloride compound, a cationic halogen-containing compound, such as cetylpyridinium chloride, Benzalkonium chloride, Benzalkonium chloride, Benzyldimethylhexadecylammonium chloride, Benzyldimethyltetradecylammonium chloride, Benzyldodecyldimethylammonium bromide, Benzyltrimethylammonium tetrachloroiodate, Dimethyldioctadecylammonium bromide, Dodecylethyldimethylammonium bromide, Dodecyltrimethylammonium bromide, Dodecyltrimethylammonium bromide, Ethylhexadecyldimethylammonium bromide, Girard's reagent T, Hexadecyltrimethylammonium bromide, Hexadecyltrimethylammonium bromide, N,N',N'-Polyoxyethylene(10)-N-tallow-1,3-diaminopropane, Thonzonium bromide, Trimethyl(tetradecyl)ammonium bromide, 1,3,5-Triazine-1,3,5(2H,4H,6H)-triethanol, 1-Decanaminium, N-decyl-N, N-dimethyl-, chloride, Didecyl dimethyl ammonium chloride, 2-(2-(p-(Diisobutyl)cresosxy)ethoxy)ethyl dimethyl benzyl ammonium chloride, 2-(2-(p-(Diisobutyl)phenoxy)ethoxy)ethyl dimethyl benzyl ammonium chloride, Alkyl 1 or 3 benzyl-1-(2-hydroxethyl)-2-imidazolinium chloride, Alkyl bis(2-hydroxyethyl) benzyl ammonium chloride, Alkyl demethyl benzyl ammonium chloride, Alkyl dimethyl 3,4-dichlorobenzyl ammonium chloride (100% C12), Alkyl dimethyl 3,4-dichlorobenzyl ammonium chloride (50% C14, 40% C12, 10% C16), Alkyl dimethyl 3,4-dichlorobenzyl ammonium chloride (55% C14, 23% C12, 20% C16), Alkyl dimethyl benzyl ammonium chloride, Alkyl dimethyl benzyl ammonium chloride (100% C14), Alkyl dimethyl benzyl ammonium chloride (100% C16), Alkyl dimethyl benzyl ammonium chloride (41% C14, 28% C12), Alkyl dimethyl benzyl ammonium chloride (47% C12, 18% C14), Alkyl dimethyl benzyl ammonium chloride (55% C16, 20% C14), Alkyl dimethyl benzyl ammonium chloride (58% C14, 28% C16), Alkyl dimethyl benzyl ammonium chloride (60% C14, 25% C12), Alkyl dimethyl benzyl ammonium chloride (61% C11, 23% C14), Alkyl dimethyl benzyl ammonium chloride (61% C12, 23% C14), Alkyl dimethyl benzyl ammonium chloride (65% C12, 25% C14), Alkyl dimethyl benzyl ammonium chloride (67% C12, 24% C14), Alkyl dimethyl benzyl ammonium chloride (67% C12, 25% C14), Alkyl dimethyl benzyl ammonium chloride (90% C14, 5% C12), Alkyl dimethyl benzyl ammonium chloride (93% C14, 4% C12), Alkyl dimethyl benzyl ammonium chloride (95% C16, 5% C18), Alkyl didecyl dimethyl ammonium chloride, Alkyl dimethyl benzyl ammonium chloride (C12-16), Alkyl dimethyl benzyl ammonium chloride (C12-18), dialkyl dimethyl benzyl ammonium chloride, Alkyl dimethyl dimethybenzyl ammonium chloride, Alkyl dimethyl ethyl ammonium bromide (90% C14, 5% C16, 5% C12), Alkyl dimethyl ethyl ammonium bromide (mixed alkyl and alkenyl groups as in the fatty acids of soybean oil), Alkyl dimethyl ethylbenzyl ammonium chloride, Alkyl dimethyl ethylbenzyl ammonium chloride (60% C14), Alkyl dimethyl isopropylbenzyl ammonium chloride (50% C12, 30% C14, 17% C16, 3% C18), Alkyl trimethyl ammonium chloride (58% C18, 40% C16, 1% C14, 1% C12), Alkyl trimethyl ammonium chloride (90% C18, 10% C16), Alkyldimethyl(ethylbenzyl) ammonium chloride (C12-18), Di-(C8-10)-alkyl dimethyl ammonium chlorides, Dialkyl dimethyl ammonium chloride, Dialkyl methyl benzyl ammonium chloride, Didecyl dimethyl ammonium chloride, Diisodecyl dimethyl ammonium chloride, Dioctyl dimethyl ammonium chloride, Dodecyl bis (2-hydroxyethyl) octyl hydrogen ammonium chloride, Dodecyl dimethyl benzyl ammonium chloride, Dodecylcarbamoyl methyl dinethyl benzyl ammonium chloride, Heptadecyl hydroxyethylimidazolinium chloride, Hexahydro-1,3,5-tris (2-hydroxyethyl)-s-triazine, Myristalkonium chloride (and) Quat RNIUM 14, N,N-Dimethyl-2-hydroxypropylammonium chloride polymer, n-Tetradecyl dimethyl benzyl ammonium chloride monohydrate, Octyl decyl dimethyl ammonium chloride, Octyl dodecyl dimethyl ammonium chloride, Octyphenoxyethoxyethyl dimethyl benzyl ammonium chloride, Oxydiethylenebis(alkyl dimethyl ammonium chloride), Trimethoxysily propyl dimethyl octadecyl ammonium chloride, Trimethoxysilyl quats, Trimethyl dodecylbenzyl ammonium chloride, semi-synthetic derivatives thereof, and combinations thereof.

Exemplary cationic halogen-containing compounds include, but are not limited to, cetylpyridinium halides, cetyltrimethylammonium halides, cetyldimethylethylammonium halides, cetyldimethylbenzylammonium halides, cetyltributylphosphonium halides, dodecyltrimethylammonium halides, or tetradecyltrimethylammonium halides. In some particular embodiments, suitable cationic halogen containing compounds comprise, but are not limited to, cetylpyridinium chloride (CPC), cetyltrimethylammonium chloride, cetylbenzyldimethylammonium chloride, cetylpyridinium bromide (CPB), cetyltrimethylammonium bromide (CTAB), cetyidimethylethylammonium bromide, cetyltributylphosphonium bromide, dodecyltrimethylammonium bromide, and tetrad ecyltrimethylammonium bromide. In particularly preferred embodiments, the cationic halogen containing compound is CPC, although the compositions of the present invention are not limited to formulation with a particular cationic containing compound.

Suitable anionic surfactants include, but are not limited to, a carboxylate, a sulphate, a sulphonate, a phosphate, chenodeoxycholic acid, chenodeoxycholic acid sodium salt, cholic acid, ox or sheep bile, Dehydrocholic acid, Deoxycholic acid, Deoxycholic acid, Deoxycholic acid methyl ester, Digitonin, Digitoxigenin, N,N-Dimethyldodecylamine N-oxide, Docusate sodium salt, Glycochenodeoxycholic acid sodium salt, Glycocholic acid hydrate, synthetic, Glycocholic acid sodium salt hydrate, synthetic, Glycodeoxycholic acid monohydrate, Glycodeoxycholic acid sodium salt, Glycolithocholic acid 3-sulfate disodium salt, Glycolithocholic acid ethyl ester, N-Lauroylsarcosine sodium salt, N-Lauroylsarcosine solution, N-Lauroylsarcosine solution, Lithium dodecyl sulfate, Lithium dodecyl sulfate, Lithium dodecyl sulfate, Lugol solution, Niaproof 4, Type 4, 1-Octanesulfonic acid sodium salt, Sodium 1-butanesulfonate, Sodium 1-decanesulfonate, Sodium 1-decanesulfonate, Sodium 1-dodecanesulfonate, Sodium 1-heptanesulfonate anhydrous, Sodium 1-heptanesulfonate anhydrous, Sodium 1-nonanesulfonate, Sodium 1-propanesulfonate monohydrate, Sodium 2-bromoethanesulfonate, Sodium cholate hydrate, Sodium choleate, Sodium deoxycholate, Sodium deoxycholate monohydrate, Sodium dodecyl sulfate, Sodium hexanesulfonate anhydrous, Sodium octyl sulfate, Sodium pentanesulfonate anhydrous, Sodium taurocholate, Taurochenodeoxycholic acid sodium salt, Taurodeoxycholic acid sodium salt monohydrate, Taurohyodeoxycholic acid sodium salt hydrate, Taurolithocholic acid 3-sulfate disodium salt, Tauroursodeoxycholic acid sodium salt, Trizma® dodecyl sulfate, TWEEN® 80, Ursodeoxycholic acid, semi-synthetic derivatives thereof, and combinations thereof.

Suitable zwitterionic surfactants include, but are not limited to, an N-alkyl betaine, lauryl amindo propyl dimethyl betaine, an alkyl dimethyl glycinate, an N-alkyl amino propionate, CHAPS, minimum 98% (TLC), CHAPS, SigmaUltra, minimum 98% (TLC), CHAPS, for electrophoresis, minimum 98% (TLC), CHAPSO, minimum 98%, CHAPSO, SigmaUltra, CHAPSO, for electrophoresis, 3-(Decyldimethylammonio)propanesulfonate inner salt, 3-Dodecyldimethylammonio)propanesulfonate inner salt, SigmaUltra, 3-(Dodecyldimethylammonio)propanesulfonate inner salt, 3-(N,N-Dimethylmyristylammonio)propanesulfonate, 3-(N,N-Dimethyloctadecylammonio)propanesulfonate, 3-(N,N-Dimethyloctylammonio)propanesulfonate inner salt, 3-(N,N-Dimethylpalmitylammonio)propanesulfonate, semi-synthetic derivatives thereof, and combinations thereof.

In some embodiments, the nanoemulsion comprises a cationic surfactant, which can be cetylpyridinium chloride. In other embodiments of the invention, the nanoemulsion comprises a cationic surfactant, and the concentration of the cationic surfactant is less than about 5.0% and greater than about 0.001%. In yet another embodiment of the invention, the nanoemulsion comprises a cationic surfactant, and the concentration of the cationic surfactant is selected from the group consisting of less than about 5%, less than about 4.5%, less than about 4.0%, less than about 3.5%, less than about 3.0%, less than about 2.5%, less than about 2.0%, less than about 1.5%, less than about 1.0%, less than about 0.90%, less than about 0.80%, less than about 0.70%, less than about 0.60%, less than about 0.50%, less than about 0.40%, less than about 0.30%, less than about 0.20%, or less than about 0.10%. Further, the concentration of the cationic agent in the nanoemulsion is greater than about 0.002%, greater than about 0.003%, greater than about 0.004%, greater than about 0.005%, greater than about 0.006%, greater than about 0.007%, greater than about 0.008%, greater than about 0.009%, greater than about 0.010%, or greater than about 0.001%. In one embodiment, the concentration of the cationic agent in the nanoemulsion is less than about 5.0% and greater than about 0.001%.

In another embodiment of the invention, the nanoemulsion comprises at least one cationic surfactant and at least one non-cationic surfactant. The non-cationic surfactant is a nonionic surfactant, such as a polysorbate (Tween), such as polysorbate 80 or polysorbate 20. In one embodiment, the non-ionic surfactant is present in a concentration of about 0.05% to about 7.0%, or the non-ionic surfactant is present in a concentration of about 0.5% to about 4%. In yet another embodiment of the invention, the nanoemulsion comprises a cationic surfactant present in a concentration of about 0.01% to about 2%, in combination with a nonionic surfactant.

5. Additional Ingredients

Additional compounds suitable for use in the nanoemulsions of the invention include but are not limited to one or more solvents, such as an organic phosphate-based solvent, bulking agents, coloring agents, pharmaceutically acceptable excipients, a preservative, pH adjuster, buffer, chelating agent, etc. The additional compounds can be admixed into a previously emulsified nanoemulsion, or the additional compounds can be added to the original mixture to be emulsified. In certain of these embodiments, one or more additional compounds are admixed into an existing nanoemulsion composition immediately prior to its use.

Suitable preservatives in the nanoemulsions of the invention include, but are not limited to, cetylpyridinium chloride, benzalkonium chloride, benzyl alcohol, chlorhexidine, imidazolidinyl urea, phenol, potassium sorbate, benzoic acid, bronopol, chlorocresol, paraben esters, phenoxyethanol, sorbic acid, alpha-tocophernol, ascorbic acid, ascorbyl palmitate, butylated hydroxyanisole, butylated hydroxytoluene, sodium ascorbate, sodium metabisulphite, citric acid, edetic acid, semi-synthetic derivatives thereof, and combinations thereof. Other suitable preservatives include, but are not limited to, benzyl alcohol, chlorhexidine (bis (p-chlorophenyldiguanido) hexane), chlorphenesin (3-(-4-chloropheoxy)-propane-1,2-diol), Kathon CG (methyl and methylchloroisothiazolinone), parabens (methyl, ethyl, propyl, butyl hydrobenzoates), phenoxyethanol (2-phenoxyethanol), sorbic acid (potassium sorbate, sorbic acid), Phenonip (phenoxyethanol, methyl, ethyl, butyl, propyl parabens), Phenoroc (phenoxyethanol 0.73%, methyl paraben 0.2%, propyl paraben 0.07%), Liquipar Oil (isopropyl, isobutyl, butylparabens), Liquipar PE (70% phenoxyethanol, 30% liquipar oil), Nipaguard MPA (benzyl alcohol (70%), methyl & propyl parabens), Nipaguard MPS (propylene glycol, methyl & propyl parabens), Nipasept (methyl, ethyl and propyl parabens), Nipastat (methyl, butyl, ethyl and propyel parabens), Elestab 388 (phenoxyethanol in propylene glycol plus chlorphenesin and methylparaben), and Killitol (7.5% chlorphenesin and 7.5% methyl parabens).

The nanoemulsion may further comprise at least one pH adjuster. Suitable pH adjusters in the nanoemulsion of the invention include, but are not limited to, diethyanolamine, lactic acid, monoethanolamine, triethylanolamine, sodium hydroxide, sodium phosphate, semi-synthetic derivatives thereof, and combinations thereof.

In addition, the nanoemulsion can comprise a chelating agent. In one embodiment of the invention, the chelating agent is present in an amount of about 0.0005% to about 1.0%. Examples of chelating agents include, but are not limited to, phytic acid, polyphosphoric acid, citric acid, gluconic acid, acetic acid, lactic acid, ethylenediamine, ethylenediaminetetraacetic acid (EDTA), and dimercaprol, and a preferred chelating agent is ethylenediaminetetraacetic acid.

The nanoemulsion can comprise a buffering agent, such as a pharmaceutically acceptable buffering agent. Examples of buffering agents include, but are not limited to, 2-Amino-2-methyl-1,3-propanediol, ≥99.5% (NT), 2-Amino-2-methyl-1-propanol, ≥99.0% (GC), L-(+)-Tartaric acid, ≥99.5% (T), ACES, ≥99.5% (T), ADA, ≥99.0% (T), Acetic acid, ≥99.5% (GC/T), Acetic acid, for luminescence, ≥99.5% (GC/T), Ammonium acetate solution, for molecular biology, ~5 M in $H_2O$, Ammonium acetate, for luminescence, ≥99.0% (calc. on dry substance, T), Ammonium bicarbonate, ≥99.5% (T), Ammonium citrate dibasic, ≥99.0% (T), Ammonium formate solution, 10 M in $H_2O$, Ammonium formate, ≥99.0% (calc. based on dry substance, NT), Ammonium oxalate monohydrate, ≥99.5% (RT), Ammonium phosphate dibasic solution, 2.5 M in $H_2O$, Ammonium phosphate dibasic, ≥99.0% (T), Ammonium phosphate monobasic solution, 2.5 M in $H_2O$, Ammonium phosphate monobasic, ≥99.5% (T), Ammonium sodium phosphate dibasic tetrahydrate, ≥99.5% (NT), Ammonium sulfate solution, for molecular biology, 3.2 M in $H_2O$, Ammonium tartrate dibasic solution, 2 M in $H_2O$ (colorless solution at 20° C.), Ammonium tartrate dibasic, ≥99.5% (T), BES buffered saline, for molecular biology, 2× concentrate, BES, ≥99.5% (T), BES, for molecular biology, ≥99.5% (T), BICINE buffer Solution, for molecular biology, 1 M in $H_2O$, BICINE, ≥99.5% (T), BIS-TRIS, ≥99.0% (NT), Bicarbonate buffer solution, ≥0.1 M $Na_2CO_3$, ≥0.2 M $NaHCO_3$, Boric acid, ≥99.5% (T), Boric acid, for molecular biology, ≥99.5% (T), CAPS, ≥99.0% (TLC), CHES, ≥99.5% (T), Calcium acetate hydrate, ≥99.0% (calc. on dried material, KT), Calcium carbonate, precipitated, ≥99.0% (KT), Calcium citrate tribasic tetrahydrate, ≥98.0% (calc. on dry substance, KT), Citrate Concentrated Solution, for molecular biology, 1 M in $H_2O$, Citric acid, anhydrous, ≥99.5% (T), Citric acid, for luminescence, anhydrous, ≥99.5% (T), Diethanolamine, ≥99.5% (GC), EPPS, ≥99.0% (T), Ethylenediaminetetraacetic acid disodium salt dihydrate, for molecular biology, ≥99.0% (T), Formic acid solution, 1.0 M in $H_2O$, Gly-Gly-Gly, ≥99.0% (NT), Gly-Gly, ≥99.5% (NT), Glycine, ≥99.0% (NT), Glycine, for luminescence, ≥99.0% (NT), Glycine, for molecular biology, ≥99.0% (NT), HEPES buffered saline, for molecular biology, 2× concentrate, HEPES, ≥99.5% (T), HEPES, for molecular biology, ≥99.5% (T), Imidazole buffer Solution, 1 M in $H_2O$, Imidazole, ≥99.5% (GC), Imidazole, for luminescence, ≥99.5% (GC), Imidazole, for molecular biology, ≥99.5% (GC), Lipoprotein Refolding Buffer, Lithium acetate dihydrate, ≥99.0% (NT), Lithium citrate tribasic tetrahydrate, ≥99.5% (NT), MES hydrate, ≥99.5% (T), MES monohydrate, for luminescence, ≥99.5% (T), MES solution, for molecular biology, 0.5 M in $H_2O$, MOPS, ≥99.5% (T), MOPS, for luminescence, ≥99.5% (T), MOPS, for molecular biology, ≥99.5% (T), Magnesium acetate solution, for molecular biology, ~1 M in $H_2O$, Magnesium acetate tetrahydrate, ≥99.0% (KT), Magnesium citrate tribasic nonahydrate, ≥98.0% (calc. based on dry substance, KT), Magnesium formate solution, 0.5 M in $H_2O$, Magnesium phosphate dibasic trihydrate, ≥98.0% (KT), Neutralization solution for the in-situ hybridization for in-situ hybridization, for molecular biology, Oxalic acid dihydrate, ≥99.5% (RT), PIPES, ≥99.5% (T), PIPES, for molecular biology, ≥99.5% (T), Phosphate buffered saline, solution (autoclaved), Phosphate buffered saline, washing buffer for peroxidase conjugates in Western Blotting, 10× concentrate, Piperazine, anhydrous, ≥99.0% (T), Potassium D-tartrate monobasic, ≥99.0% (T), Potassium acetate solution, for molecular biology, Potassium acetate solution, for molecular biology, 5 M in $H_2O$, Potassium acetate solution, for molecular biology, ~1 M in $H_2O$, Potassium acetate, ≥99.0% (NT), Potassium acetate, for luminescence, ≥99.0% (NT), Potassium acetate, for molecular biology, ≥99.0% (NT), Potassium bicarbonate, ≥99.5% (T), Potassium carbonate, anhydrous, ≥99.0% (T), Potassium chloride, ≥99.5% (AT), Potassium citrate monobasic, ≥99.0% (dried material, NT), Potassium citrate tribasic solution, 1 M in $H_2O$, Potassium formate solution, 14 M in $H_2O$, Potassium formate, ≥99.5% (NT), Potassium oxalate monohydrate, ≥99.0% (RT), Potassium phosphate dibasic, anhydrous, ≥99.0% (T), Potassium phosphate dibasic, for luminescence, anhydrous, ≥99.0% (T), Potassium phosphate dibasic, for molecular biology, anhydrous, ≥99.0% (T), Potassium phosphate monobasic, anhydrous, ≥99.5% (T), Potassium phosphate monobasic, for molecular biology, anhydrous, ≥99.5% (T), Potassium phosphate tribasic monohydrate, ≥95% (T), Potassium phthalate monobasic, ≥99.5% (T), Potassium sodium tartrate solution, 1.5 M in $H_2O$, Potassium sodium tartrate tetrahydrate, ≥99.5% (NT), Potassium tetraborate tetrahydrate, ≥99.0% (T), Potassium tetraoxalate dihydrate, ≥99.5% (RT), Propionic acid solution, 1.0 M in $H_2O$, STE buffer solution, for molecular biology, pH 7.8, STET buffer solution, for molecular biology, pH 8.0, Sodium 5,5-diethylbarbiturate, ≥99.5% (NT), Sodium acetate solution, for molecular biology, ~3 M in $H_2O$, Sodium acetate trihydrate, ≥99.5% (NT), Sodium acetate, anhydrous, ≥99.0% (NT), Sodium acetate, for luminescence, anhydrous, ≥99.0% (NT), Sodium acetate, for molecular biology, anhydrous, ≥99.0% (NT), Sodium bicarbonate, ≥99.5% (T), Sodium bitartrate monohydrate, ≥99.0% (T), Sodium carbonate decahydrate, ≥99.5% (T), Sodium carbonate, anhydrous, ≥99.5% (calc. on dry substance, T), Sodium citrate monobasic, anhydrous, ≥99.5% (T), Sodium citrate tribasic dihydrate, ≥99.0% (NT), Sodium citrate tribasic dihydrate, for luminescence, ≥99.0% (NT), Sodium citrate tribasic dihydrate, for molecular biology, ≥99.5% (NT), Sodium formate solution, 8 M in $H_2O$, Sodium oxalate, ≥99.5% (RT), Sodium phosphate dibasic dihydrate, ≥99.0% (T), Sodium phosphate dibasic dihydrate, for luminescence, ≥99.0% (T), Sodium phosphate dibasic dihydrate, for molecular biology, ≥99.0% (T), Sodium phosphate dibasic dodecahydrate, ≥99.0% (T), Sodium phosphate dibasic solution, 0.5 M in $H_2O$, Sodium phosphate dibasic, anhydrous, ≥99.5% (T), Sodium phosphate dibasic, for molecular biology, ≥99.5% (T), Sodium phosphate monobasic dihydrate, ≥99.0% (T), Sodium phosphate monobasic dihydrate, for molecular biology, ≥99.0% (T), Sodium phosphate monobasic monohydrate, for molecular biology, ≥99.5% (T), Sodium phosphate monobasic solution, 5 M in $H_2O$, Sodium pyrophosphate dibasic, ≥99.0% (T), Sodium pyrophosphate tetrabasic decahydrate, ≥99.5% (T), Sodium tartrate dibasic dihydrate, ≥99.0% (NT), Sodium tartrate dibasic solution, 1.5 M in $H_2O$ (colorless solution at 20° C.), Sodium tetraborate decahydrate, ≥99.5% (T), TAPS, ≥99.5% (T), TES, ≥99.5% (calc. based on dry substance, T), TM buffer solution, for molecular biology, pH 7.4, TNT buffer solution, for molecular biology, pH 8.0, TRIS Glycine buffer solution, 10× concentrate, TRIS acetate—EDTA buffer solution, for molecular biology, TRIS buffered saline, 10× concentrate, TRIS glycine SDS buffer solution, for electrophoresis, 10× concentrate, TRIS phosphate—EDTA buffer solution, for molecular biology, concentrate, 1 Ox concentrate, Tricine, ≥99.5% (NT), Triethanolamine, ≥99.5% (GC), Triethylamine, ≥99.5% (GC), Triethylammonium acetate buffer, volatile buffer, ~1.0 M in $H_2O$, Triethylammonium phosphate solution, volatile buffer, ~1.0 M in $H_2O$, Trimethylammonium acetate solution, volatile buffer, ~1.0 M in $H_2O$, Trimethylammonium phosphate solution, volatile buffer, ~1 M in $H_2O$, Tris-EDTA buffer solution, for molecular biology, concentrate, 100× concentrate, Tris-EDTA buffer solution, for molecular biology, pH 7.4, Tris-EDTA buffer solution, for molecular biology, pH 8.0, Trizma® acetate, ≥99.0% (NT), Trizma® base, ≥99.8% (T), Trizma® base, ≥99.8% (T), Trizma® base, for luminescence, ≥99.8% (T), Trizma® base, for molecular biology, ≥99.8% (T), Trizma® carbonate, ≥98.5% (T), Trizma® hydrochloride buffer solution, for molecular biology, pH 7.2, Trizma® hydrochloride buffer solution, for molecular biology, pH 7.4, Trizma® hydrochloride buffer solution, for molecular biology, pH 7.6, Trizma® hydrochloride buffer solution, for molecular biology, pH 8.0, Trizma® hydrochloride, ≥99.0% (AT), Trizma® hydrochloride, for luminescence, ≥99.0% (AT), Trizma® hydrochloride, for molecular biology, ≥99.0% (AT), and Trizma® maleate, ≥99.5% (NT).

The nanoemulsion can comprise one or more emulsifying agents to aid in the formation of emulsions. Emulsifying agents include compounds that aggregate at the oil/water interface to form a kind of continuous membrane that prevents direct contact between two adjacent droplets. Certain embodiments of the present invention feature nanoemulsions that may readily be diluted with water to a desired concentration without impairing their antiviral properties.

6. Active Agents Incorporated into a Nanoemulsion of the Invention

In a further embodiment of the invention, a nanoemulsion comprises an additional active agent, such as an antibiotic or a palliative agent (such as for burn wound treatment). Addition of another agent may enhance the therapeutic effectiveness of the nanoemulsion. The nanoemulsion in and of itself has anti-bacterial activity and does not need to be combined with another active agent to obtain therapeutic effectiveness. Any antibacterial (or antibiotic) agent suitable for treating a bacterial infection can be incorporated into the topical nanoemulsions of the invention.

Examples of such antibiotic agents include, but are not limited to, aminoglycosides, Ansamycins, Carbacephems, Carbapenems, Cephalosporins, Glycopeptides, Macrolides, Monobactams, Penicillins, Polypeptides, Polymyxin, Quinolones, Sulfonamides, Tetracyclines, and others (e.g., Arsphenamine, Chloramphenicol, Clindamycin, Lincomycin, Ethambutol, Fosfomycin, Fusidic acid, Furazolidone, Isoniazid, Linezolid, Metronidazole, Mupirocin, Nitrofurantoin, Platensimycin, Pyrazinamide, Quinupristin/Dalfopristin, Rifampicin (Rifampin in US), Thiamphenicol, Tinidazole, Dapsone, and lofazimine).

Examples of these classes of antibiotics include, but are not limited to, Amikacin, Gentamicin, Kanamycin, Neomycin, Netilmicin, Streptomycin, Tobramycin, Paromomycin, Geldanamycin, Herbimycin, Loracarbef, Ertapenem, Doripenem, Imipenem/Cilastatin, Meropenem, Cefadroxil, Cefazolin, Cefalotin or Cefalothin, Cefalexin, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefepime, Ceftobiprole, Teicoplanin, Vancomycin, Azithromycin, Clarithromycin, Dirithromycin, Erythromycin, Roxithromycin, Troleandomycin, Telithromycin, Spectinomycin, Aztreonam, Amoxicillin, Ampicillin, Azlocillin, Carbenicillin, Cloxacillin, Dicloxacillin, Flucloxacillin, Mezlocillin, Meticillin, Nafcillin, Oxacillin, Penicillin, Piperacillin, Ticarcillin, Bacitracin, Colistin, Polymyxin B, Ciprofloxacin, Enoxacin, Gatifloxacin, Levofloxacin, Lomefloxacin, Moxifloxacin, Norfloxacin, Ofloxacin, Trovafloxacin, Grepafloxacin, Sparfloxacin, Temafloxacin, Mafenide, Sulfonamidochrysoidine (archaic), Sulfacetamide, Sulfadiazine, Sulfamethizole, Sulfanilimide (archaic), Sulfasalazine, Sulfisoxazole, Trimethoprim, rimethoprim-Sulfamethoxazole (Co-trimoxazole) (TMP-SMX), Demeclocycline, Doxycycline, Minocycline, Oxytetracycline, and Tetracycline.

Examples of palliative agents which may be incorporated into the nanoemulsions of the invention include, but are not limited to, menthol, camphor, phenol, allantoin, benzocaine, corticosteroids, phenol, zinc oxide, camphor, pramoxine, dimethicone, meradimate, octinoxate, octisalate, oxybenzone, dyclonine, alcohols (e.g., benzyl alcohol), mineral oil, propylene glycol, titanium dioxide, silver nitrate ($AgNO_3$), silver sulfadiazine, mafenide acetate, nanocrystalline impregnated silver dressings, a p38 MAPK inhibitor, and magnesium stearate.

D. Pharmaceutical Compositions

The nanoemulsions of the invention may be formulated into pharmaceutical compositions that comprise the nanoemulsion in a therapeutically effective amount and suitable, pharmaceutically-acceptable excipients for administration to a human subject in need thereof using any conventional pharmaceutical method of administration. Such excipients are well known in the art.

By the phrase "therapeutically effective amount" it is meant any amount of the nanoemulsion that is effective in treating microorganisms by killing or inhibiting the growth of the microorganisms, causing the microorganisms to lose pathogenicity, or any combination thereof.

Exemplary dosage forms may include, but are not limited to, patches, ointments, creams, emulsions, liquids, lotions, gels, bioadhesive gels, aerosols, pastes, foams, sunscreens, capsules, microcapsules, or in the form of an article or carrier, such as a bandage, insert, syringe-like applicator, pessary, powder, and talc or other solid.

The pharmaceutical compositions may be formulated for immediate release, sustained release, controlled release, delayed release, or any combinations thereof. In some embodiments, the formulations may comprise a penetration-enhancing agent for enhancing penetration of the nanoemulsion through the stratum corneum and into the epidermis or dermis (i.e., for methods of treating burn wounds). Suitable penetration-enhancing agents include, but are not limited to, alcohols such as ethanol, triglycerides and aloe compositions. The amount of the penetration-enhancing agent may comprise from about 0.5% to about 40% by weight of the formulation.

When appropriate, for example when treating burn wounds, the nanoemulsions of the invention can be applied and/or delivered utilizing electrophoretic delivery/electrophoresis. Such transdermal methods, which comprise applying an electrical current, are well known in the art.

In another embodiment of the invention, minimal systemic absorption of the nanoemulsion occurs upon topical administration. Such minimal systemic exposure can be determined by the detection of less than 10 ng/mL, less than 8 ng/mL, less than 5 ng/mL, less than 4 ng/mL, less than 3 ng/mL, or less than 2 ng/mL of the one or more surfactants present in the nanoemulsion in the plasma of the subject. Lack of systemic absorption may be monitored, for example, by measuring the amount of the surfactant, such as the cationic surfactant, in the plasma of the human subject undergoing treatment. Amounts of surfactant of equal to or less than about 10 ng/ml in the plasma confirms minimal systemic absorption.

The pharmaceutical compositions may be applied in a single administration or in multiple administrations. The pharmaceutical compositions can be applied for at least one day, at least two days at least three days at least four days at least 5 days, once a week, at least twice a week, at least once a day, at least twice a day, multiple times daily, multiple times weekly, biweekly, at least once a month, or any combination thereof.

Following topical or intradermal administration, the nanoemulsion may be occluded or semi-occluded. Occlusion or semi-occlusion may be performed by overlaying a bandage, polyoleofin film, article of clothing, impermeabile barrier, or semi-impermeable barrier to the topical preparation.

Exemplary Nanoemulsions

Several exemplary nanoemulsions are described below, although the methods of the invention are not limited to the use of such nanoemulsions. The components and quantity of each can be varied as described herein in the preparation of other nanoemulsions. ("CPC" refers to cetylpyridinium chloride, which is a cationic surfactant present in the nanoemulsions). Compositions are w/w % unless otherwise noted.

TABLE 1

Exemplary Nanoemulsions

| Nanoemulsion | Component | Weight Percent |
|---|---|---|
| $W_{20}5EC$ ED | Distilled Water | 23.418% |
| | EDTA | 0.0745% |
| | Cetylpyridinium Chloride | 1.068% |
| | Tween 20 | 5.92% |
| | Ethanol | 6.73% |
| | Soybean Oil | 62.79% |
| $P_{407}5EC$ | Distilled Water | 23.49% |
| | CPC | 1.068% |
| | Poloxamer 407 | 5.92% |
| | Ethanol | 6.73% |
| | Soybean Oil, NP | 62.79% |
| $W_{20}5GBA_2$ (v/v%) | Distilled Water | 20.93% |
| | BTC 824 | 2% |
| | Tween 20 | 5% |
| | Glycerine | 8% |
| | Soybean Oil | 64% |
| $W_{80}5EC$ | Water | 23.490% |
| | Ethanol | 6.730% |
| | Cetylpyridinium Chloride | 1.068% |
| | Polysorbate 80 | 5.920% |
| | Refined Soybean Oil | 62.790% |
| $W_{20}5ECEDL2$ | Distilled Water | 23.418% |
| | EDTA | 0.0745% |
| | Cetylpyridinium Chloride | 1.068% |
| | Tween 20 | 5.92% |
| | Ethanol | 6.73% |
| | Soybean Oil | 62.79% |

TABLE 1-continued

Exemplary Nanoemulsions

| Nanoemulsion | Component | Weight Percent |
|---|---|---|
| $W_{20}5GBA_2ED$ (v/v%) | Distilled Water | 20.93% |
| | EDTA | 0.0745% |
| | BTC 824 | 2% |
| | Tween 20 | 5% |
| | Glycerine | 8% |
| | Soybean Oil | 64% |

The following nanoemulsions have an average particle (droplet) size of about 300 nm to about 600 nm: $W_{20}5EC$ ED, $P_{407}5EC$, $W_{20}5GBA_2$, $W_{80}5EC$, and $W_{20}5GBA_2ED$. The $W_{20}5ECEDL2$, which undergoes high pressure processing, has an average particle (droplet) size of about 150 nm to about 400 nm. The formulations listed in the table above are "neat" or "concentrated" formulations, meaning that the formulation intended for therapeutic use can be diluted as desired.

Methods of Manufacture

The nanoemulsions of the invention can be formed using classic emulsion forming techniques. See e.g., U.S. 2004/0043041. See also U.S. Pat. Nos. 6,015,832, 6,506,803, 6,559,189, 6,635,676, and US Patent Publication No. 20040043041, all of which are incorporated by reference. In addition, methods of making emulsions are described in U.S. Pat. Nos. 5,103,497 and 4,895,452 (herein incorporated by reference). In an exemplary method, the oil is mixed with the aqueous phase under relatively high shear forces (e.g., using high hydraulic and mechanical forces) to obtain a nanoemulsion comprising oil droplets having an average diameter of less than about 1000 nm. Some embodiments of the invention employ a nanoemulsion having an oil phase comprising an alcohol such as ethanol. The oil and aqueous phases can be blended using any apparatus capable of producing shear forces sufficient to form an emulsion, such as French Presses or high shear mixers (e.g., FDA approved high shear mixers are available, for example, from Admix, Inc., Manchester, N.H.). Methods of producing such emulsions are described in U.S. Pat. Nos. 5,103,497 and 4,895,452, herein incorporated by reference in their entireties.

In an exemplary embodiment, the nanoemulsions used in the methods of the invention comprise droplets of an oily discontinuous phase dispersed in an aqueous continuous phase, such as water. The nanoemulsions of the invention are stable, and do not decompose even after long storage periods. Certain nanoemulsions of the invention are non-toxic and safe when swallowed, inhaled, or contacted to the skin of a subject.

The compositions of the invention can be produced in large quantities and are stable for many months at a broad range of temperatures. The nanoemulsion can have textures ranging from that of a semi-solid cream to that of a thin lotion, and can be applied topically by hand, and can be sprayed onto a surface or nebulized.

As stated above, at least a portion of the emulsion may be in the form of lipid structures including, but not limited to, unilamellar, multilamellar, and paucliamellar lipid vesicles, micelles, and lamellar phases.

The present invention contemplates that many variations of the described nanoemulsions will be useful in the methods of the present invention. To determine if a candidate nanoemulsion is suitable for use with the present invention, three criteria are analyzed. Using the methods and standards described herein, candidate emulsions can be easily tested to determine if they are suitable. First, the desired ingredients are prepared using the methods described herein, to determine if a nanoemulsion can be formed. If a nanoemulsion cannot be formed, the candidate is rejected. Second, the candidate nanoemulsion should form a stable emulsion. A nanoemulsion is stable if it remains in emulsion form for a sufficient period to allow its intended use. For example, for nanoemulsions that are to be stored, shipped, etc., it may be desired that the nanoemulsion remain in emulsion form for months to years. Typical nanoemulsions that are relatively unstable, will lose their form within a day. Third, the candidate nanoemulsion should have efficacy for its intended use. For example, the emulsions of the invention should kill or disable microorganisms in vitro. To determine the suitability of a particular candidate nanoemulsion against a desired microorganism, the nanoemulsion is exposed to the microorganism for one or more time periods in a side-by-side experiment with an appropriate control sample (e.g., a negative control such as water) and determining if, and to what degree, the nanoemulsion kills or disables the microorganism.

The nanoemulsion of the invention can be provided in many different types of containers and delivery systems. For example, in some embodiments of the invention, the nanoemulsions are provided as a liquid, lotion, cream or other solid or semi-solid form. The nanoemulsions of the invention may be incorporated into hydrogel formulations.

The nanoemulsions can be delivered (e.g., to a subject or customers) in any suitable container. Suitable containers can be used that provide one or more single use or multi-use dosages of the nanoemulsion for the desired application. In some embodiments of the invention, the nanoemulsions are provided in a suspension or liquid form. Such nanoemulsions can be delivered in any suitable container including spray bottles (e.g., pressurized spray bottles, nebulizers).

Exemplary Methods of Use

As described in more detail throughout this application, the present invention is directed to methods of treating and/or preventing a respiratory infection in a subject having Cystic fibrosis (CF). In general, the method comprises administering a nanoemulsion to the subject, wherein the nanoemulsion comprises: (i) water; (ii) at least one organic solvent; (iii) at least one surfactant; and (iv) at least one oil; and wherein the nanoemulsion comprises droplets having an average diameter of less than about 1000 nm. In one embodiment of the invention, the subject is susceptible to or has an infection by one or more bacterial species selected from the group consisting of *Staphylococcus* spp., *Haemophilus* spp., *Pseudomonas* spp., *Burkholderia* spp., *Acinetobacter* spp, *Stenotrophomonas* spp., *Escherichia* spp., *Klebsiella* spp., and *Proteus* spp. The nanoemulsion can be delivered using any pharmaceutically acceptable means, with inhalation being one example of a useful administration method.

In yet another embodiment, the invention is directed to a method of treating or preventing an infection in a subject having a burn wound, wherein: (a) the method comprises administering a nanoemulsion to the subject; and (b) the nanoemulsion comprises: (i) water; (ii) at least one organic solvent; (iii) at least one surfactant; and (iv) at least one oil; and wherein the nanoemulsion comprises droplets having an average diameter of less than about 1000 nm. In one embodiment of the invention, the subject is susceptible to or has an infection by one or more gram-negative or gram-positive bacterial species. In another embodiment, the bacterial species are selected from the group consisting of *Staphylococcus* spp., *Haemophilus* spp., *Pseudomonas* spp., *Burkholderia* spp., *Acinetobacter* spp, *Stenotrophomonas* spp., *Escherichia* spp., *Klebsiella* spp., and *Proteus* spp. The nanoemulsion can be delivered using any pharmaceutically acceptable means, with inhalation, nebulization, and topical application to mucosal surfaces being examples of useful administration methods.

In yet another embodiment, the invention is directed to a method of treating or preventing an *Haemophilus influenzae* infection in a subject wherein: (a) the method comprises administering a nanoemulsion to the subject having or at risk of having a *Haemophilus influenzae* infection; (b) the nanoemulsion comprises: (i) water; (ii) at least one organic solvent; (iii) at least one surfactant; and (iv) at least one oil; and (c) wherein the nanoemulsion comprises droplets having an average diameter of less than about 1000 nm. The nanoemulsion can be delivered using any pharmaceutically acceptable means, with inhalation, nebulization, and delivery to a mucosal surface being examples of useful administration methods.

In one embodiment of the invention, the nanoemulsion exhibits minimal or no toxicity or side effects. Preferably, the nanoemulsion does not exhibit resistance to bacteria. This embodiment applies to all methods described herein.

If the method relates to a respiratory infection, then in one embodiment the respiratory infection may be associated with a bacterial biofilm, such as a biofilm present in the lungs of a subject.

All of the methods of the invention may further comprise administering one or more antibiotics either before, during, or after administration of the nanoemulsion. In yet another embodiment, one or more antibiotics may be incorporated into a nanoemulsion. In yet another embodiment of the invention, the nanoemulsion does not exhibit any antagonism with the antibiotic.

In one embodiment of the invention, administration of a nanoemulsion and at least one antibiotic is synergistic as defined by a fractional inhibitory concentration (FIC) index, a fractional bactericidal concentration (FBC) index, or a combination thereof. This embodiment applies to all methods described herein. Examples of such antibiotics include, but are not limited to polymyxins (colistin) and aminoglycosides (tobramycin).

In yet another embodiment, the methods of the invention may be used to treat or prevent infection by one or more bacterial species selected from the group consisting of *Pseudomonas aeruginosa, B. cenocepacia, A. baumannii, Stenotrophomonas maltophilia, Staphylococcus aureus, H. influenzae, E. coli, K. pneumoniae*, and *Proteus mirabilis*. All other gram positive or gram negative bacteria are also encompassed by the methods of the invention.

In one embodiment, the minimum inhibitory concentration (MIC), the minimum bactericidal concentration (MBC), or a combination thereof for the nanoemulsion demonstrate bacteriostatic or bactericidal activity for the nanoemulsion. This embodiment applies to all methods described herein.

In another embodiment of the invention, one or more bacterial species may exhibit resistance against one or more antibiotics. For example, the bacterial species can be methicillin-resistant *Staphylococcus aureus* (MRSA). This embodiment applies to all methods described herein.

The present invention is not limited by the type of subject administered a composition of the present invention. Each of the subjects (e.g., susceptible to respiratory infection) described above may be administered a composition of the present invention. In addition, the compositions and methods of the present invention are useful in the treatment of other respiratory diseases and disorders, such as acute bronchitis, bronchiectasis, pneumonia (including ventilator-associated pneumonia, nosocomial pneumonia, viral pneumonia, bacterial pneumonia, mycobacterial pneumonia, fungal pneumonia, eosinophilic pneumonia, and *Pneumocystis carinii* pneumonia), tuberculosis, cystic fibrosis (CF), emphysema radiation pneumonitis, and respiratory infection associated with inflammation caused by smoking, pulmonary edema, pneumoconiosis, sarcoidiosis, silicosis, asbestosis, berylliosis, coal worker's pneumonoconiosis (CWP), byssinosis, interstitial lung diseases (ILD) such as idiopathic pulmonary fibrosis, ILD associated with collagen vascular disorders, systemic lupus erythematosus, rheumatoid arthritis, ankylosing spondylitis, systemic sclerosis, and pulmonary inflammation that is a result of or is secondary to another disorder such as influenza.

The present invention is not limited by the particular formulation of a composition comprising a nanoemulsion of the present invention. Indeed, a composition comprising a nanoemulsion of the present invention may comprise one or more different agents in addition to the nanoemulsion. These agents or cofactors include, but are not limited to, adjuvants, surfactants, additives, buffers, solubilizers, chelators, oils, salts, therapeutic agents, drugs, bioactive agents, antibacterials, and antimicrobial agents (e.g., antibiotics, antivirals, etc.). In some embodiments, a composition comprising a nanoemulsion of the present invention comprises an agent and/or co-factor that enhance the ability of the nanoemulsion to kill a microbe (e.g., located in the respiratory tract). In some preferred embodiments, the presence of one or more co-factors or agents reduces the amount of nanoemulsion required for killing and/or attenuation of growth of a microbe. The present invention is not limited by the type of co-factor or agent used in a therapeutic agent of the present invention.

In some embodiments, a co-factor or agent used in a nanoemulsion composition is a bioactive agent. For example, in some embodiments, the bioactive agent may be a bioactive agent useful in a cell (e.g., a cell expressing a CFTR). Bioactive agents, as used herein, include diagnostic agents such as radioactive labels and fluorescent labels. Bioactive agents also include molecules affecting the metabolism of a cell (e.g., a cell expressing a CFTR), including peptides, nucleic acids, and other natural and synthetic drug molecules. Bioactive agents include, but are not limited to, adrenergic agent; adrenocortical steroid; adrenocortical suppressant; alcohol deterrent; aldosterone antagonist; amino acid; ammonia detoxicant; anabolic; analeptic; analgesic; androgen; anesthesia, adjunct to; anesthetic; anorectic; antagonist; anterior pituitary suppressant; anthelmintic; anti-acne agent; anti-adrenergic; anti-allergic; anti-amebic; anti-androgen; anti-anemic; anti-anginal; anti-anxiety; anti-arthritic; anti-asthmatic; anti-atherosclerotic; antibacterial; anticholelithic; anticholelithogenic; anticholinergic; anticoagulant; anticoccidal; anticonvulsant; antidepressant; antidiabetic; antidiarrheal; antidiuretic; antidote; anti-emetic; anti-epileptic; anti-estrogen; antifibrinolytic; antifungal; antiglaucoma agent; antihemophilic; antihemorrhagic; antihistamine; antihyperlipidemia; antihyperlipoproteinemic; antihypertensive; antihypotensive; anti-infective; anti-infective, topical; anti-inflammatory; antikeratinizing agent; antimalarial; antimicrobial; antimigraine; antimitotic; antimycotic, antinauseant, antineoplastic, antineutropenic, antiobessional agent; antiparasitic; antiparkinsonian; antiperistaltic, antipneumocystic; antiproliferative; antiprostatic hypertrophy; antiprotozoal; antipruritic; antipsychotic; antirheumatic; antischistosomal; antiseborrheic; antisecretory; antispasmodic; antithrombotic; antitussive; anti-ulcerative; anti-urolithic; antiviral; appetite suppressant; benign prostatic hyperplasia therapy agent; blood glucose regulator; bone resorption inhibitor; bronchodilator; carbonic anhydrase inhibitor; cardiac depressant; cardioprotectant; cardiotonic; cardiovascular agent; choleretic; cholinergic; cholinergic agonist; cholinesterase deactivator; coccidiostat; cognition adjuvant; cognition enhancer; depressant; diagnostic aid; diuretic; dopaminergic agent; ectoparasiticide; emetic; enzyme inhibitor; estrogen; fibrinolytic; fluorescent agent; free oxygen radical scavenger; gastrointestinal motility effector; glucocorticoid; gonad-stimulating principle; hair growth stimulant; hemostatic; histamine H2 receptor antagonists; hormone; hypocholesterolemic; hypoglycemic; hypolipidemic; hypotensive; imaging agent; immunizing agent; immunomodulator; immunoregulator; immunostimulant; immunosuppressant; impotence therapy adjunct; inhibitor; keratolytic; LHRH agonist; liver disorder treatment; luteolysin; memory adjuvant; mental performance enhancer; mood regulator; mucolytic; mucosal protective agent; mydriatic; nasal decongestant; neuromuscular blocking agent; neuroprotective; NMDA antagonist; non-hormonal sterol derivative; oxytocic; plasminogen activator; platelet activating factor antagonist; platelet aggregation inhibitor; post-stroke and post-head trauma treatment; potentiator; progestin; prostaglandin; prostate growth inhibitor; prothyrotropin; psychotropic; pulmonary surface; radioactive agent; regulator; relaxant; repartitioning agent; scabicide; sclerosing agent; sedative; sedative-hypnotic; selective adenosine Al antagonist; serotonin antagonist; serotonin inhibitor; serotonin receptor antagonist; steroid; stimulant; suppressant; symptomatic multiple sclerosis; synergist; thyroid hormone; thyroid inhibitor; thyromimetic; tranquilizer; amyotrophic lateral sclerosis agent; cerebral ischemia agent; Paget's disease agent; unstable angina agent; uricosuric; vasoconstrictor; vasodilator; vulnerary; wound healing agent; xanthine oxidase inhibitor.

Molecules useful as antimicrobials can be delivered by the methods and compositions of the invention, such that the respiratory infection is reduced or eliminated. Antibiotics that may find use in co-administration with a composition comprising a nanoemulsion of the present invention include, but are not limited to, agents or drugs that are bactericidal and/or bacteriostatic (e.g., inhibiting replication of bacteria or inhibiting synthesis of bacterial components required for survival of the infecting organism), including, but not limited to, almecillin, amdinocillin, amikacin, amoxicillin, amphomycin, amphotericin B, ampicillin, azacitidine, azaserine, azithromycin, azlocillin, aztreonam, bacampicillin, bacitracin, benzyl penicilloyl-polylysine, bleomycin, candicidin, capreomycin, carbenicillin, cefaclor, cefadroxil, cefamandole, cefazoline, cefdinir, cefepime, cefixime, cefinenoxime, cefinetazole, cefodizime, cefonicid, cefoperazone, ceforanide, cefotaxime, cefotetan, cefotiam, cefoxitin, cefpiramide, cefpodoxime, cefprozil, cefsulodin, ceftazidime, ceftibuten, ceftizoxime, ceftriaxone, cefuroxime, cephacetrile, cephalexin, cephaloglycin, cephaloridine, cephalothin, cephapirin, cephradine, chloramphenicol, chlortetracycline, cilastatin, cinnamycin, ciprofloxacin, clarithromycin, clavulanic acid, clindamycin, clioquinol, cloxacillin, colistimethate, colistin, cyclacillin, cycloserine, cyclosporine, cyclo-(Leu-Pro), dactinomycin, dalbavancin, dalfopristin, daptomycin, daunorubicin, demeclocycline, detorubicin, dicloxacillin, dihydrostreptomycin, dirithromycin, doxorubicin, doxycycline, epirubicin, erythromycin, eveminomycin, floxacillin, fosfomycin, fusidic acid, gemifloxacin, gentamycin, gramicidin, griseofulvin, hetacillin, idarubicin, imipenem, iseganan, ivermectin, kanamycin, laspartomycin, linezolid, linocomycin, loracarbef, magainin, meclocycline, meropenem, methacycline, methicillin, mezlocillin, minocycline, mitomycin, moenomycin, moxalactam, moxifloxacin, mycophenolic acid, nafcillin, natamycin, neomycin, netilmicin, niphimycin, nitrofurantoin, novobiocin, oleandomycin, oritavancin, oxacillin, oxytetracycline, paromomycin, penicillamine, penicillin G, penicillin V, phenethicillin, piperacillin, plicamycin, polymyxin B, pristinamycin, quinupristin, rifabutin, rifampin, rifamycin, rolitetracycline, sisomicin, spectrinomycin, streptomycin, streptozocin, sulbactam, sultamicillin, tacrolimus, tazobactam, teicoplanin, telithromycin, tetracycline, ticarcillin, tigecycline, tobramycin, troleandomycin, tunicamycin, tyrthricin, vancomycin, vidarabine, viomycin, virginiamycin, BMS-284,756, L-749,345, ER-35,786, S-4661, L-786,392, MC-02479, PepS, RP 59500, and TD-6424.

In some embodiments, a composition comprising a nanoemulsion of the present invention comprises one or more mucoadhesives (See, e.g., U.S. Pat. App. No. 20050281843, hereby incorporated by reference in its entirety). The present invention is not limited by the type of mucoadhesive utilized. Indeed, a variety of mucoadhesives are contemplated to be useful in the present invention including, but not limited to, cross-linked derivatives of poly(acrylic acid) (e.g., carbopol and polycarbophil), polyvinyl alcohol, polyvinyl pyrollidone, polysaccharides (e.g., alginate and chitosan), hydroxypropyl methylcellulose, lectins, fimbrial proteins, and carboxymethylcellulose. Although an understanding of the mechanism is not necessary to practice the present invention and the present invention is not limited to any particular mechanism of action, in some embodiments, use of a mucoadhesive (e.g., in a composition comprising a nanoemulsion) enhances killing and/or attenuation of growth of a microbe (e.g., exposed to a composition of the present invention) due to an increase in duration and/or amount of exposure to the nanoemulsion that a subject and/or microbe experiences when a mucoadhesive is used compared to the duration and/or amount of exposure to the nanoemulsion in the absence of using the mucoadhesive.

In some embodiments, a composition of the present invention may comprise sterile aqueous preparations. Acceptable vehicles and solvents include, but are not limited to, water, Ringer's solution, phosphate buffered saline and isotonic sodium chloride solution. In addition, sterile, fixed oils are conventionally employed as a solvent or suspending medium. For this purpose any bland fixed mineral or non-mineral oil may be employed including synthetic mono-ordi-glycerides. In addition, fatty acids such as oleic acid find use in the preparation of injectables. Carrier formulations suitable for mucosal, pulmonary, subcutaneous, intramuscular, intraperitoneal, intravenous, or administration via other routes may be found in Remington's Pharmaceutical Sciences, Mack Publishing Company, Easton, Pa.

A composition comprising a nanoemulsion of the present invention can be used therapeutically (e.g., to kill and/or attenuate growth of an existing infection) or as a prophylactic (e.g., to prevent microbial growth and/or colonization (e.g., to prevent signs or symptoms of disease)). A composition comprising a nanoemulsion of the present invention can be administered to a subject via a number of different delivery routes and methods.

For example, the compositions of the present invention can be administered to a subject (e.g., mucosally or by pulmonary route) by multiple methods, including, but not limited to: being suspended in a solution and applied to a surface; being suspended in a solution and sprayed onto a surface using a spray applicator; being mixed with a mucoadhesive and applied (e.g., sprayed or wiped) onto a surface (e.g., mucosal or pulmonary surface); being placed on or impregnated onto a nasal and/or pulmonary applicator and applied; being applied by a controlled-release mechanism; applied using a nebulizer, aerosolized, being applied as a liposome; or being applied on a polymer.

In some embodiments, compositions of the present invention are administered mucosally (e.g., using standard techniques; See, e.g., Remington: The Science and Practice of Pharmacy, Mack Publishing Company, Easton, Pa., 19th edition, 1995 (e.g., for mucosal delivery techniques, including intranasal and pulmonary techniques), as well as European Publication No. 517,565 and Illum et al., J. Controlled Rel., 1994, 29:133-141 (e.g., for techniques of intranasal administration), each of which is hereby incorporated by reference in its entirety). The present invention is not limited by the route of administration.

Methods of intranasal and pulmonary administration are well known in the art, including the administration of a droplet or spray form of the nanoemulsion into the nasopharynx of a subject to be treated. In some embodiments, a nebulized or aerosolized composition comprising a nanoemulsion is provided. Enteric formulations such as gastro resistant capsules for oral administration, suppositories for rectal or vaginal administration may also form part of this invention. Compositions of the present invention may also be administered via the oral route. Under these circumstances, a composition comprising a nanoemulsion may comprise a pharmaceutically acceptable excipient and/or include alkaline buffers, or enteric capsules. Formulations for nasal delivery may include those with dextran or cyclodextran and saponin as an adjuvant.

In preferred embodiments, a nanoemulsion of the present invention is administered via a pulmonary delivery route and/or means. In some embodiments, an aqueous solution containing the nanoemulsion is gently and thoroughly mixed to form a solution. The solution is sterile filtered (e.g., through a 0.2 micron filter) into a sterile, enclosed vessel. Under sterile conditions, the solution is passed through an appropriately small orifice to make droplets (e.g., between 0.1 and 10 microns).

The particles may be administered using any of a number of different applicators. Suitable methods for manufacture and administration are described in the following U.S. Pat. Nos. 6,592,904; 6,518,239; 6,423,344; 6,294,204; 6,051,256 and 5,997,848 to INHALE (now NEKTAR); and U.S. Pat. No. 5,985,309; RE37,053; U.S. Pat. Nos. 6,436,443; 6,447,753; 6,503,480; and 6,635,283, to Edwards, et al. (MIT, AIR), each of which is hereby incorporated Thus, in some embodiments, compositions of the present invention are administered by pulmonary delivery. For example, a composition of the present invention can be delivered to the lungs of a subject (e.g., a human) via inhalation (See, e.g., Adjei, et al. Pharmaceutical Research 1990; 7:565-569; Adjei, et al. Int. J. Pharmaceutics 1990; 63:135-144; Braquet, et al. J. Cardiovascular Pharmacology 1989 143-146; Hubbard, et al. (1989) Annals of Internal Medicine, Vol. III, pp. 206-212; Smith, et al. J. Clin. Invest. 1989; 84:1145-1146; Oswein, et al. "Aerosolization of Proteins", 1990; Proceedings of Symposium on Respiratory Drug Delivery II Keystone, Colorado; Debs, et al. J. Immunol. 1988; 140: 3482-3488; and U.S. Pat. No. 5,284,656 to Platz, et al, each of which are hereby incorporated by reference in its entirety). A method and composition for pulmonary delivery of drugs for systemic effect is described in U.S. Pat. No. 5,451,569 to Wong, et al., hereby incorporated by reference; See also U.S. Pat. No. 6,651,655 to Licalsi et al., hereby incorporated by reference in its entirety)). In some embodiments, a composition comprising a nanoemulsion is administered to a subject by more than one route or means (e.g., administered via pulmonary route as well as a mucosal route).

Further contemplated for use in the practice of this invention are a wide range of mechanical devices designed for pulmonary and/or nasal mucosal delivery of pharmaceutical agents including, but not limited to, nebulizers, metered dose inhalers, and powder inhalers, all of which are familiar to those skilled in the art. Some specific examples of commercially available devices suitable for the practice of this invention are the ULTRAVENT nebulizer (Mallinckrodt Inc., St. Louis, Mo.); the ACORN II nebulizer (Marquest Medical Products, Englewood, Colo.); the VENTOLIN metered dose inhaler (Glaxo Inc., Research Triangle Park, N.C.); and the SPINHALER powder inhaler (Fisons Corp., Bedford, Mass.). All such devices require the use of formulations suitable for dispensing of the therapeutic agent. Typically, each formulation is specific to the type of device employed and may involve the use of an appropriate propellant material, in addition to the usual diluents, adjuvants, surfactants, carriers and/or other agents useful in therapy. Also, the use of liposomes, microcapsules or microspheres, inclusion complexes, or other types of carriers is contemplated.

Thus, in some embodiments, a composition comprising a nanoemulsion of the present invention may be used to protect and/or treat a subject susceptible to, or suffering from, a disease by means of administering compositions comprising a nanoemulsion by mucosal, intramuscular, intraperitoneal, intradermal, transdermal, pulmonary, intravenous, subcutaneous or other route of administration described herein. Methods of systemic administration of the nanoemulsion and/or agent co-administered with the nanoemulsion may include conventional syringes and needles, or devices designed for ballistic delivery (See, e.g., WO 99/27961, hereby incorporated by reference), or needleless pressure liquid jet device (See, e.g., U.S. Pat. Nos. 4,596,556; 5,993,412, each of which are hereby incorporated by reference), or transdermal patches (See, e.g., WO 97/48440; WO 98/28037, each of which are hereby incorporated by reference). In some embodiments, the present invention provides a delivery device for systemic administration, pre-filled with the nanoemulsion composition of the present invention.

As described above, the present invention is not limited by the type of subject administered a composition of the present invention. Indeed, a wide variety of subjects are contemplated to be benefited from administration of a composition of the present invention. In preferred embodiments, the subject is a human. In some embodiments, human subjects are of any age (e.g., adults, children, infants, etc.) that have been or are likely to become exposed to a microorganism. In some embodiments, the human subjects are subjects that are more likely to receive a direct exposure to pathogenic microorganisms or that are more likely to display signs and symptoms of disease after exposure to a pathogen (e.g., subjects with CF or asthma, subjects in the armed forces, government employees, frequent travelers, persons attending or working in a school or daycare, health care workers, an elderly person, an immunocompromised person, and emergency service employees (e.g., police, fire, EMT employees)). In some embodiments, any one or all members of the general public can be administered a composition of the present invention (e.g., to prevent the occurrence or spread of disease). For example, in some embodiments, compositions and methods of the present invention are utilized to treat a group of people (e.g., a population of a region, city, state and/or country) for their own health (e.g., to prevent or treat disease) and/or to prevent or reduce the risk of disease spread from animals (e.g., birds, cattle, sheep, pigs, etc.) to humans. In some embodiments, the subjects are non-human mammals (e.g., pigs, cattle, goats, horses, sheep, or other livestock; or mice, rats, rabbits or other animal). In some embodiments, compositions and methods of the present invention are utilized in research settings (e.g., with research animals).

A composition comprising a nanoemulsion of the present invention can be administered (e.g., to a subject (e.g., via pulmonary and/or mucosal route) or to microbes (e.g., bacteria (e.g., opportunistic and/or pathogenic bacteria (e.g., residing on or within the respiratory system of a subject and/or on or within a burn wound)))) as a therapeutic or as a prophylactic to prevent microbial infection. Thus, in some embodiments, the present invention provides a method of altering microbial (e.g., bacterial (e.g., opportunistic and/or pathogenic bacterial) growth comprising administering a composition comprising a nanoemulsion to the microbes (e.g., bacteria (e.g., opportunistic and/or pathogenic bacteria). In some embodiments, administration of a composition comprising a nanoemulsion to the microbes (e.g., bacteria (e.g., opportunistic and/or pathogenic bacteria) kills the microbes. In some embodiments, administration of a composition comprising nanoemulsion to the microbes (e.g., bacteria (e.g., opportunistic and/or pathogenic bacteria) inhibits growth of the microbes. It is contemplated that a composition comprising a nanoemulsion can be administered to microbes (e.g., bacteria (e.g., opportunistic and/or pathogenic bacteria (e.g., residing within the respiratory tract))) via a number of delivery routes and/or mechanisms.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, preferably do not unduly interfere with the biological activities of the components of the compositions of the present invention. The formulations can be sterilized and, if desired, mixed with auxiliary agents (e.g., lubricants, preservatives, stabilizers, wetting agents, emulsifiers, salts for influencing osmotic pressure, buffers, colorings, flavorings and/or aromatic substances and the like) that do not deleteriously interact with the nanoemulsion. In some embodiments, nanoemulsion compositions of the present invention are administered in the form of a pharmaceutically acceptable salt. When used the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include, but are not limited to, acetic acid and a salt (1-2% w/v); citric acid and a salt (1-3% w/v); boric acid and a salt (0.5-2.5% w/v); and phosphoric acid and a salt (0.8-2% w/v). Suitable preservatives may include benzalkonium chloride (0.003-0.03% w/v); chlorobutanol (0.3-0.9% w/v); parabens (0.01-0.25% w/v) and thimerosal (0.004-0.02% w/v).

In some embodiments, a composition comprising a nanoemulsion is co-administered with one or more antibiotics. For example, one or more antibiotics may be administered with, before and/or after administration of a composition comprising a nanoemulsion. The present invention is not limited by the type of antibiotic co-administered. Indeed, a variety of antibiotics may be co-administered including, but not limited to, β-lactam antibiotics, penicillins (such as natural penicillins, aminopenicillins, penicillinase-resistant penicillins, carboxy penicillins, ureido penicillins), cephalosporins (first generation, second generation, and third generation cephalosporins), and other β-lactams (such as imipenem, monobactams,), β-lactamase inhibitors, vancomycin, aminoglycosides and spectinomycin, tetracyclines, chloramphenicol, erythromycin, lincomycin, clindamycin, rifampin, metronidazole, polymyxins, doxycycline, quinolones (e.g., ciprofloxacin), sulfonamides, trimethoprim, and quinolines.

A wide variety of antimicrobial agents are currently available for use in treating bacterial, fungal and viral infections. For a comprehensive treatise on the general classes of such drugs and their mechanisms of action, the skilled artisan is referred to Goodman & Gilman's "The Pharmacological Basis of Therapeutics" Eds. Hardman et al., 9th Edition, Pub. McGraw Hill, chapters 43 through 50, 1996, (herein incorporated by reference in its entirety). Generally, these agents include agents that inhibit cell wall synthesis (e.g., penicillins, cephalosporins, cycloserine, vancomycin, bacitracin); and the imidazole antifungal agents (e.g., miconazole, ketoconazole and clotrimazole); agents that act directly to disrupt the cell membrane of the microorganism (e.g., detergents such as polmyxin and colistimethate and the antifungals nystatin and amphotericin B); agents that affect the ribosomal subunits to inhibit protein synthesis (e.g., chloramphenicol, the tetracyclines, erthromycin and clindamycin); agents that alter protein synthesis and lead to cell death (e.g., aminoglycosides); agents that affect nucleic acid metabolism (e.g., the rifamycins and the quinolones); the antimetabolites (e.g., trimethoprim and sulfonamides); and the nucleic acid analogues such as zidovudine, gangcyclovir, vidarabine, and acyclovir which act to inhibit viral enzymes essential for DNA synthesis. Various combinations of antimicrobials may be employed.

The present invention also includes methods involving co-administration of a composition comprising a nanoemulsion with one or more additional active and/or anti-infective agents. In co-administration procedures, the agents may be administered concurrently or sequentially. In one embodiment, the compositions described herein are administered prior to the other active agent(s). The pharmaceutical formulations and modes of administration may be any of those described herein. In addition, the two or more co-administered agents may each be administered using different modes (e.g., routes) or different formulations. The additional agents to be co-administered (e.g., antibiotics, a second type of nanoemulsion, etc.) can be any of the well-known agents in the art, including, but not limited to, those that are currently in clinical use.

In some embodiments, a composition comprising a nanoemulsion is administered to a subject via more than one route. For example, a subject may benefit from receiving mucosal administration (e.g., nasal administration or other mucosal routes described herein) and, additionally, receiving one or more other routes of administration (e.g., pulmonary administration (e.g., via a nebulizer, inhaler, or other methods described herein.

Other delivery systems can include time-release, delayed release or sustained release delivery systems. Such systems can avoid repeated administrations of the compositions, increasing convenience to the subject and a physician. Many types of release delivery systems are available and known to those of ordinary skill in the art. They include polymer based systems such as poly (lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109, hereby incorporated by reference. Delivery systems also include non-polymer systems that are: lipids including sterols such as cholesterol, cholesterol esters and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, each of which is hereby incorporated by reference and (b) diffusional systems in which an active component permeates at a controlled rate from a polymer such as described in U.S. Pat. Nos. 3,854,480, 5,133,974 and 5,407,686, each of which is hereby incorporated by reference. In addition, pump-based hardware delivery systems can be used, some of which are adapted for implantation.

In preferred embodiments, a composition comprising a nanoemulsion of the present invention comprises a suitable amount of the nanoemulsion to kill and/or attenuate growth of microbes (e.g., pathogenic microbes (e.g., pathogenic bacteria, viruses, etc.)) in a subject when administered to the subject. The present invention is not limited by the amount of nanoemulsion used. In some preferred embodiments, the amount of nanoemulsion in a composition comprising a nanoemulsion is selected as that amount which kills and/or attenuates microbial growth without significant, adverse side effects. The amount will vary depending upon which specific nanoemulsion(s) is/are employed, and can vary from subject to subject, depending on a number of factors including, but not limited to, the species, age and general condition (e.g., health) of the subject, and the mode of administration. Procedures for determining the appropriate amount of nanoemulsion administered to a subject to kill and/or attenuate growth of a microbe (e.g., pathogenic microbe (e.g., pathogenic bacteria, viruses, etc.)) in a subject can be readily determined using known means by one of ordinary skill in the art.

In some embodiments, it is expected that each dose (e.g., of a composition comprising a nanoemulsion (e.g., administered to a subject to kill and/or attenuate microbial growth)) comprises 10-40% nanoemulsion, in some embodiments, 20% nanoemulsion, in some embodiments less than 20% (e.g., 15%, 10%, 8%, 5% or less nanoemulsion), and in some embodiments greater than 20% nanoemulsion (e.g., 25%, 30%, 35%, 40% or more nanoemulsion). An optimal amount for a particular administration (e.g., to kill and/or attenuate microbial growth) can be ascertained by one of skill in the art using standard studies involving observation of microbial growth and/or death and other responses in subjects.

In some embodiments, it is expected that each dose (e.g., of a composition comprising a nanoemulsion (e.g., administered to a subject to kill and/or attenuate microbial growth)) is from 0.001 to 40% or more (e.g., 0.001-10%, 0.5-5%, 1-3%, 2%, 6%, 10%, 15%, 20%, 30%, 40% or more) by weight nanoemulsion.

Similarly, the present invention is not limited by the duration of time a nanoemulsion is administered to a subject (e.g., to kill and/or attenuate microbial growth). In some embodiments, a nanoemulsion is administered one or more times (e.g. twice, three times, four times or more) daily. In some embodiments, a composition comprising a nanoemulsion is administered one or more times a day until an infection is eradicated or microbial growth and/or presence has been reduced to a desired level. In some embodiments, a composition comprising a nanoemulsion of the present invention is formulated in a concentrated dose that can be diluted prior to administration to a subject. For example, dilutions of a concentrated composition may be administered to a subject such that the subject receives any one or more of the specific dosages provided herein. In some embodiments, dilution of a concentrated composition may be made such that a subject is administered (e.g., in a single dose) a composition comprising 0.5-50% of the nanoemulsion present in the concentrated composition. Concentrated compositions are contemplated to be useful in a setting in which large numbers of subjects may be administered a composition of the present invention (e.g., a hospital). In some embodiments, a composition comprising a nanoemulsion of the present invention (e.g., a concentrated composition) is stable at room temperature for more than 1 week, in some embodiments for more than 2 weeks, in some embodiments for more than 3 weeks, in some embodiments for more than 4 weeks, in some embodiments for more than 5 weeks, and in some embodiments for more than 6 weeks.

Dosage units may be proportionately increased or decreased based on several factors including, but not limited to, the weight, age, and health status of the subject. In addition, dosage units may be increased or decreased for subsequent administrations.

In some embodiments, a composition comprising a nanoemulsion is administered to a subject under conditions such that microbes (e.g., bacteria (e.g., opportunistic and/or pathogenic bacteria)) are killed. In some embodiments, a composition comprising a nanoemulsion is administered to a subject under conditions such that microbial (e.g., bacterial (e.g., opportunistic and/or pathogenic bacterial) growth is prohibited and/or attenuated. In some embodiments, greater than 90% (e.g., greater than 95%, 98%, 99%, all detectable) of microbes (e.g., bacteria (e.g., opportunistic and/or pathogenic bacteria) are killed. In some embodiments, there is greater than 2 log (e.g., greater than 3 log, 4 log, 5 log, or more) reduction in microbe (e.g., bacteria (e.g., opportunistic and/or pathogenic bacteria) presence. In some embodiments, reduction and/or killing is observed in one hour or less (e.g., 45 minutes, 30 minutes, 15 minutes, or less). In some embodiments, reduction and/or killing is observed in 6 hours or less (e.g., 5 hours, 4, hours, 3 hours, two hours or less than one hour). In some embodiments, reduction and/or killing is observed in two days or less following initial treatment (e.g., less than 24 hours, less than 20 hours, 18 hours or less). In some embodiments, the reduction and/or killing is observed in three days or less, four days or less, or five days or less.

A composition comprising a nanoemulsion of the present invention finds use where the nature of the infectious and/or disease causing agent (e.g., causing signs, symptoms or indications of respiratory infection) is known, as well as where the nature of the infectious and/or disease causing agent is unknown (e.g., in emerging disease (e.g., of pandemic proportion (e.g., influenza or other outbreaks of disease))). For example, the present invention contemplates use of the compositions of the present invention in treatment of or prevention of infections associated with an emergent infectious and/or disease causing agent yet to be identified (e.g., isolated and/or cultured from a diseased person but without genetic, biochemical or other characterization of the infectious and/or disease causing agent).

It is contemplated that the compositions and methods of the present invention will find use in various settings, including research settings. For example, compositions and methods of the present invention also find use in studies of the immune system (e.g., characterization of adaptive immune responses (e.g., protective immune responses (e.g., mucosal or systemic immunity))). Uses of the compositions and methods provided by the present invention encompass human and non-human subjects and samples from those subjects, and also encompass research applications using these subjects. Compositions and methods of the present invention are also useful in studying and optimizing nanoemulsions, immunogens, and other components and for screening for new components. Thus, it is not intended that the present invention be limited to any particular subject and/or application setting.

The formulations can be tested in vivo in a number of animal models developed for the study of pulmonary, mucosal and other routes of delivery. As is readily apparent, the compositions of the present invention are useful for preventing and/or treating a wide variety of diseases and infections caused by viruses, bacteria, parasites, and fungi. Not only can the compositions be used prophylactically or therapeutically, as described above, the compositions can also be used in order to prepare antibodies, both polyclonal and monoclonal (e.g., for diagnostic purposes), as well as for immunopurification of an antigen of interest.

In some embodiments, the present invention provides a kit comprising a composition comprising a nanoemulsion. In some embodiments, the kit further provides a device for administering the composition. The present invention is not limited by the type of device included in the kit. In some embodiments, the device is configured for pulmonary application of the composition of the present invention (e.g., a nasal inhaler or nasal mister). In some embodiments, a kit comprises a composition comprising a nanoemulsion in a concentrated form (e.g., that can be diluted prior to administration to a subject).

In some embodiments, all kit components are present within a single container (e.g., vial or tube). In some embodiments, each kit component is located in a single container (e.g., vial or tube). In some embodiments, one or more kit components are located in a single container (e.g., vial or tube) with other components of the same kit being located in a separate container (e.g., vial or tube). In some embodiments, a kit comprises a buffer. In some embodiments, the kit further comprises instructions for use.

Therapeutic and Prophylactic Use of Immunogenic Compositions

The present invention provides immunogenic nanoemulsion compositions and methods of using the same for the induction of immune responses (e.g., innate and/or adaptive immune responses (e.g., for generation of host immunity against a bacterial species of the genus *Burkholderia* (e.g., *B. cenocepacia, B. multivorans*, etc.))). Compositions and methods of the present invention find use in, among other things, clinical (e.g. therapeutic and preventative medicine (e.g., vaccination)) and research applications.

As shown in Example 10, an immunogenic composition (e.g., comprising a nanoemulsion and *Bukholderia* antigen) of the present invention induces (e.g., when administered to a subject) both systemic and mucosal immunity. Thus, in some preferred embodiments, administration of a composition comprising a nanoemulsion and *Burkholderia* antigen to a subject results in protection against an exposure (e.g., a mucosal and/or respiratory exposure) to *Burkholderia*. Although an understanding of the mechanism is not necessary to practice the present invention and the present invention is not limited to any particular mechanism of action, mucosal administration (e.g., vaccination) provides protection against *Burkholderia* (e.g., *Burkholderia cepacia*) infection (e.g., that initiates at a mucosal surface). Although it has heretofore proven difficult to stimulate secretory IgA responses and protection against pathogens that invade at mucosal surfaces (See, e.g., Mestecky et al, Mucosal Immunology. 3ed edn. (Academic Press, San Diego, 2005)), in some embodiments, the present invention provides compositions and methods for stimulating mucosal immunity (e.g., a protective IgA response) towards a pathogen (e.g., pathogenic species of *Burkholderia, Haemophilus, Staphylococcus* or other bacterial genus) in a subject.

In some embodiments, the present invention provides a composition (e.g., a composition comprising a nanoemulsion and *Burkholderia* (e.g., *Burkholderia cenocepacia*) antigen (e.g., an immunogenic polypeptide comprising an amino acid sequence of SEQ ID NO. 1 or SEQ ID NOS. 2-16)) to serve as a mucosal vaccine. In some embodiments, an immunogenic composition comprising nanoemulsion (NE) and *Burkholderia* antigen is produced with NE and killed whole cell bacteria of the genus *Burkholderia* (e.g., *Burkholderia cepacia* (e.g., killed using nanoemulsion, alcohol (e.g., ethanol), or other methods), isolated, purified and/or recombinant protein and/or saccharide component of *Burkholderia* (e.g., protein/peptide (e.g., *Burkholderia*-derived protein, live-virus-vector-derived protein, recombinant protein, recombinant denatured protein/antigens, small peptide segments protein/antigen).

In some preferred embodiments, the present invention provides a composition for generating an immune response comprising a NE and an immunogen (e.g., a purified, isolated or synthetic *Burkholderia* protein or derivative, variant, or analogue thereof; or, one or more species of *Burkholderia* (e.g., *Burkholderia multivorans* (e.g., killed and or inactivated whole cell bacteria). When administered to a subject, a composition of the present invention stimulates an immune response against the immunogen within the subject. Although an understanding of the mechanism is not necessary to practice the present invention and the present invention is not limited to any particular mechanism of action, in some embodiments, generation of an immune response (e.g., resulting from administration of a composition comprising a nanoemulsion and an immunogen) provides total or partial immunity to the subject (e.g., from signs, symptoms or conditions of a disease associated with *Burkholderia* infection (e.g., strep throat, meningitis, bacterial *pneumoniae*, endocarditis, erysipelas and/or necrotizing fasciitis)). Without being bound to any specific theory, protection and/or immunity from disease (e.g., the ability of a subject's immune system to prevent or attenuate (e.g., suppress) a sign, symptom or condition of disease) after exposure to an immunogenic composition of the present invention is due to adaptive (e.g., acquired) immune responses (e.g., immune responses mediated by B and T cells following exposure to a NE comprising an immunogen of the present invention (e.g., immune responses that exhibit increased specificity and reactivity towards *Burkholderia* (e.g., *Burkholderia cepacia*)). Thus, in some embodiments, the compositions and methods of the present invention are used prophylactically or therapeutically to prevent or attenuate a sign, symptom or condition associated with *Burkholderia* (e.g., *Burkholderia cepacia*)).

In some embodiments, a NE comprising an immunogen (e.g., a *Burkholderia* (e.g., *Burkholderia cepacia*) antigen) is administered alone. In some embodiments, a composition comprising a NE and an immunogen (e.g., a *Burkholderia* (e.g., *Burkholderia cepacia*) antigen) comprises one or more other agents (e.g., a pharmaceutically acceptable carrier, adjuvant, excipient, and the like). In some embodiments, a composition for stimulating an immune response of the present invention is administered in a manner to induce a humoral immune response. In some embodiments, a composition for stimulating an immune response of the present invention is administered in a manner to induce a cellular (e.g., cytotoxic T lymphocyte) immune response, rather than a humoral response. In some embodiments, a composition comprising a NE and an immunogen of the present invention induces both a cellular and humoral immune response.

The present invention is not limited by the isotype, strain or species of *Burkholderia* (e.g., *Burkholderia cepacia*) used in a composition comprising a NE and immunogen. Indeed, each *Burkholderia* (e.g., *Burkholderia cepacia*) family member alone, or in combination with another family member, may be used to generate a composition comprising a NE and an immunogen (e.g., used to generate an immune response) of the present invention. Exemplary species of *Burkholderia* are described herein.

In some embodiments, the *Burkholderia* (e.g., *Burkholderia cepacia*) species utilized is a modified (e.g., genetically modified (e.g., naturally modified via natural selection or modified using recombinant genetic techniques)) species that displays greater pathogenic capacity (e.g., causes more sever *Burkholderia*—(e.g., *Burkholderia cepacia*)-induced disease (e.g., comprising enhanced and/or more severe respiratory infection, etc.)). In some embodiments, any one or more members of the genus *Burkholderia* is utilized in an immunoreactive composition of the invention including but not limited to *B. cenocepacia, B. dolosa, B. multivorans, B. ambifaria, B. vietnamiensis, B. ubonensis, B. thailandensis, B. graminis, B. oklahomensis, B. pseudomallei, B. xenovorans, B. phytofirmans, B. phymatum, R. metallidurans, R. eutropha, R. solanacearum.*

The present invention is not limited by the *Burkholderia* strain used. Indeed, a variety of *Burkholderia* strains are contemplated to be useful in the present invention including, but not limited to, classical strains, attenuated strains, non-replicating strains, modified strains (e.g., genetically or mechanically modified strains (e.g., to become more or less virulent)), or other serially diluted strains of *Burkholderia*. A composition comprising a NE and immunogen may comprise one or more strains of *Burkholderia cenocepacia* and/or other type of *Burkholderia* (e.g., *Burkholderia multivorans*). Additionally, a composition comprising a NE and immunogen may comprise one or more strains of *Burkholderia* and, in addition, one or more strains of a non-*Burkholderia* immunogen.

In some embodiments, the immunogen may comprise one or more antigens derived from a pathogen (e.g., *Burkholderia*). For example, in some embodiments, the immunogen is a purified, recombinant, synthetic, or otherwise isolated protein (e.g., added to the NE to generate an immunogenic composition). Similarly, the immunogenic protein may be a derivative, analogue or otherwise modified (e.g., conjugated) form of a protein from a pathogen.

The present invention is not limited by the particular formulation of a composition comprising a NE and immunogen of the present invention. Indeed, a composition comprising a NE and immunogen of the present invention may comprise one or more different agents in addition to the NE and immunogen. These agents or cofactors include, but are not limited to, adjuvants, surfactants, additives, buffers, solubilizers, chelators, oils, salts, therapeutic agents, drugs, bioactive agents, antibacterials, and antimicrobial agents (e.g., antibiotics, antivirals, etc.). In some embodiments, a composition comprising a NE and immunogen of the present invention comprises an agent and/or co-factor that enhance the ability of the immunogen to induce an immune response (e.g., an adjuvant). In some preferred embodiments, the presence of one or more co-factors or agents reduces the amount of immunogen required for induction of an immune response (e.g., a protective immune response (e.g., protective immunization)). In some embodiments, the presence of one or more co-factors or agents can be used to skew the immune response towards a cellular (e.g., T cell mediated) or humoral (e.g., antibody mediated) immune response. The present invention is not limited by the type of co-factor or agent used in a therapeutic agent of the present invention.

Adjuvants are described in general in Vaccine Design—the Subunit and Adjuvant Approach, edited by Powell and Newman, Plenum Press, New York, 1995. The present invention is not limited by the type of adjuvant utilized (e.g., for use in a composition (e.g., pharmaceutical composition) comprising a NE and immunogen). For example, in some embodiments, suitable adjuvants include an aluminum salt such as aluminum hydroxide gel (alum) or aluminum phosphate. In some embodiments, an adjuvant may be a salt of calcium, iron or zinc, or may be an insoluble suspension of acylated tyrosine, or acylated sugars, cationically or anionically derivatised polysaccharides, or polyphosphazenes.

In some embodiments, it is preferred that a composition comprising a NE and immunogen of the present invention comprises one or more adjuvants that induce a Th1-type response. However, in other embodiments, it will be preferred that a composition comprising a NE and immunogen of the present invention comprises one or more adjuvants that induce a Th2-type response.

In general, an immune response is generated to an antigen through the interaction of the antigen with the cells of the immune system. Immune responses may be broadly categorized into two categories: humoral and cell mediated immune responses (e.g., traditionally characterized by antibody and cellular effector mechanisms of protection, respectively). These categories of response have been termed Th1-type responses (cell-mediated response), and Th2-type immune responses (humoral response).

Stimulation of an immune response can result from a direct or indirect response of a cell or component of the immune system to an intervention (e.g., exposure to an immunogen). Immune responses can be measured in many ways including activation, proliferation or differentiation of cells of the immune system (e.g., B cells, T cells, dendritic cells, APCs, macrophages, NK cells, NKT cells etc.); up-regulated or down-regulated expression of markers and cytokines; stimulation of IgA, IgM, or IgG titer; splenomegaly (including increased spleen cellularity); hyperplasia and mixed cellular infiltrates in various organs. Other responses, cells, and components of the immune system that can be assessed with respect to immune stimulation are known in the art.

Although an understanding of the mechanism is not necessary to practice the present invention and the present invention is not limited to any particular mechanism of action, in some embodiments, compositions and methods of the present invention induce expression and secretion of cytokines (e.g., by macrophages, dendritic cells and CD4+ T cells). Modulation of expression of a particular cytokine can occur locally or systemically. It is known that cytokine profiles can determine T cell regulatory and effector functions in immune responses. In some embodiments, Th1-type cytokines can be induced, and thus, the immunostimulatory compositions of the present invention can promote a Th1 type antigen-specific immune response including cytotoxic T-cells (e.g., thereby avoiding unwanted Th2 type immune responses (e.g., generation of Th2 type cytokines (e.g., IL-13) involved in enhancing the severity of disease (e.g., IL-13 induction of mucus formation))).

Cytokines play a role in directing the T cell response. Helper (CD4+) T cells orchestrate the immune response of mammals through production of soluble factors that act on other immune system cells, including B and other T cells. Most mature CD4+ T helper cells express one of two cytokine profiles: Th1 or Th2. Th1-type CD4+ T cells secrete IL-2, IL-3, IFN-γ, GM-CSF and high levels of TNF-α. Th2 cells express IL-3, IL-4, IL-5, IL-6, IL-9, IL-10, IL-13, GM-CSF and low levels of TNF-α. Th1 type cytokines promote both cell-mediated immunity, and humoral immunity that is characterized by immunoglobulin class switching to IgG2a in mice and IgG1 in humans. Th1 responses may also be associated with delayed-type hypersensitivity and autoimmune disease. Th2 type cytokines induce primarily humoral immunity and induce class switching to IgG1 and IgE. The antibody isotypes associated with Th1 responses generally have neutralizing and opsonizing capabilities whereas those associated with Th2 responses are associated more with allergic responses.

Several factors have been shown to influence skewing of an immune response towards either a Th1 or Th2 type response. The best characterized regulators are cytokines IL-12 and IFN-γ are positive Th1 and negative Th2 regulators. IL-12 promotes IFN-γ production, and IFN-γ provides positive feedback for IL-12. IL-4 and IL-10 appear important for the establishment of the Th2 cytokine profile and to down-regulate Th1 cytokine production.

Thus, in preferred embodiments, the present invention provides a method of stimulating a Th1-type immune response in a subject comprising administering to a subject a composition comprising a NE and an immunogen. However, in other embodiments, the present invention provides a method of stimulating a Th2-type immune response in a subject (e.g., if balancing of a T cell mediated response is desired) comprising administering to a subject a composition comprising a NE and an immunogen. In further preferred embodiments, adjuvants can be used (e.g., can be co-administered with a composition of the present invention) to skew an immune response toward either a Th1 or Th2 type immune response. For example, adjuvants that induce Th2 or weak Th1 responses include, but are not limited to, alum, saponins, and SB-As4. Adjuvants that induce Th1 responses include but are not limited to MPL, MDP, ISCOMS, IL-12, IFN-γ, and SB-AS2.

Several other types of Th1-type immunogens can be used (e.g., as an adjuvant) in compositions and methods of the present invention. These include, but are not limited to, the following. In some embodiments, monophosphoryl lipid A (e.g., in particular 3-de-O-acylated monophosphoryl lipid A (3D-MPL)), is used. 3D-MPL is a well known adjuvant manufactured by Ribi Immunochem, Mont. Chemically it is often supplied as a mixture of 3-de-O-acylated monophosphoryl lipid A with either 4, 5, or 6 acylated chains. In some embodiments, diphosphoryl lipid A, and 3-O-deacylated variants thereof are used. Each of these immunogens can be purified and prepared by methods described in GB 2122204B, hereby incorporated by reference in its entirety. Other purified and synthetic lipopolysaccharides have been described (See, e.g., U.S. Pat. No. 6,005,099 and EP 0 729 473; Hilgers et al., 1986, Int. Arch. Allergy. Immunol., 79(4): 392-6; Hilgers et al., 1987, Immunology, 60(1):141-6; and EP 0 549 074, each of which is hereby incorporated by reference in its entirety). In some embodiments, 3D-MPL is used in the form of a particulate formulation (e.g., having a small particle size less than 0.2 μm in diameter, described in EP 0 689 454, hereby incorporated by reference in its entirety).

In some embodiments, saponins are used as an immunogen (e.g., Th1-type adjuvant) in a composition of the present invention. Saponins are well known adjuvants (See, e.g., Lacaille-Dubois and Wagner (1996) Phytomedicine vol 2 pp 363-386). Examples of saponins include Quil A (derived from the bark of the South American tree Quillaja *Saponaria Molina*), and fractions thereof (See, e.g., U.S. Pat. No. 5,057, 540; Kensil, Crit Rev Ther Drug Carrier Syst, 1996, 12 (1-2): 1-55; and EP 0 362 279, each of which is hereby incorporated by reference in its entirety). Also contemplated to be useful in the present invention are the haemolytic saponins QS7, QS 17, and QS21 (HPLC purified fractions of Quil A; See, e.g., Kensil et al. (1991). J. Immunology 146, 431-437, U.S. Pat. No. 5,057,540; WO 96/33739; WO 96/11711 and EP 0 362 279, each of which is hereby incorporated by reference in its entirety). Also contemplated to be useful are combinations of QS21 and polysorbate or cyclodextrin (See, e.g., WO 99/10008, hereby incorporated by reference in its entirety.

In some embodiments, an immunogenic oligonucleotide containing unmethylated CpG dinucleotides ("CpG") is used as an adjuvant in the present invention. CpG is an abbreviation for cytosine-guanosine dinucleotide motifs present in DNA. CpG is known in the art as being an adjuvant when administered by both systemic and mucosal routes (See, e.g., WO 96/02555, EP 468520, Davis et al., J. Immunol, 1998, 160(2):870-876; McCluskie and Davis, J. Immunol., 1998, 161(9):4463-6; and U.S. Pat. App. No. 20050238660, each of which is hereby incorporated by reference in its entirety). For example, in some embodiments, the immunostimulatory sequence is Purine-Purine-C-G-pyrimidine-pyrimidine; wherein the CG motif is not methylated.

Although an understanding of the mechanism is not necessary to practice the present invention and the present invention is not limited to any particular mechanism of action, in some embodiments, the presence of one or more CpG oligonucleotides activate various immune subsets including natural killer cells (which produce IFN-γ) and macrophages. In some embodiments, CpG oligonucleotides are formulated into a composition of the present invention for inducing an immune response. In some embodiments, a free solution of CpG is co-administered together with an antigen (e.g., present within a NE solution (See, e.g., WO 96/02555; hereby incorporated by reference). In some embodiments, a CpG oligonucleotide is covalently conjugated to an antigen (See, e.g., WO 98/16247, hereby incorporated by reference), or formulated with a carrier such as aluminium hydroxide (See, e.g., Brazolot-Millan et al., Proc. Natl. Acad Sci., USA, 1998, 95(26), 15553-8).

In some embodiments, adjuvants such as Complete Freunds Adjuvant and Incomplete Freunds Adjuvant, cytokines (e.g., interleukins (e.g., IL-2, IFN-γ, IL-4, etc.), macrophage colony stimulating factor, tumor necrosis factor, etc.), detoxified mutants of a bacterial ADP-ribosylating toxin such as a cholera toxin (CT), a pertussis toxin (PT), or an *E. Coli* heat-labile toxin (LT), particularly LT-K63 (where lysine is substituted for the wild-type amino acid at position 63) LT-R72 (where arginine is substituted for the wild-type amino acid at position 72), CT-S 109 (where serine is substituted for the wild-type amino acid at position 109), and PT-K9/G129 (where lysine is substituted for the wild-type amino acid at position 9 and glycine substituted at position 129) (See, e.g., WO93/13202 and WO92/19265, each of which is hereby incorporated by reference), and other immunogenic substances (e.g., that enhance the effectiveness of a composition of the present invention) are used with a composition comprising a NE and immunogen of the present invention.

Additional examples of adjuvants that find use in the present invention include poly(di(carboxylatophenoxy)phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); and *Leishmania* elongation factor (a purified *Leishmania* protein; Corixa Corporation, Seattle, Wash.).

Adjuvants may be added to a composition comprising a NE and an immunogen, or, the adjuvant may be formulated with carriers, for example liposomes, or metallic salts (e.g., aluminium salts (e.g., aluminium hydroxide)) prior to combining with or co-administration with a composition comprising a NE and an immunogen.

In some embodiments, a composition comprising a NE and an immunogen comprises a single adjuvant. In other embodiments, a composition comprising a NE and an immunogen comprises two or more adjuvants (See, e.g., WO 94/00153; WO 95/17210; WO 96/33739; WO 98/56414; WO 99/12565; WO 99/11241; and WO 94/00153, each of which is hereby incorporated by reference in its entirety).

In some embodiments, a composition comprising a NE and an immunogen of the present invention comprises one or more mucoadhesives (See, e.g., U.S. Pat. App. No. 20050281843, hereby incorporated by reference in its entirety). The present invention is not limited by the type of mucoadhesive utilized. Indeed, a variety of mucoadhesives are contemplated to be useful in the present invention including, but not limited to, cross-linked derivatives of poly(acrylic acid) (e.g., carbopol and polycarbophil), polyvinyl alcohol, polyvinyl pyrollidone, polysaccharides (e.g., alginate and chitosan), hydroxypropyl methylcellulose, lectins, fimbrial proteins, and carboxymethylcellulose. Although an understanding of the mechanism is not necessary to practice the present invention and the present invention is not limited to any particular mechanism of action, in some embodiments, use of a mucoadhesive (e.g., in a composition comprising a NE and immunogen) enhances induction of an immune response in a subject (e.g., administered a composition of the present invention) due to an increase in duration and/or amount of exposure to an immunogen that a subject experiences when a mucoadhesive is used compared to the duration and/or amount of exposure to an immunogen in the absence of using the mucoadhesive.

In some embodiments, a composition of the present invention may comprise sterile aqueous preparations. Acceptable vehicles and solvents include, but are not limited to, water, Ringer's solution, phosphate buffered saline and isotonic sodium chloride solution. In addition, sterile, fixed oils are conventionally employed as a solvent or suspending medium. For this purpose any bland fixed mineral or non-mineral oil may be employed including synthetic mono-ordi-glycerides. In addition, fatty acids such as oleic acid find use in the preparation of injectables. Carrier formulations suitable for mucosal, subcutaneous, intramuscular, intraperitoneal, intravenous, or administration via other routes may be found in Remington's Pharmaceutical Sciences, Mack Publishing Company, Easton, Pa.

A composition comprising a NE and an immunogen of the present invention can be used therapeutically (e.g., to enhance an immune response) or as a prophylactic (e.g., for immunization (e.g., to prevent signs or symptoms of disease)). A composition comprising a NE and an immunogen of the present invention can be administered to a subject via a number of different delivery routes and methods.

For example, an immunogenic compositions of the invention can be administered to a subject (e.g., mucosally (e.g., nasal mucosa, vaginal mucosa, etc.)) by multiple methods, including, but not limited to: being suspended in a solution and applied to a surface; being suspended in a solution and sprayed onto a surface using a spray applicator; being mixed with a mucoadhesive and applied (e.g., sprayed or wiped) onto a surface (e.g., mucosal surface); being placed on or impregnated onto a nasal and/or vaginal applicator and applied; being applied by a controlled-release mechanism; being applied as a liposome; or being applied on a polymer.

In some preferred embodiments, immunogenic compositions described herein are administered mucosally (e.g., using standard techniques; See, e.g., Remington: The Science and Practice of Pharmacy, Mack Publishing Company, Easton, Pa., 19th edition, 1995 (e.g., for mucosal delivery techniques, including intranasal, pulmonary, vaginal and rectal techniques), as well as European Publication No. 517,565 and Illum et al., J. Controlled Rel., 1994, 29:133-141 (e.g., for techniques of intranasal administration), each of which is hereby incorporated by reference in its entirety). Alternatively, immunogenic compositions described herein are administered dermally or transdermally, using standard techniques (See, e.g., Remington: The Science and Practice of Pharmacy, Mack Publishing Company, Easton, Pa., 19th edition, 1995). The present invention is not limited by the route of administration.

Mucosal vaccination, such as intranasal vaccination, may induce mucosal immunity not only in the nasal mucosa, but also in distant mucosal sites such as the genital mucosa (See, e.g., Mestecky, Journal of Clinical Immunology, 7:265-276, 1987). In addition to inducing mucosal immune responses, mucosal vaccination also induces systemic immunity (See, e.g., Example 10). In some embodiments, non-parenteral administration (e.g., mucosal administration of vaccines) provides an efficient and convenient way to boost systemic immunity (e.g., induced by parenteral or mucosal vaccination (e.g., in cases where multiple boosts are used to sustain a vigorous systemic immunity)).

In some embodiments, a composition comprising a NE and an immunogen of the present invention may be used to protect or treat a subject susceptible to, or suffering from, disease by means of administering a composition of the present invention via a mucosal route (e.g., an oral/alimentary or nasal route). Alternative mucosal routes include intravaginal and intra-rectal routes. In preferred embodiments of the present invention, a nasal route of administration is used, termed "intranasal administration" or "intranasal vaccination" herein. Methods of intranasal vaccination are well known in the art, including the administration of a droplet or spray form of the vaccine into the nasopharynx of a subject to be immunized. In some embodiments, a nebulized or aerosolized composition comprising a NE and immunogen is provided. Enteric formulations such as gastro resistant capsules for oral administration, suppositories for rectal or vaginal administration also form part of this invention. Immunogenic compositions described herein may also be administered via the oral route. Under these circumstances, a composition comprising a NE and an immunogen may comprise a pharmaceutically acceptable excipient and/or include alkaline buffers, or enteric capsules. Formulations for nasal delivery may include those with dextran or cyclodextran and saponin as an adjuvant.

Immunogenic compositions described herein may also be administered via a vaginal route. In such cases, a composition comprising a NE and an immunogen may comprise pharmaceutically acceptable excipients and/or emulsifiers, polymers (e.g., CARBOPOL), and other known stabilizers of vaginal creams and suppositories. In some embodiments, compositions of the present invention are administered via a rectal route. In such cases, a composition comprising a NE and an immunogen may comprise excipients and/or waxes and polymers known in the art for forming rectal suppositories.

In some embodiments, the same route of administration (e.g., mucosal administration) is chosen for both a priming and boosting vaccination. In some embodiments, multiple routes of administration are utilized (e.g., at the same time, or, alternatively, sequentially) in order to stimulate an immune response (e.g., using an immunogenic compositions described herein).

For example, in some embodiments, a composition comprising a NE and an immunogen is administered to a mucosal surface of a subject in either a priming or boosting vaccination regime. Alternatively, in some embodiments, a composition comprising a NE and an immunogen is administered systemically in either a priming or boosting vaccination regime. In some embodiments, a composition comprising a NE and an immunogen is administered to a subject in a priming vaccination regimen via mucosal administration and a boosting regimen via systemic administration. In some embodiments, a composition comprising a NE and an immunogen is administered to a subject in a priming vaccination regimen via systemic administration and a boosting regimen via mucosal administration. Examples of systemic routes of administration include, but are not limited to, a parenteral, intramuscular, intradermal, transdermal, subcutaneous, intraperitoneal or intravenous administration. A composition comprising a NE and an immunogen may be used for both prophylactic and therapeutic purposes.

In some embodiments, immunogenic compositions described herein are administered by pulmonary delivery. For example, immunogenic compositions described herein can be delivered to the lungs of a subject (e.g., a human) via inhalation (e.g., thereby traversing across the lung epithelial lining to the blood stream (See, e.g., Adjei, et al. Pharmaceutical Research 1990; 7:565-569; Adjei, et al. Int. J. Pharmaceutics 1990; 63:135-144; Braquet, et al. J. Cardiovascular Pharmacology 1989 143-146; Hubbard, et al. (1989) Annals of Internal Medicine, Vol. III, pp. 206-212; Smith, et al. J. Clin. Invest. 1989; 84:1145-1146; Oswein, et al. "Aerosolization of Proteins", 1990; Proceedings of Symposium on Respiratory Drug Delivery II Keystone, Colorado; Debs, et al. J. Immunol. 1988; 140:3482-3488; and U.S. Pat. No. 5,284,656 to Platz, et al, each of which are hereby incorporated by reference in its entirety). A method and composition for pulmonary delivery of drugs for systemic effect is described in U.S. Pat. No. 5,451,569 to Wong, et al., hereby incorporated by reference; See also U.S. Pat. No. 6,651,655 to Licalsi et al., hereby incorporated by reference in its entirety)). Further contemplated for use in the practice of delivery of immunogenic compositions described herein are the wide range of mechanical devices designed for pulmonary and/or nasal mucosal delivery of pharmaceutical agents described herein Thus, in some embodiments, an immunogenic composition described herein may be used to protect and/or treat a subject susceptible to, or suffering from, a disease by means of administering a compositions comprising a NE and an immunogen by mucosal, intramuscular, intraperitoneal, intradermal, transdermal, pulmonary, intravenous, subcutaneous or other route of administration described herein under conditions that induce an immunogen-specific immune response in the subject. Methods of systemic administration of the vaccine preparations may include conventional syringes and needles, or devices designed for ballistic delivery of solid vaccines (See, e.g., WO 99/27961, hereby incorporated by reference), or needleless pressure liquid jet device (See, e.g., U.S. Pat. Nos. 4,596,556; 5,993,412, each of which are hereby incorporated by reference), or transdermal patches (See, e.g., WO 97/48440; WO 98/28037, each of which are hereby incorporated by reference). The present invention may also be used to enhance the immunogenicity of antigens applied to the skin (transdermal or transcutaneous delivery, See, e.g., WO 98/20734; WO 98/28037, each of which are hereby incorporated by reference). Thus, in some embodiments, the present invention provides a delivery device for systemic administration, pre-filled with the vaccine composition of the present invention.

The present invention is not limited by the type of subject administered (e.g., in order to stimulate an immune response (e.g., in order to generate protective immunity (e.g., mucosal and/or systemic immunity))) a composition of the present invention. Indeed, a wide variety of subjects are contemplated to be benefited from administration of a composition of the present invention. In preferred embodiments, the subject is a human. In some embodiments, human subjects are of any age (e.g., adults, children, infants, etc.) that have been or are likely to become exposed to a microorganism (e.g., bacteria of the genus *Burkholderia*). In some embodiments, the human subjects are subjects that are more likely to suffer from opportunistic infection (e.g., a subject with CF or an immune suppressed subject (e.g., a subject with human immunodeficiency virus)). In some embodiments, the subjects are non-human mammals (e.g., pigs, cattle, goats, horses, sheep, or other livestock; or mice, rats, rabbits or other animal). In some embodiments, compositions and methods of the present invention are utilized in research settings (e.g., with research animals). In some embodiments, the present invention provides a method to elicit an immune response (e.g., protective immune response) in infants (e.g., from about 0-2 years old) by administering to the infant a safe and effective amount of an immunogenic composition of the invention (e.g., a pediatric vaccine). Further embodiments of the invention include the provision of the immunogenic *Burkholderia* nanoemulsion compositions of the invention for use in medicine and the use of the *Burkholderia* nanoemulsion compositions of the invention in the manufacture of a medicament for the prevention (or treatment) of disease caused by *Burkholderia*. In yet another embodiment, the present invention is provides a method to elicit an immune response (e.g., a protective immune response) in the elderly population (e.g., in a subject 50 years or over in age, typically over 55 years and more generally over 60 years) by administering a safe and effective amount of an immunogenic composition of the invention.

Immunogenic compositions described herein may be formulated for administration by any route, such as mucosal, oral, topical, parenteral or other route described herein. The compositions may be in any one or more different forms including, but not limited to, tablets, capsules, powders, granules, lozenges, foams, creams or liquid preparations.

Topical formulations may be presented as, for instance, ointments, creams or lotions, foams, and aerosols, and may contain appropriate conventional additives such as preservatives, solvents (e.g., to assist penetration), and emollients in ointments and creams.

Topical formulations may also include agents that enhance penetration of the active ingredients through the skin. Exemplary agents include a binary combination of N-(hydroxyethyl) pyrrolidone and a cell-envelope disordering compound, a sugar ester in combination with a sulfoxide or phosphine oxide, and sucrose monooleate, decyl methyl sulfoxide, and alcohol.

Other exemplary materials that increase skin penetration include surfactants or wetting agents including, but not limited to, polyoxyethylene sorbitan mono-oleoate (Polysorbate 80); sorbitan mono-oleate (Span 80); p-isooctyl polyoxyethylene-phenol polymer (Triton WR-1330); polyoxyethylene sorbitan tri-oleate (Tween 85); dioctyl sodium sulfosuccinate; and sodium sarcosinate (Sarcosyl NL-97); and other pharmaceutically acceptable surfactants.

In certain embodiments of the invention, compositions may further comprise one or more alcohols, zinc-containing compounds, emollients, humectants, thickening and/or gelling agents, neutralizing agents, and surfactants. Water used in the formulations is preferably deionized water having a neutral pH. Additional additives in the topical formulations include, but are not limited to, silicone fluids, dyes, fragrances, pH adjusters, and vitamins.

Topical formulations may also contain compatible conventional carriers, such as cream or ointment bases and ethanol or oleyl alcohol for lotions. Such carriers may be present as from about 1% up to about 98% of the formulation. The ointment base can comprise one or more of petrolatum, mineral oil, ceresin, lanolin alcohol, panthenol, glycerin, bisabolol, cocoa butter and the like.

Immunogenic compositions described herein may additionally contain other adjunct components conventionally found in pharmaceutical compositions. Thus, for example, the compositions may contain additional, compatible, pharmaceutically-active materials such as, for example, antipuritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, preferably do not unduly interfere with the biological activities of the immunogenic compositions described herein. The formulations can be sterilized and, if desired, mixed with auxiliary agents (e.g., lubricants, preservatives, stabilizers, wetting agents, emulsifiers, salts for influencing osmotic pressure, buffers, colorings, flavorings and/or aromatic substances and the like) that do not deleteriously interact with the NE and immunogen of the formulation. In some embodiments, immunogenic compositions described herein are administered in the form of a pharmaceutically acceptable salt. When used the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include, but are not limited to, acetic acid and a salt (1-2% w/v); citric acid and a salt (1-3% w/v); boric acid and a salt (0.5-2.5% w/v); and phosphoric acid and a salt (0.8-2% w/v). Suitable preservatives may include benzalkonium chloride (0.003-0.03% w/v); chlorobutanol (0.3-0.9% w/v); parabens (0.01-0.25% w/v) and thimerosal (0.004-0.02% w/v).

In some embodiments, a composition comprising a NE and an immunogen is co-administered with one or more antibiotics. For example, one or more antibiotics may be administered with, before and/or after administration of a composition comprising a NE and an immunogen. The present invention is not limited by the type of antibiotic co-administered. Indeed, a variety of antibiotics may be co-administered including, but not limited to, □ lactam antibiotics, penicillins (such as natural penicillins, aminopenicillins, penicillinase-resistant penicillins, carboxy penicillins, ureido penicillins), cephalosporins (first generation, second generation, and third generation cephalosporins), and other □ lactams (such as imipenem, monobactams,), β-lactamase inhibitors, vancomycin, aminoglycosides and spectinomycin, tetracyclines, chloramphenicol, erythromycin, lincomycin, clindamycin, rifampin, metronidazole, polymyxins, doxycycline, quinolones (e.g., ciprofloxacin), sulfonamides, trimethoprim, and quinolines.

There are an enormous amount of antimicrobial agents currently available for use in treating bacterial, fungal and viral infections. For a comprehensive treatise on the general classes of such drugs and their mechanisms of action, the skilled artisan is referred to Goodman & Gilman's "The Pharmacological Basis of Therapeutics" Eds. Hardman et al., 9th Edition, Pub. McGraw Hill, chapters 43 through 50, 1996, (herein incorporated by reference in its entirety). Generally, these agents include agents that inhibit cell wall synthesis (e.g., penicillins, cephalosporins, cycloserine, vancomycin, bacitracin); and the imidazole antifungal agents (e.g., miconazole, ketoconazole and clotrimazole); agents that act directly to disrupt the cell membrane of the microorganism (e.g., detergents such as polmyxin and colistimethate and the antifungals nystatin and amphotericin B); agents that affect the ribosomal subunits to inhibit protein synthesis (e.g., chloramphenicol, the tetracyclines, erythromycin and clindamycin); agents that alter protein synthesis and lead to cell death (e.g., aminoglycosides); agents that affect nucleic acid metabolism (e.g., the rifamycins and the quinolones); the antimetabolites (e.g., trimethoprim and sulfonamides); and the nucleic acid analogues such as zidovudine, gangcyclovir, vidarabine, and acyclovir which act to inhibit viral enzymes essential for DNA synthesis. Various combinations of antimicrobials may be employed.

The present invention also includes methods involving co-administration of a composition comprising a NE and an immunogen with one or more additional active and/or immunostimulatory agents (e.g., a composition comprising a NE and a different immunogen, an antibiotic, anti-oxidant, etc.). Indeed, it is a further aspect of this invention to provide methods for enhancing prior art immunostimulatory methods (e.g., immunization methods) and/or pharmaceutical compositions by co-administering a composition of the present invention. In co-administration procedures, the agents may be administered concurrently or sequentially. In one embodiment, the compositions described herein are administered prior to the other active agent(s). The pharmaceutical formulations and modes of administration may be any of those described herein. In addition, the two or more co-administered agents may each be administered using different modes (e.g., routes) or different formulations. The additional agents to be co-administered (e.g., antibiotics, adjuvants, etc.) can be any of the well-known agents in the art, including, but not limited to, those that are currently in clinical use.

In some embodiments, a composition comprising a NE and immunogen is administered to a subject via more than one route. For example, a subject that would benefit from having a protective immune response (e.g., immunity) towards a pathogenic microorganism may benefit from receiving mucosal administration (e.g., nasal administration or other mucosal routes described herein) and, additionally, receiving one or more other routes of administration (e.g., parenteral or pulmonary administration (e.g., via a nebulizer, inhaler, or other methods described herein). In some preferred embodiments, administration via mucosal route is sufficient to induce both mucosal as well as systemic immunity towards an immunogen or organism from which the immunogen is derived. In other embodiments, administration via multiple routes serves to provide both mucosal and systemic immunity. Thus, although an understanding of the mechanism is not necessary to practice the present invention and the present invention is not limited to any particular mechanism of action, in some embodiments, it is contemplated that a subject administered a composition of the present invention via multiple routes of administration (e.g., immunization (e.g., mucosal as well as airway or parenteral administration of a composition comprising a NE and immunogen of the present invention) may have a stronger immune response to an immunogen than a subject administered a composition via just one route.

Other delivery systems can include time-release, delayed release or sustained release delivery systems. Such systems can avoid repeated administrations of the compositions, increasing convenience to the subject and a physician. Many types of release delivery systems are available and known to those of ordinary skill in the art. They include polymer based systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109, hereby incorporated by reference. Delivery systems also include non-polymer systems that are: lipids including sterols such as cholesterol, cholesterol esters and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, each of which is hereby incorporated by reference and (b) diffusional systems in which an active component permeates at a controlled rate from a polymer such as described in U.S. Pat. Nos. 3,854,480, 5,133,974 and 5,407,686, each of which is hereby incorporated by reference. In addition, pump-based hardware delivery systems can be used, some of which are adapted for implantation.

In preferred embodiments, a composition comprising a NE and an immunogen of the present invention comprises a suitable amount of the immunogen to induce an immune response in a subject when administered to the subject. In preferred embodiments, the immune response is sufficient to provide the subject protection (e.g., immune protection) against a subsequent exposure to the immunogen or the microorganism (e.g., bacteria of the genus *Burkholderia*) from which the immunogen was derived. The present invention is not limited by the amount of immunogen used. In some preferred embodiments, the amount of immunogen (e.g., *Burkholderia* bacteria (e.g., *Burkholderia cepacia*) or one or more component parts thereof) in a composition comprising a NE and immunogen (e.g., for use as an immunization dose) is selected as that amount which induces an immunoprotective response without significant, adverse side effects. The amount will vary depending upon which specific immunogen or combination thereof is/are employed, and can vary from subject to subject, depending on a number of factors including, but not limited to, the species, age and general condition (e.g., health) of the subject, and the mode of administration.

In some embodiments, each dose (e.g., of a composition comprising a NE and an immunogen (e.g., administered to a subject to induce an immune response (e.g., a protective immune response (e.g., protective immunity))) comprises about 0.05-5000 μg of immunogen (e.g., recombinant and/or purified *Burkholderia* OMP protein). In some embodiments, each dose (e.g., of a composition comprising a NE and an immunogen (e.g., administered to a subject to induce an immune response (e.g., a protective immune response (e.g., protective immunity))) comprises about 0.05-5000 μg of the immunogen (e.g., recombinant and/or purified *Burkholderia* OMP protein) and comprises about 0.05-5000 μg of another immunogen (e.g., recombinant and/or purified protein, adjuvant (e.g., cholera toxin), etc.). In some embodiments, each dose will comprise 1-500 μg, in some embodiments, each dose will comprise 350-750 μg, in some embodiments, each dose will comprise 50-200 μg, in some embodiments, each dose will comprise 25-75 μg of immunogen (e.g., recombinant and/or purified protein (e.g., *Burkholderia* antigen). In some embodiments, each dose comprises an amount of the immunogen sufficient to generate an immune response. An effective amount of the immunogen in a dose need not be quantified, as long as the amount of immunogen generates an immune response in a subject when administered to the subject.

In some embodiments, it is expected that each dose (e.g., of a composition comprising a NE and an immunogen (e.g., administered to a subject to induce and immune response)) is from 0.001 to 15% or more (e.g., 0.001-10%, 0.5-5%, 1-3%, 2%, 6%, 10%, 15% or more) by weight immunogen (e.g., neutralized bacteria, or recombinant and/or purified protein). In some embodiments, an initial or prime administration dose contains more immunogen than a subsequent boost dose In some embodiments, a composition comprising a NE and an immunogen of the present invention is formulated in a concentrated dose that can be diluted prior to administration to a subject. For example, dilutions of a concentrated composition may be administered to a subject such that the subject receives any one or more of the specific dosages provided herein. In some embodiments, dilution of a concentrated composition may be made such that a subject is administered (e.g., in a single dose) a composition comprising 0.5-50% of the NE and immunogen present in the concentrated composition. In some preferred embodiments, a subject is administered in a single dose a composition comprising 1% of the NE and immunogen present in the concentrated composition. Concentrated compositions are contemplated to be useful in a setting in which large numbers of subjects may be administered a composition of the present invention (e.g., an immunization clinic, hospital, school, etc.). In some embodiments, a composition comprising a NE and an immunogen of the present invention (e.g., a concentrated composition) is stable at room temperature for more than 1 week, in some embodiments for more than 2 weeks, in some embodiments for more than 3 weeks, in some embodiments for more than 4 weeks, in some embodiments for more than 5 weeks, and in some embodiments for more than 6 weeks.

Generally, the emulsion compositions of the invention will comprise at least 0.001% to 100%, preferably 0.01 to 90%, of emulsion per ml of liquid composition. It is envisioned that the formulations may comprise about 0.001%, about 0.0025%, about 0.005%, about 0.0075%, about 0.01%, about 0.025%, about 0.05%, about 0.075%, about 0.1%, about 0.25%, about 0.5%, about 1.0%, about 2.5%, about 5%, about 7.5%, about 10%, about 12.5%, about 15%, about 20%, about 25%, about 30%, about 35%, about 40%, about 50%, about 55%, about 60%, about 65%, about 70%, about 75%, about 80%, about 85%, about 90%, about 95% or about 98% of emulsion per ml of liquid composition. It should be understood that a range between any two figures listed above is specifically contemplated to be encompassed within the metes and bounds of the present invention. Some variation in dosage will necessarily occur depending on the condition of the specific pathogen and the subject being immunized.

In some embodiments, following an initial administration of a composition of the present invention (e.g., an initial vaccination), a subject may receive one or more boost administrations (e.g., around 2 weeks, around 3 weeks, around 4 weeks, around 5 weeks, around 6 weeks, around 7 weeks, around 8 weeks, around 10 weeks, around 3 months, around 4 months, around 6 months, around 9 months, around 1 year, around 2 years, around 3 years, around 5 years, around 10 years) subsequent to a first, second, third, fourth, fifth, sixth, seventh, eighth, ninth, tenth, and/or more than tenth administration. Although an understanding of the mechanism is not necessary to practice the present invention and the present invention is not limited to any particular mechanism of action, in some embodiments, reintroduction of an immunogen in a boost dose enables vigorous systemic immunity in a subject. The boost can be with the same formulation given for the primary immune response, or can be with a different formulation that contains the immunogen. The dosage regimen will also, at least in part, be determined by the need of the subject and be dependent on the judgment of a practitioner.

Dosage units may be proportionately increased or decreased based on several factors including, but not limited to, the weight, age, and health status of the subject. In addition, dosage units may be increased or decreased for subsequent administrations (e.g., boost administrations).

It is contemplated that the compositions and methods of the present invention will find use in various settings, including research settings. For example, compositions and methods of the present invention also find use in studies of the immune system (e.g., characterization of adaptive immune responses (e.g., protective immune responses (e.g., mucosal or systemic immunity))). Uses of the compositions and methods provided by the present invention encompass human and non-human subjects and samples from those subjects, and also encompass research applications using these subjects. Compositions and methods of the present invention are also useful in studying and optimizing nanoemulsions, immunogens, and other components and for screening for new components. Thus, it is not intended that the present invention be limited to any particular subject and/or application setting.

The formulations can be tested in vivo in a number of animal models developed for the study of mucosal and other routes of delivery. As is readily apparent, the compositions of the present invention are useful for preventing and/or treating a wide variety of diseases and infections caused by viruses, bacteria, parasites, and fungi, as well as for eliciting an immune response against a variety of antigens. Not only can the compositions be used prophylactically or therapeutically, as described above, the compositions can also be used in order to prepare antibodies, both polyclonal and monoclonal (e.g., for diagnostic purposes), as well as for immunopurification of an antigen of interest. If polyclonal antibodies are desired, a selected mammal, (e.g., mouse, rabbit, goat, horse, etc.) can be immunized with the compositions of the present invention. The animal is usually boosted 2-6 weeks later with one or more—administrations of the antigen. Polyclonal antisera can then be obtained from the immunized animal and used according to known procedures (See, e.g., Jurgens et al., J. Chrom. 1985, 348:363-370).

In some embodiments, the present invention provides a kit comprising a composition comprising a NE and an immunogen. In some embodiments, the kit further provides a device for administering the composition. The present invention is not limited by the type of device included in the kit. In some embodiments, the device is configured for nasal application of the composition of the present invention (e.g., a nasal applicator (e.g., a syringe) or nasal inhaler or nasal mister). In some embodiments, a kit comprises a composition comprising a NE and an immunogen in a concentrated form (e.g., that can be diluted prior to administration to a subject).

In some embodiments, all kit components are present within a single container (e.g., vial or tube). In some embodiments, each kit component is located in a single container (e.g., vial or tube). In some embodiments, one or more kit component are located in a single container (e.g., vial or tube) with other components of the same kit being located in a separate container (e.g., vial or tube). In some embodiments, a kit comprises a buffer. In some embodiments, the kit further comprises instructions for use.

EXPERIMENTAL

The following examples are provided in order to demonstrate and further illustrate certain preferred embodiments and aspects of the present invention and are not to be construed as limiting the scope thereof.

Example 1

In vivo Toxicity Studies

A nanoemulsion composition of the present invention was tested to determine if pulmonary administration of the composition to a subject would elicit any histological changes and/or pathology.

A solution comprising 20% nanoemulsion ($W_{80}$5EC) and 0.1% EDTA was administered via a nebulizer. A custom murine nose only nebulization chamber with PARI LC nebulizer (Midlothian, Va.) and compressor was used. A 0.9% NaCl solution was used as a control. Using the nebulizer, mice were administered nebulized nanoemulsion+EDTA or NaCl solution for 10 minutes. Twenty-four hours after administration, mice were sacrificed and physical properties and histology assessed.

Upon examination, there was an absence of histological changes indicating the absence of toxicity upon administration of nebulized nanoemulsion. Physical findings were normal.

Example 2

Killing Assays Utilizing Nanoemulsion Compositions and Bacteria Found in the Respiratory Tract It was determined whether a composition comprising nanoemulsion ($W_{80}$5EC) alone or in combination with EDTA and/or the presence of a hypertonic salt solution would be able to attenuate growth and/or kill bacteria found in the respiratory tract.

An overnight culture of *Burkholderia cepacia* or *Pseudomonas aeruginosa* was started in 6 ml of cation adjusted Mueller Hinton Broth (MHB) from a frozen bacterial stock at −80° C. The culture was incubated in a shaking incubator at 37° C. The following day, bacteria were brought to logarithmic growth phase by back diluting the overnight culture 1:4 with fresh MHB. Back diluted culture was incubated at 37° C. in the shaking incubator until the OD600 reached between 0.40 to 0.45. One ml of the culture was spun down at 3500 to 4000 rpm for 15 minutes. The bacterial pellet was resuspended in 1 ml of sterile 2×PBS, 12% or 14% saline. Appropriate dilutions were done with the same solutions to get desired numbers of bacteria in 50 μl (OD600 of 0.5 approximately=$10^9$ bacteria). Dilutions of the starting bacterial suspensions were plated onto Luria Bertani (LB) agar plates to estimate the starting bacterial counts. Double the concentrations of the desired final nanoemulsion and nanoemulsion with EDTA concentrations were made with sterile milliQ water. Fifty micro liters of the nanoemulsion was mixed with 50 μl of the bacteria and vortexed to mix the reaction. The mixture was incubated at 37° C. for desired time intervals. Following incubation, the reaction was diluted with 500 μl of 1×PBS and vortexed to mix the contents. The contents were centrifuged at 4000 rpm for 15 minutes to pellet the bacteria and separate the nanoemulsion. Supernatant containing the nanoemulsion was removed and the bacterial pellet resuspended in 1×PBS. Undiluted or dilutions of the resuspended bacterial pellet was plated onto LB agar plates for colony count. Log killing of the bacteria were calculated from ratio with the starting numbers.

Figure 2:
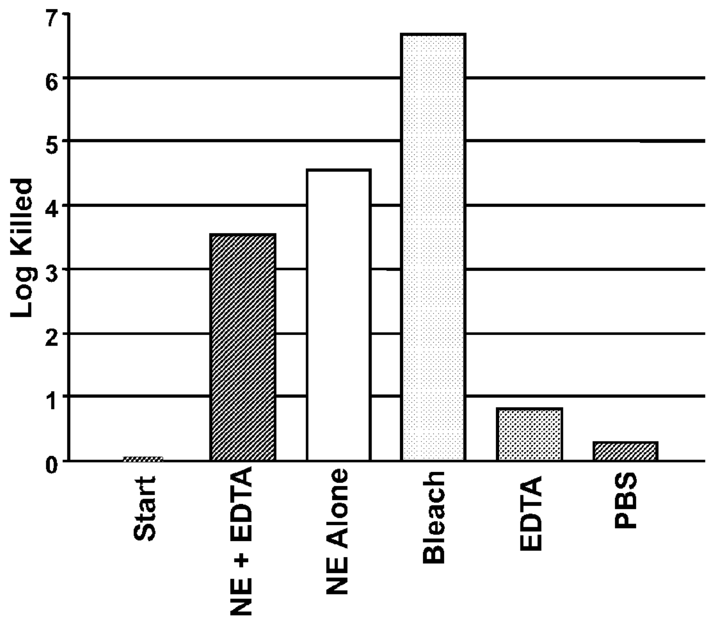
FIG. 2 shows killing of *B. cepacia* in PBS by 20% NE alone or with 20 mM EDTA in 20 minutes.
Figure 3:
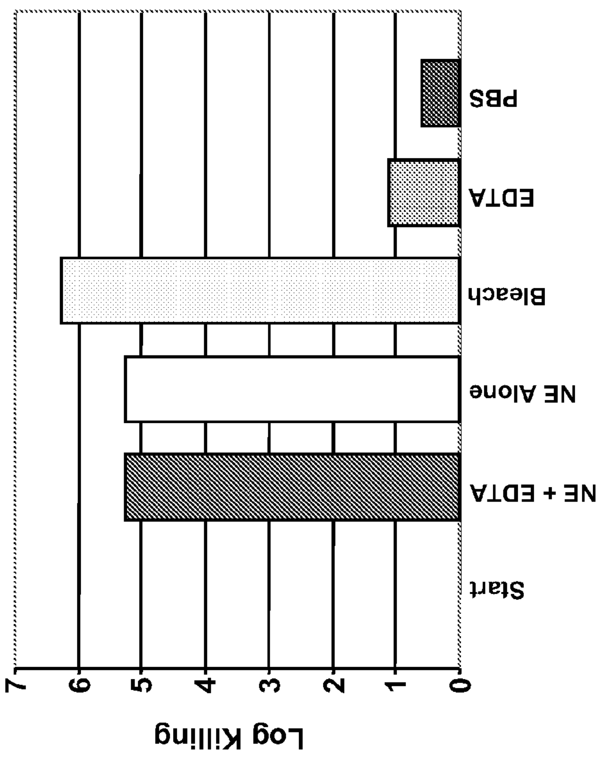
FIG. 3 shows killing of *B. cepacia* in PBS by 20% NE alone or with 20 mM EDTA in 40 minutes.
Figure 4A:
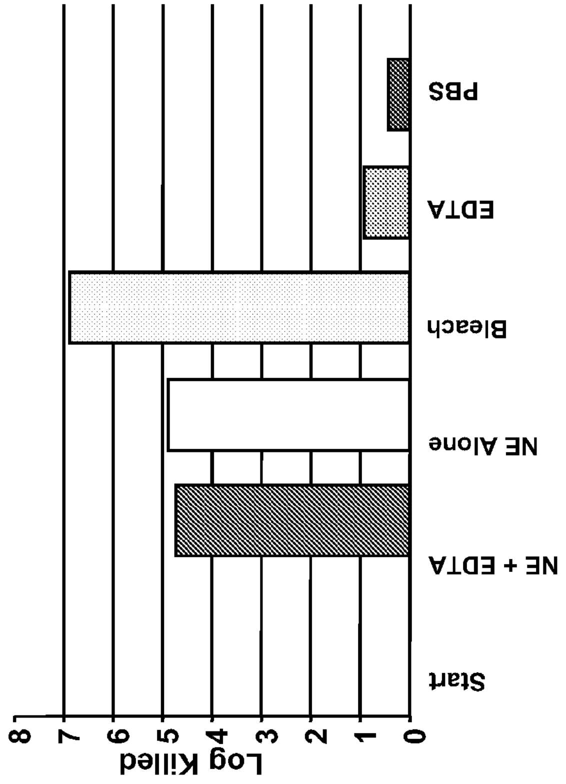
FIG. 4 shows (FIG. 4A) killing of *B. cepacia* in PBS by 20% NE alone or with 20 mM EDTA in 40 minutes.
(FIG. 4B) killing of *B. cepacia* in PBS by 20% NE alone or with 20 mM EDTA in 60 minutes.
(FIG. 4C) killing of *B. cepacia* in PBS by 20% NE alone or with 20 mM EDTA in 60 minutes.
Figure 4B:
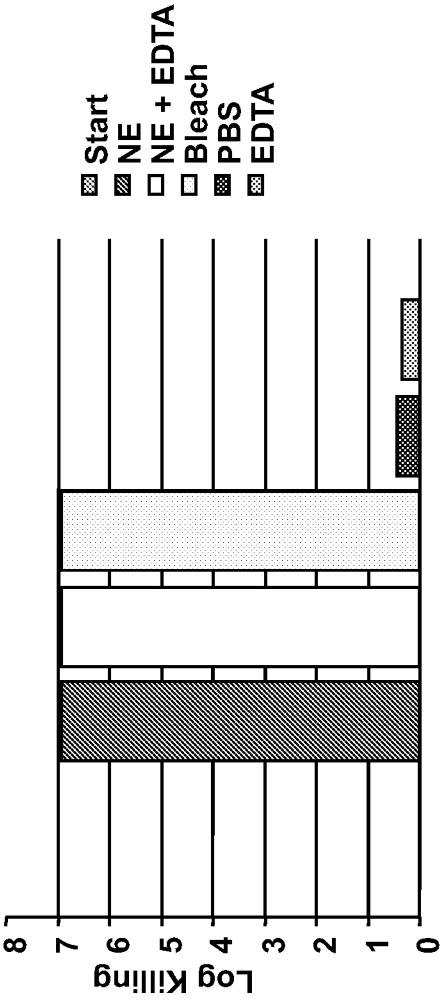
Figure 4C:
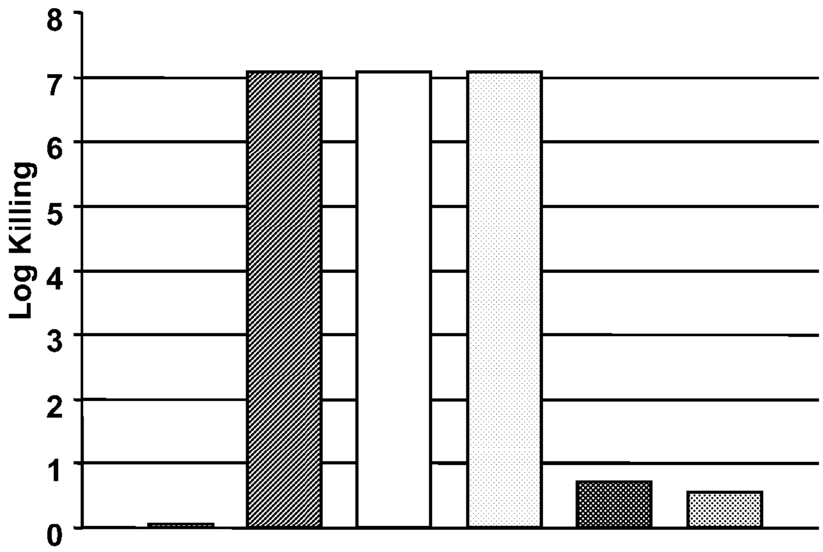
Figure 5:
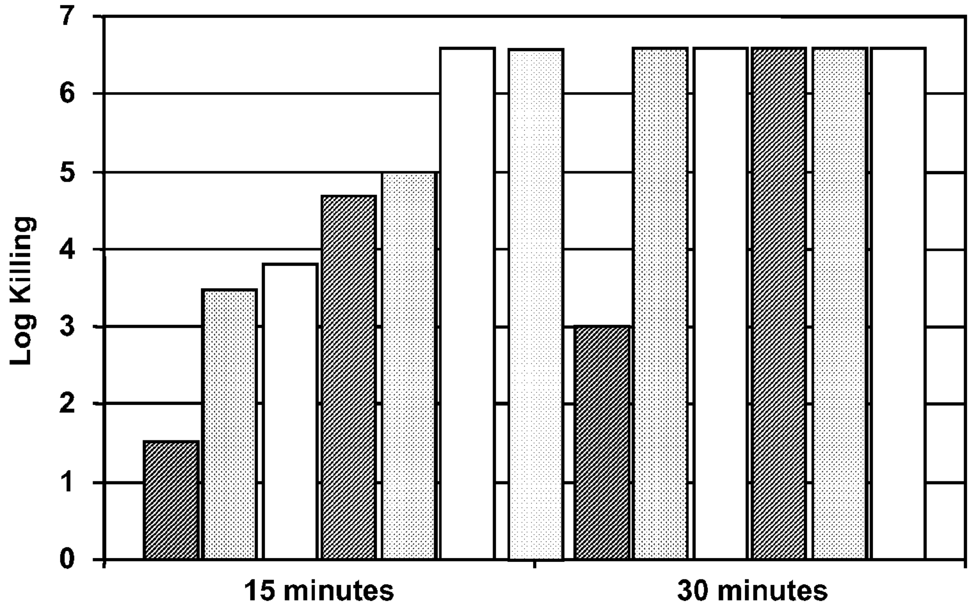
FIG. 5 shows killing of *B. cepacia* in hypertonic saline (6% NaCl) at 15 and 30 Minutes by NE alone and NE with EDTA.
Figure 6:
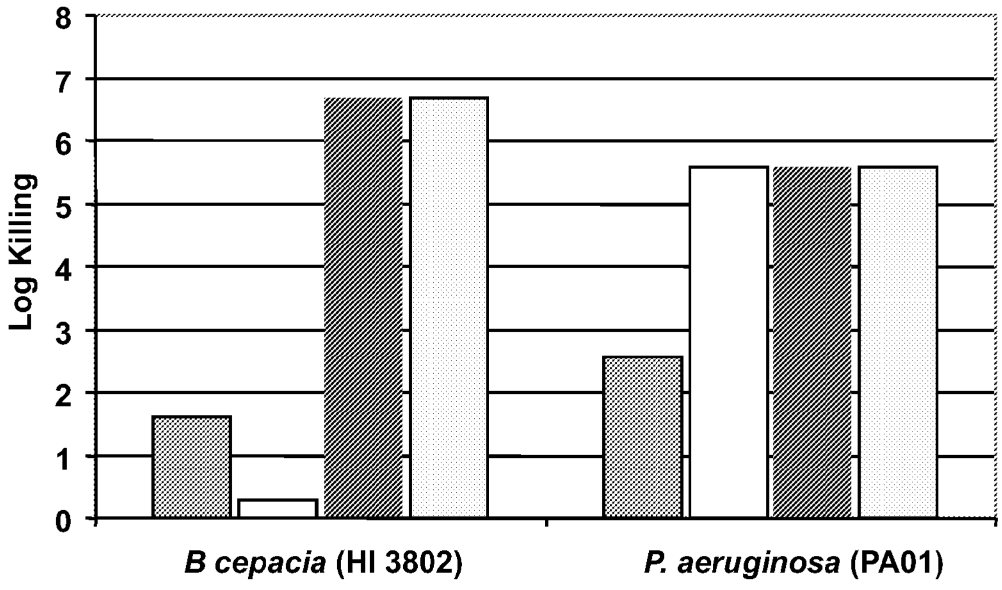
FIG. 6 shows killing of *B. cepacia* and *P. aeruginosa* in 7% NaCl within 15 min.
Figure 7:
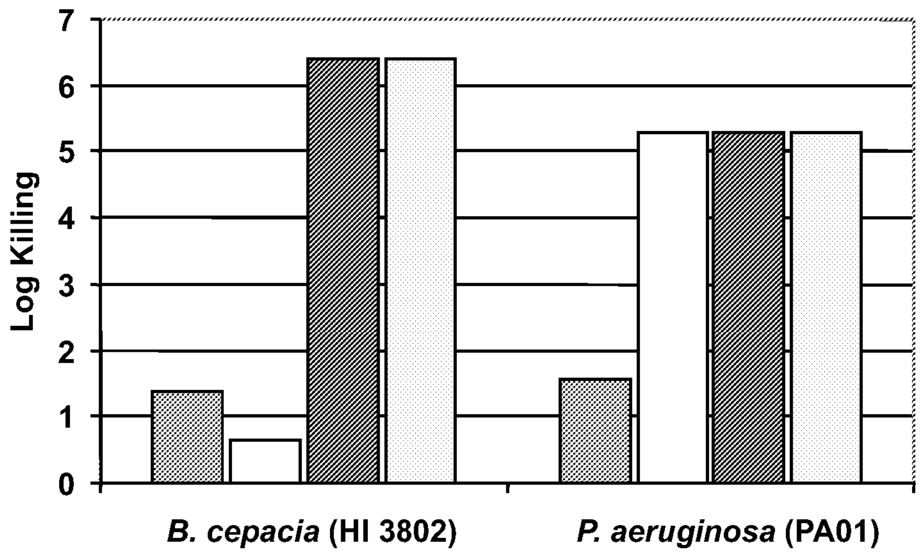
FIG. 7 shows killing of *B. cepacia* and *P. aeruginosa* (Mixed-culture) in 7% NaCl within 15 minutes.

The following killing assays were performed:

Killing of *Burkholderia cepacia* in PBS by 20% Nanemulsion (NE) alone or with 20 mM EDTA in 10 minutes (See FIG. 1);

Killing of *B. cepacia* in PBS by 20% NE alone or with 20 mM EDTA within 20 minutes (See FIG. 2);

Killing of *B. cepacia* in PBS by 20% NE alone or with 20 mM EDTA within 40 minutes (See FIG. 3);

Killing of *B. cepacia* in PBS by 20% NE alone or with 20 mM EDTA within 40 or 60 minutes (See FIG. 4);

Killing of *B. cepacia* in hypertonic saline (6% NaCl) at 15 and 30 minutes by NE alone and NE with EDTA (See FIG. 5);

Killing of *B. cepacia* and *P. aeruginosa* in 7% NaCl within 15 min (See FIG. 6); and Killing of *B. cepacia* and *P. aeruginosa* (Mixed-culture) in 7% NaCl within 15 minutes (See FIG. 7).

Nanoemulsion alone or in combination with EDTA (e.g., 10-20 mM EDTA) was able to achieve complete killing of $10^6$ bacteria in PBS in 60 minutes. In the presence of hypertonic saline (e.g., 6-7% NaCl), the killing ability of the nanoemulsion was strikingly enhanced, achieving complete killing within 15 minutes while in the presence of 20 mM EDTA. Also, nanoemulsions comprising a lower concentration of EDTA were able to achieve complete killing of bacteria in 30 minutes in the presence of hypertonic saline. Thus, the present invention provides that a nanoemulsion composition comprising EDTA can be used to kill (e.g., completely) bacteria over a short time period (e.g., <60 minutes). Moreover, the present invention provides that nanoemulsion with hypertonic saline and EDTA can be used to kill bacteria over even shorter time periods (e.g., <30 minutes, <15 minutes) and that the concentration of EDTA and hypertonic saline solution alter the pace at which the nanoemulsion is able to eradicate the bacteria. The present invention also demonstrates that compositions of the present invention are able to eradicate a mixed population of bacteria.

Example 3

Nanoemulsion Killing of Cystic Fibrosis (CF) Related Bacteria Including Multi-drug Resistant Strains Materials and Methods.

Bacterial strains and culture conditions. One hundred fifty isolates were analyzed including 75 *Burkholderia* isolates and 75 isolates belonging to other CF-relevant species, including *Pseudomonas aeruginosa, Achromobacter xylosoxidans, Stenotrophomonas maltophilia, Acinetobacter* species, *Pandoraea* species (*P. apista, P. pnomenusa, P. pulmonicola, P. norimburgensis*, and *P. sputorum*), and *Ralstonia* species (*R. mannitolilytica* and *R. pickettii*). One hundred forty-five clinical isolates were obtained from the *Burkholderia cepacia* Research Laboratory and Repository (BcRLR, University of Michigan, Ann Arbor, Mich.). These were recovered from 142 individuals between September 1997 and October 2007 and were referred to the BcRLR from 62 CF treatment centers in the U.S. for analysis. The remaining five strains included environmental isolates *B. multivorans* ATCC 17616 (American Type Culture Collection, Manassas, Va.), *P. norimburgensis* LMG $18379^T$ (BCCM/LMG Bacteria Collection, Laboratorium voor Micrbiologie Gent, Universiteit Gent, Ghent, Belgium) and *B. pyrrocinia* HI3642 (BcRLR collection), and the clinical type strains *B. cenocepacia* LMG $16656^T$ (aka J2315) and P. pulmonicola LMG $18106^T$. One hundred thirty four (91%) of the 147 clinical isolates were recovered from persons with CF; 114 (78%) of these were from sputum culture, with the remainder from throat swab (n=17), endotracheal suction/tracheal aspiration (n=5), blood (n=5), bronchial lavage (n=3), and one each from maxillary sinus, peritoneal cavity, and epiglottis. Forty nine (33%) of the 150 isolates were defined as multi-drug resistant (resistant to all drugs tested in two of three antibiotic classes: lactams including carbapenems, aminoglycosides, and quinolones; See, e.g., Taccetti et al., Eur J Epidemiol. 1999 January; 15(1):85-8) based on susceptibility testing performed at the referring microbiology laboratory; 20 (41%) of these were panresistant. Seventy two (48%) of the remaining isolates were susceptible to at least one antibiotic, and susceptibility testing results were unavailable for 29 (19%) isolates. All isolates were identified to the species level at the BcRLR by polyphasic analyses using phenotypic and genotypic assays as described (See, e.g., Reik et al., J Clin Microbiol. 2005 June; 43(6):2926-8). The exception was *Acinetobacter*, which was identified only to the genus level due to lack of definitive species-specific assays. All isolates were also subjected to repetitive extragenic element-PCR (rep-PCR) typing using the BOX AIR primer as previously described (See, e.g., Coenye et al., J Clin Microbiol. 2002 September; 40(9): 3300-7) to ensure that all 150 isolates included in the test panel were genotypically distinct. Bacteria were stored at −80° C. in skim milk or Lauria-Bertani (LB) broth with 15% glycerol and recovered from frozen stock overnight at 37° C. on Mueller-Hinton (MH) agar.

Nanoemulsion. Nanoemulsion $P_{407}5EC$, described herein, was manufactured by NANOBIO Corp. (Ann Arbor, Mich.). $P_{407}5EC$ droplets had a mean particle diameter of 400 nm. Surfactants and food substances utilized in the manufacture of $P_{407}5EC$ were 'Generally Recognized as Safe' (GRAS) by the FDA, and manufactured in accordance with Good Manufacturing Practices (GMP). The concentration of CPC was used as a surrogate for the amount of $P_{407}5EC$ used experimentally. $P_{407}5EC$ was stable for no less than 12 months at 40° C.

Susceptibility testing. Because $P_{407}5EC$ is opaque, the MICs of this compound for test bacteria were determined by using a modification of the Clinical and Laboratory Standards Institute (CLSI)-approved microtiter serial dilution method (See, e.g., Clinical and Laboratory Standards Institute. 2006. Approved standard M7-A7, seventh edition. Clinical and Laboratory Standards Institute, Wayne, Pa.). $P_{407}5EC$ was diluted to a concentration of 2 mg/ml (of CPC) in MH broth supplemented with 7% NaCl and 20 mM EDTA. Serial two-fold dilutions of this preparation were made in unsupplemented MH broth and aliquoted into 96-well flat bottom microtiter plates (100 μl/well). Bacteria from overnight growth on MH agar were suspended in MH broth to a 0.5 McFarland turbidity standard (absorbance of 0.08~0.13 at 625 nm), further diluted 1:100 in MH broth, and added (5 μl/well) to the $P_{407}5EC$ serial dilution wells. Appropriate controls, including wells with bacteria but no $P_{407}5EC$ and wells with $P_{407}5EC$ dilutions but no bacteria, were included on each plate. Microtiter plates were shaken briefly, and 1 μl was removed from wells containing bacteria but no $P_{407}5EC$, diluted in 1 ml of MH broth, plated on MH agar (100 μl), and incubated for 24-48 h at 37° C. to determine bacterial concentrations of initial inoculums. Microtiter plates were then incubated at 37° C. without shaking To determine MBCs, 10 μl were removed from each well after overnight growth, spotted on MH agar, and incubated at 37° C. Colonies were enumerated 24 h later, and MBCs were recorded as the $P_{407}5EC$ concentration with a 3 log decrease in CFU/ml compared to the initial inoculum. To determine MICs, 10 μl of resazurin (R&D SYSTEMS, Minneapolis, Minn.) were added to each well and microtiter plates were shaken briefly, covered with foil, and incubated at 37° C. without shaking Wells were visually inspected the next day, and the MIC was recorded as the lowest concentration of $P_{407}5EC$ remaining a blue color. MIC results were further quantified by recording fluorescence on a spectrofluorometer at 560 nm excitation/590 nm emission.

Biofilm growth and susceptibility testing. To identify biofilm-forming isolates, bacteria were grown overnight in tryptic soy broth, adjusted to a 0.5 McFarland turbidity standard, and further diluted 1:10 in MH broth, and 100 μl were seeded in triplicate in internal wells of 96-well flat bottom microtiter plates. Negative control wells without bacteria were included. To minimize evaporation, the remaining wells were filled with MH broth, and the plate was wrapped with plastic wrap before incubating for 48 h at 37° C. without shaking Wells were gently washed twice with phosphate buffered saline (PBS; pH 7.4), dried for 2 h at 37° C., and then stained with 1% crystal violet in water for 15 min. Stained wells were washed 3 times with PBS, and crystal violet was solubilized by the addition of absolute methanol. After incubation for 5 min at room temperature, the solubilized crystal violet was transferred to a new microtiter plate and scanned at 590 nm in a spectrophotometer. A biofilm-forming isolate was defined as one where the average absorbance of the 3 wells was greater than the average absorbance of the negative control wells plus 3 standard deviations (See, e.g., Stepanovic et al., J Microbiol Methods. 2000 April;40(2):175-9).

For biofilm susceptibility testing, isolates shown to produce biofilm by crystal violet testing were grown in triplicate for 48 h as described above. Wells were gently washed twice with PBS before addition of $P_{407}5EC$, serially diluted as described for planktonic MIC testing. After overnight incubation at 37° C., wells were again washed twice with PBS, and 100 μl of 10% resazurin in MH broth was added to wells. Plates were wrapped in plastic, covered with foil, and again incubated overnight at 37° C. without shaking Plates were visually inspected the next day, and the minimum biofilm inhibitory concentration (MBIC) was recorded as the lowest concentration of $P_{407}$5EC in which the wells were a blue color. To calculate minimum biofilm eradication concentrations (MBECs), biofilm was resuspended in the same wells used for MBIC testing by shaking the microtiter plate and then scraping the sides of the wells with a pipet tip. Ten μl were removed from each well, spotted on MH agar plates and incubated at 37° C. After overnight growth, MBECs were recorded as the lowest $P_{407}$5EC concentration resulting in no growth (See, e.g., Tomlin et al., Can J Microbiol. 2001 October; 47(10):949-54). To confirm initial inoculum concentrations and to quantify viable bacteria in biofilm grown cultures, colonies were enumerated from 10-fold serial dilutions of the 0.5 McFarland inoculating culture and from the untreated positive control wells with resuspended biofilm for MBEC calculations.

Sputum preparation. Expectorated sputum, collected from CF patients during the course of routine care, was obtained from the University of Michigan Health System clinical microbiology laboratory and stored at −80° C. Equal volumes of sputum from 15 individuals were pooled, mechanically sheared using a TISSUE MISER homogenizer (FISHER SCIENTIFIC, Pittsburgh, Pa.) at room temperature for 5 min at maximum speed, and then incubated in an 80° C. water bath for 20 min. Processed sputum was divided into 10 ml aliquots, and 100 μl from each aliquot was plated on MH agar and incubated for 48 h at 37° C. to confirm sterility. Aliquots were stored at −80° C.

Results.

Figure 8:
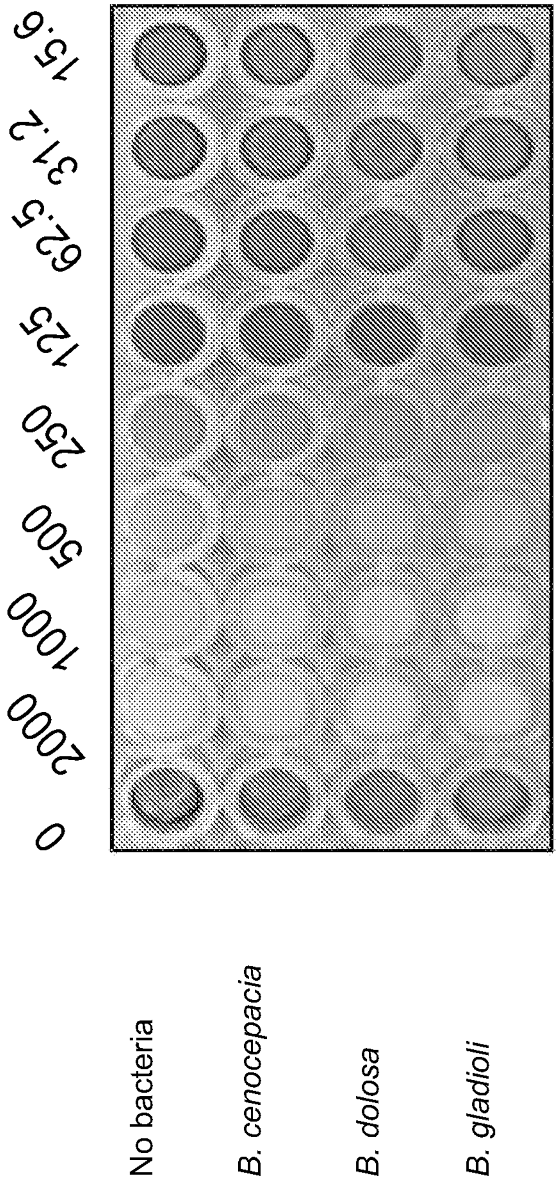
FIG. 8 shows a microtiter serial dilution MIC assay. Numbers above the plate indicate the concentration (μg/ml CPC) of $P_{407}$5EC added to each column of wells. The bacterial species added to wells in each row is indicated on the left. The MICs for these strains (top to bottom) are ≤15.6 μg/ml, 125 μg/ml, and 31.2 μg/ml.
Figure 9:
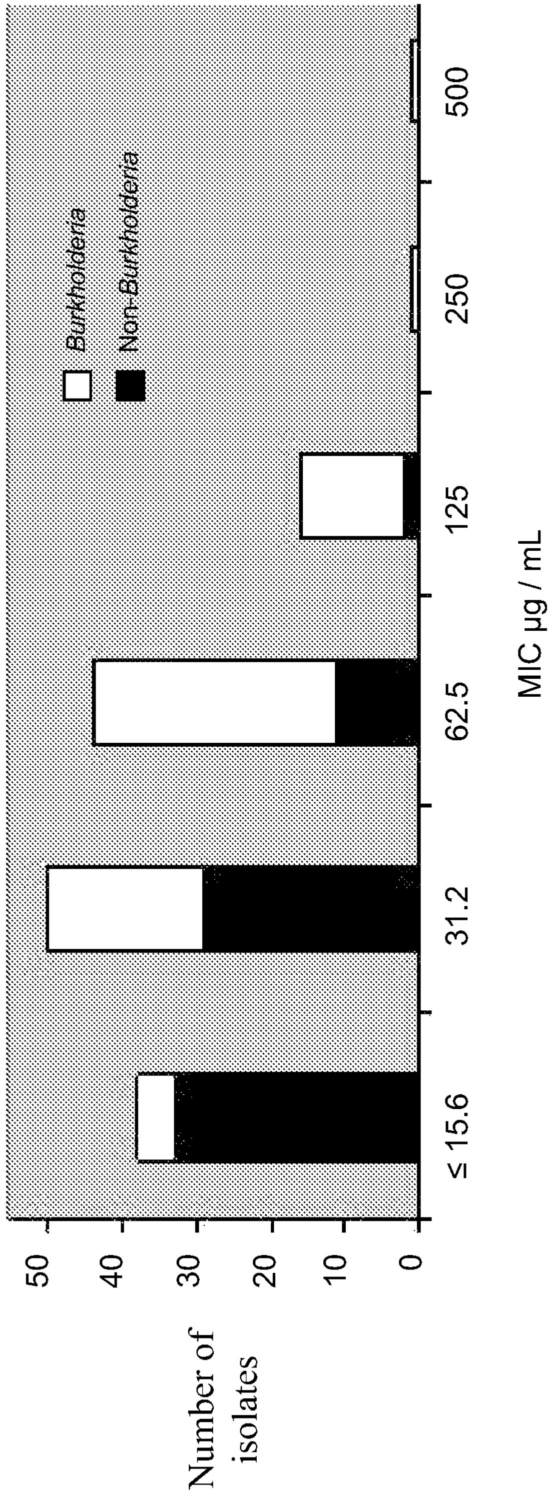
FIG. 9 shows distribution of $P_{407}$5EC MICs for 150 *Burkholderia* and non-*Burkholderia* strains

Susceptibility of planktonic bacteria. Due to the opaque white color of $P_{407}$5EC, the standard CLSI-approved microtiter serial dilution method was modified to include the addition of resazurin as an indicator of bacterial viability. $P_{407}$5EC was tested in a concentration range of 15.6-2000 μg/ml. MICs were defined as the lowest concentration of $P_{407}$5EC that did not produce a color change from blue to pink (See FIG. 8). Comparison of this visual inflection point with fluorometric analysis showed that 63% of MIC wells had ≤1% of the metabolic activity of untreated control wells; 91% had ≤5% metabolic activity, and 96% had ≤10% metabolic activity compared to control wells. The MIC results are shown in FIG. 11. All strains were inhibited by the concentrations of $P_{407}$5EC tested. The $MIC_{50}$ for the entire panel of 150 strains was 31.2 μg/ml; the $MIC_{90}$ was 125 μg/ml. Thirty eight strains (25%) were inhibited by the lowest concentration of $P_{407}$5EC tested (15.6 μg/ml), and only a single strain each required a concentration of 250 μg/ml and 500 μg/ml for inhibition. $P_{407}$5EC was slightly more active against non-*Burkholderia* strains ($MIC_{50}$ 31.2 μg/ml; $MIC_{90}$ 62.5 μg/ml) than *Burkholderia* strains ($MIC_{50}$ 62.5 μg/ml; $MIC_{90}$ 125 μg/ml) (See FIG. 9). Activity was comparable across the 10 *Burkholderia* species tested. No difference was found in the activity of $P_{407}$5EC against multi-drug resistant *Burkholderia* strains compared to strains susceptible to one or more antibiotics.

To evaluate the bactericidal activity of $P_{407}$5EC against planktonic bacteria, MBCs were determined on a subset of 34 strains including 22 *Burkholderia* and 12 non-*Burkholderia*. All MBCs were within 1 dilution of the respective MICs for this subset of strains except for a single *B. cenocepacia* strain that had a MIC of 250 μg/ml and an MBC of 2000 μg/ml. A time-kill study of *B. multivorans* ATCC 17616 showed time- and concentration-dependent killing, with a 99% decrease in bacterial viability within 90 min at a $P_{407}$5EC concentration two times greater than the MIC and complete killing within 30 min at concentrations eight times greater than the MIC (See FIG. 10A).

Susceptibility of bacteria grown in biofilm. To further assess the activity of $P_{407}$5EC, bacteria grown as biofilms were tested for susceptibility. Crystal violet staining identified 12 biofilm-forming strains from among 25 strains screened from the test panel. Nine (75%) of the 12 strains showed decreased susceptibility to $P_{407}$5EC, defined as at least a four-fold increase in the MBIC compared to the MIC, when grown as a biofilm (See FIG. 12). The median increase in MBIC compared to the respective MIC of $P_{407}$5EC for the strains in this set was eight-fold. No evidence of tolerance of biofilm bacteria to $P_{407}$5EC was observed; the MBEC was the same as the respective MBIC for 10 of the 12 strains.

Susceptibility of bacteria in CF sputum. The 12 biofilm-forming strains were also tested for susceptibility to $P_{407}$5EC in the presence of CF sputum to model more closely the CF pulmonary microenvironment. The MBCs of $P_{407}$5EC for all 12 strains, grown under planktonic conditions, increased in the presence of 43% sputum (the highest sputum concentration achievable in the microtiter assay) compared to the respective MBCs under standard conditions (See FIG. 12). Nevertheless, all strains remained susceptible to $P_{407}$5EC in the presence of sputum. CF sputum inhibited the activity of $P_{407}$5EC against planktonic bacteria in a concentration dependent manner (See FIG. 10B).

Example 4

Nanoemulsion Killing of Individual and Mixed Bacterial Biofilms

A composition comprising nanoemulsion $P_{407}$5EC, 7% saline and 20 mM EDTA was tested for its ability to kill bacteria present in biofilms (individual or mixed).

Biofilm Growth. Bacterial biofilms on polycarbonate membranes were formed following the procedure described in Current Protocols in Microbiology (John Wiley & Sons, Inc., NJ, USA). Polycarbonate membranes were sterilized by exposing the membrane to UV light for 10 minutes each side using sterile forceps or by steam sterilization at 121° C. for 20 minutes. The sterile membrane was placed on the surface of an agar medium with the shiny surface facing upwards. Overnight culture of the bacterial strain of interest was diluted with broth media to an $OD_{600}$ of 0.05 and 0.5 μl of the diluted culture placed onto the shiny surface of the polycarbonate membrane on the agar plate medium. The plate with the membrane was incubated at 37° C. for 24 hours following which; the membrane is transferred to a new agar medium for another 24 hours for biofilm formation.

Bactericidal Assay for Biofilm Bacteria. Polycarbonate membrane with the biofilm was immersed in 250 μl of 20% $P_{407}$5EC with 20 mM EDTA and 7% sodium chloride (NaCl) in a 1.5 ml eppendorf tube for 3 hours at 37° C. Seven percent NaCl served as the negative control. Following incubation, the membrane was transferred to 15 ml sterile polypropylene tubes containing 10 ml of sterile PBS. One ml of sterile PBS was added to the eppendorf reaction tubes, vortexed and spun at 3500 rpm for 15 minutes. Following centrifugation, the supernatant containing the NE was removed and the bacterial pellet resuspended in their respective 15 ml tube in which the polycarbonate membrane was collected. The 15 ml tube was then vortexed at maximum speed for 3 minutes to get bacteria from membrane into the PBS. One hundred microliters of undiluted and diluted treated and control samples were plated onto LB agar plates for colony count.

Figure 13:
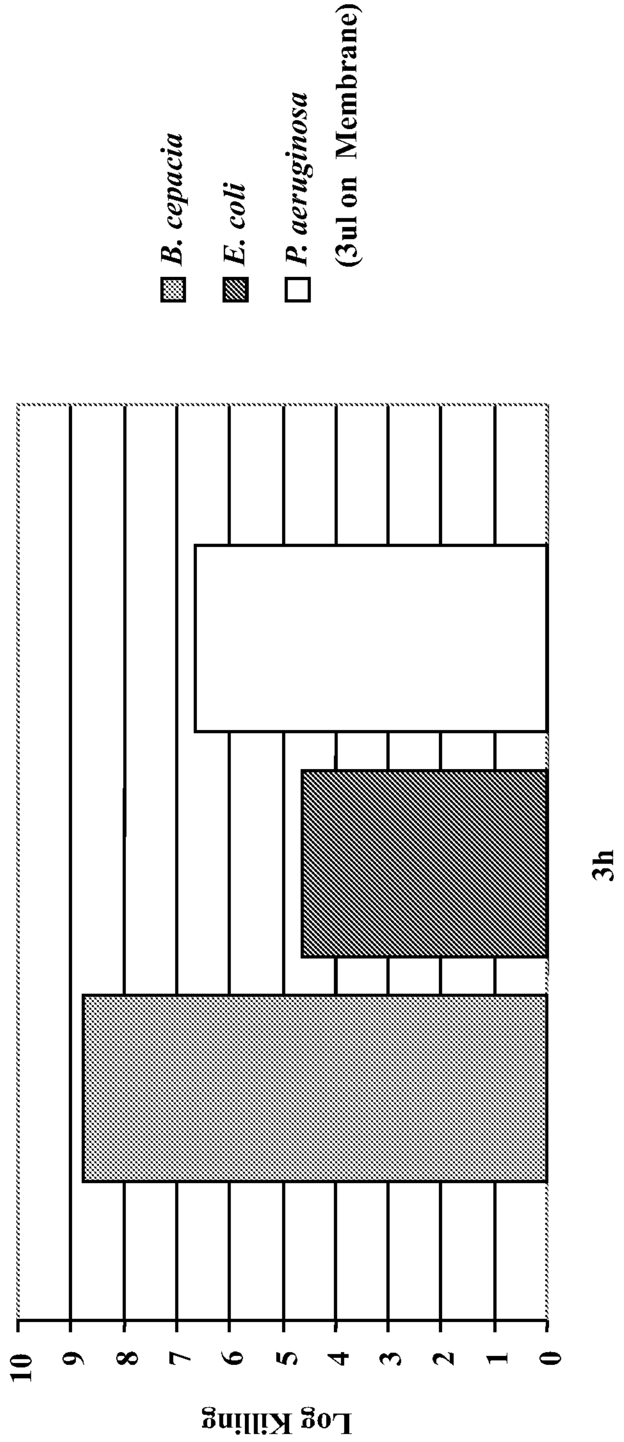
FIG. 13 shows influence of $P_{407}$5EC on *B. cepacia, P. aeruginosa* and *E. coli* individual biofilms.
Figure 14:
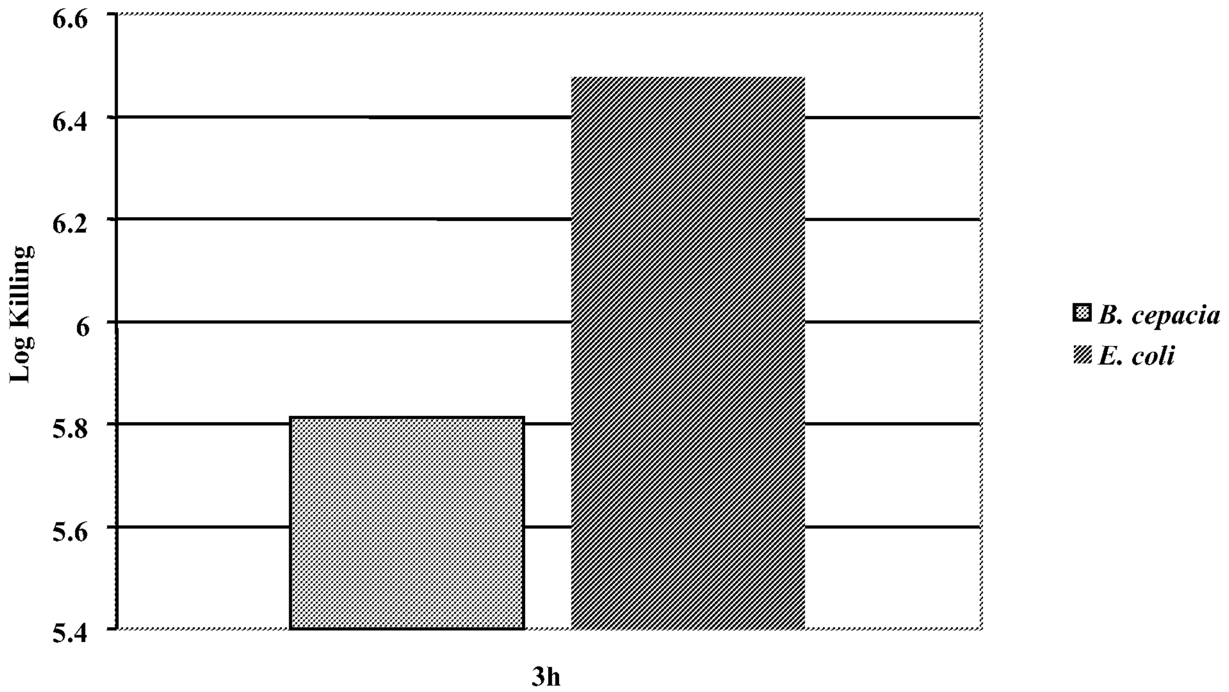
FIG. 14 shows influence of $P_{407}$5EC on mixed biofilms.
Figure 15:
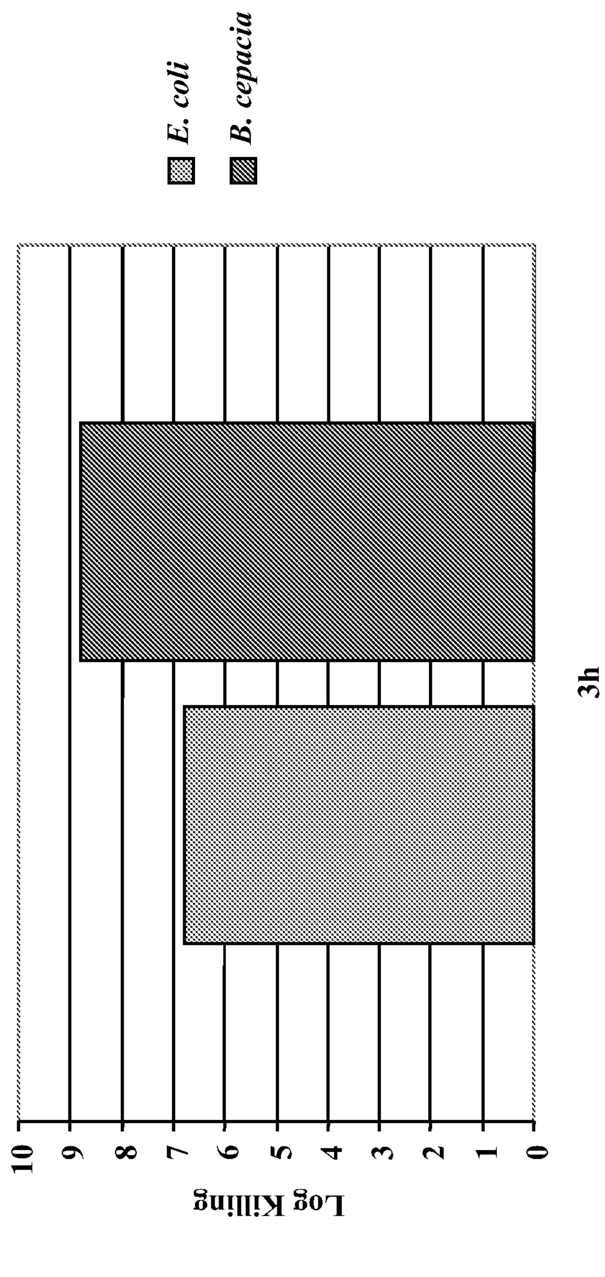
FIG. 15 shows influence of $P_{407}$5EC on mixed biofilms.
Figure 16:
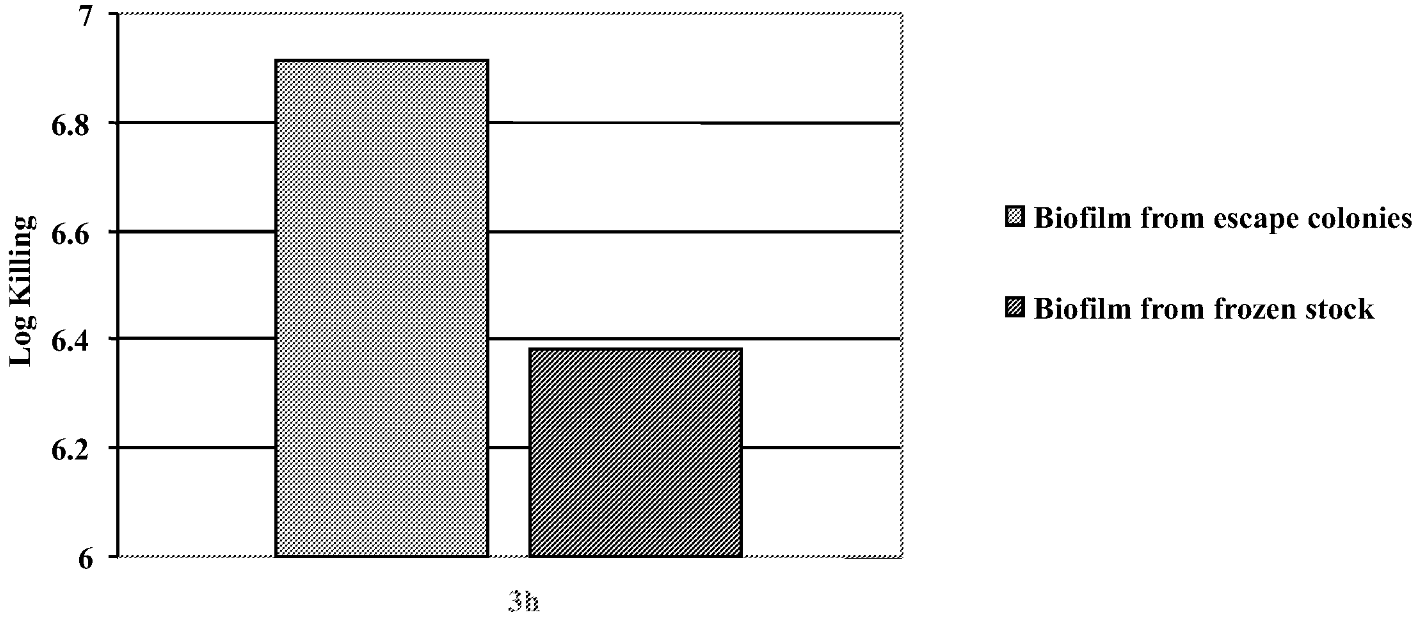
FIG. 16 shows influence of $P_{407}$5EC on escape colonies of *B. cepacia* biofilms.
Figure 18:
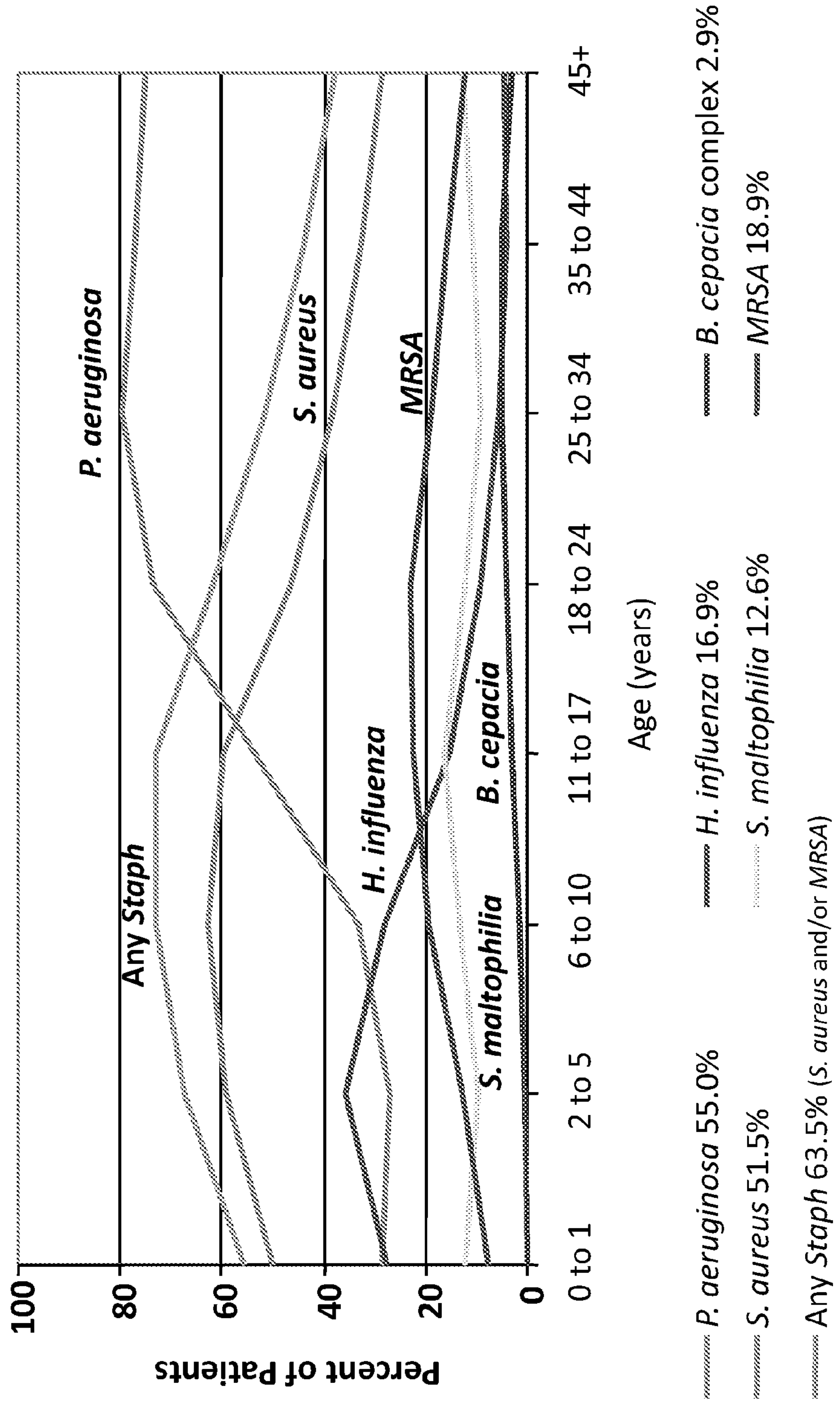
FIG. 18 shows age specific prevalence of respiratory infections in CF patients.
Figure 20A:
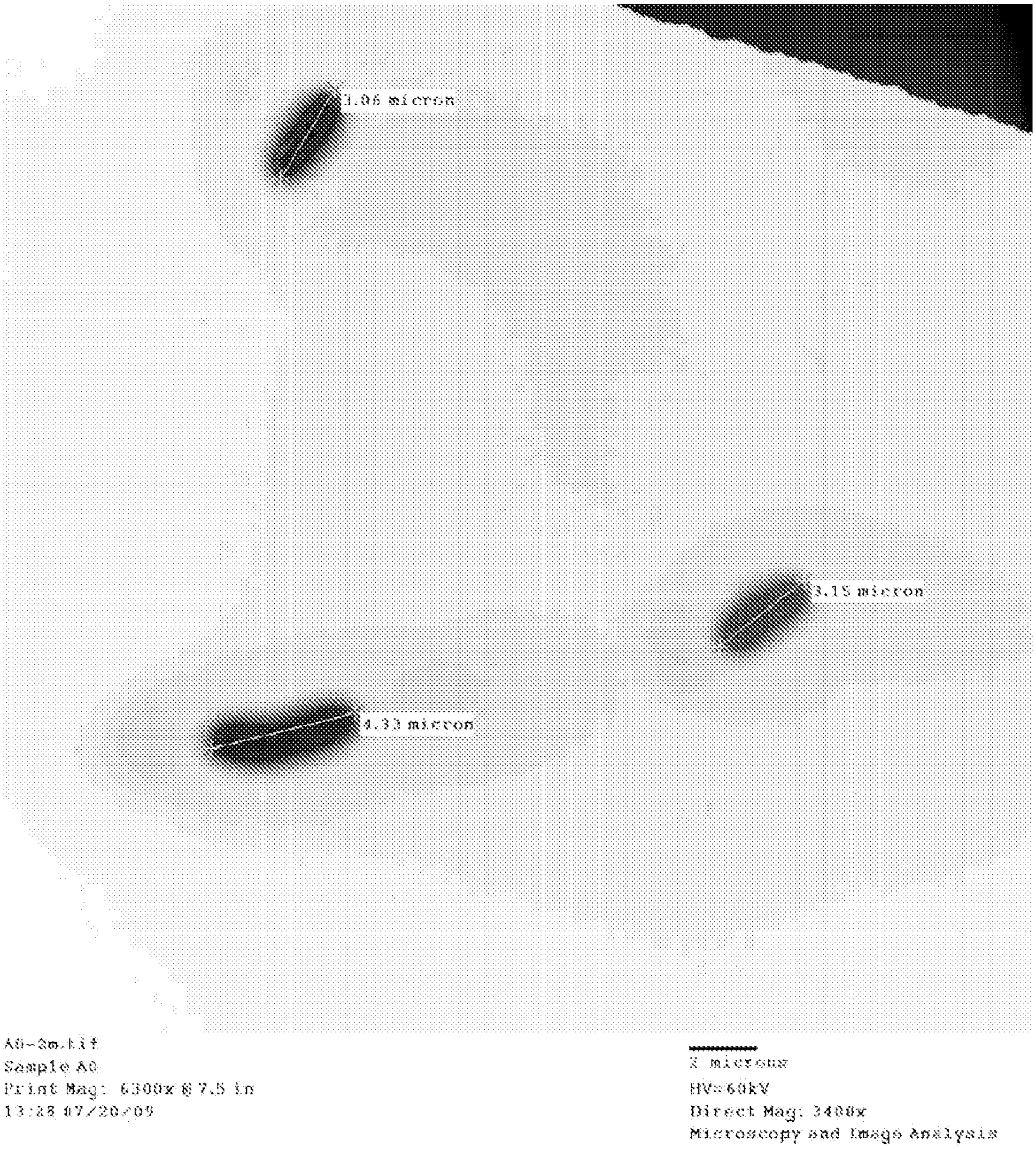
FIGS. 20A-D show figures of electron microscopy.
Figure 20B:
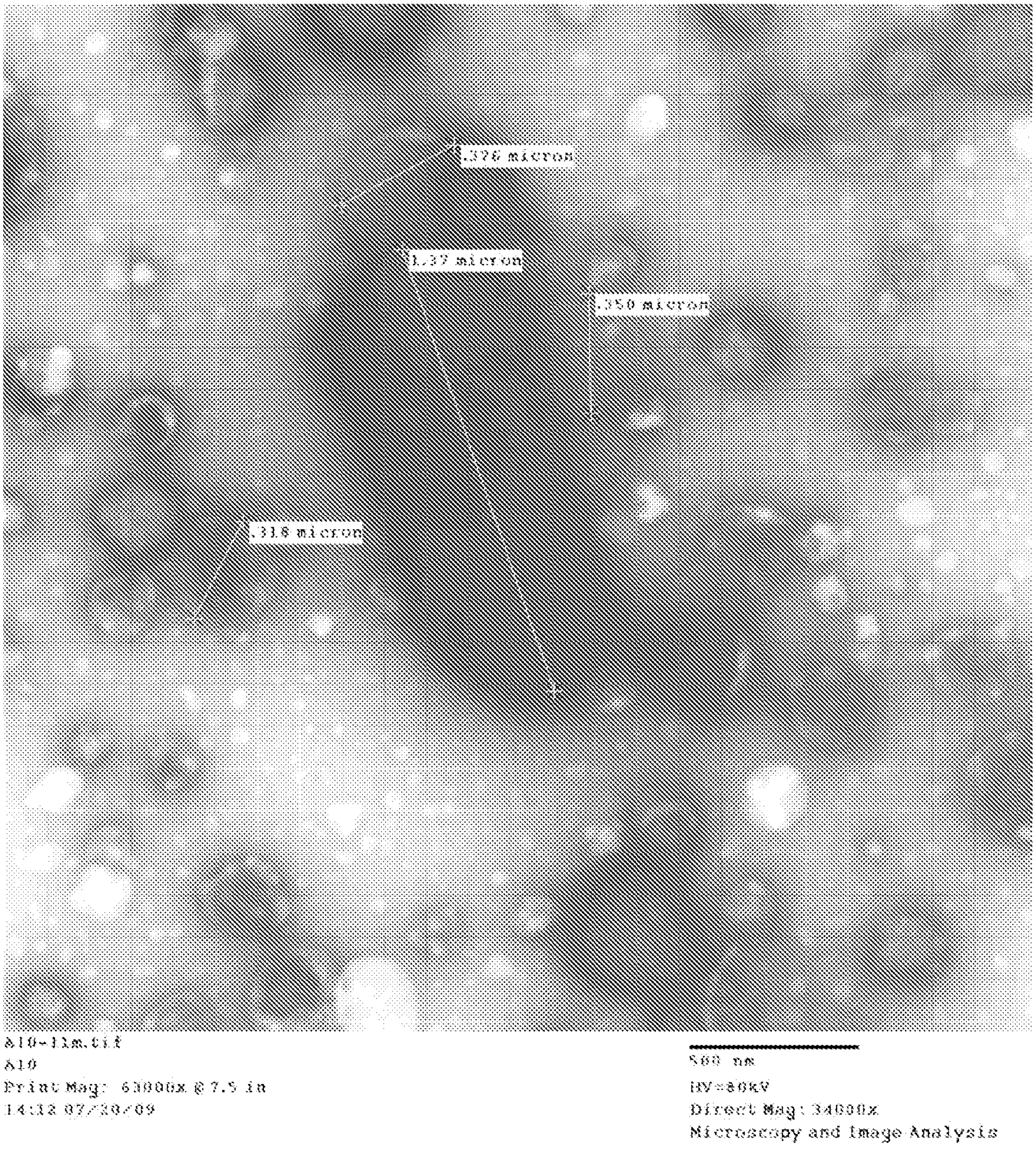
Figure 20C:
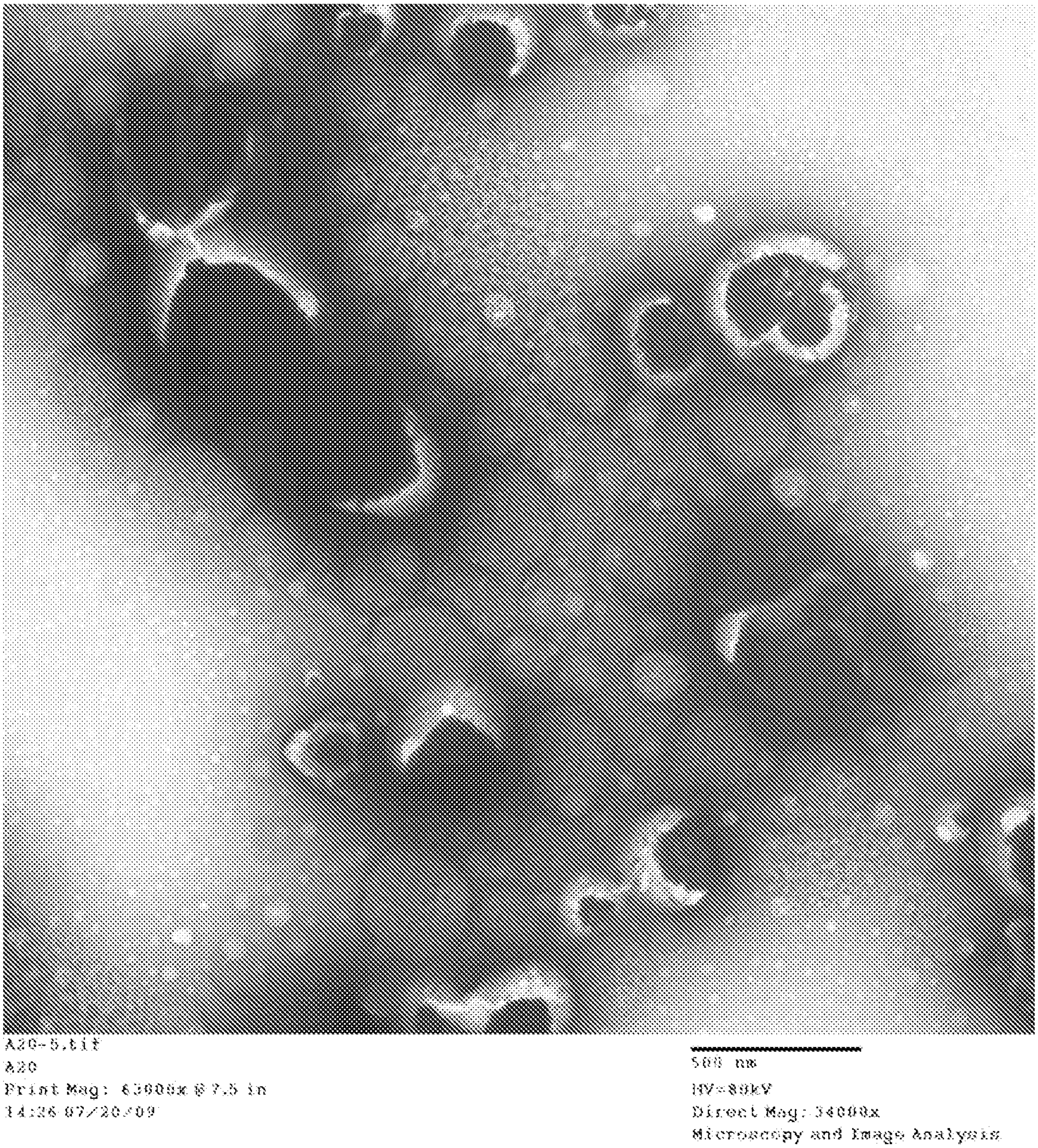
Figure 20D:
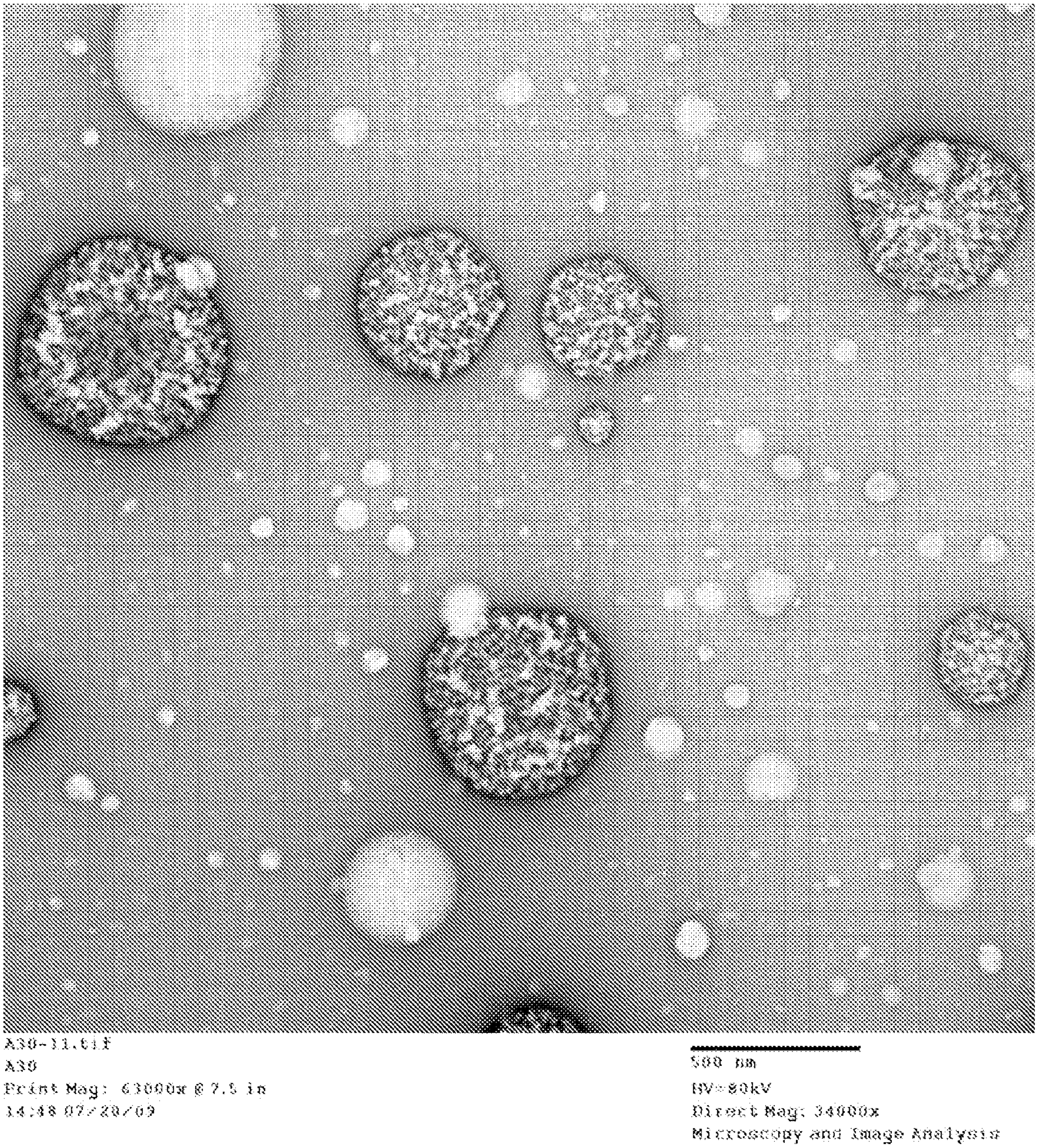

As shown in FIGS. 13-16, 20% $P_{407}$5EC with 7% saline and 20 mM EDTA was effective to kill bacteria present in biofilms comprising a single bacterial strain (See, e.g., FIG. 13, biofilms comprising a plurality of bacterial strains (See, e.g., FIGS. 14-15), as well as biofilms generated from bacteria that escaped killing in a first round of treatment (See, e.g., FIG. 16), attaining between a 4 to 9 log reduction in bacterial numbers.

Example 5

This example describes the effectiveness of various nanoemulsion formulations against various gram negative pathogens that may be associated with CF, wounds, burns and burn patients, or other environments.

As noted above, CF is characterized by chronic respiratory infection that begins early in life with *Staphylococcus aureus* and *Haemophilus influenzae* infections and later colonization with mucoid strains of *Pseudomonas aeruginosa*. In CF lung disease, early colonization with *Burkholderia cepacia* correlates with a poor prognosis in CF patients. Patients are often prescribed inhaled tobramycin to prevent exacerbations of bacteria infections. With time, patients can become unresponsive to tobramycin therapy/prophylaxis. New inhaled topical agents that are not cross-resistant to known antibiotics would be valued as an alternative to inhaled tobramycin.

Several topical nanoemulsions were evaluated for microbiological activity against gram-negative isolates, including *P. aeruginosa* and *B. cepacia*. All 3 nanoemulsions kill quickly in the presence of an outer membrane permeabilizer such as EDTA. The nanoemulsions were evaluated against 23 of the 35 gram-negative isolates for cidal activity, and all were bactericidal (85-95%). Thus, the one or more of these novel nanoemulsions can be used to prevent exacerbation of chronic pulmonary infections.

Methods: MICs and MBCs were determined using CLSI standard methods. MICs to nanoemulsions were determined in the presence of 5 mM EDTA, a known enhancer of nanoemulsion activity. The addition of alamar blue, a redeox indicator that yields a colorimetric change in response to metabolic activity, was used to determine the MICs of nanoemulsions that are opaque at higher concentrations.

Emulsion manufacturing: Nanoemulsions $W_{20}5EC$, $P_{407}5EC$, and $W_{20}5GBA_2ED$ are oil-in-water emulsions manufactured from ingredients that are Generally Recognized As Safe (GRAS) with a cationic detergent (cetylpyridinium chloride (CPC) or benzalkonium chloride (BA)) as active ingredients that have proven safe for oral human use. The emulsion is formed from highly purified oil, ethanol, a nonionic surfactant and water. The average nanoemulsion droplet size was 180 nm for $W_{20}5EC$ and 350 nm for $P_{407}5EC$ and $W_{20}5GBA_2ED$, as measured by dynamic light scattering using a Malvern Zetasizer Nano3600 (Malvern Instruments Ltd., Worcestershire, UK). The formulations for $W_{20}5EC$ and $P_{407}5EC$ are described above. $W_{20}5GBA_2ED$ (v/v %) is distilled water (18.93%), TWEEN 20 (5%), Glycerine (8%), Soybean oil (64%), BTC 824 50% (4%) (Stepan, Northfield, Ill.), and EDTA (0.0745%). The formulation may be diluted in water (e.g., 60% $W_{20}5GBA_2ED$, 40% water) to provide 60% $W_{20}5GBA_2ED$. This material may be diluted to a 10% formulation with 10 mM EDTA (e.g., 76 g water per 24 g 100 mM EDTA per 20 g 60% $W_{20}5GBA_2ED$). Thus, in some embodiments, a formulation comprising oil, water, glycerine, surfactant, and BTC (n-alkyl dimethyl benzyl ammonium chloride), and/or EDTA is provided.

Source of isolates. The source of the clinical isolates were blood stream or skin and soft tissue isolates collected by JMI Laboratories in the past 2 years.

MIC and MBC determinations. MICs of $W_{20}5EC\pm0$, 5, 10, 15, and 20 mM EDTA were evaluated in cation-adjusted Mueller-Hinton broth by microdilution per M7-A7 (2006). MICs for a panel of gram-negative isolates were determined for the nanoemulsions, W205EC, P4075EC, and W205GBA2ED in the presence of 5 mM EDTA. EDTA was used to permeabilize the gram-negative envelope, aiding infusion of the nanodroplets to the cell membrane, resulting in lysis. Alamar blue was added to the assay panels 2 hours post-inoculation for enhanced MIC endpoint detection. MBC values were assessed for all nanoemulsions and a comparator compound (fusidicacid) by plating the entire broth content from the MIC well and from those four doubling dilutions above the MIC for each selected organism onto blood agar growth media. Quantitative colony counts were performed on the initial inoculum. The lowest concentration of antimicrobial agent that killed ≥99.9% of the starting test inoculum was defined as the MBC endpoint. See Tables 2, 3, and 4.

TABLE 2

MIC values of W205EC ± EDTA

| Bacterial Isolates | 0 mM | 5 mM | 10 mM | 15 mM | 20 mM |
|---|---|---|---|---|---|
| *K. pneumoniae* 24-5A | 64 | 8-16 | 8 | 8 | 8 |
| *E. coli* ATCC 25922 | 16 | 1 | ≤0.12 | ≤0.12 | ≤0.12 |
| *P. mirabilis* 119-163A | 128 | ≤0.12* | ≤0.12 | ≤0.12 | ≤0.12 |
| *A. baumannii* 67-299A | 32 | ≤0.12* | ≤0.12 | ≤0.12 | ≤0.12 |
| *P. aeruginosa* ATCC 27853 | >256 | 32-64 | 32 | 32 | 32 |
| *B. cepacia* 30-492A | >256 | >256 | >256 | >256 | >256 |

*EDTA alone inhibited these strains.

TABLE 3

Cidality of nanoemulsions against a subset (23) of gram-negative isolates

| | | Compound (number of strains) | | | |
|---|---|---|---|---|---|
| | MBC/MIC ratio | $W_{20}5EC$ | $P_{407}5EC$ | $W_{20}5GBA_2ED$ | Levo-floxacin |
| Cidal ↑ | 1 | 7 | 10 | 9 | 9 |
| | 2 | 6 | 7 | 7 | 8 |
| | 4 | 4 | 2 | 2 | 1 |
| Static ↓ | 8 | 1 | 1 | 1 | |
| | >8x | 2 | | 1 | 5 |
| | No growth* | 3 | 3 | 3 | |

TABLE 4

| Antimicrobial agent | *Escherichia coli* (n = 5)8 $MIC_{50}$ | $MIC_{90}$ | Range | % susceptible/ resistant[a] | *Klebsiella pneumoniae* (n = 5) $MIC_{50}$ | $MIC_{90}$ | Range | % susceptible/ resistant |
|---|---|---|---|---|---|---|---|---|
| $W_{20}5EC$ | 2 | — | 1-2 | —/— | 8 | — | 4-16 | —/— |
| $P_{407}5EC$ | 4 | — | 4 | —/— | 8 | — | 8-16 | —/— |
| $W_{20}5G\ BA_2$ ED | 2 | — | 2-4 | —/— | 4 | — | 4-8 | —/— |
| Ceftazidime | <=1 | — | <=1->16 | 80.0/20.0 | <=1 | — | <=1->16 | 80.0/20.0 |
| Cefepime | <=0.12 | — | <=0.12->16 | 80.0/20.0 | <=0.12 | — | <=0.12->16 | 80.0/20.0 |
| Piperacillin/ tazobactam | 2 | — | 1-8 | 100.0/0.0 | 2 | — | 1-64 | 80.0/0.0 |
| Imipenem | 0.25 | — | <=0.12-0.5 | 100.0/0.0 | 0.25 | — | <=0.12-0.25 | 100.0/0.0 |

TABLE 4-continued

| | | | | | | | | |
|---|---|---|---|---|---|---|---|---|
| Gentamicin | <=2 | — | <=2->8 | 80.0/20.0 | <=2 | — | <=2 | 100.0/0.0 |
| Tobramycin | 0.5 | — | 0.25-16 | 80.0/20.0 | 0.25 | — | 0.25-16 | 80.0/20.0 |
| Levofloxacin | 0.03 | — | 0.03->8 | 60.0/40.0 | 0.06 | — | 0.06-8 | 80.0/20.0 |
| Tetracycline | >8 | — | 4->8 | 20.0/80.0 | <=2 | — | <=2-4 | 100.0/0.0 |
| Colistin | <=0.5 | — | <=0.5 | —/— | <=0.5 | — | <=0.5 | —/— |

| | *Proteus mirabilis* (n = 5) | | | | *Pseudomonas aeruginosa* (n = 5) | | | |
|---|---|---|---|---|---|---|---|---|
| Antimicrobial agent | $MIC_{50}$ | $MIC_{90}$ | Range | % susceptible/ resistant | $MIC_{50}$ | $MIC_{90}$ | Range | % susceptible/ resistant |
| $W_{20}5EC$ | 8 | — | 4-8 | —/— | 16 | — | 16-32 | —/— |
| $P_{407}5EC$ | 16 | — | 8-16 | —/— | 64 | — | 32-64 | —/— |
| $W_{20}5G\ BA_2$ ED | 8 | — | 4-16 | —/— | 16 | — | 8-16 | —/— |
| Ceftazidime | <=1 | — | <=1 | 100.0/0.0 | 2 | — | 2-4 | 100.0/0.0 |
| Cefepime | <=0.12 | — | <=0.12 | 100.0/0.0 | 4 | — | 1-8 | 100.0/0.0 |
| Piperacillin/ tazobactam | <=0.5 | — | <=0.5-1 | 100.0/0.0 | 2 | — | 2-16 | 100.0/0.0 |
| Imipenem | 1 | — | <=0.12-2 | 100.0/0.0 | 1 | — | 1->8 | 80.0/20.0 |
| Gentamicin | <=2 | — | <=2 | 100.0/0.0 | <=2 | — | <=2-4 | 100.0/0.0 |
| Tobramycin | 1 | — | 0.25-1 | 100.0/0.0 | 0.5 | — | 0.25-1 | 100.0/0.0 |
| Levofloxacin | 0.12 | — | 0.06-2 | 100.0/0.0 | 1 | — | 0.25-4 | 80.0/0.0 |
| Tetracycline | >8 | — | >8 | 0.0/100.0 | 8 | — | 8->8 | 0.0/40.0 |
| Colistin | >4 | — | >4 | —/— | 1 | — | <=0.5-2 | 100.0/0.0 |

| | *Acinetobacter baumannii* (n = 5)[b] | | | | *Stenotrophomonas maltophilia* (n = 5)[c] | | | |
|---|---|---|---|---|---|---|---|---|
| Antimicrobial agent | $MIC_{50}$ | $MIC_{90}$ | Range | % susceptible/ resistant | $MIC_{50}$ | $MIC_{90}$ | Range | % susceptible/ resistant |
| $W_{20}5EC$ | <=0.12 | — | <=0.12-2 | —/— | <=0.12 | — | <=0.12 | —/— |
| $P_{407}5EC$ | <=0.12 | — | <=0.12-4 | —/— | <=0.12 | — | <=0.12 | —/— |
| $W_{20}5G\ BA_2$ ED | <=0.12 | — | <=0.12-4 | —/— | <=0.12 | — | <=0.12 | —/— |
| Ceftazidime | 4 | — | <=1->16 | 80.0/20.0 | 16 | — | 2->16 | 40.0/40.0 |
| Cefepime | 2 | — | <=0.12->16 | 80.0/20.0 | >16 | — | 4->16 | —/— |
| Piperacillin/ tazobactam | 2 | — | <=0.5->64 | 80.0/20.0 | >64 | — | 8->64 | —/— |
| Imipenem | <=0.12 | — | <=0.12->8 | 80.0/20.0 | >8 | — | 4->8 | —/— |
| Gentamicin | <=2 | — | <=2->8 | 80.0/20.0 | >8 | — | <=2->8 | —/— |
| Tobramycin | 0.5 | — | 0.25->16 | 80.0/20.0 | >16 | — | 0.5->16 | —/— |
| Levofloxacin | 0.25 | — | 0.06->8 | 80.0/20.0 | 0.5 | — | 0.5-8 | 60.0/20.0 |
| Tetracycline | <=2 | — | <=2->8 | 80.0/20.0 | >8 | — | <=2->8 | —/— |
| Colistin | <=0.5 | — | <=0.5-2 | 100.0/0.0 | <=0.5 | — | <=0.5-1 | —/— |

| | *Burkholderia cepacia* (n = 5) | | | |
|---|---|---|---|---|
| Antimicrobial agent | $MIC_{50}$ | $MIC_{90}$ | Range | % susceptible/ resistant |
| $W_{20}5EC$ | 256 | — | 64->256 | —/— |
| $P_{407}5EC$ | 256 | — | 128->256 | —/— |
| $W_{20}5G\ BA_2$ ED | 128 | — | 32->256 | —/— |
| Ceftazidime | 2 | — | 2-4 | 100.0/0.0 |
| Cefepime | 8 | — | 4-16 | —/— |
| Piperacillin/ tazobactam | 4 | — | 2-32 | —/— |
| Imipenem | 8 | — | 4-8 | —/— |
| Gentamicin | >8 | — | >8 | —/— |
| Tobramycin | >16 | — | >16 | —/— |
| Levofloxacin | 2 | — | 1-2 | 100.0/0.0 |
| Tetracycline | >8 | — | >8 | —/— |
| Colistin | — | — | >4 | —/— |

Results: All 3 nanoemulsions had activity against Gram-negative isolates (EDTA alone inhibited 3 and 5 strains of *A. baumannii* and *S. maltophilia*, respectively). This included isolates that were resistant to comparator agents. MBCs were performed for 23 isolates; $W_{20}5EC$, $P_{407}5EC$, and $W_{20}5GBA_2ED$ were bactericidal against 85, 95, and 90% of the isolates, respectively. No cross-resistance to any known antibiotic was observed for any of the nanoemulsions.

Conclusions: Nanoemulsions were broadly active against Gram-negative species, including multidrug-resistant isolates. The documented MICs were within the range of concentrations achievable with topical application to skin or mucosal tissues. One or more of the nanoemulsions may be useful for prophylaxis and/or therapeutic treatment of chronic pulmonary infections in cystic fibrosis patients.

Example 6

The purpose of this example was to determine if nanoemulsions according to the invention have activity against *Haemophilus influenzae* isolates. *H. influenzae* is an important respiratory pathogen implicated in acute exacerbations of cystic fibrosis patients as well as upper and lower respiratory tract infections for non-CF normal individuals.

This example determined the minimum inhibitory concentration of three exemplary nanoemulsions ($W_{20}5EC$, $P_{407}5EC$ and $W_{20}5GBA_2$) plus comparator drugs against clinical isolates of *H. influenzae*. The results, as described in more detail below, show that $P_{407}5EC$ and $W_{20}5EC$ had similar MIC ranges of 1.88-3.75 μg/ml. $W_{20}5GBA_2$ had a MIC range of 8-16 μg/ml. The addition of EDTA at 1 mM to each well containing nanoemulsion had no effect on the MIC. Concentrations of EDTA greater than 1 mM inhibited the growth of bacteria, likely reducing the concentration of cations to levels below those that support growth. MBC data for the three nanoemulsions+1 mM EDTA were obtained for seven strains. The MBCs were within 4-fold of the respective MICs, consistent with each nanoemulsion having bactericidal activity against *H. influenzae* isolates.

A. Materials and Methods

Source of drugs. $W_{20}5EC$, lot x1151, at a concentration of 5000 μg/ml (stock concentration) was a pooled sample of clinical trial material (NB-001), manufactured at Patheon, Mississauga, Ontario, Canada. $P_{407}5EC$, lot X1138, and $W_{20}5GBA_2$, lot X1103, were manufactured at NanoBio Corporation. Comparator compounds, azithromycin, ampicillin, cefepime and clindamycin were purchased from The United States Pharmacopeia; catalog numbers were 1046056, 1033000, 1097636, 1136002, respectively. Tetracycline was purchased from Fluka Biochemika, catalog number 87128. The emulsions were produced by mixing a water immiscible oil phase with an aqueous phase. The base formulations are shown in Table 5 below and represent the neat emulsions, which were further diluted to the desired %. Compositions are w/w % unless otherwise noted.

TABLE 5

| Nanoemulsions | | |
|---|---|---|
| Nanoemulsion | Component | Weight Percent (w/w %) |
| $W_{20}5EC$ ED | Distilled Water | 23.418% |
| | EDTA | 0.0745% |
| | Cetylpyridinium Chloride | 1.068% |
| | Tween 20 | 5.92% |
| | Ethanol | 6.73% |
| | Soybean Oil | 62.79% |
| $P_{407}5EC$ | Distilled Water | 23.49% |
| | CPC | 1.068% |
| | Poloxamer 407 | 5.92% |
| | Ethanol | 6.73% |
| | Soybean Oil, NP | 62.79% |
| $W_{205}GBA_2$ (v/v %) | Distilled Water | 20.93% |
| | BTC 824 | 2% |
| | Tween 20 | 5% |
| | Glycerine | 8% |
| | Soybean Oil | 64% |

Source of bacterial strains. Ten clinical isolates of *H. influenzae* were obtained from Case Western Reserve University, Cleveland, Ohio. The quality control isolate, ATCC 49247, was obtained from the American Type Culture Collection.

Susceptibility assays. The susceptibility of *H. influenzae* isolates to five commercial antibiotics and three nanoemulsion formulations was evaluated using the guidelines published by Clinical Laboratory Standards Institute (Clinical and Laboratory Standards Institute. Performance Standards for Antimicrobial Susceptibility and Testing; Seventeenth Informational Supplement. CLSI document MI00-517 (ISBN 1-56238-625-5). CLSI, 940 West Valley Road, Suite 1400, Wayne, Pa. 19087-1988, 2007). The ranges of drug concentrations tested were as follows: Azithromycin at 0.25-128 μg/ml, Ampicillin at 0.063-32 μg/ml, Cefepime at 0.063-32 μg/ml, Clindamycin at 0.125-64 μg/ml, Tetracycline at 0.125-64 μg/ml, $P_{407}5EC$ at 0.12-60 μg/ml cetylpyridinium chloride, $W_{20}5EC$ at 0.12-60 μg/ml cetylpyridinium chloride, $W_{20}5GBA_2$ at 0.125-64 μg/ml benzalkonium chloride. Since nanoemulsions are not a single component, the MICs/MBCs are expressed as the concentration of the cationic surfactant; $W_{20}5EC$ and $P_{407}5EC$ both contain cetylpyridinium chloride (CPC) as the cationic surfactant, while $W_{20}5GBA_2$ contains benzalkonium chloride (BA) as the cationic surfactant. Isolates were also tested with the same range of nanoemulsion concentrations+1-5 mM EDTA to see if the latter enhanced the activity of the nanoemulsion. EDTA concentrations were tested alone to ensure that chelation of cations by EDTA was sufficient to inhibit bacterial growth independent of the nanoemulsion.

Minimum inhibitory concentrations (MIC) were determined visually as the first totally clear well in the series of the 10 concentrations of each drug. For the nanoemulsions, because they are intrinsically opaque, the MIC was determined as the first well observed to have some clearing from the least concentrated to the most concentrated of the serial dilution. MBC values were assessed for the nanoemulsions+1 mM EDTA for 7 clinical strains and the ATCC 49257 isolate by plating 10 μl from the well determined to be the MIC and 4 wells above the MIC onto chocolate blood agar media. The lowest concentration of antimicrobial agent that killed ≥99.9% of the starting test inoculum was defined as the MBC. A compound or nanoemulsion is defined as bactericidal if its MBC/MIC ratio was ≤4.

Results: Data for the MICs and MBCs are shown in Tables 6-7. $P_{407}5EC$, $W_{20}5EC$, and $W_{20}5GBA_2$ were equally effective antimicrobials in the presence or absence of 1 mM EDTA. The $MIC_{90}$ values for these compounds were 3.75, 3.75, and 16 μg/ml, respectively (Table 6). By $MIC_{90}$ values, the majority of isolates were susceptible to azithromycin, cefepime, tetracycline and ampicillin, but were resistant to clindamycin and ampicillin.

The MBC values were within 4-fold of the respective MICs for each isolate tested (Table 7); thus each of the nanoemulsions were bactericidal for *H. influenzae*, with a range of MBCs for $P_{407}5EC$, $W_{20}5EC$, and $W_{20}5GBA_2$ of 1.88-7.5, 1.88-7.5 and 8-16 μg/ml, respectively.

Conclusions: $P_{407}5EC$ and $W_{20}5EC$ appeared equally effective against clinical isolates of *H. influenzae*. The benzalkonium chloride formulation, $W_{20}5GBA_2$, was two- to four-fold less active than the other nanoemulsions by $MIC_{90}$ and MBC values. EDTA at concentrations ≥2 mM EDTA inhibited the growth of *H. influenzae* under these growth conditions. The addition of EDTA was not necessary to enhance the activity of any of the nanoemulsions.

TABLE 6

Susceptibility of *H. influenzae* clinical isolates to nanoemulsions and control antibiotics

| | MIC (μg/ml) | | | | | | | | | | |
|---|---|---|---|---|---|---|---|---|---|---|---|
| Strain | $P_{407}$5EC[a] | $P_{407}$5EC + 1 mM EDTA | $W_{20}$5EC[a] | $W_{20}$5EC + 1 mM EDTA | $W_{20}5GBA_2$[b] | $W_{20}5GBA_2$ + 1 mM EDTA | Azi[c] | Amp[c] | Cef[c] | Tet[c] | Cli[c] |
| 49247 | 1.88 | 1.88 | 1.88 | 0.94 | 8 | 4 | 1 | 4 | 1 | 16 | 8 |
| 30 | 1.88 | 0.94 | 1.88 | 0.94 | 4 | 8 | 2 | 0.25 | 0.125 | 0.5 | 16 |
| 32 | 1.88 | 1.88 | 1.88 | 3.75 | 8 | 4 | 8 | 32 | 0.125 | 2 | 8 |
| 33 | 3.75 | 1.88 | 3.75 | 3.75 | 8 | 8 | 1 | 0.25 | 0.0625 | 1 | 16 |
| 34 | 3.75 | 3.75 | 3.75 | 3.75 | 8 | 8 | 1 | >32 | 0.125 | 1 | 16 |
| 35 | 3.75 | 3.75 | 7.5 | 7.5 | 16 | 16 | 1 | 0.25 | 0.125 | 0.5 | 8 |
| 36 | 3.75 | 3.75 | 3.75 | 3.75 | 8 | 16 | 2 | 0.125 | 0.125 | 1 | 16 |
| 37 | 1.88 | 1.88 | 3.75 | 3.75 | 16 | 16 | 1 | >32 | 0.125 | 1 | 4 |
| 38 | 3.75 | 3.75 | 3.75 | 3.75 | 16 | 16 | 1 | 0.25 | 0.0625 | 0.5 | 16 |
| 41 | 1.88 | 0.94 | 1.88 | 0.94 | 8 | 4 | 2 | >32 | 0.25 | 1 | 8 |
| 42 | 1.88 | 1.88 | 1.88 | 3.75 | 8 | 8 | 1 | >32 | 0.125 | 1 | 4 |
| MIC range | 1.88-3.75 | 0.94-3.75 | 1.88-3.75 | 0.94-7.5 | 4-16 | 4-16 | 1-8 | 0.25->32 | 0.0625-1 | 0.5-16 | 4-16 |
| $MIC_{90}$ | 3.75 | 3.75 | 3.75 | 3.75 | 16 | 16 | 2 | >32 | 0.125 | 2 | 16 |

[a]MIC value reflects the amount of μg cetylpyridinium chloride/ml

[b]MIC values reflects the amount of μg benzalkonium chloride/ml

[c]Azi = azithromycin; Amp = ampicillin; Cef = cefepime; Tet = tetracycline; Cli = clindamycin

TABLE 7

Cidality of nanoemulsions against *H. influenzae* clinical isolate

| | MBC (μg/ml) | | |
|---|---|---|---|
| Strain | P407 5EC + 1 mM EDTA | $W_{20}$5EC + 1 mM EDTA | $W_{20}5GBA_2$ + 1 mM EDTA |
| 49247 | 1.88 | 1.88 | 8 |
| 30 | 1.88 | 1.88 | 8 |
| 32 | 3.75 | 3.75 | 8 |
| 34 | 7.5 | 3.75 | 8 |
| 35 | 7.5 | 7.5 | 16 |
| 36 | 7.5 | 7.5 | 16 |
| 37 | 3.75 | 3.75 | 8 |
| 38 | 7.5 | 7.5 | 16 |

For Table 8 below, drug concentrations are in μg/ml for the comparators, as μg cetylpyridinium chloride (CPC)/ml for $W_{20}$5EC and $P_{407}$5EC and as μg benzalkonium chloride (BA)/ml for $W_{20}5GBA_2$. NC is for Negative Control and GC is for Growth Control. The chart describes the wells of a 96 well microtiter plate. The rows listed as I, J, K, and L are the rows of a partial plate used to evaluate the nanoemulsions with different EDTA concentrations. For each clinical strain and control strain, the chart below was used for tracking the MIC and MBC data. If the wells were too opaque to read the MIC( ), the MBC was relied upon to provide the MIC. In Table 8, rows with light highlighting contain plate counts for MBC. The second number is the plate count of a 10 μl sample from the microtiter plate used to determine the MBC. The MBC was defined as ≥3-log reduction of the inoculum. The darker highlighting corresponds to MIC.

TABLE 8

*H. influenzae* MIC of Nanoemulsions with EDTA
*Haemophilus influenzae* MIC of Nanoemulsions with EDTA of Sep. 18, 2008

ATCC *H. influenzae* 49247, 1.1E+06 cfu/ml (initial inoculum concentration)

| Quality Control Isolate | | 1 | 2 | 3 | 4 | 5 | 6 | 7 | 8 | 9 | 10 | 11 | 12 |
|---|---|---|---|---|---|---|---|---|---|---|---|---|---|
| A (QC MIC range is 1-4) | Azi | 128 | 64 | 32 | 16 | 8 | 4 | 2 | 1 | 0.5 | 0.25 | NC | GC |
| B (QC MIC range 2-8) | Amp | 32 | 16 | 8 | 4 | 2 | 1 | 0.5 | 0.25 | 0.13 | 0.063 | NC | GC |
| C (QC MIC range 0.5-2) | Cef | 32 | 16 | 8 | 4 | 2 | 1 | 0.5 | 0.25 | 0.13 | 0.063 | NC | GC |
| D (n/a) | Cli | 64 | 32 | 16 | 8 | 4 | 2 | 1 | 0.5 | 0.25 | 0.13 | NC | GC |
| E (QC MIC range 4-32) | Tet | 64 | 32 | 16 | 8 | 4 | 2 | 1 | 0.5 | 0.25 | 0.13 | NC | GC |
| F-μg CPC/ml | $P_{407}$5EC | 60 | 30 | 15 | 7.5 | 3.75 | 1.88 | 0.94 | 0.47 | 0.23 | 0.12 | NC | GC |
| G-μg CPC/ml | $W_{20}$5EC | 60 | 30 | 15 | 7.5 | 3.75 | 1.88 | 0.94 | 0.47 | 0.23 | 0.12 | NC | GC |
| H-μg BA/ml | $W_{20}5GBA_2$ | 64 | 32 | 16 | 8 | 4 | 2 | 1 | 0.5 | 0.25 | 0.13 | NC | GC |
| With 1 mM EDTA | | | | | | | | | | | | | |
| I | $P_{407}$5EC | 60 | 30 | 15 | 7.5, 0 | 3.75, 0 | 1.88, 0 | 0.94, tntc | 0.47 | 0.23 | 0.12 | NC | GC |
| J | $W_{20}$5EC | 60 | 30 | 15 | 7.5, 0 | 3.75, 0 | 1.88, 0 | 0.94, tntc | 0.47 | 0.23 | 0.12 | NC | GC |
| K | $W_{20}5GBA_2$ | 64 | 32.0 | 16, 0 | 8, 0 | 4, 0 | 2 | 1 | 0.5 | 0.25 | 0.13 | NC | GC |
| L | 1 mM EDTA | 1 | 1 | 1 | 1 | 1 | 1 | 1 | 1 | 1 | 1 | NC | GC |

TABLE 8-continued

| | | | | | | | | | | | | | |
|---|---|---|---|---|---|---|---|---|---|---|---|---|---|
| With 2 mM EDTA | | | | | | | | | | | | | |
| I | $P_{407}$5EC | 60 | 30 | 15 | 7.5 | 3.75 | 1.88 | 0.94 | 0.47 | 0.23 | 0.12 | NC | GC |
| J | $W_{20}$5EC | 60 | 30 | 15 | 7.5 | 3.75 | 1.88 | 0.94 | 0.47 | 0.23 | 0.12 | NC | GC |
| K | $W_{20}5GBA_2$ | 64 | 32 | 16 | 8 | 4 | 2 | 1 | 0.5 | 0.25 | 0.13 | NC | GC |
| L | 2 mM EDTA | 2 | 2 | 2 | 2 | 2 | 2 | 2 | 2 | 2 | 2 | NC | GC |
| With 3 mM EDTA | | | | | | | | | | | | | |
| I | $P_{407}$5EC | 60 | 30 | 15 | 7.5 | 3.75 | 1.88 | 0.94 | 0.47 | 0.23 | 0.12 | NC | GC |
| J | $W_{20}$5EC | 60 | 30 | 15 | 7.5 | 3.75 | 1.88 | 0.94 | 0.47 | 0.23 | 0.12 | NC | GC |
| K | $W_{20}5GBA_2$ | 64 | 32 | 16 | 8 | 4 | 2 | 1 | 0.5 | 0.25 | 0.13 | NC | GC |
| L | 3 mM EDTA | 3 | 3 | 3 | 3 | 3 | 3 | 3 | 3 | 3 | 3 | NC | GC |
| With 4 mM EDTA | | | | | | | | | | | | | |
| I | $P_{407}$5EC | 60 | 30 | 15 | 7.5 | 3.75 | 1.88 | 0.94 | 0.47 | 0.23 | 0.12 | NC | GC |
| J | $W_{20}$5EC | 60 | 30 | 15 | 7.5 | 3.75 | 1.88 | 0.94 | 0.47 | 0.23 | 0.12 | NC | GC |
| K | $W_{20}5GBA_2$ | 64 | 32 | 16 | 8 | 4 | 2 | 1 | 0.5 | 0.25 | 0.13 | NC | GC |
| L | 4 mM EDTA | 4 | 4 | 4 | 4 | 4 | 4 | 4 | 4 | 4 | 4 | NC | GC |
| With 5 mM EDTA | | | | | | | | | | | | | |
| I | $P_{407}$5EC | 60 | 30 | 15 | 7.5 | 3.75 | 1.88 | 0.94 | 0.47 | 0.23 | 0.12 | NC | GC |
| J | $W_{20}$5EC | 60 | 30 | 15 | 7.5 | 3.75 | 1.88 | 0.94 | 0.47 | 0.23 | 0.12 | NC | GC |
| K | $W_{20}5GBA_2$ | 64 | 32 | 16 | 8 | 4 | 2 | 1 | 0.5 | 0.25 | 0.13 | NC | GC |
| L | 5 mM EDTA | 5 | 5 | 5 | 5 | 5 | 5 | 5 | 5 | 5 | 5 | NC | GC |

| | 2.2E+06 cfu/mL (initial inoculum concentration) | | | | | | | | | | | | |
|---|---|---|---|---|---|---|---|---|---|---|---|---|---|
| #30 neg | | 1 | 2 | 3 | 4 | 5 | 6 | 7 | 8 | 9 | 10 | 11 | 12 |
| A | Azi | 128 | 64 | 32 | 16 | 8 | 4 | 2 | 1 | 0.5 | 0.25 | NC | GC |
| B | Amp | 32 | 16 | 8 | 4 | 2 | 1 | 0.5 | 0.25 | 0.13 | 0.063 | NC | GC |
| C | Cef | 32 | 16 | 8 | 4 | 2 | 1 | 0.5 | 0.25 | 0.13 | 0.063 | NC | GC |
| D | Cli | 64 | 32 | 16 | 8 | 4 | 2 | 1 | 0.5 | 0.25 | 0.13 | NC | GC |
| E | Tet | 64 | 32 | 16 | 8 | 4 | 2 | 1 | 0.5 | 0.25 | 0.13 | NC | GC |
| F | $P_{407}$5EC | 60 | 30 | 15 | 7.5 | 3.75 | 1.88 | 0.94 | 0.47 | 0.23 | 0.12 | NC | GC |
| G | $W_{20}$5EC | 60 | 30 | 15 | 7.5 | 3.75 | 1.88 | 0.94 | 0.47 | 0.23 | 0.12 | NC | GC |
| H | $W_{20}5GBA_2$ | 64 | 32 | 16 | 8 | 4 | 2 | 1 | 0.5 | 0.25 | 0.13 | NC | GC |
| With 1 mM EDTA | | | | | | | | | | | | | |
| I | $P_{407}$5EC | 60 | 30 | 15 | 7.5, 0 | 3.75, 0 | 1.88, 0 | 0.94, tntc | 0.47 | 0.23 | 0.12 | NC | GC |
| J | $W_{20}$5EC | 60 | 30 | 15 | 7.5, 0 | 3.75, 0 | 1.88, 0 | 0.94, tntc | 0.47 | 0.23 | 0.12 | NC | GC |
| K | $W_{20}5GBA_2$ | 64, 0 | 32, 0 | 16, 0 | 8, 0 | 4 | 2 | 1 | 0.5 | 0.25 | 0.13 | NC | GC |
| L | 1 mM EDTA | 1 | 1 | 1 | 1 | 1 | 1 | 1 | 1 | 1 | 1 | NC | GC |
| With 2 mM EDTA | | | | | | | | | | | | | |
| I | $P_{407}$5EC | 60 | 30 | 15 | 7.5 | 3.75 | 1.88 | 0.94 | 0.47 | 0.23 | 0.12 | NC | GC |
| J | $W_{20}$5EC | 60 | 30 | 15 | 7.5 | 3.75 | 1.88 | 0.94 | 0.47 | 0.23 | 0.12 | NC | GC |
| K | $W_{20}5GBA_2$ | 64 | 32 | 16 | 8 | 4 | 2 | 1 | 0.5 | 0.25 | 0.13 | NC | GC |
| L | 2 mM EDTA | 2 | 2 | 2 | 2 | 2 | 2 | 2 | 2 | 2 | 2 | NC | GC |
| With 3 mM EDTA | | | | | | | | | | | | | |
| I | $P_{407}$5EC | 60 | 30 | 15 | 7.5 | 3.75 | 1.88 | 0.94 | 0.47 | 0.23 | 0.12 | NC | GC |
| J | $W_{20}$5EC | 60 | 30 | 15 | 7.5 | 3.75 | 1.88 | 0.94 | 0.47 | 0.23 | 0.12 | NC | GC |
| K | $W_{20}5GBA_2$ | 64 | 32 | 16 | 8 | 4 | 2 | 1 | 0.5 | 0.25 | 0.13 | NC | GC |
| L | 3 mM EDTA | 3 | 3 | 3 | 3 | 3 | 3 | 3 | 3 | 3 | 3 | NC | GC |

TABLE 8-continued

| | | | | | | | | | | | | | |
|---|---|---|---|---|---|---|---|---|---|---|---|---|---|
| With 4 mM EDTA | | | | | | | | | | | | | |
| I | $P_{407}$5EC | 60 | 30 | 15 | 7.5 | 3.75 | 1.88 | 0.94 | 0.47 | 0.23 | 0.12 | NC | GC |
| J | $W_{20}$5EC | 60 | 30 | 15 | 7.5 | 3.75 | 1.88 | 0.94 | 0.47 | 0.23 | 0.12 | NC | GC |
| K | $W_{20}5GBA_2$ | 64 | 32 | 16 | 8 | 4 | 2 | 1 | 0.5 | 0.25 | 0.13 | NC | GC |
| L | 4 mM EDTA | 4 | 4 | 4 | 4 | 4 | 4 | 4 | 4 | 4 | 4 | NC | GC |
| With 5 mM EDTA | | | | | | | | | | | | | |
| I | $P_{407}$5EC | 60 | 30 | 15 | 7.5 | 3.75 | 1.88 | 0.94 | 0.47 | 0.23 | 0.12 | NC | GC |
| J | $W_{20}$5EC | 60 | 30 | 15 | 7.5 | 3.75 | 1.88 | 0.94 | 0.47 | 0.23 | 0.12 | NC | GC |
| K | $W_{20}5GBA_2$ | 64 | 32 | 16 | 8 | 4 | 2 | 1 | 0.5 | 0.25 | 0.13 | NC | GC |
| L | 5 mM EDTA | 5 | 5 | 5 | 5 | 5 | 5 | 5 | 5 | 5 | 5 | NC | GC |

| | | 2.6E+06 cfu/mL (initial inoculum concentration) | | | | | | | | | | | |
|---|---|---|---|---|---|---|---|---|---|---|---|---|---|
| #32 pos | | 1 | 2 | 3 | 4 | 5 | 6 | 7 | 8 | 9 | 10 | 11 | 12 |
| A | Azi | 128 | 64 | 32 | 16 | 8 | 4 | 2 | 1 | 0.5 | 0.25 | NC | GC |
| B | Amp | 32 | 16 | 8 | 4 | 2 | 1 | 0.5 | 0.25 | 0.13 | 0.063 | NC | GC |
| C | Cef | 32 | 16 | 8 | 4 | 2 | 1 | 0.5 | 0.25 | 0.13 | 0.063 | NC | GC |
| D | Cli | 64 | 32 | 16 | 8 | 4 | 2 | 1 | 0.5 | 0.25 | 0.13 | NC | GC |
| E | Tet | 64 | 32 | 16 | 8 | 4 | 2 | 1 | 0.5 | 0.25 | 0.13 | NC | GC |
| F | $P_{407}$5EC | 60 | 30 | 15 | 7.5 | 3.75 | 1.88 | 0.94 | 0.47 | 0.23 | 0.12 | NC | GC |
| G | $W_{20}$5EC | 60 | 30 | 15 | 7.5 | 3.75 | 1.88 | 0.94 | 0.47 | 0.23 | 0.12 | NC | GC |
| H | $W_{20}5GBA_2$ | 64 | 32 | 16 | 8 | 4 | 2 | 1 | 0.5 | 0.25 | 0.13 | NC | GC |
| With 1 mM EDTA | | | | | | | | | | | | | |
| I | $P_{407}$5EC | 60 | 30 | 15, 0 | 7.5, 0 | 3.75, 0 | 1.88, tntc | 0.94 | 0.47 | 0.23 | 0.12 | NC | GC |
| J | $W_{20}$5EC | 60 | 30, 0 | 15, 0 | 7.5, 0 | 3.75, 0 | 1.88 | 0.94 | 0.47 | 0.23 | 0.12 | NC | GC |
| K | $W_{20}5GBA_2$ | 64 | 32, 0 | 16, 0 | 8, 0 | 4, 41 | 2 | 1 | 0.5 | 0.25 | 0.13 | NC | GC |
| L | 1 mM EDTA | 1 | 1 | 1 | 1 | 1 | 1 | 1 | 1 | 1 | 1 | NC | GC |
| With 2 mM EDTA | | | | | | | | | | | | | |
| I | $P_{407}$5EC | 60 | 30 | 15 | 7.5 | 3.75 | 1.88 | 0.94 | 0.47 | 0.23 | 0.12 | NC | GC |
| J | $W_{20}$5EC | 60 | 30 | 15 | 7.5 | 3.75 | 1.88 | 0.94 | 0.47 | 0.23 | 0.12 | NC | GC |
| K | $W_{20}5GBA_2$ | 64 | 32 | 16 | 8 | 4 | 2 | 1 | 0.5 | 0.25 | 0.13 | NC | GC |
| L | 2 mM EDTA | 2 | 2 | 2 | 2 | 2 | 2 | 2 | 2 | 2 | 2 | NC | GC |
| With 3 mM EDTA | | | | | | | | | | | | | |
| I | $P_{407}$5EC | 60 | 30 | 15 | 7.5 | 3.75 | 1.88 | 0.94 | 0.47 | 0.23 | 0.12 | NC | GC |
| J | $W_{20}$5EC | 60 | 30 | 15 | 7.5 | 3.75 | 1.88 | 0.94 | 0.47 | 0.23 | 0.12 | NC | GC |
| K | $W_{20}5GBA_2$ | 64 | 32 | 16 | 8 | 4 | 2 | 1 | 0.5 | 0.25 | 0.13 | NC | GC |
| L | 3 mM EDTA | 3 | 3 | 3 | 3 | 3 | 3 | 3 | 3 | 3 | 3 | NC | GC |
| With 4 mM EDTA | | | | | | | | | | | | | |
| I | $P_{407}$5EC | 60 | 30 | 15 | 7.5 | 3.75 | 1.88 | 0.94 | 0.47 | 0.23 | 0.12 | NC | GC |
| J | $W_{20}$5EC | 60 | 30 | 15 | 7.5 | 3.75 | 1.88 | 0.94 | 0.47 | 0.23 | 0.12 | NC | GC |
| K | $W_{20}5GBA_2$ | 64 | 32 | 16 | 8 | 4 | 2 | 1 | 0.5 | 0.25 | 0.13 | NC | GC |
| L | 4 mM EDTA | 4 | 4 | 4 | 4 | 4 | 4 | 4 | 4 | 4 | 4 | NC | GC |
| With 5 mM EDTA | | | | | | | | | | | | | |
| I | $P_{407}$5EC | 60 | 30 | 15 | 7.5 | 3.75 | 1.88 | 0.94 | 0.47 | 0.23 | 0.12 | NC | GC |
| J | $W_{20}$5EC | 60 | 30 | 15 | 7.5 | 3.75 | 1.88 | 0.94 | 0.47 | 0.23 | 0.12 | NC | GC |
| K | $W_{20}5GBA_2$ | 64 | 32 | 16 | 8 | 4 | 2 | 1 | 0.5 | 0.25 | 0.13 | NC | GC |
| L | 5 mM EDTA | 5 | 5 | 5 | 5 | 5 | 5 | 5 | 5 | 5 | 5 | NC | GC |

TABLE 8-continued

| #33 neg | 2.4E+06 cfu/mL (initial inoculum concentration) | 1 | 2 | 3 | 4 | 5 | 6 | 7 | 8 | 9 | 10 | 11 | 12 |
|---|---|---|---|---|---|---|---|---|---|---|---|---|---|
| A | Azi | 128 | 64 | 32 | 16 | 8 | 4 | 2 | 1 | 0.5 | 0.25 | NC | GC |
| B | Amp | 32 | 16 | 8 | 4 | 2 | 1 | 0.5 | 0.25 | 0.13 | 0.063 | NC | GC |
| C | Cef | 32 | 16 | 8 | 4 | 2 | 1 | 0.5 | 0.25 | 0.13 | 0.063 | NC | GC |
| D | Cli | 64 | 32 | 16 | 8 | 4 | 2 | 1 | 0.5 | 0.25 | 0.13 | NC | GC |
| E | Tet | 64 | 32 | 16 | 8 | 4 | 2 | 1 | 0.5 | 0.25 | 0.13 | NC | GC |
| F | $P_{407}5EC$ | 60 | 30 | 15 | 7.5 | 3.75 | 1.88 | 0.94 | 0.47 | 0.23 | 0.12 | NC | GC |
| G | $W_{20}5EC$ | 60 | 30 | 15 | 7.5 | 3.75 | 1.88 | 0.94 | 0.47 | 0.23 | 0.12 | NC | GC |
| H | $W_{20}5GBA_2$ | 64 | 32 | 16 | 8 | 4 | 2 | 1 | 0.5 | 0.25 | 0.13 | NC | GC |
| With 1 mM EDTA | | | | | | | | | | | | | |
| I | $P_{407}5EC$ | 60 | 30 | 15 | 7.5 | 3.75 | 1.88 | 0.94 | 0.47 | 0.23 | 0.12 | NC | GC |
| J | $W_{20}5EC$ | 60 | 30 | 15 | 7.5 | 3.75 | 1.88 | 0.94 | 0.47 | 0.23 | 0.12 | NC | GC |
| K | $W_{20}5GBA_2$ | 64 | 32 | 16 | 8 | 4 | 2 | 1 | 0.5 | 0.25 | 0.13 | NC | GC |
| L | 1 mM EDTA | 1 | 1 | 1 | 1 | 1 | 1 | 1 | 1 | 1 | 1 | NC | GC |
| With 2 mM EDTA | | | | | | | | | | | | | |
| I | $P_{407}5EC$ | 60 | 30 | 15 | 7.5 | 3.75 | 1.88 | 0.94 | 0.47 | 0.23 | 0.12 | NC | GC |
| J | $W_{20}5EC$ | 60 | 30 | 15 | 7.5 | 3.75 | 1.88 | 0.94 | 0.47 | 0.23 | 0.12 | NC | GC |
| K | $W_{20}5GBA_2$ | 64 | 32 | 16 | 8 | 4 | 2 | 1 | 0.5 | 0.25 | 0.13 | NC | GC |
| L | 2 mM EDTA | 2 | 2 | 2 | 2 | 2 | 2 | 2 | 2 | 2 | 2 | NC | GC |
| With 3 mM EDTA | | | | | | | | | | | | | |
| I | $P_{407}5EC$ | 60 | 30 | 15 | 7.5 | 3.75 | 1.88 | 0.94 | 0.47 | 0.23 | 0.12 | NC | GC |
| J | $W_{20}5EC$ | 60 | 30 | 15 | 7.5 | 3.75 | 1.88 | 0.94 | 0.47 | 0.23 | 0.12 | NC | GC |
| K | $W_{20}5GBA_2$ | 64 | 32 | 16 | 8 | 4 | 2 | 1 | 0.5 | 0.25 | 0.13 | NC | GC |
| L | 3 mM EDTA | 3 | 3 | 3 | 3 | 3 | 3 | 3 | 3 | 3 | 3 | NC | GC |
| With 4 mM EDTA | | | | | | | | | | | | | |
| I | $P_{407}5EC$ | 60 | 30 | 15 | 7.5 | 3.75 | 1.88 | 0.94 | 0.47 | 0.23 | 0.12 | NC | GC |
| J | $W_{20}5EC$ | 60 | 30 | 15 | 7.5 | 3.75 | 1.88 | 0.94 | 0.47 | 0.23 | 0.12 | NC | GC |
| K | $W_{20}5GBA_2$ | 64 | 32 | 16 | 8 | 4 | 2 | 1 | 0.5 | 0.25 | 0.13 | NC | GC |
| L | 4 mM EDTA | 4 | 4 | 4 | 4 | 4 | 4 | 4 | 4 | 4 | 4 | NC | GC |
| With 5 mM EDTA | | | | | | | | | | | | | |
| I | $P_{407}5EC$ | 60 | 30 | 15 | 7.5 | 3.75 | 1.88 | 0.94 | 0.47 | 0.23 | 0.12 | NC | GC |
| J | $W_{20}5EC$ | 60 | 30 | 15 | 7.5 | 3.75 | 1.88 | 0.94 | 0.47 | 0.23 | 0.12 | NC | GC |
| K | $W_{20}5GBA_2$ | 64 | 32 | 16 | 8 | 4 | 2 | 1 | 0.5 | 0.25 | 0.13 | NC | GC |
| L | 5 mM EDTA | 5 | 5 | 5 | 5 | 5 | 5 | 5 | 5 | 5 | 5 | NC | GC |

TABLE 8-continued

| | | 3.0E+06 cfu/mL (initial inoculum concentration) | | | | | | | | | | | |
|---|---|---|---|---|---|---|---|---|---|---|---|---|---|
| #34 pos | | 1 | 2 | 3 | 4 | 5 | 6 | 7 | 8 | 9 | 10 | 11 | 12 |
| A | Azi | 128 | 64 | 32 | 16 | 8 | 4 | 2 | 1 | 0.5 | 0.25 | NC | GC |
| B | Amp | 32 | 16 | 8 | 4 | 2 | 1 | 0.5 | 0.25 | 0.13 | 0.063 | NC | GC |
| C | Cef | 32 | 16 | 8 | 4 | 2 | 1 | 0.5 | 0.25 | 0.13 | 0.063 | NC | GC |
| D | Cli | 64 | 32 | 16 | 8 | 4 | 2 | 1 | 0.5 | 0.25 | 0.13 | NC | GC |
| E | Tet | 64 | 32 | 16 | 8 | 4 | 2 | 1 | 0.5 | 0.25 | 0.13 | NC | GC |
| F | $P_{407}$5EC | 60 | 30 | 15 | 7.5 | 3.75 | 1.88 | 0.94 | 0.47 | 0.23 | 0.12 | NC | GC |
| G | $W_{20}$5EC | 60 | 30 | 15 | 7.5 | 3.75 | 1.88 | 0.94 | 0.47 | 0.23 | 0.12 | NC | GC |
| H | $W_{20}$5GBA$_2$ | 64 | 32 | 16 | 8 | 4 | 2 | 1 | 0.5 | 0.25 | 0.13 | NC | GC |
| With 1 mM EDTA | | | | | | | | | | | | | |
| I | $P_{407}$5EC | 60, 0 | 30, 0 | 15, 0 | 7.5, 0 | 3.75 | 1.88 | 0.94 | 0.47 | 0.23 | 0.12 | NC | GC |
| J | $W_{20}$5EC | 60 | 30, 0 | 15, 0 | 7.5, 0 | 3.75, 0 | 1.88 | 0.94 | 0.47 | 0.23 | 0.12 | NC | GC |
| K | $W_{20}$5GBA$_2$ | 64, 0 | 32, 0 | 16, 0 | 8, 1 | 4 | 2 | 1 | 0.5 | 0.25 | 0.13 | NC | GC |
| L | 1 mM EDTA | 1 | 1 | 1 | 1 | 1 | 1 | 1 | 1 | 1 | 1 | NC | GC |
| With 2 mM EDTA | | | | | | | | | | | | | |
| I | $P_{407}$5EC | 60 | 30 | 15 | 7.5 | 3.75 | 1.88 | 0.94 | 0.47 | 0.23 | 0.12 | NC | GC |
| J | $W_{20}$5EC | 60 | 30 | 15 | 7.5 | 3.75 | 1.88 | 0.94 | 0.47 | 0.23 | 0.12 | NC | GC |
| K | $W_{20}$5GBA$_2$ | 64 | 32 | 16 | 8 | 4 | 2 | 1 | 0.5 | 0.25 | 0.13 | NC | GC |
| L | 2 mM EDTA | 2 | 2 | 2 | 2 | 2 | 2 | 2 | 2 | 2 | 2 | NC | GC |
| With 3 mM EDTA | | | | | | | | | | | | | |
| I | $P_{407}$5EC | 60 | 30 | 15 | 7.5 | 3.75 | 1.88 | 0.94 | 0.47 | 0.23 | 0.12 | NC | GC |
| J | $W_{20}$5EC | 60 | 30 | 15 | 7.5 | 3.75 | 1.88 | 0.94 | 0.47 | 0.23 | 0.12 | NC | GC |
| K | $W_{20}$5GBA$_2$ | 64 | 32 | 16 | 8 | 4 | 2 | 1 | 0.5 | 0.25 | 0.13 | NC | GC |
| L | 3 mM EDTA | 3 | 3 | 3 | 3 | 3 | 3 | 3 | 3 | 3 | 3 | NC | GC |
| With 4 mM EDTA | | | | | | | | | | | | | |
| I | $P_{407}$5EC | 60 | 30 | 15 | 7.5 | 3.75 | 1.88 | 0.94 | 0.47 | 0.23 | 0.12 | NC | GC |
| J | $W_{20}$5EC | 60 | 30 | 15 | 7.5 | 3.75 | 1.88 | 0.94 | 0.47 | 0.23 | 0.12 | NC | GC |
| K | $W_{20}$5GBA$_2$ | 64 | 32 | 16 | 8 | 4 | 2 | 1 | 0.5 | 0.25 | 0.13 | NC | GC |
| L | 4 mM EDTA | 4 | 4 | 4 | 4 | 4 | 4 | 4 | 4 | 4 | 4 | NC | GC |
| With 5 mM EDTA | | | | | | | | | | | | | |
| I | $P_{407}$5EC | 60 | 30 | 15 | 7.5 | 3.75 | 1.88 | 0.94 | 0.47 | 0.23 | 0.12 | NC | GC |
| J | $W_{20}$5EC | 60 | 30 | 15 | 7.5 | 3.75 | 1.88 | 0.94 | 0.47 | 0.23 | 0.12 | NC | GC |
| K | $W_{20}$5GBA$_2$ | 64 | 32 | 16 | 8 | 4 | 2 | 1 | 0.5 | 0.25 | 0.13 | NC | GC |
| L | 5 mM EDTA | 5 | 5 | 5 | 5 | 5 | 5 | 5 | 5 | 5 | 5 | NC | GC |

TABLE 8-continued

| #35 neg | | 1 | 2 | 3 | 4 | 5 | 6 | 7 | 8 | 9 | 10 | 11 | 12 |
|---|---|---|---|---|---|---|---|---|---|---|---|---|---|
| | 2.7E+06 cfu/mL (initial inoculum concentration) | | | | | | | | | | | | |
| A | Azi | 128 | 64 | 32 | 16 | 8 | 4 | 2 | 1 | 0.5 | 0.25 | NC | GC |
| B | Amp | 32 | 16 | 8 | 4 | 2 | 1 | 0.5 | 0.25 | 0.13 | 0.063 | NC | GC |
| C | Cef | 32 | 16 | 8 | 4 | 2 | 1 | 0.5 | 0.25 | 0.13 | 0.063 | NC | GC |
| D | Cli | 64 | 32 | 16 | 8 | 4 | 2 | 1 | 0.5 | 0.25 | 0.13 | NC | GC |
| E | Tet | 64 | 32 | 16 | 8 | 4 | 2 | 1 | 0.5 | 0.25 | 0.13 | NC | GC |
| F | $P_{407}5EC$ | 60 | 30 | 15 | 7.5 | 3.75 | 1.88 | 0.94 | 0.47 | 0.23 | 0.12 | NC | GC |
| G | $W_{20}5EC$ | 60 | 30 | 15 | 7.5 | 3.75 | 1.88 | 0.94 | 0.47 | 0.23 | 0.12 | NC | GC |
| H | $W_{20}5GBA_2$ | 64 | 32 | 16 | 8 | 4 | 2 | 1 | 0.5 | 0.25 | 0.13 | NC | GC |
| With 1 mM EDTA | | | | | | | | | | | | | |
| I | $P_{407}5EC$ | 60 | 30, 0 | 15, 0 | 7.5, 0 | 3.75, 48 | 1.88 | 0.94 | 0.47 | 0.23 | 0.12 | NC | GC |
| J | $W_{20}5EC$ | 60, 0 | 30, 0 | 15, 0 | 7.5, 0 | 3.75 | 1.88 | 0.94 | 0.47 | 0.23 | 0.12 | NC | GC |
| K | $W_{20}5GBA_2$ | 64, 0 | 32, 0 | 16, 0 | 8, lawn | 4 | 2 | 1 | 0.5 | 0.25 | 0.13 | NC | GC |
| L | 1 mM EDTA | 1 | 1 | 1 | 1 | 1 | 1 | 1 | 1 | 1 | 1 | NC | GC |
| With 2 mM EDTA | | | | | | | | | | | | | |
| I | $P_{407}5EC$ | 60 | 30 | 15 | 7.5 | 3.75 | 1.88 | 0.94 | 0.47 | 0.23 | 0.12 | NC | GC |
| J | $W_{20}5EC$ | 60 | 30 | 15 | 7.5 | 3.75 | 1.88 | 0.94 | 0.47 | 0.23 | 0.12 | NC | GC |
| K | $W_{20}5GBA_2$ | 64 | 32 | 16 | 8 | 4 | 2 | 1 | 0.5 | 0.25 | 0.13 | NC | GC |
| L | 2 mM EDTA | 2 | 2 | 2 | 2 | 2 | 2 | 2 | 2 | 2 | 2 | NC | GC |
| With 3 mM EDTA | | | | | | | | | | | | | |
| I | $P_{407}5EC$ | 60 | 30 | 15 | 7.5 | 3.75 | 1.88 | 0.94 | 0.47 | 0.23 | 0.12 | NC | GC |
| J | $W_{20}5EC$ | 60 | 30 | 15 | 7.5 | 3.75 | 1.88 | 0.94 | 0.47 | 0.23 | 0.12 | NC | GC |
| K | $W_{20}5GBA_2$ | 64 | 32 | 16 | 8 | 4 | 2 | 1 | 0.5 | 0.25 | 0.13 | NC | GC |
| L | 3 mM EDTA | 3 | 3 | 3 | 3 | 3 | 3 | 3 | 3 | 3 | 3 | NC | GC |
| With 4 mM EDTA | | | | | | | | | | | | | |
| I | $P_{407}5EC$ | 60 | 30 | 15 | 7.5 | 3.75 | 1.88 | 0.94 | 0.47 | 0.23 | 0.12 | NC | GC |
| J | $W_{20}5EC$ | 60 | 30 | 15 | 7.5 | 3.75 | 1.88 | 0.94 | 0.47 | 0.23 | 0.12 | NC | GC |
| K | $W_{20}5GBA_2$ | 64 | 32 | 16 | 8 | 4 | 2 | 1 | 0.5 | 0.25 | 0.13 | NC | GC |
| L | 4 mM EDTA | 4 | 4 | 4 | 4 | 4 | 4 | 4 | 4 | 4 | 4 | NC | GC |
| With 5 mM EDTA | | | | | | | | | | | | | |
| I | $P_{407}5EC$ | 60 | 30 | 15 | 7.5 | 3.75 | 1.88 | 0.94 | 0.47 | 0.23 | 0.12 | NC | GC |
| J | $W_{20}5EC$ | 60 | 30 | 15 | 7.5 | 3.75 | 1.88 | 0.94 | 0.47 | 0.23 | 0.12 | NC | GC |
| K | $W_{20}5GBA_2$ | 64 | 32 | 16 | 8 | 4 | 2 | 1 | 0.5 | 0.25 | 0.13 | NC | GC |
| L | 5 mM EDTA | 5 | 5 | 5 | 5 | 5 | 5 | 5 | 5 | 5 | 5 | NC | GC |

TABLE 8-continued

| #36 neg | | 2.0E+06 cfu/mL (initial inoculum concentration) 1 | 2 | 3 | 4 | 5 | 6 | 7 | 8 | 9 | 10 | 11 | 12 |
|---|---|---|---|---|---|---|---|---|---|---|---|---|---|
| A | Azi | 128 | 64 | 32 | 16 | 8 | 4 | 2 | 1 | 0.5 | 0.25 | NC | GC |
| B | Amp | 32 | 16 | 8 | 4 | 2 | 1 | 0.5 | 0.25 | 0.13 | 0.063 | NC | GC |
| C | Cef | 32 | 16 | 8 | 4 | 2 | 1 | 0.5 | 0.25 | 0.13 | 0.063 | NC | GC |
| D | Cli | 64 | 32 | 16 | 8 | 4 | 2 | 1 | 0.5 | 0.25 | 0.13 | NC | GC |
| E | Tet | 64 | 32 | 16 | 8 | 4 | 2 | 1 | 0.5 | 0.25 | 0.13 | NC | GC |
| F | $P_{407}5EC$ | 60 | 30 | 15 | 7.5 | 3.75 | 1.88 | 0.94 | 0.47 | 0.23 | 0.12 | NC | GC |
| G | $W_{20}5EC$ | 60 | 30 | 15 | 7.5 | 3.75 | 1.88 | 0.94 | 0.47 | 0.23 | 0.12 | NC | GC |
| H | $W_{20}5GBA_2$ | 64 | 32 | 16 | 8 | 4 | 2 | 1 | 0.5 | 0.25 | 0.13 | NC | GC |
| With 1 mM EDTA | | | | | | | | | | | | | |
| I | $P_{407}5EC$ | 60 | 30 | 15, 0 | 7.5, 0 | 3.75, 48 | 1.88, tntc | 0.94 | 0.47 | 0.23 | 0.12 | NC | GC |
| J | $W_{20}5EC$ | 60 | 30 | 15, 0 | 7.5, 0 | 3.75, tntc | 1.88, lawn | 0.94 | 0.47 | 0.23 | 0.12 | NC | GC |
| K | $W_{20}5GBA_2$ | 64, 0 | 32, 0 | 16, 0 | 8, lawn | 4 | 2 | 1 | 0.5 | 0.25 | 0.13 | NC | GC |
| L | 1 mM EDTA | 1 | 1 | 1 | 1 | 1 | 1 | 1 | 1 | 1 | 1 | NC | GC |
| With 2 mM EDTA | | | | | | | | | | | | | |
| I | $P_{407}5EC$ | 60 | 30 | 15 | 7.5 | 3.75 | 1.88 | 0.94 | 0.47 | 0.23 | 0.12 | NC | GC |
| J | $W_{20}5EC$ | 60 | 30 | 15 | 7.5 | 3.75 | 1.88 | 0.94 | 0.47 | 0.23 | 0.12 | NC | GC |
| K | $W_{20}5GBA_2$ | 64 | 32 | 16 | 8 | 4 | 2 | 1 | 0.5 | 0.25 | 0.13 | NC | GC |
| L | 2 mM EDTA | 2 | 2 | 2 | 2 | 2 | 2 | 2 | 2 | 2 | 2 | NC | GC |
| With 3 mM EDTA | | | | | | | | | | | | | |
| I | $P_{407}5EC$ | 60 | 30 | 15 | 7.5 | 3.75 | 1.88 | 0.94 | 0.47 | 0.23 | 0.12 | NC | GC |
| J | $W_{20}5EC$ | 60 | 30 | 15 | 7.5 | 3.75 | 1.88 | 0.94 | 0.47 | 0.23 | 0.12 | NC | GC |
| K | $W_{20}5GBA_2$ | 64 | 32 | 16 | 8 | 4 | 2 | 1 | 0.5 | 0.25 | 0.13 | NC | GC |
| L | 3 mM EDTA | 3 | 3 | 3 | 3 | 3 | 3 | 3 | 3 | 3 | 3 | NC | GC |
| With 4 mM EDTA | | | | | | | | | | | | | |
| I | $P_{407}5EC$ | 60 | 30 | 15 | 7.5 | 3.75 | 1.88 | 0.94 | 0.47 | 0.23 | 0.12 | NC | GC |
| J | $W_{20}5EC$ | 60 | 30 | 15 | 7.5 | 3.75 | 1.88 | 0.94 | 0.47 | 0.23 | 0.12 | NC | GC |
| K | $W_{20}5GBA_2$ | 64 | 32 | 16 | 8 | 4 | 2 | 1 | 0.5 | 0.25 | 0.13 | NC | GC |
| L | 4 mM EDTA | 4 | 4 | 4 | 4 | 4 | 4 | 4 | 4 | 4 | 4 | NC | GC |
| With 5 mM EDTA | | | | | | | | | | | | | |
| I | $P_{407}5EC$ | 60 | 30 | 15 | 7.5 | 3.75 | 1.88 | 0.94 | 0.47 | 0.23 | 0.12 | NC | GC |
| J | $W_{20}5EC$ | 60 | 30 | 15 | 7.5 | 3.75 | 1.88 | 0.94 | 0.47 | 0.23 | 0.12 | NC | GC |
| K | $W_{20}5GBA_2$ | 64 | 32 | 16 | 8 | 4 | 2 | 1 | 0.5 | 0.25 | 0.13 | NC | GC |
| L | 5 mM EDTA | 5 | 5 | 5 | 5 | 5 | 5 | 5 | 5 | 5 | 5 | NC | GC |

TABLE 8-continued

| | | 1.7E+06 cfu/mL (initial inoculum concentration) | | | | | | | | | | | |
|---|---|---|---|---|---|---|---|---|---|---|---|---|---|
| #37 pos | | 1 | 2 | 3 | 4 | 5 | 6 | 7 | 8 | 9 | 10 | 11 | 12 |
| A | Azi | 128 | 64 | 32 | 16 | 8 | 4 | 2 | 1 | 0.5 | 0.25 | NC | GC |
| B | Amp | 32 | 16 | 8 | 4 | 2 | 1 | 0.5 | 0.25 | 0.13 | 0.063 | NC | GC |
| C | Cef | 32 | 16 | 8 | 4 | 2 | 1 | 0.5 | 0.25 | 0.13 | 0.063 | NC | GC |
| D | Cli | 64 | 32 | 16 | 8 | 4 | 2 | 1 | 0.5 | 0.25 | 0.13 | NC | GC |
| E | Tet | 64 | 32 | 16 | 8 | 4 | 2 | 1 | 0.5 | 0.25 | 0.13 | NC | GC |
| F | $P_{407}$5EC | 60 | 30 | 15 | 7.5 | 3.75 | 1.88 | 0.94 | 0.47 | 0.23 | 0.12 | NC | GC |
| G | $W_{20}$5EC | 60 | 30 | 15 | 7.5 | 3.75 | 1.88 | 0.94 | 0.47 | 0.23 | 0.12 | NC | GC |
| H | $W_{20}$5GBA$_2$ | 64 | 32 | 16 | 8 | 4 | 2 | 1 | 0.5 | 0.25 | 0.13 | NC | GC |
| With 1 mM EDTA | | | | | | | | | | | | | |
| I | $P_{407}$5EC | 60 | 30 | 15, 0 | 7.5, 0 | 3.75, 0 | 1.88, lawn | 0.94 | 0.47 | 0.23 | 0.12 | NC | GC |
| J | $W_{20}$5EC | 60 | 30, 0 | 15, 0 | 7.5, 0 | 3.75, 0 | 1.88 | 0.94 | 0.47 | 0.23 | 0.12 | NC | GC |
| K | $W_{20}$5GBA$_2$ | 64, 0 | 32, 0 | 16, 0 | 8, 4 | 4 | 2 | 1 | 0.5 | 0.25 | 0.13 | NC | GC |
| L | 1 mM EDTA | 1 | 1 | 1 | 1 | 1 | 1 | 1 | 1 | 1 | 1 | NC | GC |
| With 2 mM EDTA | | | | | | | | | | | | | |
| I | $P_{407}$5EC | 60 | 30 | 15 | 7.5 | 3.75 | 1.88 | 0.94 | 0.47 | 0.23 | 0.12 | NC | GC |
| J | $W_{20}$5EC | 60 | 30 | 15 | 7.5 | 3.75 | 1.88 | 0.94 | 0.47 | 0.23 | 0.12 | NC | GC |
| K | $W_{20}$5GBA$_2$ | 64 | 32 | 16 | 8 | 4 | 2 | 1 | 0.5 | 0.25 | 0.13 | NC | GC |
| L | 2 mM EDTA | 2 | 2 | 2 | 2 | 2 | 2 | 2 | 2 | 2 | 2 | NC | GC |
| With 3 mM EDTA | | | | | | | | | | | | | |
| I | $P_{407}$5EC | 60 | 30 | 15 | 7.5 | 3.75 | 1.88 | 0.94 | 0.47 | 0.23 | 0.12 | NC | GC |
| J | $W_{20}$5EC | 60 | 30 | 15 | 7.5 | 3.75 | 1.88 | 0.94 | 0.47 | 0.23 | 0.12 | NC | GC |
| K | $W_{20}$5GBA$_2$ | 64 | 32 | 16 | 8 | 4 | 2 | 1 | 0.5 | 0.25 | 0.13 | NC | GC |
| L | 3 mM EDTA | 3 | 3 | 3 | 3 | 3 | 3 | 3 | 3 | 3 | 3 | NC | GC |
| With 4 mM EDTA | | | | | | | | | | | | | |
| I | $P_{407}$5EC | 60 | 30 | 15 | 7.5 | 3.75 | 1.88 | 0.94 | 0.47 | 0.23 | 0.12 | NC | GC |
| J | $W_{20}$5EC | 60 | 30 | 15 | 7.5 | 3.75 | 1.88 | 0.94 | 0.47 | 0.23 | 0.12 | NC | GC |
| K | $W_{20}$5GBA$_2$ | 64 | 32 | 16 | 8 | 4 | 2 | 1 | 0.5 | 0.25 | 0.13 | NC | GC |
| L | 4 mM EDTA | 4 | 4 | 4 | 4 | 4 | 4 | 4 | 4 | 4 | 4 | NC | GC |
| With 5 mM EDTA | | | | | | | | | | | | | |
| I | $P_{407}$5EC | 60 | 30 | 15 | 7.5 | 3.75 | 1.88 | 0.94 | 0.47 | 0.23 | 0.12 | NC | GC |
| J | $W_{20}$5EC | 60 | 30 | 15 | 7.5 | 3.75 | 1.88 | 0.94 | 0.47 | 0.23 | 0.12 | NC | GC |
| K | $W_{20}$5GBA$_2$ | 64 | 32 | 16 | 8 | 4 | 2 | 1 | 0.5 | 0.25 | 0.13 | NC | GC |
| L | 5 mM EDTA | 5 | 5 | 5 | 5 | 5 | 5 | 5 | 5 | 5 | 5 | NC | GC |

TABLE 8-continued

| | | 9.5E+05 cfu/mL (initial inoculum concentration) | | | | | | | | | | | |
|---|---|---|---|---|---|---|---|---|---|---|---|---|---|
| #38 neg | | 1 | 2 | 3 | 4 | 5 | 6 | 7 | 8 | 9 | 10 | 11 | 12 |
| A | Azi | 128 | 64 | 32 | 16 | 8 | 4 | 2 | 1 | 0.5 | 0.25 | NC | GC |
| B | Amp | 32 | 16 | 8 | 4 | 2 | 1 | 0.5 | 0.25 | 0.13 | 0.063 | NC | GC |
| C | Cef | 32 | 16 | 8 | 4 | 2 | 1 | 0.5 | 0.25 | 0.13 | 0.063 | NC | GC |
| D | Cli | 64 | 32 | 16 | 8 | 4 | 2 | 1 | 0.5 | 0.25 | 0.13 | NC | GC |
| E | Tet | 64 | 32 | 16 | 8 | 4 | 2 | 1 | 0.5 | 0.25 | 0.13 | NC | GC |
| F | $P_{407}5EC$ | 60 | 30 | 15 | 7.5 | 3.75 | 1.88 | 0.94 | 0.47 | 0.23 | 0.12 | NC | GC |
| G | $W_{20}5EC$ | 60 | 30 | 15 | 7.5 | 3.75 | 1.88 | 0.94 | 0.47 | 0.23 | 0.12 | NC | GC |
| H | $W_{20}5GBA_2$ | 64 | 32 | 16 | 8 | 4 | 2 | 1 | 0.5 | 0.25 | 0.13 | NC | GC |
| With 1 mM EDTA | | | | | | | | | | | | | |
| I | $P_{407}5EC$ | 60, 1 | 30, 0 | 15, 0 | 7.5, 0 | 3.75 | 1.88 | 0.94 | 0.47 | 0.23 | 0.12 | NC | GC |
| J | $W_{20}5EC$ | 60, 0 | 30, 0 | 15, 0 | 7.5, 0 | 3.75 | 1.88 | 0.94 | 0.47 | 0.23 | 0.12 | NC | GC |
| K | $W_{20}5GBA_2$ | 64, 0 | 32, 0 | 16, 0 | 8, lawn | 4 | 2 | 1 | 0.5 | 0.25 | 0.13 | NC | GC |
| L | 1 mM EDTA | 1 | 1 | 1 | 1 | 1 | 1 | 1 | 1 | 1 | 1 | NC | GC |
| With 2 mM EDTA | | | | | | | | | | | | | |
| I | $P_{407}5EC$ | 60 | 30 | 15 | 7.5 | 3.75 | 1.88 | 0.94 | 0.47 | 0.23 | 0.12 | NC | GC |
| J | $W_{20}5EC$ | 60 | 30 | 15 | 7.5 | 3.75 | 1.88 | 0.94 | 0.47 | 0.23 | 0.12 | NC | GC |
| K | $W_{20}5GBA_2$ | 64 | 32 | 16 | 8 | 4 | 2 | 1 | 0.5 | 0.25 | 0.13 | NC | GC |
| L | 2 mM EDTA | 2 | 2 | 2 | 2 | 2 | 2 | 2 | 2 | 2 | 2 | NC | GC |
| With 3 mM EDTA | | | | | | | | | | | | | |
| I | $P_{407}5EC$ | 60 | 30 | 15 | 7.5 | 3.75 | 1.88 | 0.94 | 0.47 | 0.23 | 0.12 | NC | GC |
| J | $W_{20}5EC$ | 60 | 30 | 15 | 7.5 | 3.75 | 1.88 | 0.94 | 0.47 | 0.23 | 0.12 | NC | GC |
| K | $W_{20}5GBA_2$ | 64 | 32 | 16 | 8 | 4 | 2 | 1 | 0.5 | 0.25 | 0.13 | NC | GC |
| L | 3 mM EDTA | 3 | 3 | 3 | 3 | 3 | 3 | 3 | 3 | 3 | 3 | NC | GC |
| With 4 mM EDTA | | | | | | | | | | | | | |
| I | $P_{407}5EC$ | 60 | 30 | 15 | 7.5 | 3.75 | 1.88 | 0.94 | 0.47 | 0.23 | 0.12 | NC | GC |
| J | $W_{20}5EC$ | 60 | 30 | 15 | 7.5 | 3.75 | 1.88 | 0.94 | 0.47 | 0.23 | 0.12 | NC | GC |
| K | $W_{20}5GBA_2$ | 64 | 32 | 16 | 8 | 4 | 2 | 1 | 0.5 | 0.25 | 0.13 | NC | GC |
| L | 4 mM EDTA | 4 | 4 | 4 | 4 | 4 | 4 | 4 | 4 | 4 | 4 | NC | GC |
| With 5 mM EDTA | | | | | | | | | | | | | |
| I | $P_{407}5EC$ | 60 | 30 | 15 | 7.5 | 3.75 | 1.88 | 0.94 | 0.47 | 0.23 | 0.12 | NC | GC |
| J | $W_{20}5EC$ | 60 | 30 | 15 | 7.5 | 3.75 | 1.88 | 0.94 | 0.47 | 0.23 | 0.12 | NC | GC |
| K | $W_{20}5GBA_2$ | 64 | 32 | 16 | 8 | 4 | 2 | 1 | 0.5 | 0.25 | 0.13 | NC | GC |
| L | 5 mM EDTA | 5 | 5 | 5 | 5 | 5 | 5 | 5 | 5 | 5 | 5 | NC | GC |

TABLE 8-continued

| | | 2.0E+06 cfu/mL (initial inoculum concentration) | | | | | | | | | | | |
|---|---|---|---|---|---|---|---|---|---|---|---|---|---|
| #41 pos | | 1 | 2 | 3 | 4 | 5 | 6 | 7 | 8 | 9 | 10 | 11 | 12 |
| A | Azi | 128 | 64 | 32 | 16 | 8 | 4 | 2 | 1 | 0.5 | 0.25 | NC | GC |
| B | Amp | 32 | 16 | 8 | 4 | 2 | 1 | 0.5 | 0.25 | 0.13 | 0.063 | NC | GC |
| C | Cef | 32 | 16 | 8 | 4 | 2 | 1 | 0.5 | 0.25 | 0.13 | 0.063 | NC | GC |
| D | Cli | 64 | 32 | 16 | 8 | 4 | 2 | 1 | 0.5 | 0.25 | 0.13 | NC | GC |
| E | Tet | 64 | 32 | 16 | 8 | 4 | 2 | 1 | 0.5 | 0.25 | 0.13 | NC | GC |
| F | $P_{407}$5EC | 60 | 30 | 15 | 7.5 | 3.75 | 1.88 | 0.94 | 0.47 | 0.23 | 0.12 | NC | GC |
| G | $W_{20}$5EC | 60 | 30 | 15 | 7.5 | 3.75 | 1.88 | 0.94 | 0.47 | 0.23 | 0.12 | NC | GC |
| H | $W_{20}$5$GBA_2$ | 64 | 32 | 16 | 8 | 4 | 2 | 1 | 0.5 | 0.25 | 0.13 | NC | GC |
| With 1 mM EDTA | | | | | | | | | | | | | |
| I | $P_{407}$5EC | 60 | 30 | 15 | 7.5 | 3.75 | 1.88 | 0.94 | 0.47 | 0.23 | 0.12 | NC | GC |
| J | $W_{20}$5EC | 60 | 30 | 15 | 7.5 | 3.75 | 1.88 | 0.94 | 0.47 | 0.23 | 0.12 | NC | GC |
| K | $W_{20}$5$GBA_2$ | 64 | 32 | 16 | 8 | 4 | 2 | 1 | 0.5 | 0.25 | 0.13 | NC | GC |
| L | 1 mM EDTA | 1 | 1 | 1 | 1 | 1 | 1 | 1 | 1 | 1 | 1 | NC | GC |
| With 2 mM EDTA | | | | | | | | | | | | | |
| I | $P_{407}$5EC | 60 | 30 | 15 | 7.5 | 3.75 | 1.88 | 0.94 | 0.47 | 0.23 | 0.12 | NC | GC |
| J | $W_{20}$5EC | 60 | 30 | 15 | 7.5 | 3.75 | 1.88 | 0.94 | 0.47 | 0.23 | 0.12 | NC | GC |
| K | $W_{20}$5$GBA_2$ | 64 | 32 | 16 | 8 | 4 | 2 | 1 | 0.5 | 0.25 | 0.13 | NC | GC |
| L | 2 mM EDTA | 2 | 2 | 2 | 2 | 2 | 2 | 2 | 2 | 2 | 2 | NC | GC |
| With 3 mM EDTA | | | | | | | | | | | | | |
| I | $P_{407}$5EC | 60 | 30 | 15 | 7.5 | 3.75 | 1.88 | 0.94 | 0.47 | 0.23 | 0.12 | NC | GC |
| J | $W_{20}$5EC | 60 | 30 | 15 | 7.5 | 3.75 | 1.88 | 0.94 | 0.47 | 0.23 | 0.12 | NC | GC |
| K | $W_{20}$5$GBA_2$ | 64 | 32 | 16 | 8 | 4 | 2 | 1 | 0.5 | 0.25 | 0.13 | NC | GC |
| L | 3 mM EDTA | 3 | 3 | 3 | 3 | 3 | 3 | 3 | 3 | 3 | 3 | NC | GC |
| With 4 mM EDTA | | | | | | | | | | | | | |
| I | $P_{407}$5EC | 60 | 30 | 15 | 7.5 | 3.75 | 1.88 | 0.94 | 0.47 | 0.23 | 0.12 | NC | GC |
| J | $W_{20}$5EC | 60 | 30 | 15 | 7.5 | 3.75 | 1.88 | 0.94 | 0.47 | 0.23 | 0.12 | NC | GC |
| K | $W_{20}$5$GBA_2$ | 64 | 32 | 16 | 8 | 4 | 2 | 1 | 0.5 | 0.25 | 0.13 | NC | GC |
| L | 4 mM EDTA | 4 | 4 | 4 | 4 | 4 | 4 | 4 | 4 | 4 | 4 | NC | GC |
| With 5 mM EDTA | | | | | | | | | | | | | |
| I | $P_{407}$5EC | 60 | 30 | 15 | 7.5 | 3.75 | 1.88 | 0.94 | 0.47 | 0.23 | 0.12 | NC | GC |
| J | $W_{20}$5EC | 60 | 30 | 15 | 7.5 | 3.75 | 1.88 | 0.94 | 0.47 | 0.23 | 0.12 | NC | GC |
| K | $W_{20}$5$GBA_2$ | 64 | 32 | 16 | 8 | 4 | 2 | 1 | 0.5 | 0.25 | 0.13 | NC | GC |
| L | 5 mM EDTA | 5 | 5 | 5 | 5 | 5 | 5 | 5 | 5 | 5 | 5 | NC | GC |

| | | 2.5E+06 cfu/mL (initial inoculum concentration) | | | | | | | | | | | |
|---|---|---|---|---|---|---|---|---|---|---|---|---|---|
| #42 pos | | 1 | 2 | 3 | 4 | 5 | 6 | 7 | 8 | 9 | 10 | 11 | 12 |
| A | Azi | 128 | 64 | 32 | 16 | 8 | 4 | 2 | 1 | 0.5 | 0.25 | NC | GC |
| B | Amp | 32 | 16 | 8 | 4 | 2 | 1 | 0.5 | 0.25 | 0.13 | 0.063 | NC | GC |
| C | Cef | 32 | 16 | 8 | 4 | 2 | 1 | 0.5 | 0.25 | 0.13 | 0.063 | NC | GC |
| D | Cli | 64 | 32 | 16 | 8 | 4 | 2 | 1 | 0.5 | 0.25 | 0.13 | NC | GC |
| E | Tet | 64 | 32 | 16 | 8 | 4 | 2 | 1 | 0.5 | 0.25 | 0.13 | NC | GC |
| F | $P_{407}$5EC | 60 | 30 | 15 | 7.5 | 3.75 | 1.88 | 0.94 | 0.47 | 0.23 | 0.12 | NC | GC |
| G | $W_{20}$5EC | 60 | 30 | 15 | 7.5 | 3.75 | 1.88 | 0.94 | 0.47 | 0.23 | 0.12 | NC | GC |
| H | $W_{20}$5$GBA_2$ | 64 | 32 | 16 | 8 | 4 | 2 | 1 | 0.5 | 0.25 | 0.13 | NC | GC |
| With 1 mM EDTA | | | | | | | | | | | | | |
| I | $P_{407}$5EC | 60 | 30 | 15 | 7.5 | 3.75 | 1.88 | 0.94 | 0.47 | 0.23 | 0.12 | NC | GC |
| J | $W_{20}$5EC | 60 | 30 | 15 | 7.5 | 3.75 | 1.88 | 0.94 | 0.47 | 0.23 | 0.12 | NC | GC |
| K | $W_{20}$5$GBA_2$ | 64 | 32 | 16 | 8 | 4 | 2 | 1 | 0.5 | 0.25 | 0.13 | NC | GC |
| L | 1 mM EDTA | 1 | 1 | 1 | 1 | 1 | 1 | 1 | 1 | 1 | 1 | NC | GC |

TABLE 8-continued

| | | | | | | | | | | | | | |
|---|---|---|---|---|---|---|---|---|---|---|---|---|---|
| With 2 mM EDTA | | | | | | | | | | | | | |
| I | $P_{407}$5EC | 60 | 30 | 15 | 7.5 | 3.75 | 1.88 | 0.94 | 0.47 | 0.23 | 0.12 | NC | GC |
| J | $W_{20}$5EC | 60 | 30 | 15 | 7.5 | 3.75 | 1.88 | 0.94 | 0.47 | 0.23 | 0.12 | NC | GC |
| K | $W_{20}$5GB$A_2$ | 64 | 32 | 16 | 8 | 4 | 2 | 1 | 0.5 | 0.25 | 0.13 | NC | GC |
| L | 2 mM EDTA | 2 | 2 | 2 | 2 | 2 | 2 | 2 | 2 | 2 | 2 | NC | GC |
| With 3 mM EDTA | | | | | | | | | | | | | |
| I | $P_{407}$5EC | 60 | 30 | 15 | 7.5 | 3.75 | 1.88 | 0.94 | 0.47 | 0.23 | 0.12 | NC | GC |
| J | $W_{20}$5EC | 60 | 30 | 15 | 7.5 | 3.75 | 1.88 | 0.94 | 0.47 | 0.23 | 0.12 | NC | GC |
| K | $W_{20}$5GB$A_2$ | 64 | 32 | 16 | 8 | 4 | 2 | 1 | 0.5 | 0.25 | 0.13 | NC | GC |
| L | 3 mM EDTA | 3 | 3 | 3 | 3 | 3 | 3 | 3 | 3 | 3 | 3 | NC | GC |
| With 4 mM EDTA | | | | | | | | | | | | | |
| I | $P_{407}$5EC | 60 | 30 | 15 | 7.5 | 3.75 | 1.88 | 0.94 | 0.47 | 0.23 | 0.12 | NC | GC |
| J | $W_{20}$5EC | 60 | 30 | 15 | 7.5 | 3.75 | 1.88 | 0.94 | 0.47 | 0.23 | 0.12 | NC | GC |
| K | $W_{20}$5GB$A_2$ | 64 | 32 | 16 | 8 | 4 | 2 | 1 | 0.5 | 0.25 | 0.13 | NC | GC |
| L | 4 mM EDTA | 4 | 4 | 4 | 4 | 4 | 4 | 4 | 4 | 4 | 4 | NC | GC |
| With 5 mM EDTA | | | | | | | | | | | | | |
| I | $P_{407}$5EC | 60 | 30 | 15 | 7.5 | 3.75 | 1.88 | 0.94 | 0.47 | 0.23 | 0.12 | NC | GC |
| J | $W_{20}$5EC | 60 | 30 | 15 | 7.5 | 3.75 | 1.88 | 0.94 | 0.47 | 0.23 | 0.12 | NC | GC |
| K | $W_{20}$5GB$A_2$ | 64 | 32 | 16 | 8 | 4 | 2 | 1 | 0.5 | 0.25 | 0.13 | NC | GC |
| L | 5 mM EDTA | 5 | 5 | 5 | 5 | 5 | 5 | 5 | 5 | 5 | 5 | NC | GC |

| | | | | | | | | |
|---|---|---|---|---|---|---|---|---|
| Highlighted in Green are rows containing plate counts for the MBC. The second number is the plate count of a 10 μl sample from the microtiter plate used to determine the MBC. The MBC was defined as ≥ 3-log reduction of the inoculum. | | | | | | | | |
| No inhibition of Growth | | MIC | | | Deduced MIC from MBC | | | |

Azi = azithromycin;
Amp = ampicillin;
Cef = cefepine;
Cli = clindamycin;
Tet = tetracycline.

Example 7

The purpose of this study was to determine the MIC and MBC of four nanoemulsions (NEs) according to the invention and compare the performance of the NEs to conventional antibiotics against MRSA. MRSA is one of the microorganisms that cause lung infections in young cystic fibrosis patients and is also implicated in infections of skin and soft tissue, including burn wound infections. Because of its varied virulence mechanisms, infections caused by MRSA can be lethal.

The purpose of this example was to evaluate 4 nanoemulsions according to the invention for use in the topical treatment of infectious diseases. The nanoemulsions tested were $W_{80}$5EC, $W_{20}$5ECEDL2, $W_{20}$ 5GB$A_2$ED and $P_{407}$5EC. This example determined the minimum inhibitory concentration (MIC) of the four nanoemulsions plus comparator drugs against 29 clinical isolates of methicillin-resistant *Staphylococcus aureus* (MRSA).

The results shown below demonstrate that the MIC ranges for the nanoemulsions were 0.5-2 ($W_{80}$5EC), 0.5-4 ($W_{20}$5ECEDL2), 1-4 ($W_{20}$5GB$A_2$ED), 1-4 μg/ml ($P_{407}$5EC), respectively. Minimum bactericidal concentration (MBC) data was also collected and the MBC ranges were 0.5-16 ($W_{80}$5EC), 1->32 ($W_{20}$5ECEDL2), 2-16 ($W_{20}$5GB$A_2$ED), and 1->16 μg/ml ($P_{407}$5EC), respectively.

A. Methods and Materials

Source of drugs and isolates. Twelve comparator compounds, clindamycin (USP #1136002), doxycycline (USP #1226003), erythromycin (Sigma #E0774), levofloxacin (Sigma #28266), mafenide acetate (USP #1373008), mupirocin (Sigma #M7694), silvadene (USP #61260), vancomycin (Sigma #V1764), Oxacillin (Sigma #28221), sulfamethoxazole (USP #1631001), trimethoprim (USP #1692505), and silver nitrate (VWR #VW3462-0) were compared to the four nanoemulsions. The four nanoemulsions were (a) $W_{80}$5EC, (b) $W_{20}$5ECEDL2, (c) $W_{20}$5GB$A_2$ED and (d) $P_{407}$5EC. See Table 10, which provides drug panel templates (with increasing dilutions across the panel). The emulsions were produced by mixing a water immiscible oil phase with an aqueous phase. The $W_{20}$5ECEDL2 formulation was microfluidized. The base formulations are shown in Table 9 below and represent the neat emulsions, which were further diluted to the desired %. Compositions are w/w % unless otherwise noted.

TABLE 9

| Nanoemulsions | | |
|---|---|---|
| Nanoemulsion | Component | Weight Percent (w/w %) |
| $W_{80}$5EC | Water | 23.490% |
| | Ethanol | 6.730% |
| | Cetylpyridinium Chloride | 1.068% |
| | Polysorbate 80 | 5.920% |
| | Refined Soybean Oil | 62.790% |

TABLE 9-continued

| Nanoemulsions | | |
|---|---|---|
| Nanoemulsion | Component | Weight Percent (w/w %) |
| $W_{20}5ECEDL2$ | Distilled Water | 23.418% |
| | EDTA | 0.0745% |
| | Cetylpyridinium Chloride | 1.068% |
| | Tween 20 | 5.92% |
| | Ethanol | 6.73% |
| | Soybean Oil | 62.79% |
| $W_{20}5GBA_2ED$ (v/v %) | Distilled Water | 20.93% |
| | EDTA | 0.0745% |
| | BTC 824 | 2% |
| | Tween 20 | 5% |
| | Glycerine | 8% |
| | Soybean Oil | 64% |
| $P_{407}5EC$ | Distilled Water | 23.49% |
| | CPC | 1.068% |
| | Poloxamer 407 | 5.92% |
| | Ethanol | 6.73% |
| | Soybean Oil, NP | 62.79% |

TABLE 10

| Drug Panel Templates<br>Drug Panel Templates | | | | | | | | | | | | | |
|---|---|---|---|---|---|---|---|---|---|---|---|---|---|
| | | Compound in μg/ml (% for $AgNO_3$) | | | | | | | | | | | |
| | Compound | 1 | 2 | 3 | 4 | 5 | 6 | 7 | 8 | 9 | 10 | 11 | 12 |
| A | Clindamycin | 64 | 32 | 16 | 8 | 4 | 2 | 1 | 0.5 | 0.25 | 0.125 | NC | GC |
| B | Doxycycline | 128 | 64 | 32 | 16 | 8 | 4 | 2 | 1 | 0.5 | 0.25 | NC | GC |
| C | Erythromycin | 128 | 64 | 32 | 16 | 8 | 4 | 2 | 1 | 0.5 | 0.25 | NC | GC |
| D | Levofloxacin | 64 | 32 | 16 | 8 | 4 | 2 | 1 | 0.5 | 0.25 | 0.125 | NC | GC |
| E | Mafenide acetate | 128 | 64 | 32 | 16 | 8 | 4 | 2 | 1 | 0.5 | 0.25 | NC | GC |
| F | Mupirocin | 64 | 32 | 16 | 8 | 4 | 2 | 1 | 0.5 | 0.25 | 0.125 | NC | GC |
| G | Silvadene | 128 | 64 | 32 | 16 | 8 | 4 | 2 | 1 | 0.5 | 0.25 | NC | GC |
| H | Vancomycin | 64 | 32 | 16 | 8 | 4 | 2 | 1 | 0.5 | 0.25 | 0.125 | NC | GC |
| A | Oxacillin | 16 | 8 | 4 | 2 | 1 | 0.5 | 0.25 | 0.125 | 0.0625 | 0.03125 | NC | GC |
| B | Sulfamethazole | 32 | 16 | 8 | 4 | 2 | 1 | 0.5 | 0.25 | 0.125 | 0.0625 | NC | GC |
| C | Trimethoprim | 64 | 32 | 16 | 8 | 4 | 2 | 1 | 0.5 | 0.25 | 0.125 | NC | GC |
| D | $AgNO_3$ | 0.01 | 0.005 | 0.0025 | 0.00125 | 0.00063 | 0.00031 | 0.00016 | 0.00008 | 0.00004 | 0.00002 | NC | GC |
| E | $P_{407}5EC$ | 32 | 16 | 8 | 4 | 2 | 1 | 0.5 | 0.25 | 0.125 | 0.0625 | NC | GC |
| F | $W_{20}5ECEDL2$ | 32 | 16 | 8 | 4 | 2 | 1 | 0.5 | 0.25 | 0.125 | 0.0625 | NC | GC |
| G | $W_{20}5GBA_2ED$ | 64 | 32 | 16 | 8 | 4 | 2 | 1 | 0.5 | 0.25 | 0.125 | NC | GC |
| H | $W_{80}5EC$ | 32 | 16 | 8 | 4 | 2 | 1 | 0.5 | 0.25 | 0.125 | 0.0625 | NC | GC |

Source of bacterial strains. Twenty-nine clinical isolates of MRSA were obtained from the University of Dentistry and Medicine of New Jersey. The quality control isolate, ATCC 29213, was obtained from the American Type Culture Collection. Table 11 below provides the phenotype/genotype of each strain.

TABLE 11

| Phenotype and genotype of MRSA isolates | | | | | | |
|---|---|---|---|---|---|---|
| Strain | Phenotype or Genotype | | | | | |
| Number | MLST | spatype | spa repeat pattern | SCCmec | PFGE | PVL |
| 2394 | ST59 | 17 | Z1-D1-M1-D1-M1-N1-K1-B1 | IV | USA1000 | + |
| 2402 | | | | | | |
| 2926 | ST5 | 2 | T1-J1-M1-B1-M1-D1-M1-G1-M1-K1 | II | | – |
| 9897 | ST1 | 131 | U1-I1-J1-F1-K1-B1-P1-E1 | IV | USA400 | + |
| 11118 | | 131 | U1-I1-J1-F1-K1-B1-P1-E1 | IV | USA400 | + |
| 11512 | ST36 | 16 | W1-G1-K1-A1-K1-A1-O1-M1-Q1-Q1-Q1 | II | | – |
| 11540 | ST8 | 1 | Y1-H1-G1-F1-M1-B1-Q1-B1-L1-O1 | IV | USA300 | + |
| 11554 | | 1 | Y1-H1-G1-F1-M1-B1-Q1-B1-L1-O1 | IV | | + |
| 13219 | | 2 | T1-J1-M1-B1-M1-D1-M1-G1-M1-K1 | IV | | – |
| 13367 | | 2 | T1-J1-M1-B1-M1-D1-M1-G1-M1-K1 | II | | – |
| 13386 | | 2 | T1-J1-M1-B1-M1-D1-M1-G1-M1-K1 | II | | – |
| 13408 | | 2 | T1-J1-M1-B1-M1-D1-M1-G1-M1-K1 | IV | | – |
| 13606 | | 2 | T1-J1-M1-B1-M1-D1-M1-G1-M1-K1 | II | | – |
| 13610 | | 1 | Y1-H1-G1-F1-M1-B1-Q1-B1-L1-O1 | I | | – |
| 13643 | | 1 | Y1-H1-G1-F1-M1-B1-Q1-B1-L1-O1 | IV | | + |
| 13693 | | 7 | Y1-H1-G1-C1-M1-B1-Q1-B1-L1-O1 | IV | | – |
| 13701 | | 2 | T1-J1-M1-B1-M1-D1-M1-G1-M1-K1 | II | | |
| 13722 | | 2 | T1-J1-M1-B1-M1-D1-M1-G1-M1-K1 | II | | – |
| 13756 | | 2 | T1-J1-M1-B1-M1-D1-M1-G1-M1-K1 | II | | – |
| 13759 | | 1 | Y1-H1-G1-F1-M1-B1-Q1-B1-L1-O1 | IV | | – |

TABLE 11-continued

Phenotype and genotype of MRSA isolates

| Strain Number | MLST | spatype | spa repeat pattern | SCCmec | PFGE | PVL |
|---|---|---|---|---|---|---|
| 13868 | | 2 | T1-J1-M1-B1-M1-D1-M1-G1-M1-K1 | II | | – |
| 15337 | | 18 | W1-F1-K1-A1-O1-M1-Q1 | II | | – |
| 18998 (MUP-R) | | 1 | Y1-H1-G1-F1-M1-B1-Q1-B1-L1-O1 | IV | USA300 | + |
| 19001 (MUP-R) | | 1 | Y1-H1-G1-F1-M1-B1-Q1-B1-L1-O1 | IV | USA300 | + |
| 19017 (MUP-R) | | 1 | Y1-H1-G1-F1-M1-B1-Q1-B1-L1-O1 | IV | USA300 | + |
| 19024 (MUP-R) | | 1 | Y1-H1-G1-F1-M1-B1-Q1-B1-L1-O1 | IV | USA300 | + |
| 19047 (MUP-R) | | 1 | Y1-H1-G1-F1-M1-B1-Q1-B1-L1-O1 | IV | | + |
| 19069 (MUP-R) | ST8 | 1 | Y1-H1-G1-F1-M1-B1-Q1-B1-L1-O1 | IV | USA300 | + |
| 19156 (MUP-R) | | 1 | Y1-H1-G1-F1-M1-B1-Q1-B1-L1-O1 | IV | | + |

Susceptibility assays. The susceptibility of MRSA to twelve traditional antimicrobials and four nanoemulsion formulations was tested using the guidelines published by the Clinical Laboratory Standards Institute (Clinical and Laboratory Standard Institute, "Antimicrobial Susceptibility and Testing; Seventeenth Informational Supplement. CLSI document M100-S17 (ISBN 1-56238-625-5), CLSI, Wayne, Pa.). The ranges of drug concentrations were as follows: clindamycin (64-0.125 μg/ml), doxycycline (128-0.25 μg/ml), erythromycin (128-0.25 μg/ml), levofloxacin (64-0.125 μg/ml), mafenide acetate (128-0.25 μg/ml), mupirocin (64-0.125 μg/ml), silvadene (128-0.25 μg/ml), vancomycin (64-0.125 μg/m), oxacillin (16-0.03125 μg/ml), sulfamethoxazole (32-0.0625 μg/ml), trimethoprim (64-125 μg/ml), silver nitrate (0.01-0.00002%), $W_{80}$5EC (32-0.0625 μg/ml), $W_{20}$5ECEDL2 (32-0.0625 μg/ml), $W_{20}$5GBA$_2$ED (64-0.125 μg/ml), and $P_{407}$5EC (32-0.0625 μg/ml).

Minimum inhibitory concentrations (MIC) were determined visually as the first totally clear well in the series of the 10 concentrations of each drug. For the nanoemulsions, because they are intrinsically opaque, the MIC was called as the first well observed to have some clearing from the least concentrated to the most concentrated. Minimum bactericidal concentrations (MBC) values were assessed for all the antimicrobials tested. The lowest concentration of antimicrobial agent that killed 2: 99.9% of the starting test inoculum was defined as the MBC. A compound or nanoemulsion is defined as bactericidal if its MBC/MIC ratio was ~4.

B. Results

Data for the MICs and MBCs are shown in Tables 11 and 12. All four nanoemulsions were potent against the clinical isolates of MRSA, with no differential activity noted for community-acquired MRSA (SCCmec type IV) or hospital-associated MRSA (SCCmec types I-III). Further, there appeared to be no cross-resistance of the nanoemulsions to any of the known antibiotics. The $MIC_{90}$ values were 2 μg/ml for $P_{407}$5EC, $W_{20}$5ECEDL2 and $W_{80}$5EC. $W_{20}$5GBA$_2$ED had a $MIC_{90}$ Of 4 μg/ml. The $MIC_{90}$ values indicated that this collection of MRSA was susceptible to oral antibiotics, doxycyline ($MIC_{90}$=4 μg/ml), sulfamethoxazole ($MIC_{90}$=4 μg/ml), trimethoprim ($MIC_{90}$=0.5 μg/ml), and vancomycin ($MIC_{90}$=1 μg/ml). Isolates were generally resistant to oral antibiotics levofloxacin ($MIC_{90}$=32 μg/ml), clindamycin ($MIC_{90}$=>64 μg/ml) and erythromycin ($MIC_{90}$=>128 μg/ml). Topical antibiotics that are used in the treatment of burn wound infections, silvadene and silver nitrate, had $MIC_{90}$ values of 32 μg/ml and 0.00063%, respectively. Mafenide acetate (Sulfamylon) is another topical treatment for burn wound infections, but it was uniformly inactive against MRSA ($MIC_{90}$=>128 μg/ml). Mupirocin is a topical treatment for skin and soft tissue infections and is also used to eradicate carriage of MRSA; 31% of the isolates were resistant to this antibiotic.

The $MBC_{90}$ values for all of the nanoemulsions were within four-fold of the respective $MIC_{90}$ values, indicating that the nanoemulsions are bactericidal to ~90% of the isolates. Among the other 12 antibiotics, only vancomycin was bactericidal.

TABLE 12

Susceptibility of MRSA to nanoemulsions and comparator compounds: MIC analysis

| Rank Order | MIC (μg/ml) Clind | Dox | Eryth | Levo | Maf. Acet | Mup | Silva | Vanco | Ox |
|---|---|---|---|---|---|---|---|---|---|
| 29 | >64 | 4 | >128 | >64 | >128 | >64 | 64 | 2 | >16 |
| 28 | >64 | 4 | >128 | >64 | >128 | >64 | 64 | 1 | >16 |
| 27 | >64 | 4 | >128 | 32 | >128 | >64 | 32 | 1 | >16 |
| 26 | >64 | 4 | >128 | 32 | >128 | >64 | 32 | 1 | >16 |
| 25 | >64 | 0.25 | >128 | 32 | >128 | >64 | 32 | 1 | >16 |
| 24 | >64 | 0.25 | >128 | 32 | >128 | >64 | 32 | 1 | >16 |
| 23 | >64 | 0.25 | >128 | 32 | >128 | >64 | 32 | 1 | >16 |
| 22 | >64 | 0.25 | >128 | 16 | >128 | >64 | 32 | 1 | >16 |
| 21 | >64 | 0.25 | >128 | 16 | >128 | 16 | 32 | 1 | >16 |

TABLE 12-continued

Susceptibility of MRSA to nanoemulsions and comparator compounds: MIC analysis

| | | | | | | | | | |
|---|---|---|---|---|---|---|---|---|---|
| 20 | >64 | 0.25 | >128 | 16 | >128 | 0.25 | 32 | 1 | >16 |
| 19 | >64 | 0.25 | >128 | 16 | >128 | 0.25 | 32 | 1 | >16 |
| 18 | >64 | 0.25 | >128 | 8 | >128 | 0.25 | 32 | 1 | >16 |
| 17 | >64 | 0.25 | >128 | 8 | >128 | 0.25 | 32 | 1 | >16 |
| 16 | >64 | 0.25 | 128 | 8 | >128 | 0.25 | 32 | 1 | >16 |
| 15 | >64 | 0.25 | 64 | 8 | >128 | 0.25 | 32 | 1 | >16 |
| 14 | >64 | 0.25 | 64 | 8 | >128 | 0.25 | 32 | 1 | >16 |
| 13 | >64 | 0.25 | 64 | 4 | >128 | 0.25 | 32 | 1 | >16 |
| 12 | 0.125 | 0.25 | 64 | 4 | >128 | 0.25 | 32 | 1 | >16 |
| 11 | 0.125 | 0.25 | 64 | 4 | >128 | 0.125 | 32 | 1 | >16 |
| 10 | 0.125 | 0.25 | 64 | 4 | >128 | 0.125 | 32 | 1 | >16 |
| 9 | 0.125 | 0.25 | 32 | 4 | >128 | 0.125 | 32 | 0.5 | >16 |
| 8 | 0.125 | 0.25 | 32 | 2 | >128 | 0.125 | 32 | 0.5 | >16 |
| 7 | 0.125 | 0.25 | 32 | 0.5 | >128 | 0.125 | 32 | 0.5 | >16 |
| 6 | 0.125 | 0.25 | 16 | 0.25 | >128 | 0.125 | 16 | 0.5 | >16 |
| 5 | 0.125 | 0.25 | 8 | 0.25 | >128 | 0.125 | 8 | 0.5 | >16 |
| 4 | 0.125 | 0.25 | 0.25 | 0.25 | >128 | 0.125 | 8 | 0.5 | >16 |
| 3 | 0.125 | 0.25 | 0.25 | 0.125 | >128 | 0.125 | 8 | 0.5 | 16 |
| 2 | 0.125 | 0.25 | 0.25 | 0.125 | >128 | 0.125 | 8 | 0.5 | 16 |
| 1 | 0.125 | 0.25 | 0.25 | 0.125 | 128 | 0.125 | 8 | 0.5 | 0.5 |
| $MIC_{90}$ (15) | >64 | 0.25 | 64 | 8 | >128 | 0.25 | 32 | 1 | >16 |
| $MIC_{90}$ (26) | >64 | 4 | >128 | 32 | >128 | >64 | 32 | 1 | >16 |

| | MIC (µg/ml) | | | | | | |
|---|---|---|---|---|---|---|---|
| Rank Order | Sulfa | Trim | Silver Nitrate | $P_{407}$5EC | $W_{20}$5EC ED L2 | $W_{20}$5G $BA_2$ ED | $W_{80}$5EC |
| 29 | >32 | >64 | 0.00250 | 4 | 4 | 4 | 2 |
| 28 | >32 | 1 | 0.00125 | 4 | 2 | 4 | 2 |
| 27 | 4 | 1 | 0.00125 | 2 | 2 | 4 | 2 |
| 26 | 4 | 0.5 | 0.000626 | 2 | 2 | 4 | 2 |
| 25 | 2 | 0.25 | 0.000626 | 2 | 2 | 4 | 2 |
| 24 | 2 | 0.125 | 0.000626 | 2 | 2 | 4 | 2 |
| 23 | 2 | 0.125 | 0.000626 | 2 | 2 | 2 | 2 |
| 22 | 1 | 0.125 | 0.000626 | 2 | 2 | 2 | 1 |
| 21 | 1 | 0.125 | 0.000626 | 2 | 2 | 2 | 1 |
| 20 | 1 | 0.125 | 0.000626 | 2 | 2 | 2 | 1 |
| 19 | 1 | 0.125 | 0.000312 | 2 | 1 | 2 | 1 |
| 18 | 1 | 0.125 | 0.000312 | 2 | 1 | 2 | 1 |
| 17 | 1 | 0.125 | 0.000312 | 1 | 1 | 2 | 1 |
| 16 | 1 | 0.125 | 0.000312 | 1 | 1 | 2 | 1 |
| 15 | 1 | 0.125 | 0.000312 | 1 | 1 | 2 | 1 |
| 14 | 1 | 0.125 | 0.000312 | 1 | 1 | 2 | 1 |
| 13 | 1 | 0.125 | 0.000312 | 1 | 1 | 2 | 1 |
| 12 | 0.5 | 0.125 | 0.000312 | 1 | 1 | 2 | 1 |
| 11 | 0.5 | 0.125 | 0.000312 | 1 | 1 | 2 | 1 |
| 10 | 0.5 | 0.125 | 0.000312 | 1 | 1 | 2 | 1 |
| 9 | 0.5 | 0.125 | 0.000312 | 1 | 1 | 2 | 1 |
| 8 | 0.5 | 0.125 | 0.000312 | 1 | 1 | 2 | 1 |
| 7 | 0.5 | 0.125 | 0.000312 | 1 | 1 | 2 | 1 |
| 6 | 0.25 | 0.125 | 0.000312 | 1 | 1 | 2 | 1 |
| 5 | 0.25 | 0.125 | 0.000312 | 1 | 1 | 2 | 1 |
| 4 | 0.25 | 0.125 | 0.000312 | 1 | 1 | 2 | 1 |
| 3 | 0.25 | 0.125 | 0.000312 | 1 | 1 | 1 | 0.5 |
| 2 | 0.25 | 0.125 | 0.000312 | 1 | 0.5 | 1 | 0.5 |
| 1 | 0.0625 | 0.125 | 0.000312 | 1 | 0.5 | 1 | 0.5 |
| $MIC_{90}$ (15) | 1 | 0.125 | 0.00031 | 1 | 1 | 2 | 1 |
| $MIC_{90}$ (26) | 4 | 0.5 | 0.00063 | 2 | 2 | 4 | 2 |

TABLE 13

Susceptibility of MRSA to nanoemulsions and comparator compounds: MBC analysis

| | MBC (µg/ml) | | | | | | | | |
|---|---|---|---|---|---|---|---|---|---|
| Rank Order | Clind | Dox | Eryth | Levo | Maf. Acet. | Mup | Silva. | Vanco | Ox | Sulfa |
| 29 | >64 | >128 | >128 | >64 | >128 | >64 | >128 | 4 | >16 | >32 |
| 28 | >64 | >64 | >128 | >64 | >128 | >64 | >128 | 4 | >16 | >32 |
| 27 | >64 | >64 | >128 | >64 | >128 | >64 | >128 | 4 | >16 | >32 |
| 26 | >64 | >64 | >128 | >64 | >128 | >64 | >128 | 2 | >16 | >32 |

TABLE 13-continued

Susceptibility of MRSA to nanoemulsions and comparator compounds: MBC analysis

| | | | | | | | | | | |
|---|---|---|---|---|---|---|---|---|---|---|
| 25 | >64 | >64 | >128 | >64 | >128 | >64 | >128 | 2 | >16 | >32 |
| 24 | >64 | >4 | >128 | >64 | >128 | >64 | >128 | 2 | >16 | >32 |
| 23 | >64 | >4 | >128 | 64 | >128 | >64 | >128 | 2 | >16 | >32 |
| 22 | >64 | >4 | >128 | 64 | >128 | >64 | >128 | 2 | >16 | >16 |
| 21 | >64 | >4 | >128 | >32 | >128 | >64 | >128 | 2 | >16 | >16 |
| 20 | >64 | >4 | >128 | 32 | >128 | >8 | >128 | 2 | >16 | >16 |
| 19 | >64 | >4 | >128 | 32 | >128 | >4 | >128 | 1 | >16 | >16 |
| 18 | >64 | >4 | >128 | 32 | >128 | >4 | >128 | 1 | >16 | >16 |
| 17 | >64 | >4 | >128 | 32 | >128 | >4 | >128 | 1 | >16 | >16 |
| 16 | >64 | >4 | >128 | 32 | >128 | >4 | >128 | 1 | >16 | >16 |
| 15 | >64 | >4 | >128 | 16 | >128 | >4 | >128 | 1 | >16 | >16 |
| 14 | >64 | >4 | >128 | 16 | >128 | >2 | 128 | 1 | >16 | >16 |
| 13 | >64 | >4 | >128 | 16 | >128 | >2 | 128 | 1 | >16 | >16 |
| 12 | >2 | >4 | >128 | 8 | >128 | >2 | 128 | 1 | >16 | >8 |
| 11 | >2 | >4 | >128 | 8 | >128 | >2 | 128 | 1 | >16 | >8 |
| 10 | >2 | >4 | >128 | 8 | >128 | >2 | 128 | 1 | >16 | >8 |
| 9 | >2 | >4 | >128 | 8 | >128 | >2 | 128 | 1 | >16 | >8 |
| 8 | >2 | >4 | >128 | 4 | >128 | >2 | 128 | 1 | >16 | >8 |
| 7 | >2 | >4 | >128 | 1 | >128 | >2 | 128 | 1 | >16 | >4 |
| 6 | >2 | >4 | >128 | 0.5 | >128 | >2 | 64 | 1 | >16 | >4 |
| 5 | >2 | >4 | 64 | 0.25 | >128 | >2 | 64 | 1 | >16 | >4 |
| 4 | >2 | >4 | >4 | 0.25 | >128 | >2 | 64 | 1 | >16 | >4 |
| 3 | >2 | 2 | >4 | 0.25 | >128 | 1 | 64 | 0.5 | >16 | >1 |
| 2 | 2 | 1 | >4 | 0.25 | >128 | 1 | 64 | 0.5 | >16 | 1 |
| 1 | 1 | 1 | >4 | 0.25 | >128 | 1 | 64 | 0.5 | 1 | 0.0625 |
| $MBC_{90}$ (15) | >64 | >4 | >128 | 16 | >128 | >2 | 128 | 1 | >16 | >16 |
| $MBC_{90}$ (26) | >64 | >64 | >128 | >64 | >128 | >64 | >128 | 2 | >16 | >32 |

| | MBC (μg/ml) | | | | | |
|---|---|---|---|---|---|---|
| Rank Order | Trim | Silver Nitrate | $P_{407}5EC$ | $W_{20}5EC$ ED L2 | $W_{20}5G$ $BA_2$ ED | $W_{80}5EC$ |
| 29 | >64 | 0.01 | >16 | >32 | 16 | 16 |
| 28 | >16 | >0.01 | 16 | 8 | 8 | 4 |
| 27 | >16 | >0.01 | 16 | 8 | 8 | 4 |
| 26 | >4 | >0.01 | 8 | 8 | 8 | 4 |
| 25 | >2 | >0.005 | 8 | 8 | 8 | 4 |
| 24 | >2 | >0.005 | 8 | 4 | 8 | 4 |
| 23 | >2 | >0.005 | 4 | 4 | 4 | 4 |
| 22 | 4 | 0.005 | 4 | 4 | 4 | 4 |
| 21 | 2 | 0.0025 | 4 | 4 | 4 | 4 |
| 20 | 2 | 0.0025 | 4 | 4 | 4 | 4 |
| 19 | 2 | 0.0025 | 4 | 4 | 4 | 4 |
| 18 | 1 | 0.0025 | 4 | 4 | 4 | 2 |
| 17 | 1 | 0.0025 | 4 | 4 | 4 | 2 |
| 16 | 0.5 | 0.0025 | 4 | 4 | 4 | 2 |
| 15 | 0.5 | 0.0025 | 2 | 4 | 4 | 2 |
| 14 | 0.5 | 0.0025 | 2 | 2 | 4 | 2 |
| 13 | 0.5 | 0.0025 | 2 | 2 | 4 | 2 |
| 12 | 0.5 | 0.0025 | 2 | 2 | 4 | 2 |
| 11 | 0.25 | 0.0025 | 2 | 2 | 4 | 2 |
| 10 | 0.25 | 0.0025 | 2 | 2 | 4 | 2 |
| 9 | 0.25 | 0.00125 | 2 | 2 | 4 | 2 |
| 8 | 0.25 | 0.00125 | 2 | 2 | 4 | 2 |
| 7 | 0.25 | 0.00125 | 2 | 2 | 4 | 2 |
| 6 | 0.25 | 0.00125 | 2 | 2 | 4 | 2 |
| 5 | 0.125 | 0.00125 | 2 | 2 | 4 | 1 |
| 4 | 0.125 | 0.00125 | 2 | 2 | 4 | 1 |
| 3 | 0.125 | 0.00125 | 2 | 2 | 2 | 1 |
| 2 | 0.125 | 0.00125 | 1 | 1 | 2 | 1 |
| 1 | 0.0125 | 0.00125 | 1 | 1 | 2 | 0.5 |
| $MBC_{90}$ (15) | 0.5 | 0.0025 | 2 | 2 | 4 | 2 |
| $MBC_{90}$ (26) | >4 | >0.01 | 8 | 8 | 8 | 4 |

C. Conclusions $W_{80}5EC$, $W_{20}5ECEDL2$, $W_{20}5GBA_2ED$ and $P_{407}5EC$ appeared equally effective against clinical isolates of MRSA, with $MIC_{90}$ values of 2 or 4 μg/ml. In addition, based on the ratio of $MBC_{90}/MIC_{90}$, the four nanoemulsions were bactericidal. As expected, the MRSA were multidrug-resistant, emphasizing the need for new agents for treating MRSA infections. Since nanoemulsions according to the invention also have activity against serious gram-negative pathogens, such as *Pseudomonas aeruginosa* and *Burkholderia* spp. (LiPuma et al., "In vitro activities of a novel nanoemulsion against *Burkholderia* and other multidrug-resistant cystic fibrosis-associated bacterial species," Antimicrob. Agents Chemother., 53:249-255 (2009)), the nanoemulsions are useful for inhalation treatment/maintenance of cystic fibrosis patients. In addition, the nanoemulsions are useful in treating burn wounds to prevent/treat infections of the pathogenic agents described herein.

Example 8

The purpose of this example was to determine the minimum inhibitory concentration (MIC) and the minimum bactericidal concentration (MBC) of an exemplary nanoemulsion ($P_{407}$5EC) side by side with comparator drugs against clinical isolates of *Pseudomonas aeruginosa, Burkholderia cenocepacia, Acinetobater baumanni, Stenotrophomonas maltophilia* from patients suffering from cystic fibrosis (CF).

Summary of Results for MIC and MBC: $P_{407}$5EC+EDTA had an MIC range of <4-16, <4-64, 2-8, <1-16 μg CPC/ml, respectively. The addition of EDTA at 5 mM for the *Pseudomonas* and *Burkholderia* and 1 mM to *Acinetobacter* and *Stenotrophomonas* to each well containing nanoemulsion improved the MIC. MBC data for the nanoemulsion+EDTA were obtained for 20 *Pseudomonas,* 10 *Burkholderia,* 10 *Acinetobacter* and 11 *Stenotrophomonas*. For three genera of bacteria tested, the data suggested bacteriostatic activity. The MBCs were within 4-fold of the respective MICs for the *Stenotrophomonas*, consistent with the nanoemulsion having bactericidal activity.

Summary of Synergy Results: In addition to the standardized MIC and MBC determinations, checkerboard synergy studies were conducted to evaluate the potential of $P_{407}$5EC+EDTA to synergize or antagonize traditional antimicrobials commonly used to treat patients with cystic fibrosis. The fractional inhibitory concentration (FIC) index and the fractional bactericidal concentration (FBC) index were determined to judge if a two drug combination was synergistic, antagonistic or indifferent to one another. Ten strains of *Burkholderia,* 10 strains of *Stenotrophomonas* and 10 strains of *Acinetobacter* were tested to determine a shift in MIC when $P_{407}$5EC+EDTA was in combination with either colistin or tobramycin, two traditional antimicrobials used in the lungs of CF patients to treat chronic lung infections. $P_{407}$5EC+EDTA in combination with colistin was found to be synergistic for 90% (in terms of the FIC) and 70% (in terms of the FBC) of the *Stenotrophomonas* strains, but indifferent, only 20% synergy in by the FIC and 0% by the FBC, when in combination with tobramycin. For the *Acinetobacter* strains, $P_{407}$5EC+EDTA in combination with colistin was found to be indifferent, only 20% synergy in by the FIC and 0% by the FBC, as well as when in combination with tobramycin, only 10% synergy in by the FIC and 10% by the FBC. For the *Burkholderia* strains, $P_{407}$5EC+EDTA in combination with colistin was found to be indifferent, only 30% synergy in by the FIC and 10% by the FBC, but when in combination with tobramycin, 50% synergy in by the FIC and 20% by the FBC.

A. Materials and Methods

Multidrug-resistant Gram-negative bacteria isolated from CF patients were tested in this example. MICs and MBCs were determined using CLSI guidelines and standard methods M7-A7 and M100-S17. Depending on the genus, MICs were performed in the presence of 1 or 5 mM EDTA, a permeability enhancer of NE activity. *Stenotrophomonas* and *Acintetobacter* had 1 mMEDTA in the nanoemulsion. *Pseudomonas* and *Burkholderia* had 5 mM EDTA in the nanoemulsion. This was the case during the standard MIC and MBC determination as well as the Checkerboard synergy work and time kill study to be described below. The addition of alamar blue, a redox indicator that yields a colorimetric change in response to metabolic activity, was used to determine the MICs of the NE ($P_{407}$5EC) because of opacity at higher concentrations.

Checkerboard synergy studies were carried out by using the MIC and MBC data collected, microtiter plates with a combination for $P_{407}$5EC+EDTA and colistin or $P_{407}$5EC+EDTA and tobramycin.

The Fractional Inhibitory Concentration (FIC) Index (see e.g., FIG. 19) examines the ratio of the MIC of a single drug when in combination with another to the MIC of that drug alone. The reduction of the MIC when a drug is in combination results in a fraction that is less than one.

$$X\text{=MIC of Drug in Combination/MIC of Drug along}$$

This ratio is calculated for both drug A and drug B. The fractions are added together. The summation is compared to the following ranges:

Synergism: Sum of FIC for the two drugs ≤0.5;

Indifference: Sum of FIC for the two drugs >0.5 to ≤4;

Antagonism: Sum of FIC for the two drugs >4.

In FIG. 19A, Row D denotes the previously determined MIC used to chose the flanking concentrations of the two drugs being combined. In FIG. 19B, the horizontal slash marks on the X and Y axis indicate typical MIC concentration of each drug alone.

The time-kill study was done over a brief time curve of 10, 20, 30 minutes including a 0 minute non-treated control was conducted to fix samples for pictures under the electron microscope.

B. Source of Isolates 46 isolates were evaluated, all of which were obtained from the University of Maryland-Baltimore School of Dentistry. The isolates received were as follows: 20 *Pseudomonas,* 11 *Burkholderia,* 10 *Acinetobacter* and 5 *Stenotrophomonas*. The *P. aeruginosa* isolates had defined lipid A modifications that have been documented in many CF patients. 10 additional isolates of *Stenotrophomonas* were received from a second source (Eurofins, Va.). These 10 are the last on the list and are the isolates with the ages of the individuals the samples were taken from. The isolates are summarized in Table 14 below.

TABLE 14

*Pseudomonas aeruginosa*, *Burkholderia cenocepacia*, *Acinetobacter baumannii*, *Stenotrophomonas maltophilia* isolates

| *Pseudomonas aeruginosa* | NanoBio number | Aminoarabinose modification Probable colistin resistance | Isolate Location | Patient Identifier |
|---|---|---|---|---|
| 1 | NB1 | − | CF Patient | A |
| 2 | NB2 | − | CF Patient | A |
| 3 | NB3 | + | CF Patient | B |
| 4 | NB4 | + | CF Patient | B |
| 5 | NB5 | + | CF Patient | C |

TABLE 14-continued

| *Pseudomonas aeruginosa*, *Burkholderia cenocepacia*, *Acinetobacter baumannii*, *Stenotrophomonas maltophilia* isolates | | | | |
|---|---|---|---|---|
| 6 | NB6 | + | CF Patient | C |
| 7 | NB7 | + | CF Patient | D |
| 8 | NB8 | + | CF Patient | D |
| 9 | NB9 | − | CF Patient | E |
| 10 | NB10 | − | CF Patient | E |
| 11 | NB11 | − | CF Patient | F |
| 12 | NB12 | − | CF Patient | G |
| 13 | NB13 | − | CF Patient | G |
| 14 | NB14 | − | CF Patient | H |
| 15 | NB15 | − | CF Patient | I |
| 16 | NB16 | + | CF Patient | J |
| 17 | NB17 | − | CF Patient | K |
| 18 | NB18 | − | CF Patient | L |
| 19 | NB19 | − | CF Patient | M |
| 20 | NB20 | + | CF Patient | N |
| *Burkholderia cenocepacia* | Nano Bio number | Genomovar | Isolate Location | Patient Identifier |
| 1 | NB21 | *B. c.* Genomovar I | CF Patient | A |
| 2 | NB22 | *B. c.* Genomovar I | CF Patient | B |
| 3 | NB23 | *B. c.* Genomovar III | CF Patient | C |
| 4 | NB24 | *B. c.* Genomovar III | CF Patient | D |
| 5 | NB25 | *B. c.* Genomovar III | CF Patient | E |
| 6 | NB26 | *B. c.* Genomovar III | CF Patient | F |
| 7 | NB27 | *B. c.* Genomovar III | CF Patient | G |
| 8 | NB28 | *B. c.* Genomovar IV | CF Patient | H |
| 9 | NB29 | *B. c.* Genomovar IV | CF Patient | I |
| 10 | NB30 | *B. c.* Genomovar IV | CF Patient | J |
| 11 | NB28b | *B. vietnamienis* Genomovar V | | |
| *Acinetobacter baumannii* | Nano Bio number | Colistin Susceptibility | Isolate Location | Patient Identifier |
| 1 | NB31 | Sensitive | wound, intraabdominal | Unknown |
| 2 | NB32 | Sensitive | abcess | Unknown |
| 3 | NB33 | Resistant | peritoneal fluid | Unknown |
| 4 | NB34 | Sensitive | sub-clav blood | Unknown |
| 5 | NB35 | Resistant | blood | Unknown |
| 6 | NB36 | Resistant | wound | Unknown |
| 7 | NB37 | Sensitive | tissue | Unknown |
| 8 | NB38 | Sensitive | urine | Unknown |
| 9 | NB39 | Resistant | CSF | Unknown |
| 10 | NB40 | Resistant | urine | Unknown |
| *Stenotrophomonas* | Nano Bio number | | Isolate Locution | Patient Identifier |
| 1 | NB41 | | CF Patient | A |
| 2 | NB42 | | CF Patient | B |
| 3 | NB43 | | CF Patient | C |
| 4 | NB44 | | CF Patient | D |
| 5 | NB45 | | CF Patient | E |

| *Stenotrophomonas maltophilia* | Short Id. | Region | Date Isolation Year | Source Description | Age |
|---|---|---|---|---|---|
| 2482274 | 1 | NEW ENGLAND | 2006 | Sputum | 14 |
| 2482270 | 2 | EAST NORTH CENTRAL | 2007 | Sputum | 10 |
| 2482275 | 3 | MOUNTAIN | 2007 | Sputum | 17 |
| 2482269 | 4 | MID ATLANTIC | 2008 | Sputum | 15 |
| 2482273 | 5 | SOUTH ATLANTIC | 2008 | Sputum | 17 |
| 2482276 | 6 | EAST SOUTH CENTRAL | 2008 | Sputum | 9 |
| 2482267 | 7 | WEST NORTH CENTRAL | 2008 | Sputum | 13 |
| 2482271 | 8 | WEST SOUTH CENTRAL | 2008 | Sputum | 4 |
| 2482272 | 9 | PACIFIC | 2008 | Sputum | 16 |
| 2482268 | 10 | SOUTH ATLANTIC | 2008 | Sputum | 1 |

C. Source of Drugs

The drugs and the source thereof used in the drug panel plates are summarized in the table below.

TABLE 15

Drugs used in drug panel plates.

| Ingredient | Manufacturer | Lot # |
|---|---|---|
| Cefepime | USP | H0G27S |
| Colistin | USP | G-1 |
| Imipenem | USP | H0E040 |
| Levofloxacin | Sigma | 1333515 |
| Ceftazidime | USP | H |
| Tobramycin | USP | L0E077 |
| Ceftoxin | USP | J0E038 |
| Piperacillin | USP | H |
| P407-5EC | NanoBio | XI138 and XI180 |

The composition of the $P_{407}$-5EC is provided in Table 16, below. The emulsion was produced by mixing a water immiscible oil phase with an aqueous phase. The base formulation is below and represents the neat emulsion, which was further diluted to the desired %.

TABLE 16

Lot # A0499
Neat $P_{407}$ SEC

| Ingredient | w/w % |
|---|---|
| Sterile distilled water | 23.49 |
| CPC | 1.068 |
| Poloxamer 407 | 5.92 |
| Ethanol | 6.73 |
| Soybean oil | 62.79 |

D. Preparation of Drug Concentrations

The preparation of drug concentration is described below in Tables 17 and 18. Specifically, Table 17 provides details regarding the preparation of the 96-well drug panel plates, and Table 18 provides details regarding the preparation of the 96-well checkerboard synergy plates.

TABLE 17

Details describing the preparation of the 96-well drug panel plates.

| Name & Lot # | Molecular Weight g/mole | Potency (ug/mg) | Exp. Concentrations Starting at X ug/mL: | Solvent/Diluent | Stock Volume in mL | Required Concentration (ug/mL) | Weight Needed (mg) |
|---|---|---|---|---|---|---|---|
| Cefepime-USP Lot H0G278 | 571.5 | 865 | 32 | Phos. Buffer pH 6 | 5.00 | 3200 | 18.50 |
| Colistin (Polymyxin E)-USP Lot G-1 | 1163 | 629 | 8 | water | 10.00 | 800 | 12.72 |
| Imipenem-USP Lot H0E040 | 317.36 | 929 | 32 | Phos. Buffer pH 7.2 | 5.00 | 3200 | 17.22 |
| Levofloxacin-Sigma 1333515 | 361.37 | 999.00 | 16 | ½ volume water, then 0.1 mol/L NaOH dropwise to dissolve | 10.00 | 1600 | 16.02 |
| Piperacillin-USP Lot H | 535.57 | 984 | 1024 | ½ volume water, then 0.1 mol/L NaOH dropwise to dissolve | 2.00 | 102400 | 208.13 |
| Tobramycin-USP Lot L0E077 | 467.52 | 970 | 32 | water | 5.00 | 3200 | 16.49 |
| Cefoxitin-USP Lot J0E038 | 449.44 | 992 | 256 | ½ volume water, then 0.1 mol/L NaOH dropwise to dissolve | 2.00 | 25600 | 51.61 |
| Ceftazidime-Lot H | 535.57 | 852 | 32 | Calcium Carbonate Sln 10% of the weight of compound to be dissolved | 2.00 | 3200 | 7.51 |

YELLOW HIGHLIGHT INDICATES POTENCY TAKEN FROM PERCENT PURITY (99% = 999 ug/mg).
1st Dilute ½, nine times from stock in solvent
2nd Dilute 1/50 in medium in a respective well of a 12 well trough.
3rd Transfer 50 uL from each well of the reservoir into the respective well for each agent at each concentration.

| Nanoemulsion | with or without EDTA | Solvent and Volume | Stock Volume in mL | Required Concentration (mM or ug/mL) | Volume Needed of Initial Stock (mL) | Volume Needed of broth (mL) |
|---|---|---|---|---|---|---|
| X1138 or X1180 = $P_{407}$5EC (@ 6 mg/mL) | with 1 mM | Water | 4.00 | 512 | 0.68 | 3.32 |

TABLE 17-continued

| | | | | | | |
|---|---|---|---|---|---|---|
| X1138 or X1180 = $P_{407}$5EC (@ 6 mg/mL) | with 5 mM | Water | 4.00 | 2056 | 2.74 | 1.26 |

** Because of the high concentration of this test antimicrobial, a 100x stock could not be made.
The calculations provided a 2x stock that is diluted in broth from the start and through the nine ½ dilutions.
A 1/50 dilution at any time is not required because the dilutions are made directly in broth.

| | X mM EDTA Diluted in Broth @ 100x | Broth volume | EDTA Stock Volume | Total Volume |
|---|---|---|---|---|
| EDTA Stock solution starting at 500 mM EDTA used to make these dilutions. | 100 | 800 | 200 | 1000 |
| | 500 | 0 | 1000 | 1000 |

For the required concentration of EDTA, a 1/50 dilution of the EDTA 100x stock was made in each well of the 12 well trough containing nanoemulsion.
Only 10 wells of the 12 well trough contain drug, the last two wells are for broth only which set up the negative and positive growth controls.

TABLE 18

Details describing the preparation of the 96-well checkerboard synergy plates.

| Nanoemulsion | with or without EDTA | Solvent and Volume | Stock Volume in mL | Required Concentration (mM or ug/mL) | Volume Needed of Initial Stock (mL) | Volume Needed of broth (mL) |
|---|---|---|---|---|---|---|
| X1180 = $P_{407}$5EC (@ 6 mg/mL) | with 1 or 5 mM | Broth | 4.00 | Varied on plate for each strain of bacteria | | |
| Colistin (Polymyxin E)-USP Lot G-1 | no | Broth | 4.00 | Varied on plate for each strain of bacteria | | |
| Tobramycin-USP Lot L0E077 | no | Broth | 4.00 | Varied on plate for each strain of bacteria | | |

** Because of the high concentration of this test antimicrobial, a 100x stock could not be made.
The calculations provided a 4x stock that is diluted in broth from the start and through the nine ½ dilutions.

E. Determination of MICs and MBCs

In the 96 well microtiter plate, the inoculated wells were observed after 20 hours of incubation at 35 degrees C. In each row, there is a range from high to low concentrations of the drug respective of the row from left to right, each well ½ the concentration of the adjacent well to the left. The first clear well in the series was called the MIC. This is the concentration of drug that inhibited the growth of the bacteria from turning the broth turbid. Because of the nanoemulsions intrinsic turbidity, alamar blue (CellTiter Blue, Promega) was added for the row containing nanoemulsion at a rate of 20 uL to 100 uL of culture volume. The plate was returned to the incubator for one hour and the first blue well was called the MIC (wells with bacterial growth turned pink at lower concentrations of nanoemulsion). The starting inoculum in each well was generally between 2-7×10^5 cfu/mL. The specific concentration for starting inoculum was determined for each test plate by sampling the inoculum used to inoculate the microtiter plate at the time it was set up. The exact concentration of bacteria was used to determine the MBC for each drug in the panel for each test plate. The MBC is defined as the concentration of drug that reduced the number of bacteria 99.9%. The MIC is the landmark used to begin sampling 10 uL/well from the MIC plus four wells to the left and put on agar plates, one sample per plate. The agar plates were incubated for 24 hours at 35 degrees C. and colonies were counted. The resulting colony counts were compared to the starting concentration of the inoculum to determine which well, that is which concentration of drug, resulted in a three log drop in cfu/mL.

F. Checkerboard Synergy Study

The starting inoculum in each well was generally between 2-7×10^5 cfu/mL. The specific concentration for starting inoculum was determined for each test plate by sampling the inoculum used to inoculate the microtiter plate at the time it was set up. Those exact concentrations of bacteria were used to determine the MBC for each drug in the panel for each test plate. The MBC is defined as the concentration of drug that reduced the number of bacteria 99.9%, a three log drop from the original concentration of bacteria. The MIC is the landmark used to begin sampling 10 uL/well from the MIC plus all wells through to column 11 to the right and put on agar plates, one sample per plate. The agar plates were incubated for 24 hours at 35 degrees C. and colonies were counted. The resulting colony counts were compared to the starting concentration of the inoculum to determine which well, that is which concentration of drug, resulted in a three log drop in cfu/mL.

In the 96 well microtiter plate, the inoculated wells were observed after 20 hours of incubation at 35 degrees C. In each row, there is a range from high to low concentrations of the drug respective of the row from right to left, each well ½ the concentration of the adjacent well to the left. Typically, but not always, the rows contained the nanoemulsion, drug A. Going up and down in the columns is drug B and here is the second drug tested in combination going high to low from A to G, respectively. Row H did not contain the second drug for it to act as the control for drug A. Column 1 did not contain any drug A so that column 1 could be the control for drug B. Traditionally, first clear well in the series from right to left in the rows was called the MIC. This is the concentration of drug that inhibited the growth of the bacteria from turning the broth turbid, in this case as indicated by a color change from blue to pink since alamar blue was used to find the metabolic activity to define the MIC. To each well 20 uL of CellTiter Blue from Promega was added. That is 20% of the original culture volume.

The well with the MIC and the well with the MBC were noted for each row. All wells noted for the MIC of the two drugs in combination were compared to the MIC of concentration of drug A and drug B each acting alone. For example, a well that contained 2 ug/mL of drug A and 8 ug/mL of drug B would have the concentration of A at 1 ug/mL when in combination divided by 16 ug/mL when acting alone. This renders a ratio of 0.125. Further in this example, 8 ug/mL of drug B would be divided by 32 ug/mL of B acting alone. The ratio for drug B in combination:alone is then 0.25. In this example the FIC index is said to be 0.125 for drug A and 0.25 for drug B, the sum is 0.325 in this example. The definition of synergy is for the sum to be equal to 0.5 or less. Indifference is greater than 0.5 to less than or equal to four. Antagonism is greater than four. See e.g., FIG. 19 for a detailed illustration.

G. Time-kill Study

A bacterial suspension of *Burkholderia* NB 29 @ O.D. 0.14-0.20 was made up. In a saline tube, 500 uL saline and 500 uL of the bacterial suspension was mixed for the TO, non-treated control, then mixed one to one with TA (Trypton-Azolectin) broth with 5 mM $CaCl_2$ to be diluted and plated as described below. In a treatment tube, added one to one the bacterial suspension to the treatment mix (2×P4075EC at 64 ug/mL CPC and 10 mM EDTA) and after 10, 20 and 30 minutes drew 400 uL at each time point and mixed with 400 uL TA broth with 5 mM $CaCl_2$. Next, 100 uL were drawn to be diluted serially 1/10 in saline to $10^{-8}$. 100 uL were then drawn from each dilution tube in the series and plated in triplicate. These plates were incubated at 35° C. overnight and counted to determine the cfu/mL at each time point. Simultaneously at the time the sample of untreated or treated bacteria was added to the neutralization TA solution, a sample of 450 uL was added to 113 uL of glutaraldehyde for each respective time point.

H. Scanning Electron Microscopy (SEM)

For scanning electron microscopy (SEM), 113 ul of 10% aqueous solution of gluteraldehyde in Sorenson's buffer, pH 7.4, was mixed with 450 uL of the bacterial suspension that underwent the exposure to nanoemulsion. Mixtures were vortexed and placed at 4° C. for at least 18 hours. Table 19 provides the procedure for fixing and staining the samples for scanning electron microscopy.

TABLE 19

Method for fixing and staining samples for SEM

| Step | |
|---|---|
| 1 | Samples were fixed in 2.5% glutaraldehyde in Sorenson's buffer, pH 7.4 then agitated on a rotary stirrer at each step |
| 2 | Samples were rinsed twice for 15 minutes each in 0.1 Sorensen's buffer |
| 3 | samples were fixed in 1.0% $OsO_4$ in Sorenson's buffer |
| 4 | samples were rinsed twice for 5 minutes each in 0.1M Sorenson's buffer |
| 5 | Samples were dehydrated for 15 minutes each in each of the following: 30% EtOH, 50% EtOH, 70% EtOH, 90% EtOH, 100% EtOH, 100% EtOH |
| 6 | Samples were immersed in four, 15 minutes changes of hexamethyldisilazane (HMDS) |
| 7 | Samples were removed following the fourth change of HMDS and replaced with just enough HMDS to cover tissue. Samples were allowed to evaporate in the hood overnight |
| 8 | Samples were mounted on SEM stubs, using the mixture of Colloidal graphite and duco cement |
| 9 | Samples were placed in a vacuum desiccator overnight |
| 10 | Samples were sputter-coated with gold using "Polaron" sputter coater |
| 11 | Samples were examined on an "Amray 1910 FE" Sacnning Electron Microscope and digitally imaged using "Xstream" imaging software |

I. Results a. MIC and MBC Data

The $MIC_{90}/MBC_{90}$ values for $P_{407}5EC$ were 8/64 μg/ml for *P. aeruginosa,* 64/>514 μg/ml for *B. cenocepacia*, 8/64 μg/ml for *A. baumannii* and 8/32 μg/ml for *S. maltophilia*. Colistin had $MIC_{90}/MBC_{90}$ values of 2/8, >32/>32, 1/>16 and >32/>32 for *P. aeruginosa, B. cenocepacia, A. baumannii* and *S. maltophilia*, respectively. Cefepime, imipenem, levofloxacin and tobramycin had $MIC_{90}/MBC_{90}$ values of ≥32/>32, ≥32/>32, 16/16 and >32/>32 μg/ml, respectively, against all strains.

b. Synergy Data

Ten strains of *Burkholderia, Stenotrophomonas* and 10 strains of *Acinetobacter* were tested to determine a shift in MIC when $P_{407}5EC$+EDTA was in combination with either colistin or tobramycin, two traditional antimicrobials used in the lungs of CF patients to treat chronic lung infections. $P_{407}5EC$+EDTA in combination with colistin was found to be synergistic for 90% (in terms of the FIC) and 70% (in terms of the FBC) of the *Stenotrophomonas* strains, but indifferent, only 20% synergy in by the FIC and 0% by the FBC, when in combination with tobramycin. For the *Acinetobacter* strains, $P_{407}5EC$+EDTA in combination with colistin was found to be indifferent, only 20% synergy in by the FIC and 0% by the FBC, as well as when in combination with tobramycin, only 10% synergy in by the FIC and 10% by the FBC. For the *Burkholderia* strains, $P_{407}5EC$+EDTA in combination with colistin was found to be indifferent, only 30% synergy in by the FIC and 10% by the FBC, but when in combination with tobramycin, 50% synergy in by the FIC and 20% by the FBC.

c. Time-kill Study

Time-kill resulted in an overall 4.44 log reduction in cfu/ml from the untreated beginning to the 30 minute time point. Each 10 minute time point had between 1-2 log reduction as follows: from the untreated to the 10 minute point there was a 1.40 log reduction, from the 10 to 20 minute time points there was a 1.91 log reduction and from the 20 to 30 minute time points there was a 1.13 log reduction. See FIGS. 20A-20D.

TABLE 20

A comparison of MIC (μg/ml) of $P_{407}$5EC and comparator drugs.

MIC & MBC 50 & 90 CF *Pseudomonas* Isolates
All Drug Values in ug/mL

| | *Pseudo-* | Cefepime | | Tobramycin | | Cefoxitin | | Colistin | | Levofloxacin | | Imipenem | | Ceftazidime | | Pipercillin | | P407-5EC & 5 mM EDTA | | P407-5EC & 0 mM EDTA | |
|---|---|---|---|---|---|---|---|---|---|---|---|---|---|---|---|---|---|---|---|---|---|
| count | *monas* | MIC | MBC | MIC | MBC | MIC | MBC | MIC | MBC | MIC | MBC | MIC | MBC | MIC | MBC | MIC | MBC | MIC | MBC | MIC | MBC |
| 1 | NB1 | 2 | 8 | 1 | 16 | >256 | >256 | 2 | >8 | 0.5 | 1 | 1 | 8 | n/a | n/a | 1024 | 1024 | 16.0625 | 64.25 | n/a | |
| 2 | NB2 | 0.13 | 0.125 | 0.25 | 2 | >256 | >256 | 1 | 8 | 0.5 | 0.5 | 2 | 2 | n/a | n/a | 128 | 128 | 8.03125 | 32.125 | n/a | |
| 3 | NB3 | 1 | 2 | 0.5 | 4 | >256 | >256 | 1 | 8 | 0.25 | 0.5 | 2 | 16 | n/a | n/a | >1024 | >1024 | 4.015625 | 16.0625 | n/a | |
| 4 | NB4 | 1 | 1 | 0.5 | 4 | >256 | >256 | 2 | 4 | 0.25 | 0.5 | 4 | 8 | n/a | n/a | 512 | 1024 | 4.015625 | 16.0625 | n/a | |
| 5 | NB5 | 2 | 4 | 0.5 | 4 | >256 | >256 | 2 | 8 | 0.5 | 1 | 2 | 16 | n/a | n/a | >1024 | >1024 | 8.03125 | 32.125 | n/a | |
| 6 | NB6 | 2 | 4 | 0.5 | 4 | >256 | >256 | 2 | 4 | 0.5 | 1 | 1 | 2 | n/a | n/a | 1024 | >1024 | 4.015625 | 16.0625 | n/a | |
| 7 | NB7 | 2 | 2 | 1 | >16 | >256 | >256 | 2 | 4 | 0.5 | 1 | 4 | 16 | n/a | n/a | 512 | 1024 | 4.015625 | 16.0625 | n/a | |
| 8 | NB8 | 2 | 2 | 1 | 8 | >256 | >256 | 2 | 8 | 0.5 | 0.5 | 4 | 4 | n/a | n/a | >1024 | >1024 | 4.015625 | 8.03125 | n/a | |
| 9 | NB9 | 2 | 2 | 1 | 8 | >256 | >256 | 2 | 8 | 0.5 | 0.5 | 4 | >32 | n/a | n/a | 512 | >1024 | 4.015625 | 64.25 | n/a | |
| 10 | NB10 | 2 | 2 | 0.5 | 4 | >256 | >256 | 2 | 2 | 0.5 | 0.5 | 4 | 8 | n/a | n/a | 256 | 512 | 8.03125 | 64.25 | n/a | |
| 11 | NB11 | 16 | 32 | 2 | 4 | >256 | >256 | 1 | 4 | 8 | 16 | 2 | 8 | n/a | n/a | n/a | n/a | <4.015625 | 16.0625 | n/a | |
| 12 | NB12 | 4 | 32 | 0.5 | 8 | >256 | >256 | 4 | 8 | 0.25 | 1 | >32 | >32 | 256 | 512 | n/a | n/a | <4.015625 | 16.0625 | 514 | >2056 |
| 13 | NB13 | 4 | 16 | 1 | 4 | >256 | >256 | 2 | 8 | 0.5 | 2 | 8 | 16 | 512 | 512 | n/a | n/a | 8.03125 | 16.0625 | 514 | >2056 |
| 14 | NB14 | 32 | >32 | 32 | >32 | >256 | >256 | 2 | 4 | 16 | >16 | >32 | >32 | 1024 | >1024 | n/a | n/a | <4.015625 | 32.156 | 4.01563 | >64.25 |
| 15 | NB15 | 8 | >32 | 0.5 | 8 | >256 | >256 | 2 | 8 | 2 | 4 | 8 | >32 | 256 | 512 | n/a | n/a | <4.015625 | 16.0625 | 1028 | >2056 |
| 16 | NB16 | 16 | 16 | 2 | 16 | >256 | >256 | 2 | 4 | 2 | 8 | 8 | 32 | 256 | >1024 | n/a | n/a | <4.015625 | >64.25 | 2056 | >2056 |
| 17 | NB17 | >32 | >32 | 16 | 32 | >256 | >256 | 1 | 4 | 16 | 16 | >32 | >32 | n/a | n/a | n/a | n/a | <4.015625 | 16.0625 | n/a | |
| 18 | NB18 | >32 | >32 | 16 | >32 | >256 | >256 | 1 | 4 | 4 | 8 | >32 | >32 | n/a | n/a | n/a | n/a | <4.015625 | <4.015625 | n/a | |
| 19 | NB19 | 16 | 32 | 2 | 16 | >256 | >256 | 2 | 4 | 2 | 4 | >32 | >32 | 512 | 1024 | n/a | n/a | <4.015625 | 8.03125 | 1028 | >2056 |
| 20 | NB20 | 8 | 8 | 0.5 | 8 | >256 | >256 | 2 | >8 | 0.5 | 1 | 2 | 16 | 256 | 512 | n/a | n/a | 8.03125 | 8.03125 | 1028 | >2056 |
| | MIC 50 | Cefe-pime | 2 | Tobramycin | 1 | Cefoxitin | >256 | Colistin | 2 | Levo-floxacin | 0.5 | Imipenem | 4 | Ceftaz-idime | n/a | Pipercillin | n/a | P407-5EC & 5 mM EDTA | 4.015625 | P407-5EC & 0 mM EDTA | n/a |
| | MIC 90 | | 32 | | 16 | | >256 | | 2 | | 8 | | >32 | | n/a | | n/a | | 8.03125 | | n/a |
| | MBC 50 | Cefe-pime | 8 | Tobramycin | 8 | Cefoxitin | >256 | Colistin | 4 | Levo-floxacin | 1 | Imipenem | 16 | Ceftaz-idime | n/a | Pipercillin | n/a | P407-5EC & 5 mM EDTA | 16.0625 | P407-5EC & 0 mM EDTA | n/a |
| | MBC 90 | | >32 | | >16 | | >256 | | 8 | | 16 | | >32 | | n/a | | n/a | | 64.25 | | n/a |

TABLE 20-continued

A comparison of MIC (μg/ml) of $P_{407}$5EC and comparator drugs.

MIC & MBC 50 & 90 CF *Burkholderia* Isolates
All Drug Values in ug/mL

| | | Cefepime | | Colistin | | Imipenem | | Levofloxacin | | Ceftazidime | | Tobramycin | | Cefoxitin | | P407-5EC & 5 mM EDTA | |
|---|---|---|---|---|---|---|---|---|---|---|---|---|---|---|---|---|---|
| count | *Burkholderia* | MIC | MBC | MIC | MBC | MIC | MBC | MIC | MBC | MIC | MBC | MIC | MBC | MIC | MBC | MIC | MBC |
| 1 | NB21 | 32 | >32 | >32 | >32 | 16 | 16 | 2 | 2 | 8 | >32 | 32 | >32 | 256 | >256 | 32.125 | 514 |
| 2 | NB22 | >32 | >32 | >32 | >32 | 16 | 16 | 1 | 4 | 8 | >32 | >32 | >32 | 128 | 256 | 32.125 | >514 |
| 3 | NB23 | >32 | >32 | >32 | >32 | >32 | >32 | 8 | >16 | >32 | >32 | >32 | >32 | >256 | >256 | <4.015625 | 64.25 |
| 4 | NB24 | 32 | >32 | >32 | >32 | 32 | >32 | 8 | 16 | 4 | 32 | >32 | >32 | 128 | >256 | 32.125 | 514 |
| 5 | NB25 | >32 | >32 | >32 | >32 | 32 | >32 | 4 | 8 | 16 | 32 | >32 | >32 | 128 | 256 | 64.25 | 257 |
| 6 | NB26 | >32 | >32 | 32 | >32 | >32 | >32 | 8 | 8 | 16 | 32 | >32 | >32 | 128 | 256 | <4.01563 | 64.25 |
| 7 | NB27 | >32 | >32 | >32 | >32 | 16 | >32 | 4 | 8 | 8 | 16 | >32 | >32 | 128 | >256 | 32.125 | 257 |
| 8 | NB29 | 8 | >32 | >32 | >32 | 8 | 16 | 1 | 4 | 4 | >32 | >32 | >32 | 256 | >256 | 16.0625 | >514 |
| 9 | NB30 | 8 | 16 | >32 | >32 | 4 | 4 | 1 | 1 | 2 | 2 | 32 | 32 | 128 | 128 | <4.015625 | >64.25 |
| 10 | NB28b | 4 | 4 | >32 | >32 | 0.5 | 0.5 | 1 | 2 | 16 | 16 | 1 | 4 | 16 | 16 | <4.015625 | >64.25 |
| | MIC 50 | Cefepime | 32 | Colistin | >32 | Imipenem | 16 | Levofloxacin | 2 | Ceftazidime | 8 | Tobramycin | >32 | Cefoxitin | 128 | P407-5EC & 5 mM EDTA | 16.0625 |
| | MIC 90 | | >32 | | >32 | | >32 | | 8 | | 16 | | >32 | | 256 | | 64.25 |
| | MBC 50 | Cefepime | >32 | Colistin | >32 | Imipenem | 32 | Levofloxacin | 4 | Ceftazidime | 32 | Tobramycin | >32 | Cefoxitin | 256 | P407-5EC & 5 mM EDTA | 128.5 |
| | MBC 90 | | >32 | | >32 | | >32 | | >16 | | >32 | | >32 | | >256 | | >514 |

MIC & MBC 50 & 90 CF *Acinetobacter* Isolates
All Drug Values in ug/mL

| | | Cefepime | | Colistin | | Imipenem | | Levofloxacin | | Ceftazidime | | Tobramycin | | Cefoxitin | | P407-5EC & 1 mM EDTA | |
|---|---|---|---|---|---|---|---|---|---|---|---|---|---|---|---|---|---|
| count | *Acinetobacter* | MIC | MBC | MIC | MBC | MIC | MBC | MIC | MBC | MIC | MBC | MIC | MBC | MIC | MBC | MIC | MBC |
| 1 | NB31 | 16 | 16 | 1 | 1 | 1 | 1 | 16 | 16 | >32 | >32 | 1 | 1 | >256 | >256 | 4 | 16 |
| 2 | NB32 | 32 | >32 | 1 | 8 | 32 | 32 | 8 | 8 | >32 | >32 | 1 | 4 | 256 | 256 | 4 | 64 |
| 3 | NB33 | >32 | >32 | 1 | 4 | 32 | >32 | 8 | 8 | >32 | >32 | 2 | 8 | >256 | >256 | 4 | 64 |
| 4 | NB34 | 32 | 32 | 1 | 1 | 32 | 32 | 16 | 16 | 32 | 32 | 16 | >32 | >256 | >256 | 4 | 8 |
| 5 | NB35 | 32 | >32 | 1 | 4 | 8 | 8 | >16 | >16 | >32 | >32 | 2 | 16 | >256 | >256 | 8 | 32 |
| 6 | NB36 | 2 | 2 | 1 | 1 | 0.125 | 0.125 | 1 | 1 | 2 | 4 | 0.5 | 0.5 | 128 | 128 | 2 | 16 |
| 7 | NB37 | 32 | >32 | 1 | >16 | 4 | 8 | 16 | 16 | 32 | 32 | 0.5 | 2 | >256 | >256 | 2 | 16 |
| 8 | NB38 | >32 | >32 | 1 | >16 | 32 | >32 | 8 | >16 | >32 | >32 | 1 | 16 | >256 | >256 | 4 | 64 |
| 9 | NB39 | >32 | 32 | 1 | 8 | 2 | 2 | 16 | 16 | 32 | >32 | 2 | 4 | >256 | >256 | 2 | 16 |
| 10 | NB40 | >32 | >32 | 1 | >16 | 2 | 32 | >16 | >16 | >32 | >32 | >32 | >32 | >256 | >256 | 8 | >128 |
| | MIC 50 | Cefepime | 32 | Colistin | 1 | Imipenem | 4 | Levofloxacin | 16 | Ceftazidime | >32 | Tobramycin | 1 | Cefoxitin | >256 | P407-5EC & 1 mM EDTA | 4 |
| | MIC 90 | | >32 | | 1 | | 32 | | >16 | | >32 | | 16 | | >256 | | 8 |
| | MBC 50 | Cefepime | >32 | Colistin | 4 | Imipenem | 8 | Levofloxacin | 16 | Ceftazidime | >32 | Tobramycin | 4 | Cefoxitin | >256 | P407-5EC & 1 mM EDTA | 16 |
| | MBC 90 | | >32 | | >16 | | >32 | | >16 | | >32 | | >32 | | >256 | | 64 |

TABLE 20-continued

A comparison of MIC (μg/ml) of $P_{407}$5EC and comparator drugs.

MIC & MBC 50 & 90 CF *Stenotrophomonas* Isolates
All Drug Values in ug/mL

| | | Cefepime | | Colistin | | Imipenem | | Levofloxacin | | Ceftazidime | | Tobramycin | | Cefoxitin | | P407-5EC & 1 mM EDTA | |
|---|---|---|---|---|---|---|---|---|---|---|---|---|---|---|---|---|---|
| count | *Stenotrophomonas* | MIC | MBC | MIC | MBC | MIC | MBC | MIC | MBC | MIC | MBC | MIC | MBC | MIC | MBC | MIC | MBC |
| 1 | NB41 | 32 | >32 | 2 | 32 | >32 | >32 | 2 | 4 | >32 | >32 | >32 | >32 | >256 | >256 | 8 | 8 |
| 2 | NB42 | >32 | >32 | 2 | 8 | >32 | >32 | 8 | 16 | 8 | >32 | 32 | >32 | >256 | >256 | 16 | 16 |
| 3 | NB43 | >32 | >32 | 16 | >32 | >32 | >32 | 2 | 4 | >32 | >32 | >32 | >32 | >256 | >256 | 8 | 16 |
| 4 | NB44 | >32 | >32 | 32 | >32 | >32 | >32 | 8 | 16 | >32 | >32 | >32 | >32 | 256 | >256 | <1 | 16 |
| 5 | NB45 | 32 | >32 | 8 | 16 | >32 | >32 | 1 | 2 | >32 | >32 | >32 | >32 | >256 | >256 | 8 | 16 |
| 6 | Steno 1 | >32 | >32 | >32 | >32 | >32 | >32 | 1 | 4 | >32 | >32 | >32 | >32 | >256 | >256 | 8 | 16 |
| 7 | Steno 2 | >32 | >32 | 32 | >32 | 32 | >32 | 4 | 8 | >32 | >32 | >32 | >32 | >256 | >256 | 4 | 16 |
| 8 | Steno 3 | >32 | >32 | >32 | >32 | >32 | >32 | 1 | 4 | >32 | >32 | >32 | >32 | 256 | >256 | 8 | 32 |
| 9 | Steno 4 | 16 | >32 | 1 | 4 | >32 | >32 | 0.5 | 2 | 2 | 16 | >32 | >32 | 256 | 256 | 2 | 32 |
| 10 | Steno 6 | >32 | >32 | 16 | >32 | 32 | 32 | 2 | 4 | 32 | >32 | 16 | 32 | 128 | 256 | 8 | 32 |
| 11 | Steno 8 | >32 | >32 | 8 | 32 | >32 | >32 | 2 | 2 | 16 | >32 | >32 | >32 | >256 | >256 | 8 | 16 |
| | MIC 50 | Cefepime | >32 | Colistin | 16 | Imipenem | >32 | Levofloxacin | 2 | Ceftazidime | >32 | Tobramycin | >32 | Cefoxitin | >256 | P407-5EC & 1 mM EDTA | 8 |
| | MIC 90 | | >32 | | >32 | | >32 | | 8 | | >32 | | >32 | | >256 | | 8 |
| | MBC 50 | Cefepime | >32 | Colistin | >32 | Imipenem | >32 | Levofloxacin | 4 | Ceftazidime | >32 | Tobramycin | >32 | Cefoxitin | >256 | P407-5EC & 1 mM EDTA | 16 |
| | MBC 90 | | >32 | | >32 | | >32 | | 16 | | >32 | | >32 | | >256 | | 32 |

TABLE 21

Collapsed Summary of Data Table 20

| | Cefepime | Colistin | Imipenem | Levofloxacin | Ceftazidime | Tobramycin | Cefoxitin | P407-5EC & 5 mM EDTA |
|---|---|---|---|---|---|---|---|---|
| | | | | *Pseudomonas* | | | | |
| MIC 50 | 2 | 2 | 4 | 0.5 | Not Tested | 1 | >256 | 4.015625 |
| MIC 90 | 32 | 2 | >32 | 8 | Not Tested | 16 | >256 | 8.03125 |
| MBC 50 | 8 | 4 | 16 | 1 | Not Tested | 8 | >256 | 16.0625 |
| MBC 90 | >32 | 8 | >32 | 16 | Not Tested | >16 | >256 | 64.25 |
| | | | | *Burkholderia* | | | | |
| MIC 50 | 32 | >32 | >32 | 2 | 8 | >32 | 128 | 16.0625 |
| MIC 90 | >32 | >32 | >32 | 8 | 16 | >32 | 256 | 64.25 |
| MBC 50 | >32 | >32 | 32 | 4 | 32 | >32 | 256 | 128.5 |
| MBC 90 | >32 | >32 | >32 | >16 | >32 | >32 | >256 | >514 |
| | | | | *Acinetobacter* | | | | |
| MIC 50 | 32 | 1 | 4 | 16 | >32 | 1 | >256 | 4 |
| MIC 90 | >32 | 1 | 32 | >16 | >32 | 16 | >256 | 8 |
| MBC 50 | >32 | 4 | 8 | 16 | >32 | 4 | >256 | 16 |
| MBC 90 | >32 | >16 | >32 | >16 | >32 | >32 | >256 | 64 |
| | | | | *Stenotrophomonas* | | | | |
| MIC 50 | >32 | 16 | >32 | 2 | >32 | >32 | >256 | 8 |
| MIC 90 | >32 | >32 | >32 | 8 | >32 | >32 | >256 | 8 |
| MBC 50 | >32 | >32 | >32 | 4 | >32 | >32 | >256 | 16 |
| MBC 90 | >32 | >32 | >32 | 16 | >32 | >32 | >256 | 32 |

| Isolate | FIC | Synergy | FBC | Synergy | Isolate | FIC | Synergy | FBC | Synergy |
|---|---|---|---|---|---|---|---|---|---|
| | | | | Checkerboard Synergy Study Results; *Acinetobacter* | | | | | |
| NB31 Colistin | 0.83 | indifferent | 2.44 | indifferent | NB31 Tobra | 0.98 | indifferent | 1.50 | no |
| NB32 Colistin | 0.58 | indifferent | 1.36 | indifferent | NB32 Tobra | 0.88 | indifferent | 1.79 | no |
| NB33 Colistin | 0.33 | yes | 2 | indifferent | NB33 Tobra | 1.27 | indifferent | 1.75 | no |
| NB34 Colistin | 0.46 | yes | 1.10 | indifferent | NB34 Tobra | 0.41 | yes | 0.24 | yes |
| NB35 Colistin | 0.72 | indifferent | 0.97 | indifferent | NB35 Tobra | 1.21 | indifferent | 1.44 | no |
| NB36 Colistin | 0.56 | indifferent | 2 | indifferent | NB36 Tobra | 3.30 | indifferent | 2.29 | no |
| NB37 Colistin | 0.63 | indifferent | 1.00 | indifferent | NB37 Tobra | 0.75 | indifferent | 1.72 | no |
| NB38 Colistin | 0.77 | indifferent | 0.68 | indifferent | NB38 Tobra | 1.05 | indifferent | 1.57 | no |
| NB39 Colistin | 0.72 | indifferent | 1.22 | indifferent | NB39 Tobra | 3.30 | indifferent | 3.52 | no |
| NB40 Colistin | 0.63 | indifferent | 0.91 | indifferent | NB40 Tobra | 3.01 | indifferent | 3.01 | no |
| | | 20% | | 0% | | | 10% | | 10% |
| | | | | Checkerboard Synergy Study Results; *Stenotrophomonas* | | | | | |
| NB42 Colistin | 0.08 | yes | 1.28 | indifferent | NB42 Tobra | 0.14 | yes | 2.15 | indifferent |
| NB43 Colistin | 0.08 | yes | 0.15 | yes | NB43 Tobra | 1.40 | indifferent | 2.29 | indifferent |
| NB44 Colistin | 1.01 | indifferent | 0.57 | indifferent | NB44 Tobra | 1.5 | indifferent | 2.86 | indifferent |
| NB45 Colistin | 0.04 | yes | 0.45 | yes | NB45 Tobra | 0.97 | indifferent | 1.50 | indifferent |
| Steno 1 Colistin | 0.08 | yes | 0.11 | yes | Steno 1 Tobra | 0.79 | indifferent | 1.57 | indifferent |
| Steno 2 Colistin | 0.09 | yes | 0.04 | yes | Steno 2 Tobra | 0.04 | yes | 2.23 | indifferent |
| Steno 3 Colistin | 0.09 | yes | 0.14 | yes | Steno 3 Tobra | 0.79 | indifferent | 1.29 | indifferent |
| Steno 4 Colistin | 0.46 | yes | 1.14 | indifferent | Steno 4 Tobra | 1.72 | indifferent | 1.61 | indifferent |
| Steno 6 Colistin | 0.09 | yes | 0.02 | yes | Steno 6 Tobra | 0.59 | indifferent | 0.89 | indifferent |
| Steno 8 Colistin | 0.09 | yes | 0.07 | yes | Steno 8 Tobra | 0.63 | indifferent | 1.15 | indifferent |
| | | 90% | | 70% | | | 20% | | 0% |
| | | | | Checkerboard Synergy Study Results; *Burkholderia* | | | | | |
| NB21 Colistin | 1.45 | indifferent | 2.07 | indifferent | NB21 Tobra | 0.27 | yes | 0.48 | yes |
| NB22 Colistin | 1.37 | indifferent | 2.29 | indifferent | NB22Tobra | 0.35 | yes | 1.23 | indifferent |
| NB23 Colistin | 1.01 | indifferent | 2.00 | indifferent | NB23 Tobra | 1.06 | indifferent | 1.09 | indifferent |
| NB24 Colistin | 1.72 | indifferent | 2.00 | indifferent | NB24 Tobra | 1.31 | indifferent | 1.36 | indifferent |
| NB25 Colistin | 2.00 | indifferent | 3.00 | indifferent | NB25 Tobra | 1.45 | indifferent | 0.99 | indifferent |
| NB26 Colistin | 0.56 | yes | 0.04 | yes | NB26 Tobra | 0.12 | yes | 0.92 | indifferent |
| NB27 Colistin | 1.93 | indifferent | 1.64 | indifferent | NB27 Tobra | 1.44 | indifferent | 1.27 | indifferent |
| NB28b Colistin | 0.29 | yes | 1.54 | indifferent | NB28b Tobra | 0.54 | yes | 1.06 | indifferent |
| NB29 Colistin | 1.61 | indifferent | 1.68 | indifferent | NB29 Tobra | 0.32 | yes | 0.07 | yes |
| NB30 Colistin | 0.02 | yes | 1.86 | indifferent | NB30 Tobra | 0.27 | yes | 0.54 | yes |
| | | 30% | | 10% | | | 50% | | 30% |

TABLE 22

Summary of Synergy Data with Comparison to Original MIC/MBC Data of Each Drug Alone

| *Stenotrophomonas* | Colistin | Tobramycin | $P_{407}$5EC & 1 mM EDTA |
|---|---|---|---|
| MIC 50 | 16 | >32 | 8 |
| MBC 50 | >32 | >32 | 16 |
| MIC 90 | >32 | >32 | 8 |
| MBC 90 | >32 | >32 | 32 |
| % FIC Synergy | 90% | 20% | |
| % FBC Synergy | 70% | 0% | |
| | Synergy | No Interference | |

| *Acinetobacter* | Colistin | Tobramycin | $P_{407}$5EC & 1 mM EDTA |
|---|---|---|---|
| MIC 50 | 1 | 1 | 4 |
| MBC 50 | 4 | 4 | 16 |
| MIC 90 | 1 | 16 | 8 |

TABLE 22-continued

Summary of Synergy Data with Comparison to Original MIC/MBC Data of Each Drug Alone

| | | | |
|---|---|---|---|
| MBC 90 | >16 | >32 | 64 |
| % FIC Synergy | 20% | 10% | |
| % FBC Synergy | 0% | 10% | |
| | No Interference | No Interference | |

| *Burkholderia* | Colistin | Tobramycin | $P_{407}$5EC & 5 mM EDTA |
|---|---|---|---|
| MIC 50 | >32 | >32 | 16 |
| MBC 50 | >32 | >32 | 64 |
| MIC 90 | >32 | >32 | 128 |
| MBC 90 | >32 | >32 | >514 |
| % FIC Synergy | 30% | 50% | |
| % FBC Synergy | 10% | 30% | |
| | No Interference | No Interference | |

TABLE 23

Time Kill with additional 5 mM EDTA

*Pseudomonas* with W205EC at 4 ug/mL + 5 mM EDTA, 1 min resulted in a 2 log drop in count.

*Burkholderia* — *Burkholderia* MIC 50 = 16 ug/mL and 90 = 64 ug/mL

NB29 MIC = 16

32 ug/mL P4075EC + 5mM EDTA — Starting Bacteria at 0.159 O.D. at 625 nm = ----8.24 × 10^7 cfu/mL

| Set Average | 0 min (Saline) | 8.24E+07 | Set Average | 10 min | 3.27E+06 | Set Average | 20 min | 4.00E+04 | Set Average | 30 min | 2.99E+03 |
|---|---|---|---|---|---|---|---|---|---|---|---|
| | 0 min (Saline) | | | 10 min | | | 20 min | | | 30 min | |
| Set A | | cfu/mL | Set A | | cfu/mL | Set A | | cfu/mL | Set A | | cfu/mL |
| 2.00E+09 | 0 | | 2.00E+09 | 0 | | 2.00E+09 | 0 | | 2.00E+09 | 0 | |
| 2.00E+08 | 0 | | 2.00E+08 | 0 | | 2.00E+08 | 0 | | 2.00E+08 | 0 | |
| 2.00E+07 | 5 | 1.00E+08 | 2.00E+07 | 0 | | 2.00E+07 | 0 | | 2.00E+07 | 0 | |
| 2.00E+06 | 44 | 8.80E+07 | 2.00E+06 | 0 | | 2.00E+06 | 0 | | 2.00E+06 | 0 | |
| 2.00E+05 | 128 | 2.56E+07 | 2.00E+05 | 23 | 4.60E+06 | 2.00E+05 | 1 | | 2.00E+05 | 0 | |
| 2.00E+04 | TNTC | | 2.00E+04 | 180 | 3.60E+06 | 2.00E+04 | 1 | 2.00E+04 | 2.00E+04 | 0 | |
| 2.00E+03 | Lawn | | 2.00E+03 | TNTC | | 2.00E+03 | 19 | 3.80E+04 | 2.00E+03 | 2 | 4.00E+03 |
| 2.00E+02 | Lawn | | 2.00E+02 | TNTC | | 2.00E+02 | 151 | 3.02E+04 | 2.00E+02 | 7 | 1.40E+03 |
| 2.00E+01 | Lawn | | 2.00E+01 | Lawn | | 2.00E+01 | TNTC | | 2.00E+01 | 134 | 2.68E+03 |
| | Average | 7.12E+07 | | Average | 4.10E+06 | | Average | 2.94E+04 | | Average | 2.69E+03 |
| Set B | | cfu/mL | Set B | | cfu/mL | Set B | | cfu/mL | Set B | | cfu/mL |
| 2.00E+09 | 0 | | 2.00E+09 | 0 | | 2.00E+09 | 0 | | 2.00E+09 | 0 | |
| 2.00E+08 | 0 | | 2.00E+08 | 0 | | 2.00E+08 | 0 | | 2.00E+08 | 0 | |
| 2.00E+07 | 5 | 1.00E+08 | 2.00E+07 | 0 | | 2.00E+07 | 0 | | 2.00E+07 | 0 | |
| 2.00E+06 | 39 | 7.80E+07 | 2.00E+06 | 1 | 2.00E+06 | 2.00E+06 | 0 | | 2.00E+06 | 0 | |
| 2.00E+05 | 234 | 4.68E+07 | 2.00E+05 | 11 | 2.20E+06 | 2.00E+05 | 1 | | 2.00E+05 | 0 | |
| 2.00E+04 | TNTC | | 2.00E+04 | 155 | 3.10E+06 | 2.00E+04 | 6 | 1.20E+05 | 2.00E+04 | 0 | |
| 2.00E+03 | TNTC | | 2.00E+03 | TNTC | | 2.00E+03 | 14 | 2.80E+04 | 2.00E+03 | 0 | |
| 2.00E+02 | Lawn | | 2.00E+02 | Lawn | | 2.00E+02 | 177 | 3.54E+04 | 2.00E+02 | 18 | 3.60E+03 |
| 2.00E+01 | Lawn | | 2.00E+01 | Lawn | | 2.00E+01 | TNTC | | 2.00E+01 | 128 | 2.56E+03 |
| | Average | 7.49E+07 | | Average | 2.43E+06 | | Average | 6.11E+04 | | Average | 3.08E+03 |
| Set C | | cfu/mL | Set C | | cfu/mL | Set C | | cfu/mL | Set C | | cfu/mL |
| 2.00E+09 | 0 | | 2.00E+09 | 0 | | 2.00E+09 | 0 | | 2.00E+09 | 0 | |
| 2.00E+08 | 0 | | 2.00E+08 | 0 | | 2.00E+08 | 0 | | 2.00E+08 | 0 | |
| 2.00E+07 | 6 | 1.20E+08 | 2.00E+07 | 1 | | 2.00E+07 | 0 | | 2.00E+07 | 0 | |
| 2.00E+06 | 41 | 8.20E+07 | 2.00E+06 | 1 | 2.00E+06 | 2.00E+06 | 0 | | 2.00E+06 | 0 | |
| 2.00E+05 | TNTC | | 2.00E+05 | 22 | 4.40E+06 | 2.00E+05 | 0 | | 2.00E+05 | 0 | |
| 2.00E+04 | TNTC | | 2.00E+04 | 172 | 3.44E+06 | 2.00E+04 | 1 | 2.00E+04 | 2.00E+04 | 0 | |
| 2.00E+03 | Lawn | | 2.00E+03 | TNTC | | 2.00E+03 | 18 | 3.60E+04 | 2.00E+03 | 2 | 4.00E+03 |
| 2.00E+02 | Lawn | | 2.00E+02 | TNTC | | 2.00E+02 | 164 | 3.28E+04 | 2.00E+02 | 12 | 2.40E+03 |
| 2.00E+01 | Lawn | | 2.00E+01 | Lawn | | 2.00E+01 | TNTC | | 2.00E+01 | 161 | 3.22E+03 |
| | Average | 1.01E+08 | | Average | 3.28E+06 | | Average | 2.96E+04 | | Average | 3.20E+03 |

J. Conclusions

This examples demonstrates that nanoemulsions, such as the tested $P_{407}5EC$, are effective against strains that are multidrug-resistant, including colistin-resistant isolates of *Burkholderia* and *Stenotrophomonas*. None of the described lipid A modifications in *Pseudomonas* species impacted the MIC/MBCs with $P_{407}5EC$. No evidence of antagonism with two major antibiotics, colistin and tobramycin, was observed and in the case of the *Stenotrophomonas*, synergy was evident. This is valuable because the treatment of patients with CF should not need their normal antibiotic regime suspended in order to use the nanoemulsion, complicating their treatment programs. The SEM images demonstrate the kill on contact mechanism, here in this case a Gram negative bacterium with a reputation of having a tough outer membrane.

Example 9

Topical Nanoemulsion Therapy Reduces Bacterial Wound Infection and Inflammation Following Burn Injury Materials and Methods Reagents. Unless otherwise indicated, all reagents were purchased from Sigma-Aldrich Corp. (St. Louis, Mo.).

Animals. Male specific pathogen-free Sprague-Dawley rats (Harlan, Indianapolis, Ind.) weighing approximately 250-300 g were used in all experiments. Rats were housed in standard cages and allowed to acclimate to their surroundings for 7 days prior to being used in experiments. They were kept on a 12 hour light cycle and provided with unrestricted access to standard rat chow and water throughout the study. Experiments were performed in accordance with National Institutes of Health guidelines for care and use of animals. Approval for the experimental protocol was obtained from the University of Michigan Animal Care and Use Committee.

Burn model. Animals were anesthetized with a 40 mg/kg intraperitoneal (ip) injection of sodium pentobarbital (Nembutal; Abbott Laboratories, North Chicago, Ill.). Dorsal hair was closely clipped and removed using Nair depilatory cream (Church & Dwight Inc., Princeton, N.J.) resulting in a thorough and uniform removal of fur. Each rat was placed in an insulated, custom-made mold, which exposes the dorsal region over 20% of the total body surface area. The burn surface area as a fraction of total body surface area was determined using Meeh's formula: body surface area $(cm^2)=9.46\times(\text{animal weight (g)})^{2/3}$ (See Gilpin, Burns 22(8): 607-611, 1996). Partial thickness scald burn injury was achieved by placing the exposed skin of the rat in a 60° C. water bath for 27 seconds. Sham burn animals received the same treatment except they were immersed in room temperature water (21-24° C.). The burn wound was scrub-débrided with dry sterile gauze and rinsed with 0.9% sterile NaCl. Each animal was resuscitated with 4 mL Ringer's lactate/% total body surface area burn/kg body weight. One half of this fluid volume was given intraperitoneally and half subcutaneously immediately following the burn injury. The burn injured skin was left uncovered to air dry. After drying, an occlusive dressing of sterile TELFA (Kendall Co., Tyco Healthcare Group LP, Mansfield, Mass.) and TEGADERM HP (3M Health Care, St Paul, Minn.) was applied to prevent wound contamination. During experiments each rat was singly housed and received 0.01 mg/kg buprenorphine subcutaneously at the time of burn and at 16 hours for post burn pain control.

Local wound treatment. Stock nanoemulsion $W_{20}5GBA_2ED$ was obtained from NanoBio Corporation (Ann Arbor, Mich.). This nanoemulsion was manufactured by emulsification of super-refined soybean oil and water with surfactants and alcohol as described herein. The resultant droplets had a mean particle diameter of 350 nm. The experimental solution was made by diluting 1 mL of the 60% stock formulation with 4.88 mL sterile saline and adding 120 μL of 1 M ethylenediaminetetraacetic acid (EDTA) giving a final concentration of 10% $W_{20}5GBA_2ED$ and 20 mM EDTA. A placebo nanoemulsion ($W_{20}5GBA_2ED$ placebo) compound was manufactured in the same manner as $W_{20}5GBA_2ED$, but benzalkonium chloride was omitted from the formulation. 5% Sulfamylon (UDL Laboratories, Inc., Rockford, Ill.) solution was formulated by mixing 50 g of mafenide acetate powder in 1 L of 0.9% sterile saline. The control reagent used was 0.9% sterile saline. Experimental groups consisted of sham, burn, burn+$W_{20}5GBA_2ED$, burn+bacteria+saline, burn+bacteria+placebo, burn+bacteria+$W_{20}5GBA_2ED$, and burn+bacteria+Sulfamylon. Sixteen hours following burn injury animals were anesthetized with inhaled isoflurane. The occlusive dressing and TELFA was removed. Nanoemulsion ($W_{20}5GBA_2ED$), placebo, Sulfamylon or sterile saline was applied in a uniform fashion to the burn wound surface using a spray bottle. Animals in the sham or burn group received no topical treatment, but did undergo dressing change under anesthesia. The burn wound was then redressed with TELFA and a TEGADERM occlusive dressing. This treatment and dressing change was repeated at 24 hours following burn injury.

Bacterial culture and inoculation. *Pseudomonas aeruginosa* isolated from a human burn patient was previously provided by the Department of Pathology at the University of Michigan. This bacterial isolate is sensitive to the topical agent Silvadene and Sulfamylon. A bacterial inoculum was prepared by thawing an aliquot (0.5 mL, stored in 50% skim milk at −80° C.) in 40 mL of Trypticase soy broth (Becton Dickinson, Franklin Lakes, N.J.) and grown overnight at 37° C. with constant shaking at 275 rpm. A sample of the resulting stationary-phase culture was transferred to 35 mL of fresh Trypticase soy broth and incubated for 2.5 hours to reach the log-phase. This subculture was transferred to a 50 mL conical polystyrene tube and centrifuged for 10 minutes at 4° C. and 880 g. The bacterial pellet was washed with 0.9% sterile saline, and resuspended in 10 mL of ice-cold saline. The optical density of the suspension was measured at 620 nm and bacterial concentration (colony forming units (CFU)/mL) calculated using the formula $OD_{620}\times2.5\times10^8$. The bacterial suspension was diluted with 0.9% sterile saline to a final concentration of $1\times10^6$ CFU per 100 μL. Eight hours following burn injury animals were anesthetized with inhaled isoflurane. The rats then underwent topical application of $1\times10^6$ CFUs of log-phase *Pseudomonas aeruginosa* in 100 μL of sterile saline pipetted onto a piece of TELFA in a uniform fashion followed by coverage with a TEGADERM occlusive dressing.

Tissue harvest. Thirty-two hours after thermal injury the animals were sacrificed and skin tissue samples harvested using sterile technique Skin samples were used immediately or frozen in liquid nitrogen.

Quantitation of bacterial wound infection. A 100 mg piece of excised skin tissue was mechanically homogenized in 1 mL of 0.9 NaCl. This homogenate was then further diluted with 9 mL of sterile saline. Serial dilutions were performed and skin homogenates plated in triplicate on blood agar plates (Becton Dickinson, Franklin Lakes, N.J.). Culture plates were incubated for 24 hours at 37° C. and CFUs counted.

Dermal cytokine analysis (ELISA). A 100 mg sample of dorsal skin was homogenized in 1 mL of ice-cold lysis buffer consisting of 50 mL of PBS and protease inhibitor (Complete X, Roche, Indianapolis, Ind.) and 50 μL of Triton X (Roche). Homogenates were centrifuged at 3000 g for 5 minutes and the supernatants collected and stored frozen at −80° C. until use. Rat IL1-β, IL-6, TNF-α, CINC-1, CINC-3, IL-10 and TGF-β were measured by sandwich enzyme-linked immunosorbent assay (ELISA) using antibodies and reagents from R&D Systems, Inc. (Minneapolis, Minn.). The assay was carried out in 96-well microplates (Immunoplate Maxisorb, Nunc, Neptune, N.J.) according to the kit instructions and samples were read using a microplate reader (Biotek Instruments, Winooski, Vt.) at 450 nm with a wavelength correction of 540 nm. Cytokine concentrations were determined using the plate reader software and a 7-point standard curve. Results were adjusted for previous dilution and expressed as pg/mL.

Detection of neutrophil sequestration (Myeloperoxidase assay). 100 mg of skin tissue was mechanically homogenized in 1 mL ice cold potassium phosphate buffer consisting of 115 mM monobasic potassium phosphate (Sigma Aldrich, Milwaukee, Wis.). Homogenates were centrifuged at 3000 g for 10 min at 4° C., the supernatants were removed and the pellets were re-suspended in 1 mL C-TAB buffer consisting of dibasic potassium phosphate, cetyltrimethylammonium bromide, and acetic acid (Sigma Aldrich, Milwaukee, Wis.). The suspensions were sonicated (Branson Sonifier 250, Danbury, Conn.) on ice for 40 seconds. Homogenates were centrifuged at 3000 g for 10 min at 4° C. and the supernatant collected. Supernatants were incubated in 60° C. water bath for 2 hours (Shaker Bath, 2568; Forma Scientific, Marietta, Ohio). Samples were stored at −80° C. until needed or assayed immediately.

20 μL standards (Calbiochem, Gibbstown, N.J.) or samples were added to a 96-well immunosorbent micro-plates (NUNC, Rochester, N.Y.), followed by the addition of 155 μL of 20 mM TMB/DMF consisting of 3,3',5,5'-tetramethylbenzidine/N,N-dimethylformamide in 115 mM potassium phosphate buffer (Fischer Scientific, Pittsburgh, Pa.) to each well. The samples were mixed well, after which 20 μL of 3 mM $H_2O_2$ was rapidly added to each well. The reaction was stopped immediately by adding 50 μL/well of 0.061 mg/mL Catalase (Roche, Indianapolis, Ind.). The plates were read using a microplate reader at 620 nm. Myeloperoxidase (MPO) concentrations were calculated using a linear standard curve and adjusted for previous dilution. The final concentrations were expressed as μg/mL.

Determination of dermal capillary leak and tissue edema (Evans blue). Animals were anesthetized 90 minutes before tissue harvest. 50 mg/kg body weight of 10% Evans blue (Merck KgaA, Darmstadt, Germany) was injected ip into the burned animal at time 30.5 hours following thermal injury. At the tissue harvest time point animals were exsanguinated by incision of the inferior vena cava. Systemic Evans blue was washed out by inserting a 20 G angiocatheter into the apex of the left ventricle past the aortic valve and into the ascending aorta. A total of four times the blood volume (7.46 mL/100 g body weight) of 0.9 NaCl with 100 units/mL heparin was used to flush the vasculature and administered via a perfusion pump at a constant flow rate. By the end of the perfusing period the effluent from the right atrium had turned clear. Dorsal skin samples were harvested and a 100 mg sample was placed in 4 mL 99.5% formamide in polyethylene tubes. Tubes were placed on a shaker at room temperature for 48 hours for Evans blue extraction. Supernatants were collected and the absorbance read on a microplate reader at 620 nm. Concentrations were calculated from an Evans blue in formamide standard curve. Results are expressed as micrograms of Evans blue per mg of skin tissue.

Histology. Skin samples were fixed in 10% buffered formalin and embedded in paraffin. Eight μm thick sections were affixed to slides, deparaffinized, and stained with hematoxylin and eosin to assess morphologic changes.

Detection of hair follicle cell apoptosis (TUNEL assay). Animals were anesthetized and underwent creation of a 20% partial thickness scald burn wound or sham injury. Treatment groups consisted of sham, burn+saline, burn+placebo, and burn+$W_{20}5GBA_2ED$. Treatment and dressing changes were performed at 0 and 8 hours post-burn. No bacterial infection was created in this experiment. Full-thickness skin samples were taken from three locations across the entire burn wound at 12, and 24 hours post thermal injury for determination of hair follicle cell apoptosis. There were four animals per treatment group per time sample.

Apoptosis was detected in situ with fluorescein based labeling of DNA strand breaks using terminal deoxynucleotidyl transferase dUTP nick end labeling (TUNEL) assay (ApopTag, CHEMICON International, Inc, Temecula, Calif.). The three fresh skin samples for each animal were placed in disposable vinyl cryomolds filled with optimal cutting temperature compound (Sakura Finetek, U.S.A., Inc., Torrance, Calif.), and frozen at −80° C. until ready for use. Frozen embedded skin specimens were cut into 4-mm-thick serial sections in a cryostat and collected on Superfrost Plus glass slides (Fisher Scientific, Pittsburgh, PN). Sections were fixed in 1% paraformaldehyde in PBS overnight at 4° C. for indirect immunofluorescence according to the manufacturer's instructions. After 2 washes with PBS, sections were post-fixed in a 2:1 solution of ethanol:acetic acid for 5 minutes at −20° C. Following 2 additional washes with PBS, sections were incubated in equilibrium buffer for 5 minutes. Sections were then incubated with terminal deoxynucleotidyl transferase enzyme in a humidified chamber for 1 h at 37° C. The reaction was terminated by rinsing the sections in a stop/wash buffer. Sections were incubated in a humidified chamber at room temperature with antidigoxigenin fluorescein (fluorescein isothiocyanate, FITC) for 30 min and rinsed 3 times in PBS. After aspiration, sections were washed once with water and coverslips applied using ProLong Gold Antifade (Molecular Probes, Inc, Eugene, Oreg.), which included $4^1$ 6-diamidino-2-phenylindole dihydrochloride (DAPI) counterstaining The TUNEL assay slides were blinded to groups, and under the microscope appropriate hair follicle cells in a randomly chosen high-power field were identified. Appropriate hair follicles for analysis were those sectioned in the mid-sagittal or mid-coronal plane. A total of 3-6 hair follicles were selected from among the three skin samples present on a slide. Fluorescent-labeled TUNEL slides were captured digitally at identical time post-labeling to control fading of fluorescence using an Olympus BX-51 fluorescence microscope at fixed image capture settings and 40× magnification. Each hair follicle was selected and first digitally captured by visualizing counterstained nuclei present using the DAPI excitation/emission channel. Then for each hair follicle analyzed, the excitation/filter channel was changed to visualize the fluorescein-labeled TUNEL-positive cells, and images again digitally captured. Within the captured images a region of interest (ROI) was digitally defined, set to include only hair follicle cells and exclude bright fluorescing hair shafts and surrounding cells (NIH Image J software, NIH, Bethesda, Md.). Fluorescence of TUNEL-positive cells was quantified, normalized to ROI size, and expressed as pixels/area fraction, controlling for differences in ROI size.

Statistical methods. Statistical analysis and graphs were performed using GraphPad Prism 5.0 software (GraphPad Software, La Jolla, Calif.). Results are presented as mean values±the SEM unless otherwise noted. Continuous variables were analyzed using an unpaired two-tailed Student's t-test and/or One-way ANOVA followed by Tukeys post-test comparisons. The Kruskal-Wallis test with Dunn's multiple comparisons was used to evaluate differences in medians for data with a non-parametric distribution. Discrete variables were compared using Fisher's exact test. Statistical significance was defined as a p-value <0.05.

Figure 21:
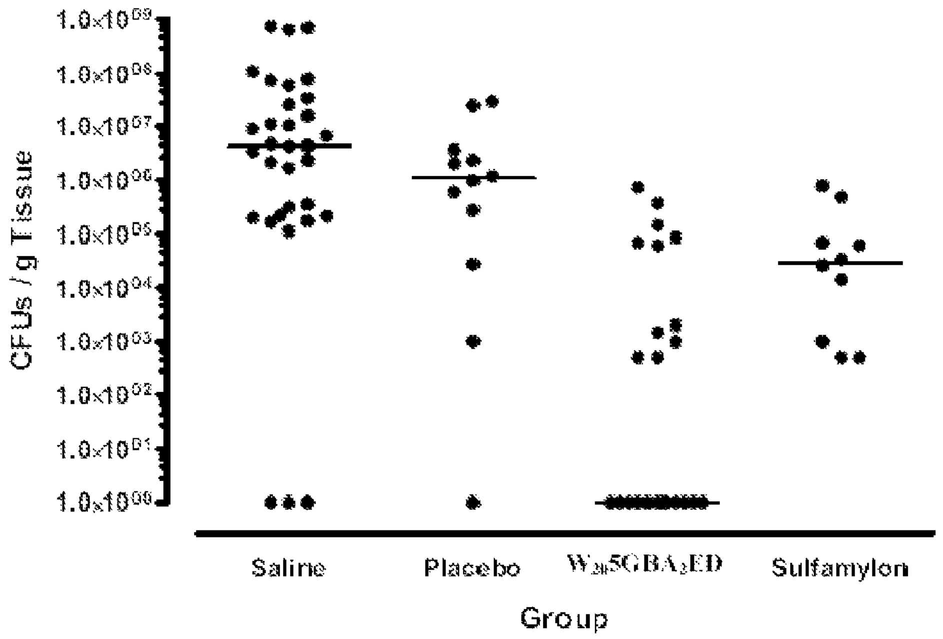
FIG. 21 shows topical application of nanoemulsion reduces *P. aeruginosa* growth in burn wounds. Male Sprague-Dawley rats received partial thickness burn wounds. At 8 hours post-injury, animals were inoculated with $10^6$ CFU *P. aeruginosa*. At 16 and 24 hours post-burn the animals were treated with topical saline (Control), placebo ($W_{20}5GBA_2ED$ without benzalkonium chloride), $W_{20}5GBA_2ED$ (nanoemulsion), or Sulfamylon (mafenide acetate). At 32 hours, animals were sacrificed, skin samples obtained and homogenized, plated, and CFUs counted. The scatter plot represents cultured CFUs for each individual animal. The median value for each group is plotted as a horizontal line. There was minimal pathogen growth in 12 out of 23 of the NB-201 treated animals. A majority of the control (29/32) and placebo (9/12) animals with burn injury had evidence of wound infection based on a positive quantitative wound culture with significantly more bacteria present in the wound than those animals treated with $W_{20}5GBA_2ED$. $p<0.0001$, Kruskal-Wallis test, $p<0.05$ for saline vs. $W_{20}5GBA_2ED$, placebo vs. $W_{20}5GBA_2ED$, and saline vs. Sulfamylon, Dunn's multiple comparison test.

Topical Application of Nanoemulsion Reduces *P. aeruginosa* Growth in Burn Wounds Animals treated with nanoemulsion had a decreased mean ($6.5\times10^4$ vs. $7.9\times10^7$, p=0.07) and median (0 vs. $4.4\times10^6$, p<0.05) number of CFUs of bacteria per gram of skin tissue when compared to the saline treated controls (See FIG. 21) A similar reduction in skin bacterial counts was found for $W_{20}5GBA_2ED$ treated animals vs. those treated with the $W_{20}5GBA_2ED$ placebo (mean: $6.5\times10^4$ vs. $5.5\times10^6$, p=0.02). When performing quantitative wound culture on clinical tissue samples a positive result is generally considered to be growth of organisms at greater than $1\times10^5$ CFUs per g of tissue (See, e.g., Neal et al., J Burn Care Rehabil 2:35-39, 1981; Taddonio et al., Burns Incl Therm Inj 14(3):180-184, 1988; Uppal et al., Burns 33(4):460-463, 2007). Using these criteria, 29 of 32 animals in the control group exhibited evidence of a positive quantitative wound culture and only 3 of 23 animals in the nanoemulsion group demonstrated proof of this level of wound infection (91% vs. 13%, p<0.0001, See Table 24, below). The Sulfamylon treated animals also demonstrated a significant reduction in the median wound bacterial level when compared to the saline controls ($3\times10^4$ vs. $4.4\times10^6$, p<0.05). Treatment with nanoemulsion or Sulfamylon produced a similar reduction in the level of *Pseudomonas* cultured from the burn wound when compared to the saline treated animals. However, there was no statistically significant difference between the placebo and Sulfamylon groups whereas there was a difference for the $W_{20}5GBA_2ED$ group compared to the $W_{20}5GBA_2ED$ placebo.

TABLE 24

Quantitative Wound Culture Results

| | Saline | Placebo | NB-201 | Sulfamyton |
|---|---|---|---|---|
| Total Animals, n | 32 | 12 | 23 | 10 |
| Animals with CFU's/g > $1\times10^5$, n (%) | 29 (91) | 9 (75) | 3 (13)* | 2 (20)* |

*p < 0.05, vs. saline control, Fishers exact test

Figure 22:
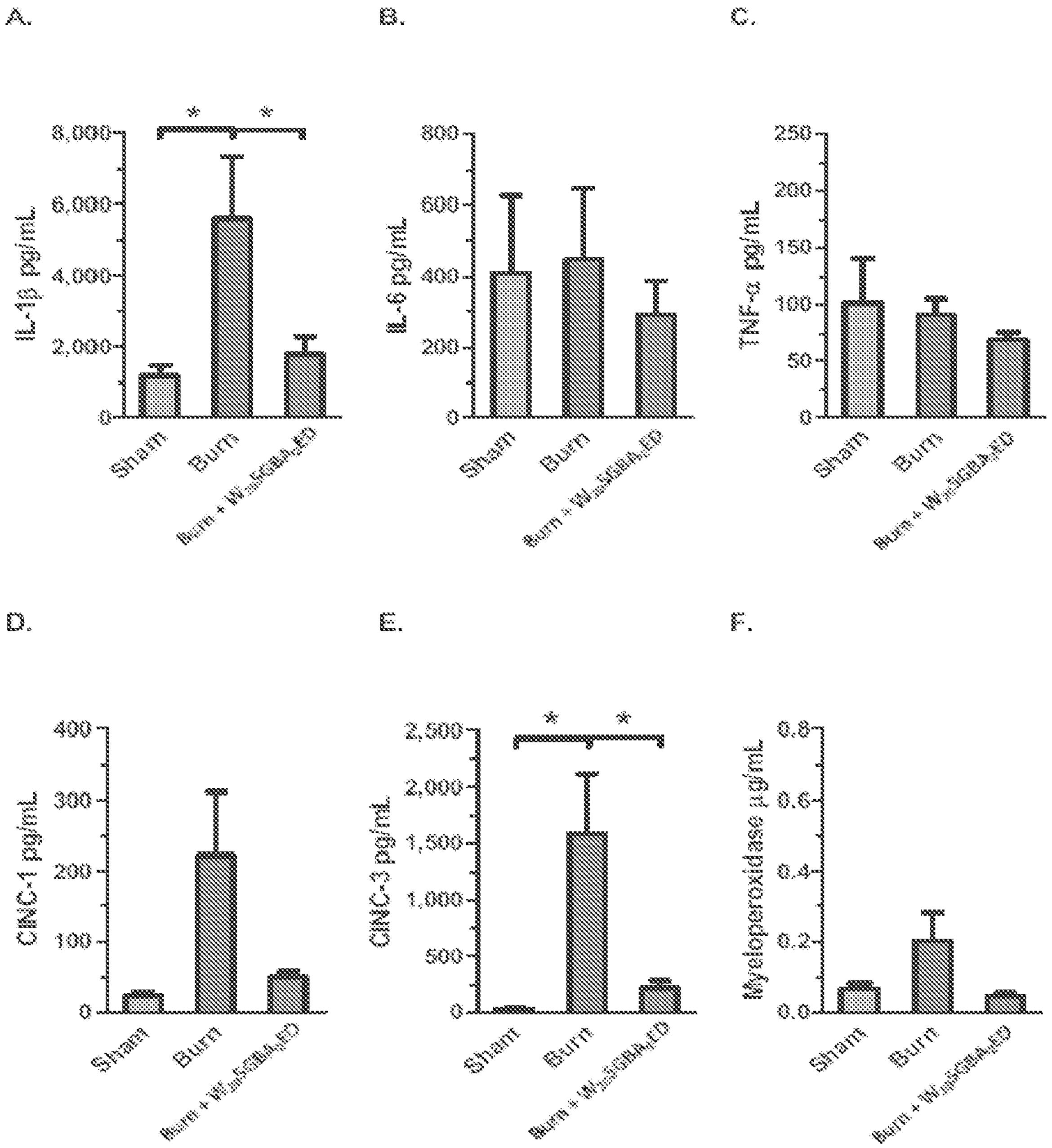
FIG. 22 shows nanoemulsion treatment following burn injury attenuates dermal proinflammatory cytokine expression. Groups were sham, burn, and burn with $W_{20}5GBA_2ED$ treatment (n=8-10 per group). A) IL-1β (p=0.02, 1-way ANOVA), B) IL-6 (p=0.8), C) TNF-α (p=0.5), D) CINC-1 (p=0.04), E) CINC-3 (p=0.005), and F) Myeloperoxidase (p=0.07). Burn injured animals treated with nanoemulsion had decreased levels of IL-1β (1773±516 vs. 5625±1743 pg/mL) and CINC-3 (225±66 vs. 1589±527 pg/mL) when compared to untreated partial thickness burned animals. *$p<0.05$, t-test or Tukey's multiple comparison test.

Nanoemulsion Treatment Following Burn Injury Attenuates Dermal Pro-inflammatory Cytokine Levels Scald injury resulting in a partial thickness burn produced differences in dermal levels of IL-1β and cytokine-induced neutrophil chemoattractant-3 (CINC-3) within skin homogenates obtained 32 hours post-injury compared to sham injured animals (See FIGS. 22A and E). Treatment with $W_{20}5GBA_2ED$ at 16 and 24 hours post-burn reduced the dermal level of these two inflammatory mediators back down to the baseline (sham) in the absence of bacterial infection. In experiments where a bacterial wound infection was not created, a difference in neutrophil sequestration as measured by myeloperoxidase assay was not observed despite the rise in the rat CXC chemokine CINC-3 within burned skin. A difference was found between all three groups (sham, burn, and burn+$W_{20}5GBA_2ED$) for CINC-1 (p=0.04, ANOVA), however the values for intergroup comparison did not reach statistical significance.

Figure 23:
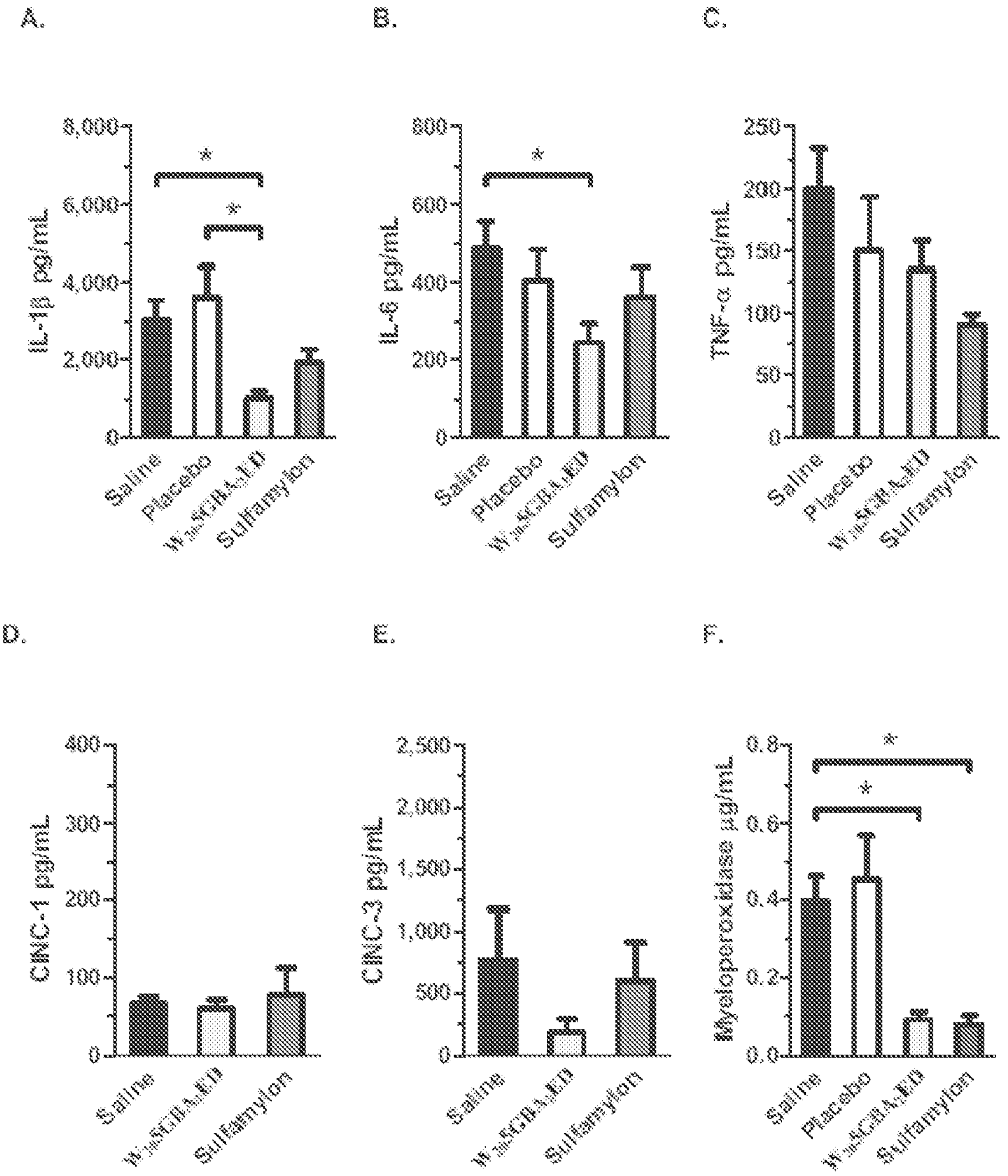
FIG. 23 shows nanoemulsion treatment following burn wound infection with *P. aeruginosa* attenuates dermal proinflammatory cytokine expression. All animals received burn injury and groups were saline, placebo, $W_{20}5GBA_2ED$, and Sulfamylon (n=10-30 per group). A) IL-1β (p=0.001, 1-way ANOVA), B) IL-6 (p=0.07), C) TNF-α (p=0.3), D) CINC-1 (p=0.8), E) CINC-3 (p=0.4), and F) Myeloperoxidase (p=0.0001). Burn wound infected animals treated with nanoemulsion had decreased levels of IL-1β (1007±157 vs. 3054±499 pg/mL) and IL-6 (244±51 vs. 485±73 pg/mL). The nanoemulsion and Sulfamylon treatment groups demonstrated reduced dermal neutrophil sequestration when compared to saline and placebo as evidenced on myeloperoxidase assay ($W_{20}5GBA_2ED$: 0.09±0.02, Sulfamylon: 0.08±0.02, Saline: 0.40±0.06, Placebo: 0.45±0.11 μg/mL). *$p<0.05$, Tukey's multiple comparison test.

Nanoemulsion Treatment Following Burn Wound Infection with *P. aeruginosa* Attenuates Dermal Cytokine Levels and Results in Reduced Neutrophil Sequestration Skin homogenates from the nanoemulsion treated group had levels of IL-1β and IL-6 that were considerably diminished when compared to the levels measured in the saline treated animals (See FIGS. 23A and B). There was no statistically significant difference seen in the level of TNF-α between the two experimental groups of animals (See FIGS. 22 C and D). Treatment of the infected burn wound with Sulfamylon did not result in any significant alteration of dermal levels of the measured proinflammatory cytokines (IL-1β, IL-6, TNF-α, CINC-1 or CINC-3) when compared to controls. Treatment with either $W_{20}5GBA_2ED$ or Sulfamylon reduced the level of myeloperoxidase found in the infected burn wound at 32 hours post-injury. Thus, in some embodiments, treatment with a nanoemulsion and/or antimicrobial reduces the level of neutrophil sequestration into a partial thickness burn wound.

Figure 24:
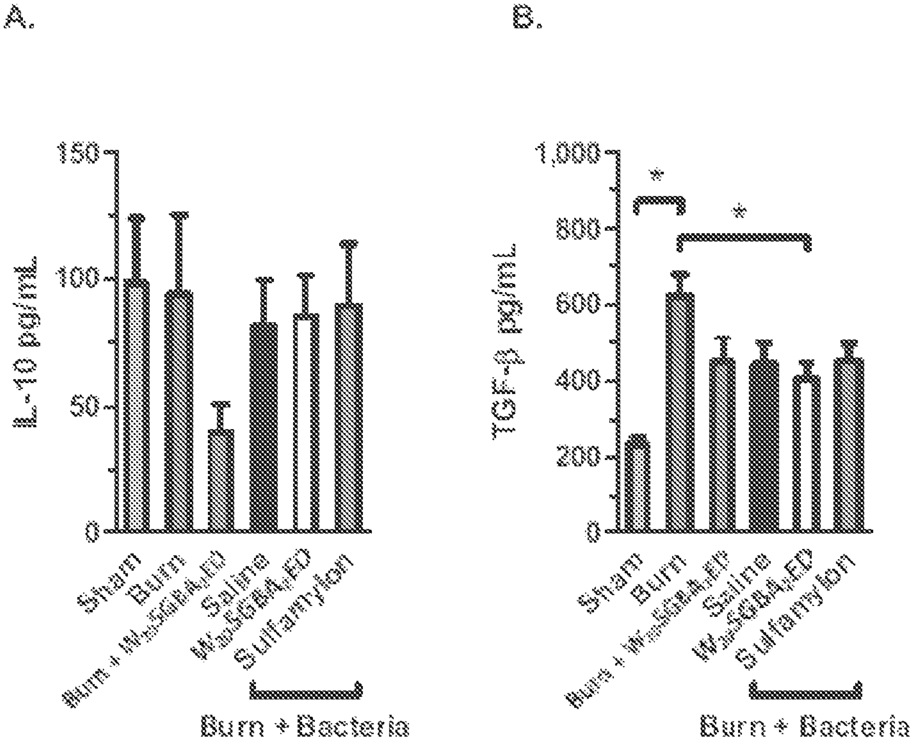
FIG. 24 shows burn injury upregulates dermal TGF-β expression and treatment with nanoemulsion in the setting of burn wound infection decreases the level of TGF-β in the wound. Dermal levels of the anti-inflammatory cytokines IL-10 and TGF-β were measured in the burn wound 32 hours after thermal injury in animals treated with nanoemulsion, and in animals exposed to bacteria and treated with nanoemulsion or Sulfamylon. A) IL-10 (p=0.4, 1-way ANOVA), and B) TGF-β (p=0.0001). Partial thickness burn increased the presence of dermal TGF-β as compared to sham (624±55 vs. 232±17 pg/mL). Treatment of an infected burn wound with $W_{20}5GBA_2ED$ significantly reduced the dermal level of TGF-β compared to the untreated burn group (404±43 vs. 624±55 pg/mL). Sulfamylon treatment did not suppress the level of IL-10 or TGF-β in the infected burn wound. *$p<0.05$, Tukey's multiple comparison test.

Burn injury caused a rise in the level of the anti-inflammatory cytokine TGF-β, but not IL-10 when compared to the sham injured animals (See FIG. 24). $W_{20}5GBA_2ED$ treatment reduced the amount of TGF-β present in the infected burn wound as compared to the level found in the burn wound alone. Accordingly, in some embodiments, the present invention provides that $W_{20}5GBA_2ED$ can be utilized to reduce acute burn wound dermal inflammation, and in further embodiments, can be utilized to reduce the eventual immunosuppression created by thermal injury.

Figure 25:
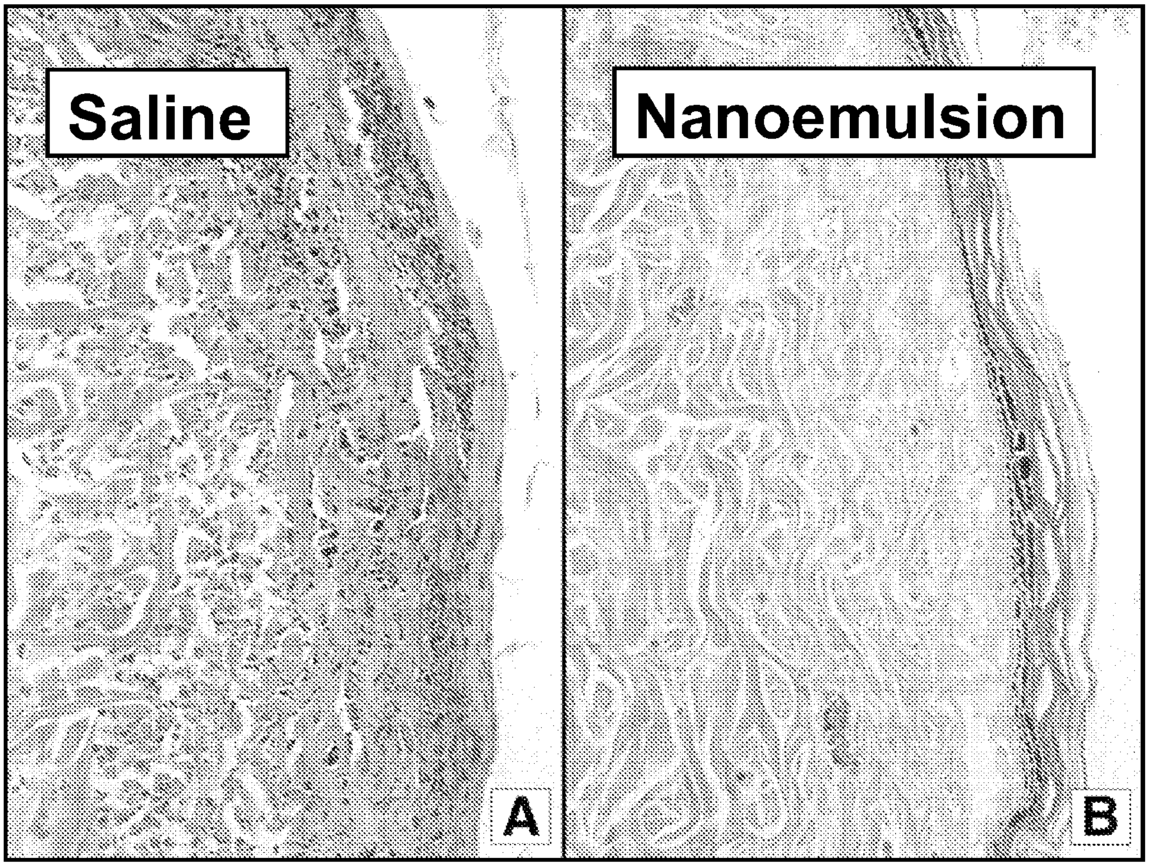
FIG. 25 shows cross sectional histology of burn skin following infection with *P. aeruginosa* and treatment with saline or nanoemulsion. Both views of skin are 32 hours after burn injury. A) Representative section from saline (control) treated animal (Hematoxylin and eosin×40). B) Representative cross-section from $W_{20}5GBA_2ED$ (nanoemulsion) treated animal (Hematoxylin and eosin×40).

On histological examination of skin from the saline control animals, there is loss of most of the epidermis and a diffuse cellular infiltrate in the subepidermal region, extending into the lower dermal connective tissue in which collagen fibrils are separated by the infiltrating leukocytes and edema fluid (See FIG. 25A). At a higher power, the cellular infiltrate between the collagen bundles consists almost entirely of neutrophils. Edema fluid causes separation of the collagen fibrils. In FIG. 25B, the skin was subjected to thermal injury followed by application of *P. aeruginosa* after which the nanoemulsion was topically applied to the burned area. The keratin layers of the epidermis are separating and some of the keratin has been lost. There is a barely detectable intradermal presence of neutrophils together with neutrophils that are adhering to the wall of a venule, which has been longitudinally sectioned (in the center of the microphotograph). The changes in this microphotograph are substantially less extensive than those seen in FIG. 25A.

Quantification of Capillary Leak and Tissue Edema

Figure 26:
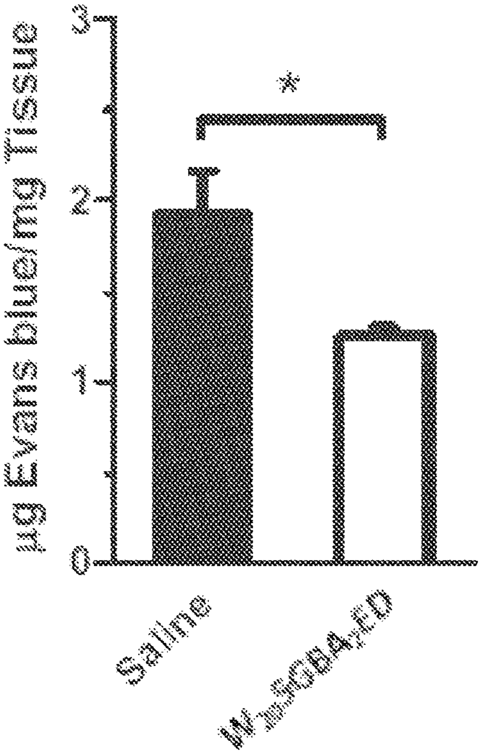
FIG. 26 shows evans blue assay to quantify capillary leak and tissue edema. Evans blue is a dye that binds to serum albumin and can be quantitated to determine vascular permeability. Topical nanoemulsion treatment resulted in less capillary leak following thermal injury and bacterial inoculation of the wound when compared to saline treated control animals (1.26±0.05 vs. 1.93±0.24 μg Evans blue/mg tissue, n=8 per group). *p=0.02, t-test.

Burn wounds are associated with significant levels of capillary leak. This can lead to depletion of the intravascular volume and a need for large amounts of intravenous crystalloid fluid administration. To assess whether therapeutic treatment with a nanoemulsion reduced capillary leak in conjunction with reducing inflammation, an Evans blue assay was utilized to measure vascular permeability. Quantitative measurement of the amount of this dye leaching out of the blood stream and into the skin tissue revealed that the nanoemulsion treated animals had less evidence of post-burn capillary leak and tissue edema than the saline treated controls (See FIG. 26).

Treatment with Nanoemulsion Reduces Burn Induced Hair-follicle Apoptosis

Figure 27:
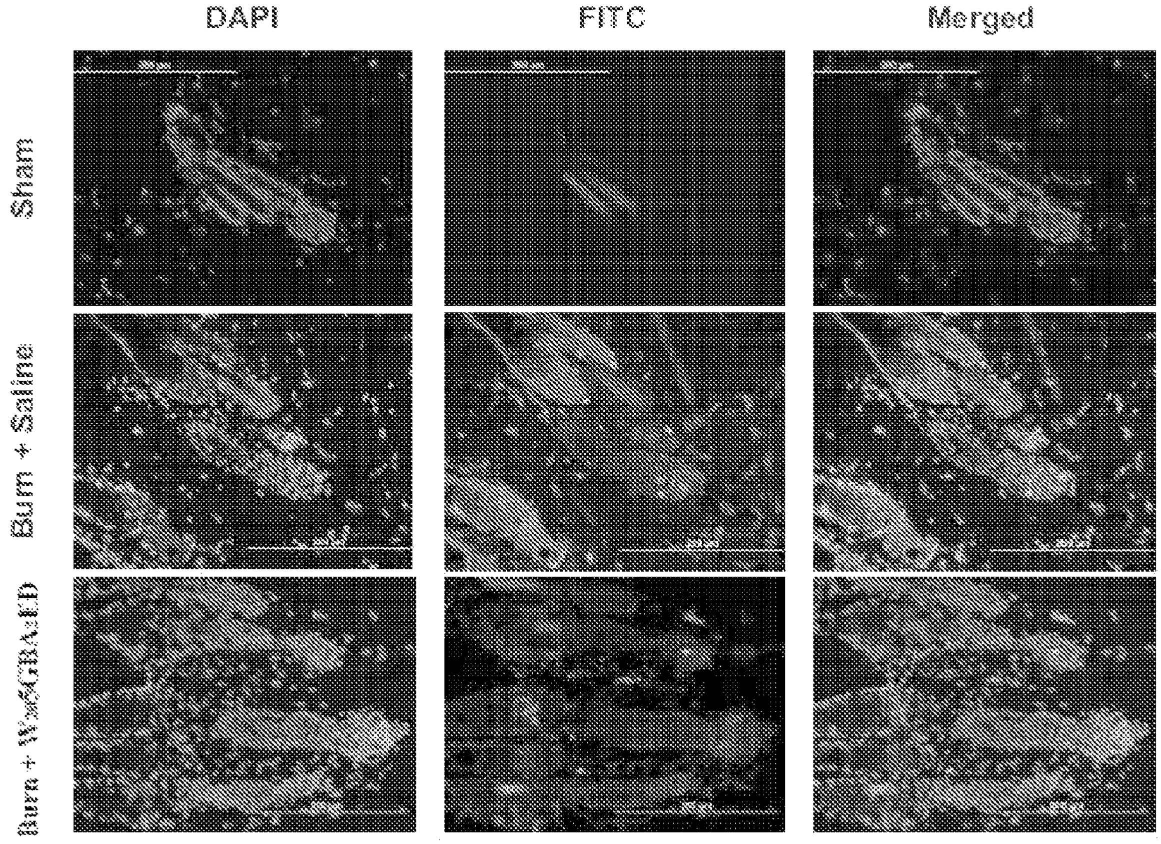
FIG. 27 shows photomicrographs of partial thickness burned skin with fluorescence labeled TUNEL staining to detect hair follicle cell apoptosis. Skin samples were harvested at 12 hours post-burn. Treatment was performed at 0 and 8 hours following thermal injury. All images are at 40× magnification.
Figure 28:
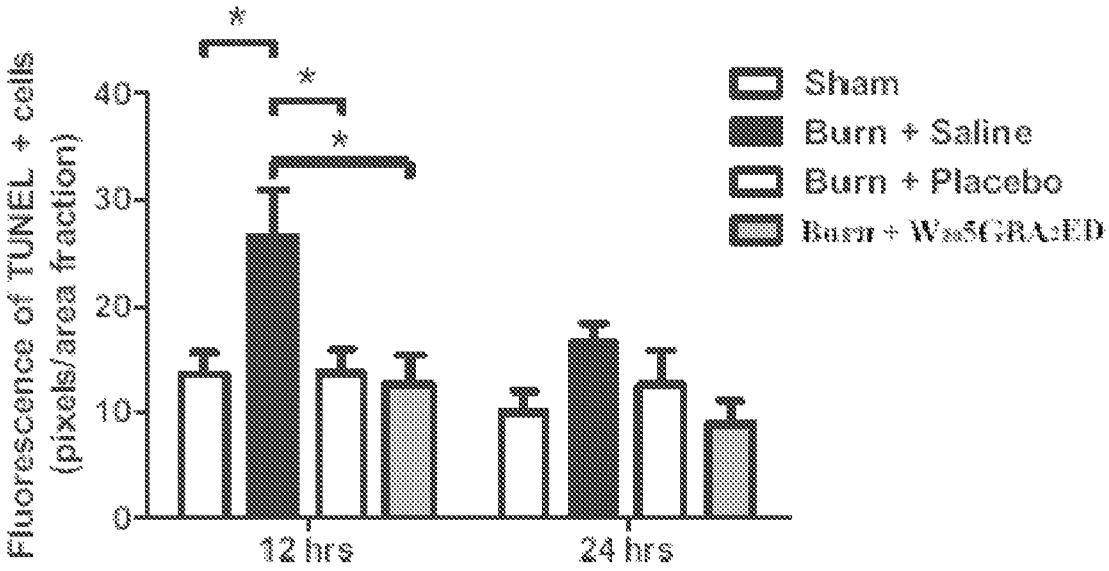
FIG. 28 shows TUNEL assay for hair follicle cell apoptosis following a partial thickness burn injury. Skin samples from sham, burn+saline (control), burn+placebo ($W_{20}5GBA_2ED$ without benzalkonium chloride), and burn+$W_{20}5GBA_2ED$ were sectioned for fluorescein-labeled TUNEL assay. Treatment was performed at time 0 and 8 hours post injury. No bacterial inoculation of the burned skin was done in this experiment. There was a significant reduction in the degree of hair follicle apoptosis among burn injured and treated animals for tissue samples harvested at 12 hours post injury (p=0.006, 1-way ANOVA). Differences were found for sham vs. burn+saline, burn+saline vs. burn+placebo, and burn+saline vs. burn+$W_{20}5GBA_2ED$ (*$p<0.05$, Tukey's multiple comparison test).

Dermal apoptosis occurs in the hair follicle cells following thermal injury. Using a fluorescence labeled TUNEL assay the burn wounds treated with saline showed evidence of intense FITC-TUNEL positive cells which appear green (See FIG. 27). The DAPI nuclear stain allows identification of coronal or sagittally sectioned hair follicles with the cells staining blue. FITC-TUNEL positive cells appear green and are representative of apoptotic cells. In the merged images, the apoptotic hair follicle cells are evident in slides from the burn+saline animals and these changes are diminished in the burn+$W_{20}5GBA_2ED$ treated animals. Counting the pixels of TUNEL positive cells within a hair follicle region of interest allowed quantification of the reduction in hair follicle cell apoptosis by treatment with topical nanoemulsion (See FIG. 28). The saline treated control animals had an increased amount of TUNEL positive cells when compared to the sham burn animals. Both the $W_{20}5GBA_2ED$ and placebo treatment resulted in a decrease in hair follicle cell apoptosis following partial thickness burn injury in tissue harvested 12 hours following thermal injury. This difference was not evident in the dermal skin sampled at 24 hours post-burn. Thus, in some embodiments, the present invention provides a method of reducing apoptotic cell death in hair follicles in the early post-burn period comprising administering a nanoemulsion (e.g., $W_{20}5GBA_2ED$) to a burn wound during an early post-burn period.

Example 10

Immunogenic Compositions Comprising Nanoemulsion and *Burkholderia* Immunogen and Methods of Inducing Protective Immunity Against *Burkholderia* Species in a Subject Materials and Methods

*B. cenocepacia* Strain K56-2 Stock Maintenance and Culture. *Burkholderia cenocepacia* strain K56-2 was generously provided by Dr. Pam Sokol (University of Calgary). K56-2 is a clinical isolate and has been used for *Burkholderia* molecular microbiology and genomic studies (See, e.g., Goldberg, 2007 *Burkholderia* Molecular Microbiology and Genomics. Gent, Belgium: Taylor & Francis). It is a representative of the transmissible and virulent *B. cenocepacia* ET12 lineage (See, e.g., Johnson et al., 1994, J Clin Microbiol 32, 924-930; Saijan et al., 2008, Infect Immun 76, 5447-5455). *Burkholderia multivorans* ATCC 17616 was used for cross-strain neutralization assays. Both K56-2 and ATCC 17616 strains were stored at −80° C. in Luria-Bertani broth with 15% glycerol and recovered from frozen stock on brain-heart infusion agar overnight at 37° C.

*B. cenocepacia* Outer Membrane Protein (OMP) Preparation. An overnight culture of K56-2 in brain-heart infusion media was centrifuged at 3500 rpm for 20 minutes. The cell pellet was washed several times with PBS (pH 7.4), re-suspended in 1 mM EDTA in PBS (pH 8.0), then incubated for 30 minutes at room temperature. Post-incubation, the bacteria were passed several times through a 26-gauge needle (Becton Dickinson) using high pressure. Cell lysis was achieved with Triton X-100 (Sigma) added to a final concentration of 2% and incubated for 10 minutes at room temperature. Mechanical separation was performed with multiple rounds of sonication (1 minute each). The sonicated lysates were then centrifuged twice for 10 minutes at 6000×g (Beckman Optima XL-100k ultracentrifuge, 25° C.) with the supernatant retained after each spin. Following the second centrifugation, the supernatant was centrifuged at 100,000×g for 1 hour at 4° C. The resulting pellet was resuspended in endotoxin-free PBS. The rough OMP preparation was purified (endotoxin-depleted OMP) with an endotoxin-removal column (Pierce) according to the manufacturer's instructions. The flow-through fractions were stored at −80° C. until used.

OMP Analysis. The protein contained within the OMP preparation was quantified using BCA Assay (Pierce). Western blotting and silver staining were performed according to established protocol as described previously (See, e.g., Makidon et al., 2008, PLoS ONE 3, e2954). To quantify endotoxin contaminate, OMP was analyzed using the LAL Kinetic-QCL (Lonza). Endotoxin was detected at 1.93 endotoxin units/mg in the endotoxin-depleted OMP preparation. DNA contaminant removal was verified by agarose-EtBr gel electrophoresis and imaged on a UV table (See FIG. 29A). Oligonucleotides contaminants were not detected in either the crude OMP or the endotoxin-depleted OMP preparations.

OMP Sequencing and Verification.

Sample Preparation. The protein sample was separated by SDS-PAGE (See FIG. 29B). The protein band immunostained with the highest intensity (~17 KDa) on western blot (See FIG. 29C) was excised and subjected to in-gel digestion. In-gel digestion was performed at the Protein Structure Facility at the University of Michigan according to procedures by Rosenfeld et al. and Hellman et al. See, e.g., Hellman et al., 1995, Analytical Biochemistry 224, 451-455; Rosenfeld et al., 1992, Analytical Biochemistry 203, 173-179). A gel slice containing 5-ρmol bovine serum albumin (BSA) was analyzed in parallel as a positive control.

Mass Spectrometry. HPLC-Electrospray Ionization (ESI) Tandem Mass Spectrometry (MS/MS) was performed on a Q-tof premier mass spectrometer (Waters Inc) fitted with a nanospray source (Waters Inc.). The mass spectrometer was calibrated with a mass accuracy within 3 ppm. On-line capillary HPLC was performed using a Waters UPLC system with an Atlantis C18 column (Waters, 100-mm inner diameter, 100-mm length, 3-mm particle size). Digests were desalted using an online trapping column (Waters, Symmetry C18, 180-mm inner diameter, 20-mm length, 5-mm particle size) before being loaded onto the Atlantis column. A data-dependent tandem mass spectrometry approach was utilized to identify peptides in which a full scan spectrum (survey scan) was used, followed by collision-induced dissociation (CID) mass spectra of all ions in the survey scan with a peak intensity rising above 20 counts per second. The survey scan was acquired in V+ mode over a mass range of 50-2000 Da with lockmass correction (Gu-Fibrinopeptide B, $(M+H)^{2+}$: 785.8426) and charge state peak selection (2+, 3+ and 4+). The MS/MS scans were acquired for 5 seconds with collision energy control by charge state recognition.

Data Analysis and Bioinformatics. Tandem mass spectra were acquired using Mass Lynx software (Version 4.1). Raw data files were first processed for lockmass correction, noise reduction, centering, and deisotoping using the Protein Lynx Global Server software Ver. 4.25 (Waters Inc.). The generated peaklist files containing the fragment mass spectra were subjected to database searches using the ProteinLynxGlobal Server and Mascot (Matrix Science Inc., Boston, Mass.) search engines and Swiss Prot and NCBI databases, as well as the *Burkholderia cenocepacia* database downloaded from the Sanger Institute web site.

Preparation of Nanoemulsion-based OMP (OMP-NE) vaccine. Nanoemulsion ($W_{80}5EC$: 5 vol. % of TWEEN 80, 8 vol. % of ethanol, 1 vol. % of CPC, 64 vol. % of soybean oil) and 22 vol. % of $DiH_2O$) was provided by NanoBio Corporation (Ann Arbor, Mich.), the droplets having a particle diameter of 200-400 nm. OMP-NE formulations were prepared by vigorously mixing the endotoxin-depleted OMP preparation (See FIG. 29B, Lane F) with concentrated NE, using PBS as the diluent. For the intranasal immunizations, OMP-NEs were formulated to contain either 0.25 μg/μL or 0.75 μg/uL OMPs mixed in 20% (v/v) NE.

Animals and immunization procedures. Pathogen-free, outbred CD-1 mice (females 6-8 weeks old) were purchased from Charles River Laboratories. The mice were housed in accordance to the standards of the American Association for Accreditation of Laboratory Animal Care. The use of these mice was approved by the University of Michigan University Committee on Use and Care of Animals (UCUCA). The mice (n=10 per group) were vaccinated with two administrations of either OMP-NE vaccines four weeks apart. Intranasal (i.n.) immunizations were performed in mice anaesthetized with isoflurane using the IMPAC6 anesthesia delivery system. The anesthetized animals were held in a supine position and 20 μL (10 μL/nare) of OMP-NE vaccine was administered slowly to the nares using a micropipette tip. Mice were immunized with either 15 μg OMP with NE, 15 μg OMP in PBS, 5 μg OMP with NE, or 5 μg OMP in PBS.

Phlebotomy, bronchoalveolar lavage, and splenocyte collection. Blood was collected from the saphenous vein every 21 days throughout the duration of the study. The terminal sample was obtained by cardiac puncture immediately following euthanasia. Whole blood samples were separated by centrifugation at 3500 rpm (15 minutes) following coagulation. The serum samples were stored at −20° C. until analyzed. Bronchoalveolar lavage (BAL) fluid was obtained from the mice immediately following euthanasia as described (See Makidon et al., 2008, PLoS ONE 3, e2954). In vitro measurement of the cytokine response was determined using the spleens of the vaccinated mice. Spleens were mechanically disrupted to obtain single-cell splenocyte suspension in PBS. Red blood cells were lysed with ACK buffer (150 mM NH4Cl, 10 mM KHCO3, 0.1 mM Na2EDTA) and removed by washing the cell suspension twice in PBS. The splenocytes were then resuspended in RPMI 1640 medium supplemented with 2% FBS, 200 nM L-glutamine, and penicillin/streptomycin (100 U/mL and 100 mg/mL).

Enzyme-linked immunosorbent assay (ELISA). Serum IgG and mucosal secretory IgA (sIgA) were determined by ELISA against endotoxin-depleted OMP. The OMP was prepared at 15 μg/mL in coating buffer (Sigma) and 100 μL was applied per well to Polysorb plates (Nunc) for a 4° C. overnight incubation. Serum was serially diluted in 0.1% BSA/PBS. Either diluted serum or undiluted BAL was then added to the plates for an overnight incubation at 4° C. Following a 16 hour incubation, the plates were washed and an alkaline phosphatase conjugated anti-mouse IgG (H&L), IgG1, IgG2a, IgG2b, sIgA (a chain-specific) (Rockland Immunochemicals, Inc) antibody was added at 1:2000 or 1:1000 in 0.1% BSA/PBS. The plates were read at $OD_{405}$ and end titers based on naïve animal levels. Levels of sIgA were normalized to total protein content.

Analysis of antigens recognized by serum IgG. In addition to western blot analysis, serum lipoprotein-specific and lipopolysaccharide-specific IgG antibodies in serum were measured using ELISA. Briefly, 96-well Polysorb assay plates (Nunc) were coated with 0.05 μg/well of crude OMP preparation, endotoxin-depleted OMP, or LPS (List Biological Laboratories). Serum was collected from mice immunized with OMP+NE 8 weeks following prime vaccination. The serum was serially diluted in 0.1% BSA/PBS and then added to the coated wells. The ELISA procedure was performed as described supra. To evaluate the immunogenic contribution of protein and LPS contained within the OMP-based vaccine, an enzymatic protein digest was performed using 250 μg of PCR-grade recombinant proteinase K (Roche) in 100 μl of either the crude OMP preparation or the endotoxin-depleted OMP preparation. Proteinase K was incubated with the OMP preparations for 16 hours at room temperature. The protein digestion was verified using a silver-stained SDS-PAGE. LPS and OMP-protein specific epitopes were evaluated using western blot analysis probing with serum from mice vaccinated with either OMP-NE or OMP in PBS, or probing with an anti-*Pseudomonas mallei* LPS antibody (GeneTex).

Analysis of cytokine expression. Freshly isolated mouse murine splenocytes were seeded at $4\times10^6$ cells/mL (RPMI 1640, 2% FBS) onto a 24-well plate and incubated for 72 hours with OMPs (15 μg/mL) or PHA-P mitogen (2 μg/mL) as a control. Cell culture supernatants were collected and analyzed for the presence of cytokines using LUMINEX multi-analyte profiling beads (LUMINEX Corporation, Austin, Tex.), according to the manufacturer's instructions.

Measurement of serum antibody neutralization. *B. cenocepacia* strain K56-2 and *B. multivorans* strain ATCC 17616 antibody-complement neutralization activity was assayed using serum harvested from mice 6 weeks following primary i.n. vaccination. Twenty-five μL of serum (serially diluted 1×, 2×, 3×, 4×, or 5×) was added to 25 μL of a solution containing $1\times10^3$ K56-2 or *B. multivorans* supplementing MH medium in microculture plates (Nunc). The plates were incubated at 37° C. for 48 hours. Controls included 25 μL serum with 25 μL of sterile 1×PBS and 50 μL of MH medium containing $1\times10^3$ bacteria. Following incubation, the wells were mixed and 10 μL of solution was plated on *Burkholderia* selective agar (BCSA) media (See Henry et al., 1997, J Clin Microbiol 35, 614-619) on polystyrene culture plates (Fisherbrand) then incubated 72 hours at 37° C. prior to manual colony forming units (cfu) enumeration.

Pulmonary bacterial challenge. Bacterial challenge studies were performed in immunized mice (n=5 per group) or non-vaccinated control mice (n=10) 10 weeks following primary vaccination using a modified version of the chronic pulmonary model of *B. cepacia* infection described (See Bertot et al., 2007, Infect Immun 75, 2740-2752; Chu et al., 2002 Infect Immun 70, 2715-2720; Chu et al., 2004, Infect Immun 72, 6142-6147). Briefly, $5\times10^7$ of K56-2 suspended in 85 μL of PBS was instilled through a trans-tracheal catheter extending to the bifurcation of the main-stem bronchi in anesthetized mice. The mice were maintained for a period of 6 days. Prior to the challenge study, the mice were non-surgically implanted with programmable temperature transponders (IPTT-3000, Bio Medic Data Systems, Inc.) for non-invasive subcutaneous temperature measurement with a handheld portable scanner (DAS-6002, Bio Medic Data Systems, Inc.). In-life analysis included monitoring the clinical status of each animal by evaluating the following metrics: body weight, body temperature, food consumption, and activity. Immediately following euthanasia, pulmonary tissues and the spleen were collected in sterile conditions and each organ was placed into individual containers containing 1 mL of 1×PBS (Mediatec Inc). The tissue was then homogenized using a Tissue TEAROR (Biospec Products Inc.) for 50 seconds on ice. Serial dilutions ($1:10^2$ to $1:10^8$) of the homogenate were plated onto separated BCSA plates. All plates were then incubated for 72 hours at 37° C. prior to manual cfu enumeration. Whole blood was collected in tubes containing EDTA (BD) immediately following euthanasia. Anti-coagulated blood was processed to determine total peripheral lymphocytes and mononuclear lymphocytes by the Animal Diagnostic Laboratory at the University of Michigan, using a HEMAVETH 950 hematology analyzer (Drew Scientific, Inc.) in accordance to manufacturer's recommendation.

Statistics. Antibody end-titer results are expressed as mean±standard error of the mean (SEM) or ±standard deviation (SD). The statistical significance was determined by ANOVA (analysis of variance) using the Student t and Fisher exact two-tailed tests. For the bacterial challenge studies, the distribution of the colonization was highly skewed, and therefore the data was transformed (natural log transformation) for data normalization. The normalized mean bacterial response in the lung and spleen were compared using an independent samples test with a two sided p-value. $p<0.05$ was considered to be statistically significant. All analyses were done with 95% confidence limits.

Identification of Immunoreactive Proteins

Figure 29:
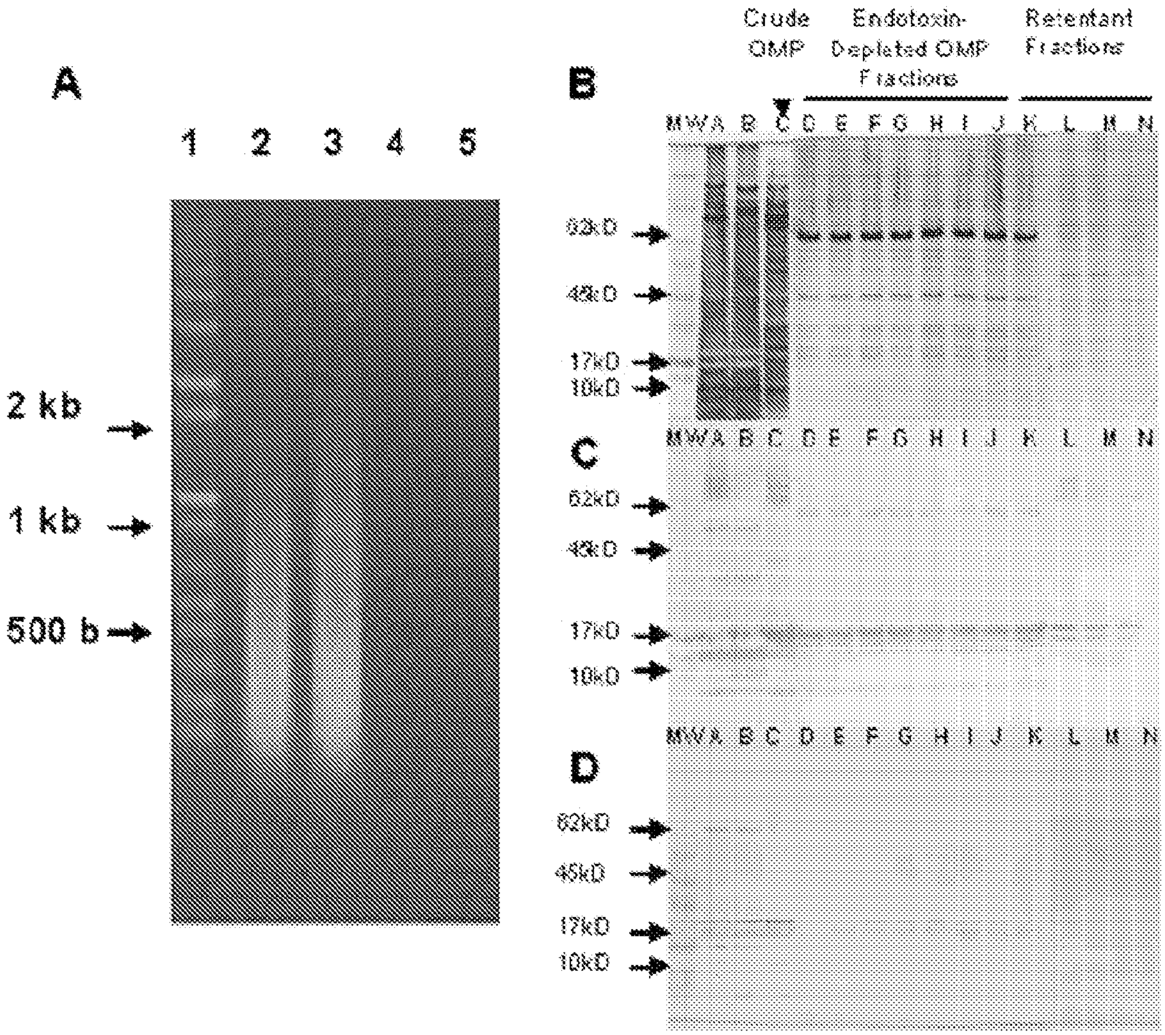
FIG. 29 shows characterization of the OMP preparation. A) Agarose gel electrophoresis and ethidium bromide-staining Lane 1. DNA ladder; Lane 2. Whole Cell lysate (WCL) before separation by high speed centrifugation; Lane 3. Supernatant following the 100,000×g spin (lane B in B, C, & D); Lane 4. Crude OMP preparation (lane C in B, C, & D); Lane 5. Endotoxin (ET) depleted OMP fraction (lane E in B, C, & D). Volumetrically-loaded silver stain B) and western blot of OMP preparation (C-D). Lane A. Protein from the supernatant produced after the 6000×g centrifugation was loaded; Lane B. An equal volume of the supernatant from the 100,000×g centrifugation; Lane C. Crude OMP (the re-suspended pellet fraction of the 100,000×g spin); Lanes D-J. Endotoxin-depleted OMP fractions (the successive flow-through portions of the endotoxin column); Lanes K-N. Endotoxin column retentant fractions (the successive fluid regenerated from the column after the addition of sodium deoxycholate). C) Western blot probed with serum from mice immunized with the endotoxin-depleted OMP-NE preparation. D) Western blot probed with serum from mice immunized with the OMP in PBS preparation.

Immunoreactive OMP proteins were identified via silver stain (See FIG. 29B) and western blot (See FIGS. 29C and D). Major reactive bands were documented at 62, 45, 17, and 10 KDa in both cases; however, the intensity of the bands was much higher with serum from mice immunized with the NE-based vaccine (See FIG. 29C) as compared to the blot probed with an equivalent serum dilution from mice immunized with the OMP in PBS preparation (See FIG. 29D).

The band with the highest intensity was located at ~17 KDa (See FIG. 29C). For the purpose of identification, the 17 KDa band was isolated from the gel and identified by MALDI-TOF analysis. The protein was identified as *Burkholderia cepacia* outer membrane lipoprotein A (OmpA) with a MW of 16.396 KDa (See, e.g., Ortega et al., 2005 J Bacteriol 187, 1324-1333; Plesa et al., 2004, J Med Microbiol 53, 389-398). Sequence analysis using National Center for Biotechnology Information (NCBI) protein BLAST confirmed that these proteins are present in other closely related *Burkholderia* species (See Table 25, below). A high degree of protein homology (87.9% sequence homology) was identified in numerous strains of *Burkholderia* and *Ralstonia* organisms and highly conserved amino acids from the OmpA family residues are present in the 17 KDa protein sequence (See Table 25). Thus, the present invention identified and provides immunoreactive OMP proteins from *B. cepacia* as well as proteins from related strains of *Burkholderia* species displaying a high degree of homology to the identified immunoreactive OMP proteins from *B. cepacia* (e.g., that find use in immunogenic compositions comprising a nanoemulsion (e.g., that are administered to a subject in order generate a specific immune response in the subject toward the immunogenic composition comprising nanoemulsion and immunoreactive OMP proteins or homologues)).

TABLE 25

Protein sequence alignment of OmpA-like protein family.

| Organisms | Omp-A like sequences alignment | Identity (%) |
|---|---|---|
| *B. centocepacia* | LDDKANAGAVSTOPSADNV SIYFDF DSYSVKDEYQPLLQQQGNTDERSTSEYN ALALLGV VSLGKEKP LATGHDEASWA<br>AQVNVDPLNDPNSPLAKR HAQYLKSHPQRHVL LALGQKRAEAVRR ADSQMEA QNRRADLVYQQ | 100 |
| *B. dolosa* | LDDKANAGAVSTQPSADNV SIYFDF DSYSVKDEYQPLLQQQGNTDERSTSEYN ALALLGV VSLGKEKP LATGHDEASWA<br>AQVNVDPLNDPNSPLAKR HAQYLKSHPQRHVL LALGQKRAEAVRR ADSQMEA QNRRADLVYQQ | 100 |
| *B. multivorans* | LDDKANAGA+STQPSADNV SIYFDF DSYSVKDEYQPLLQQQGNTDERSTSEYN ALALLGV VSLGKEKP LATGHDEASWA<br>AQVNVDPLNDPNSPLAKR HAQYLKSHPQRHVL LALGQKRAEAVRR ADSQMEA QNRRADLVYQQ | 98 |
| *B. ambifaria* | LDDKANAGAVSTQPSADNV SIYFDF DSYSVKDEYQPL+QQQGNTDERSTSEYN A+ALLGV VSLGKEKP LA+GHDEASWA<br>AQVNVDPLNDPNSPLAKR HAQYLKSHPQRHVL LALGQKRAEAVRR DSQMEA QNRRALDVYQQ | 96 |
| *B. vietnamiensis* | LDDKAN-AGAVSTQPSADN SIYFDF DSYSVKDEYQPLLQQQGNTDERSTSEYN A+ALLGV VSLGKEKP LATGHDEASWA<br>VAQVNRVDPLNDPNSPLAK HAQYLKSHPQRHVL LALGQKRAEAVRR DSQMEA QNRRADLVYQQ | 97 |
| *B. ubanensis* | LD+KNAGA+STQP+ +NVA SIYFDF DSYSVKDEYQPL+QQQGNTDERSTSEYN A+ALLGV VSLGKEKP LA GHDEASWA<br>QV VDPLNDPNSPLAKR HAQYLKSHPQRHVL LALGQKRAEAVRR ADSQMEA QNRR+DLVYQQ | 92 |
| *B. thailandensis* | LD+ AN-GAVSTQP+ +NA SIYFDF DSYSV+D+YQPLLQQQGNTDERSTSEYN AL+LLGV VSLGKEKP LA GHDEASWA<br>QV VDPLNDPNSPLAKR HAQYLKSHPQRH+L LALGQKRAEAVRR DSQMEA QNRRADLVYQQ | 88 |
| *B. graninis* | LD+ AN- GAVSTQP+++V SIYFDF DSYSVKD+YQPLLQQQGNTDERSTSEYN AL+L+GV VSLGKEKP LATGHDE +SW<br>AQVNVDPLNDPNSPLAKR H+QYLKSHPQRHVL LALGQKRAEAVRR DSQMEA QNRRADLVYQQ | 88 |
| *B. aklahomensis* | LD+ AN-GAVSTQP++NVA SIYFDF DSYSV+D+YQPLLQQQGNTDERSTSEYN AL+LLGV VSLGKEKP LA GHDEASWA<br>QV VDPLNDPNSPLAKRS HAQYLK HPQRH+L LALGQKRAEAVRR DSQMEA QNRRADLVYQQ | 87 |
| *B. pseudomallei* | LD+ AN G-AVSTQP+ +N SIYFDF DSYSV+D+YQ LLQQQGNTDERSTSEYN AL+LLGV VSLGKEKP LA GHDEASWA<br>VAQV VDPLNDPNSPLAKR HAQYLKSHPQRH+L LALGQKRAEAVRR D+QMEA QNRRADLVYQQ | 87 |
| *B. xenovarans* | LD+ AN G-+VS QP+++V SIYFDF DSYSVKD+YQ LLQQQGNTDERSTSEYN AL+L+GV VSLGKEKP LATGHDE+SWA<br>A V VDPLNDPNSPLAKR HAQYLKSHPQRH+L LALGQKRAEAVRR DSQMEA QNRRADLVYQQ | 86 |
| *B. phytafirmans* | LD+ AN- G VS QP+ ++ SIYFDF DSYSVKD+YQ LLQQQGNTDERSTSEYN AL+L+GV VSLGKEKP LATGHDE+SWA<br>VA VNVDPLNDPNSPLAKR HAQYLKSHPQRHVL LALGQKRAEAVRR DSQMEA QRNRADLVYQQ | 86 |
| *B. phymanon* | LD+ A - GA QP+ ++VA SIYFDF DSYSVKD+YQPLLQQQGNTDERSTSEYN AL+LLGV VSLGKEKP LATGHDEASWA<br>VNVDPLNDPNSPLAKR HAQYLKSHPQRHVL LALGQKRAEAVRR DS+MEA QNRRADLVYQQ | 86 |
| *R. metallidurans* | LDD + + GA- ANVA V+ SIYFDF SDYSVK +YQ +LQ QGNTDERSTSEYN +LA +GV VSLGKEKP ATGHD+ASWA+<br>V-DPLNDPNPLAKR H+QVL S+ R+LQ LALGQKRAEAVRR DSQMEA NRRAD+VY | 73 |
| *R. entropha* | LDD ANAGA AD- V V+V SIYFDF SDYSVK EYQ +L +QGNTDERSTSEYN +LA +GV VSLGKEKP +TGHDEA+WA+<br>-DPLNDPNSPLAKR HA+YL S+ R +L LALGQKRAEAVRR +DSQMEA NRRAD+ Y | 73 |
| *R. solanacearan* | LDD-K G +T NV V+V-D SIYFDF DSY+VK EYQ LL QQGNTDERSTSEYN AL+ GV VSLGKEKP ATGHDESWAQN<br>L DPNSPLAKR HA+YL+SH QR VL LALGQKRAEAVRR DSQMEA RR+D+ VY | 74 |

Intranasal Immunization with OMP-NE Induces Anti-OMP Specific Antibodies

Figure 30:
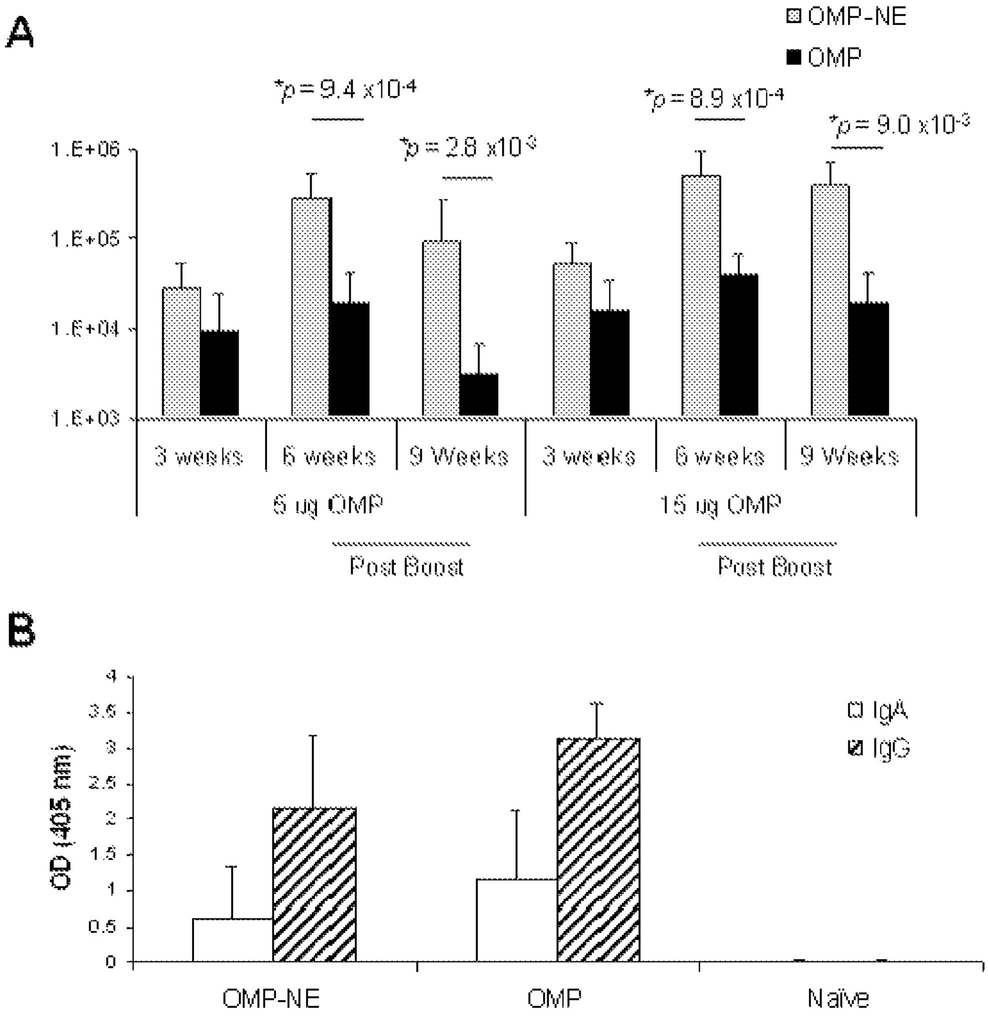
FIG. 30 shows antibody responses against *B. cenocepacia* OMP. A) ELISA results of the IgG response in serum post-immunization with the OMP preparation with or without nanoemulsion. Serum anti-OMP IgG antibody concentrations are presented as mean of endpoint titers in individual sera±SEM. * indicates a statistical difference ($p<0.05$) in the anti-OMP IgG titers. B) Mucosal antibodies sIgA and IgG against the OMP after nasal vaccine with or without nanoemulsion. sIgA and IgG were measured in BAL solution. The OD levels were normalized to total protein content within the samples.

The humoral immune responses against the OMP induced by nasal vaccine with OMP were characterized in vivo in the CD-1 mice. Intranasal vaccination with either 5 μg or 15 μg OMP preparations+NE (OMP-NE) resulted in high serum titers of OMP-specific IgG antibodies of $2.8\times10^5$ and $5.1\times10^5$ at 6 weeks, respectively, following primary vaccination (See FIG. 30A). OMPs without adjuvant were immunogenic and resulted in serum anti-OMP IgG titers of $1.9\times10^4$ and $3.8\times10^4$ six weeks following primary i.n. immunization. However, treatment groups with NE as an adjuvant responded significantly higher (13 to 30 fold) than groups without adjuvant at all time points following the boost ($p<0.05$). Further, mice immunized with OMP in PBS did not demonstrate a significant boost effect following the second vaccination (See FIG. 30A).

To further characterize the OMP-NE vaccine, the OMP-NE composition's ability to elicit specific antibody production in bronchiolar secretions was evaluated. Mucosal antibody production may be important for protection against *Burkholderia* colonization since secretory antibodies are thought to be critical effectors in protection against mucosal respiratory pathogens (See, e.g., Nelson et al., 1993, J Med Microbiol 39, 39-47). Mucosal immune responses were evaluated in bronchoalveolar lavage (BAL) fluid of animals immunized with 5 μg OMP-NE or 5 μg OMP in PBS. Comparable levels of anti-OMP antibodies in BALs were detected in mice immunized either with OMP-NE or OMP without NE adjuvant (See FIG. 30B).

OMP-NE Immunization Yields a Balanced Th1/Th2 Cellular Response

Figure 31:
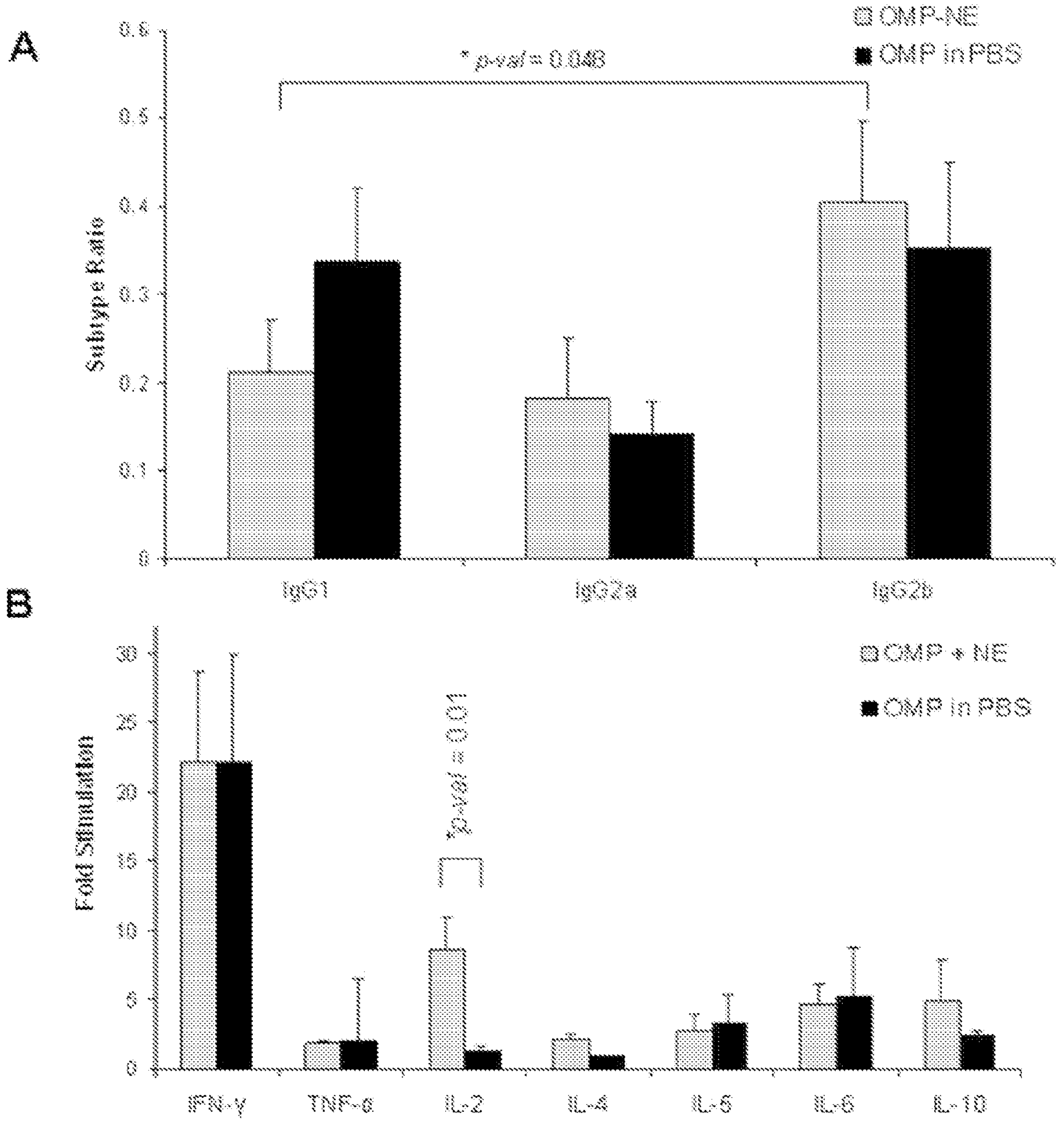
FIG. 31 shows type of cellular immune responses induced by nasal OMP-NE vaccine. A) Serum from mice immunized with 5 μg OMP mixed with either NE (OMP-NE) or with PBS (OMP-PBS) was analyzed for antibody subtype distribution. The results are presented as ratio of the specific subclass IgG to the overall IgG titer. *: indicates statistical difference ($p<0.05$) between IgG2b and IgG1 subtypes. B) Cytokine profiling of splenocytes of mice immunized with 5 μg. mixed with either NE (OMP-NE) or with PBS (OMP-PBS) Data is represented as fold change±SEM comparing OMP-activated versus non activated splenocytes and is normalized to responses in non-vaccinated mice. *: indicates statistical difference ($p<0.05$) between OMP-NE and OMP in PBS groups.

The analysis of the serum IgG subclass was performed to determine the T helper-type bias of the cellular response. The pattern of IgG subclass distribution shows that i.n. immunization with OMP-NE produced increased levels of Th1-type IgG2b versus Th2-type IgG1 subclass antibodies ($p=0.048$) (See FIG. 31A). In comparison, immunization with OMP in PBS produced similar levels of IgG1 and IgG2b antibodies (See FIG. 31A).

OMP-specific cellular responses were characterized in splenocytes obtained 6 weeks following primary vaccination with OMP-NE. The cells were stimulated with endotoxin-depleted OMP and then evaluated for specific cytokine production. In splenocytes collected from OMP-NE vaccinated mice, Th1 cytokines IFN-γ and IL-2 production increased 22.1 and 18.6-fold respectively over that of splenocytes from non-vaccinated mice ($p=0.01$ and 0.003, respectively) (See FIG. 31B). IFN-γ was equally induced in splenocytes from mice immunized with OMP in PBS. The Th2 cytokines IL-4, IL-5, IL-6, and IL-10 were minimally induced (≤5.22-fold increase) in both OMP-NE and OMP immunized mice in equivalent amounts. The pattern of splenic cytokine expression and the IgG subclass distribution results indicated a balanced Th1/Th2 response to OMP-NE vaccination.

Antibody Response is Directed Toward OMP Lipoprotein and LPS

It has been previously documented that LPS is intrinsically associated with *Burkholderia* spp. OMP preparations (See, e.g., Bertot et al., 2007, Infect Immun 75, 2740-2752). To investigate the specificity of immune response and to evaluate the possible immune enhancing role of endotoxin in *B. cencocepacia* OMP preparations, serum from mice immunized with OMP-NE was analyzed using ELISA with either crude OMP, endotoxin-depleted OMP, or LPS. The highest IgG reactivity was against the endotoxin-depleted and crude OMP preparations. The statistical analysis indicated a significantly higher response in endotoxin-depleted OMP versus LPS ($OD_{405}=2.37\pm0.11$ ($p=0.001$)) and crude OMP versus LPS ($OD_{405}=1.49\pm0.14$ ($p=0.01$)). However, the serum also contained significant levels of IgG anti-LPS antibodies ($OD_{405}=0.59\pm0.05$).

Figure 32:
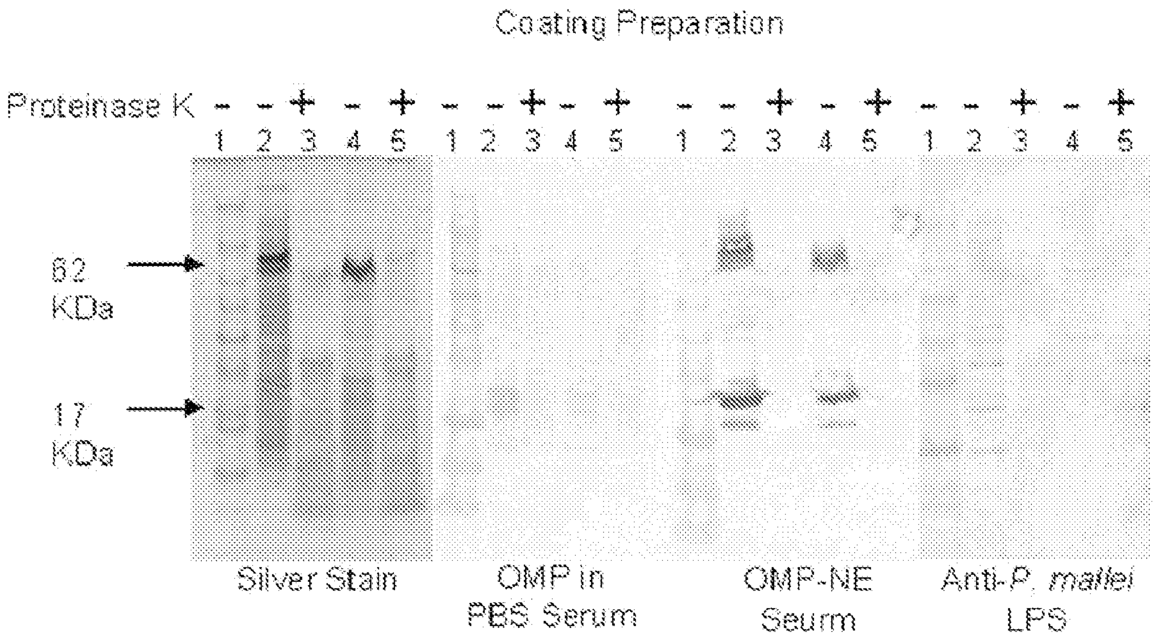
FIG. 32 shows identification of protein epitopes and LPS in OMP preparations. Lane 1. Protein ladder; Lane 2. Crude OMP preparation; Lane 3. Proteinase K digested crude OMP preparation; Lane 4. Endotoxin-depleted OMP; Lane 5; Proteinase K digested endotoxin-depleted OMP. Western blots were probed with serum from either OMP in PBS or OMP-NE immunized mice or with a monoclonal anti-*Pseudomonas mallei* LPS antibody as indicated.

To clarify the role of endotoxin in the OMP preparation, a proteolytic digest of the crude OMP and endotoxin-depleted OMP preparations were performed with proteinase K. The immunogenic epitopes were determined by western blot analysis comparing serum antibodies generated in mice vaccinated with OMP in PBS versus from mice vaccinated with OMP-NE (See FIG. 32). The results clearly indicated that antibody response was directed mainly toward 62 KDa and 17 KDa proteins contained within the OMP preparation. This was confirmed by the complete absence of the protein bands in the proteolytically digested OMP preparations (See FIG. 32 OMP-NE serum western blot). Further, when the OMP preparations were probed with commercial monoclonal anti-LPS antibody, LPS was detected as an intrinsic part of the OMP preparation. However, the proteolytic digest diminished the LPS detection but not totally. Overall, the present invention provides that nasal immunization with OMP-NE enhances the production of antibodies specific against OMP proteins (See FIG. 32).

Intranasal Vaccination with OMP-NE Results in Cross-protective Neutralizing Serum Antibody

Figure 33:
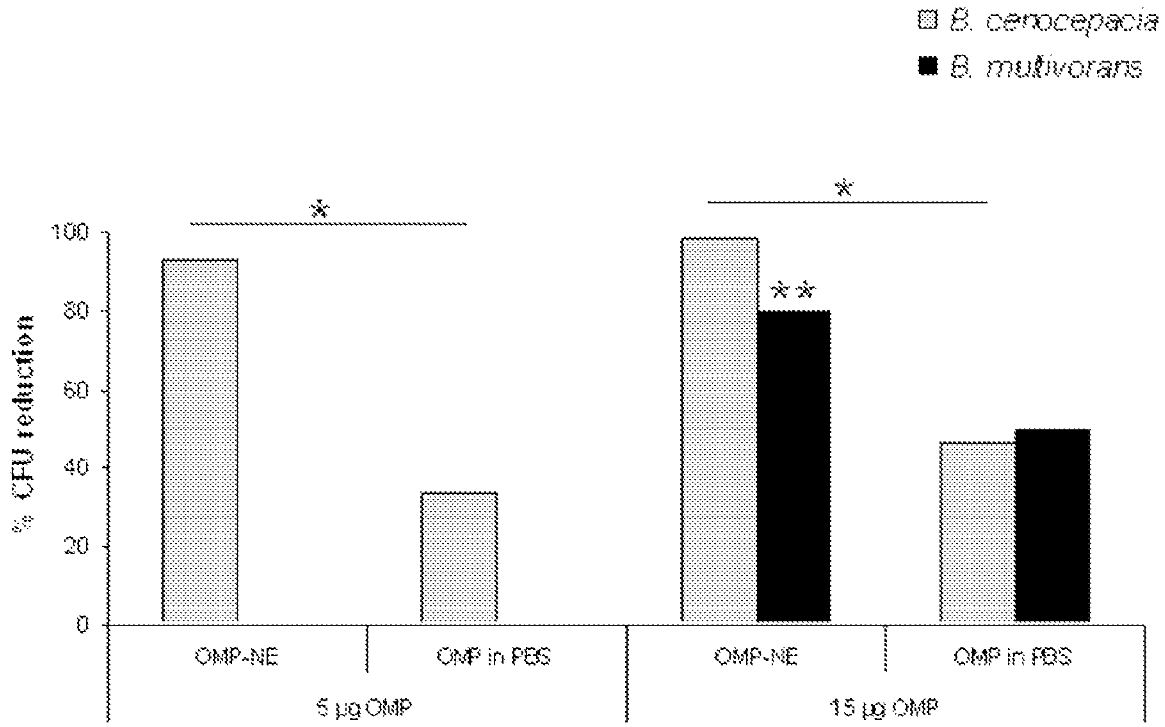
FIG. 33 shows serum neutralization assay. Percent reduction of *B. cenocepacia* or *B. multivorans* cfu plotted against samples with naïve serum. A statistical difference in *B. cenocepacia* neutralizing activity was observed between serum from mice immunized with OMP-NE and serum from mice immunized with OMP in PBS formulations ($p=9.9\times10^{-5}$ for 5 ug OMP-NE and 0.03 for 15 ug OMP-NE). *B. multivorans* cross-neutralizing activity was observed between serum from mice immunized with OMP-NE and serum from naïve mice ($p=0.04$). * indicates a statistically significant ($p<0.05$) difference in neutralizing activity between OMP-NE and OMP in PBS. ** indicates a statistically significant ($p<0.05$) difference in neutralizing activity between OMP-NE vaccinated and naïve mice.

*B. cenocepacia* neutralizing antibodies were determined using a colony reduction assay. The mice intranasally vaccinated with 5 μg or 15 μg OMP-NE produced serum-neutralizing antibodies that inhibited 92.5% or 98.3% of *B. cenocepacia* colonies, respectively, as compared to serum from non-vaccinated mice (See FIG. 33). The mice vaccinated with OMP lacking adjuvant also demonstrated a relatively high level of inhibition, resulting in 33.3% and 46.7% (for 5 μg and 15 μg OMP-PBS, respectively) cfu reduction. The statistical analysis showed that *B. cenocepacia* growth was significantly inhibited by serum derived from OMP-NE as compared to serum from those who were immunized with the OMP preparation alone (See FIG. 33).

To evaluate if the OMP-NE can produce cross-reactive protection from other bacterial strains, serum from mice vaccinated with 15 μg OMP-NE was also incubated with *B. multivorans*. The *B. multivorans* was selected because it is the most common isolate cultured from CF patients infected with Bcc organisms (See, e.g., Baldwin et al., 2008, J Clin Microbiol 46, 290-295). The serum inhibited *B. multivorans* growth by 80.1% and by 49.8% derived from mice vaccinated with OMP-NE and OMP without adjuvant, respectively, suggesting significant cross-protective antibodies following immunization with either OMP-NE or OMP in PBS (See FIG. 33).

Immunization with OMP-NE Protects Against Pulmonary *B. cenocepacia* Challenge and Reduces Incidence of Sepsis The protective effect of intranasal immunization was further tested in vivo in a lung infection model. The clearance of *B. cenocepacia* from pulmonary tissue was evaluated 6 days following intra-tracheal inoculation in mice that were intranasally immunized with the OMP-NE or the OMP without an adjuvant. Vaccination with 15 μg OMP-NE resulted in significantly higher rates of pulmonary clearance ($p=9.2\times10^{-3}$) as compared to the non-vaccinated mice (See FIG. 34A). At day 6, the average pulmonary bacterial load was 22.5±26.2 cfu in mice vaccinated with 15 μg OMP-NE, compared to $1.28\times10^6\pm3.36\times10^6$ cfu per lung in non-vaccinated mice, representing a greater than 5-log reduction in the bacterial load.

Splenic colonization following pulmonary inoculation with *B. cenocepacia* was evaluated as a means of assessing sepsis (See FIG. 34B). Vaccination with 15 μg OMP-NE significantly reduced the incidence of bacteria in the spleens 6 days following the pulmonary challenge of individual mice from an average of $3.54\times10^3\pm6.97\times10^3$ cfu per spleen in non-vaccinated mice to 2.5±5 cfu per spleen in vaccinates (p=0.0307).

Intranasal Immunization with OMP-NE Attenuates Systemic Illness after *B. cenocepacia* Infection

*B. cenocepacia* infection resulted in greater loss of thermoregulation by day 6 in the non-vaccinated mice than in the mice immunized with OMP-NE or OMP without the adjuvant. The mean body temperature 6 days following infection with *B. cenocepacia* was significantly lower in non-vaccinated mice (35.4° C.±0.7) as compared to mice vaccinated with 15 μg OMP—NE (36.8° C.±0.31, p=0.008), 5 μg OMP-NE (37.1° C.±0.42, p=0.008), or 5 μg OMP without the adjuvant (36.8° C.±0.61, p=0.01).

The total peripheral leukocyte counts determined at the time of sacrifice in the non-vaccinated mice were significantly higher from the values observed for the mice vaccinated with 15 μg OMP-NE (p=0.047), 5 μg OMP-NE (p=0.026), or 15 μg OMP in PBS (p=0.032). The ratio of polymorphonuclear leukocytes to total peripheral leukocytes were also significantly higher in non-vaccinated mice (76.0%) compared to mice vaccinated with 15 μg OMP-NE (47.7%, p=0.02), 5 μg OMP-NE (45.6%, p=0.024), or 15 μg OMP in PBS (48.7%, p=0.04) (See Table 26, below). In combination with the splenic colonization results described above (See FIG. 39B), the present invention provides that immunization with OMP-NE resulted in significantly decreased systemic disease following infection with *B. cenocepacia*.

TABLE 26

Ratio of polymorphonuclear leukocytes to total peripheral leukocytes.

| | Mean Polymorphonuclear Leukocytes | |
|---|---|---|
| Immunization Group | Concentration ($10^9$/L) | % Total Pertipheral Leukocyte Count |
| 5 μg OMP-NE | 1.99 ± 0.20* | 45.6* |
| 5 μg OMP in PBS | 3.23 ± 0.29 | 59.7 |
| 15 μg OMP-NE | 2.58 ± 0.48* | 47.7* |
| 15 μg OMP in PBS | 2.56 ± 0.55* | 48.7* |
| Non-Vaccinated | 7.29 ± 1.35 | 76.0 |

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:

1. A method of treating an infection of a wound comprising administering a composition comprising a therapeutically effective amount of a nanoemulsion, wherein the nanoemulsion comprises:

1. 30-90%, 60-80%, or 60-70% by volume oil;
2. 3-15% by volume solvent; wherein said solvent is selected from the group consisting of ethanol and glycerol;
3. 0.05-10.0% by volume non-ionic surfactant and 0.001-5.0% by volume cationic surfactant;
4. ethylenediaminetetraacetic acid (EDTA); and
5. water to said wound, wherein said composition kills or inhibits growth of bacteria within the wound infection in the absence of increased inflammation and edema at the site of the wound.

2. The method of claim 1, wherein said wound infection comprises *Staphylococcus aureus*.

3. The method of claim 2, wherein said *Staphylococcus aureus* are antibiotic resistant.

4. The method of claim 1, wherein said wound infection comprises *Pseudomonas aeruginosa*.

5. The method of claim 1, wherein said composition is co-administered with a bioactive agent.

6. The method of claim 1, wherein said nanoemulsion comprises:

a) water;
b) polyoxyethylenesorbitan monolaurate;
c) glycerol or ethanol;
d) oil;
e) dimethyl benzyl ammonium chloride; and
f) ethylenediaminetetraacetic acid (EDTA).

7. The method of claim 1, wherein said nanoemulsion comprises:

a) water;
b) a non-ionic surfactant selected from the group consisting of polyoxyethylenesorbitan monolaurate, polyoxyethylenesorbitan monooleate, and a poloxamer;
c) glycerol or ethanol;
d) oil;
e) a cationic surfactant selected from the group consisting of cetylpyridinium chloride (CPC), benzalkonium chloride, and alkyl dimethyl benzyl ammonium chloride; and
f) ethylenediaminetetraacetic acid (EDTA).

8. The method of claim 1, wherein said nanoemulsion has a mean particle size of 0.2-0.8 microns.

9. The method of claim 1, wherein said nanoemulsion has a mean particle size less than 0.5 microns.

10. The method of claim 1, further comprising the step of co-administering an antimicrobial agent to said wound.

11. The method of claim 10, wherein said antimicrobial agent is an antibiotic.

12. The method of claim 1, wherein said nanoemulsion comprises:

a) water;
b) 0.05-10.0% polyoxyethylene sorbitan monolaurate;
c) 3-15% glycerol;
d) oil;
e) 0.001-5.0% benzalkonium chloride; and
f) ethylenediaminetetraacetic acid (EDTA).

* * * * *